US008691256B2

(12) United States Patent
Enan

(10) Patent No.: US 8,691,256 B2
(45) Date of Patent: Apr. 8, 2014

(54) PEST CONTROL COMPOSITIONS AND METHODS

(75) Inventor: Essam Enan, Davis, CA (US)

(73) Assignee: Tyratech, Inc., Melbourne, FL (US)

( * ) Notice: Subject to any disclaimer, the term of this patent is extended or adjusted under 35 U.S.C. 154(b) by 229 days.

(21) Appl. No.: 12/936,039

(22) PCT Filed: Mar. 19, 2009

(86) PCT No.: PCT/US2009/037733
§ 371 (c)(1),
(2), (4) Date: Jan. 28, 2011

(87) PCT Pub. No.: WO2009/117621
PCT Pub. Date: Sep. 24, 2009

(65) Prior Publication Data
US 2011/0124502 A1 May 26, 2011

Related U.S. Application Data

(60) Provisional application No. 61/070,137, filed on Mar. 19, 2008, provisional application No. 61/043,084, filed on Apr. 7, 2008, provisional application No. 61/048,477, filed on Apr. 28, 2008, provisional application No. 61/087,140, filed on Aug. 7, 2008.

(51) Int. Cl.
*A01N 25/32* (2006.01)

(52) U.S. Cl.
USPC ........... 424/406; 424/405; 424/745; 514/341; 514/398; 514/552; 514/739

(58) Field of Classification Search
None
See application file for complete search history.

(56) References Cited

U.S. PATENT DOCUMENTS

| 4,320,113 A | 3/1982 | Kydonieus |
| 4,943,435 A | 7/1990 | Baker |
| 5,980,931 A | 11/1999 | Fowler |

(Continued)

FOREIGN PATENT DOCUMENTS

| WO | WO 00/05964 | * 2/2000 |
| WO | WO 2004/006968 | 1/2004 |

(Continued)

OTHER PUBLICATIONS

Appert-Collin, A., "Regulation of g protein-coupled receptor signaling by a-kinase anchoring proteins," Recept. Signal Transduct. Res., vol. 26, p. 631-646, 2006.

(Continued)

*Primary Examiner* — Neil Levy
(74) *Attorney, Agent, or Firm* — Davis Wright Tremaine LLP

(57) ABSTRACT

Embodiments of the present invention provide compositions for controlling a target pest including a first agent and a second agent comprising a pest control product or a signal cascade modulator, wherein the first agent and the second agent act synergistically to control the target pest. The first agent can be capable of interacting with a receptor in the target pest. The pest control product can have a first activity against the target pest when applied without the active agent and the compositions can have a second activity against the target pest; and the second activity can be greater than the first activity. Embodiments of the invention can include compositions that modulate the signal cascade initiated by the binding of ligands to, for example, cell surface receptors. Methods of screening such compositions are also disclosed.

6 Claims, 37 Drawing Sheets

(56) References Cited

U.S. PATENT DOCUMENTS

| | | | |
|---|---|---|---|
| 6,360,477 | B1 | 3/2002 | Flashinski |
| 6,610,254 | B1 | 8/2003 | Furner |
| 6,849,614 | B1* | 2/2005 | Bessette et al. ............... 514/72 |
| 2003/0060379 | A1* | 3/2003 | Souter et al. ............... 510/131 |
| 2003/0194454 | A1* | 10/2003 | Bessette et al. ............. 424/745 |
| 2003/0198659 | A1 | 10/2003 | Hoffmann |
| 2004/0185080 | A1 | 9/2004 | Hojo |
| 2005/0008714 | A1 | 1/2005 | Enan |
| 2005/0214267 | A1 | 9/2005 | Enan |
| 2006/0121126 | A1 | 6/2006 | McFadden |
| 2006/0263403 | A1 | 11/2006 | Enan |
| 2007/0232495 | A1 | 10/2007 | Nappa |
| 2007/0264297 | A1 | 11/2007 | Scialdone |
| 2007/0272281 | A1 | 11/2007 | Pel |
| 2008/0020078 | A1 | 1/2008 | Enan |
| 2008/0047312 | A1* | 2/2008 | Hill et al. ...................... 71/21 |
| 2008/0075796 | A1 | 3/2008 | Enan |
| 2008/0118585 | A1* | 5/2008 | Nouvel ...................... 424/739 |

FOREIGN PATENT DOCUMENTS

| | | |
|---|---|---|
| WO | WO 2006/061803 | 6/2006 |
| WO | WO 2008/088827 | 7/2008 |
| WO | WO 2009/117621 | 9/2009 |

OTHER PUBLICATIONS

Baxter, G.D., et al., "Isolation of a cDNA for an octopamine-like, G-protein coupled receptor from the cattle tick, *Boophilus microplus*," Insect Biochem. Mol. Biol., vol. 29, p. 461-467, 1999.

Colby, S.R., "Calculating synergistic and antagonistic responses of herbicide combinations," Weeds, vol. 15:1, p. 20-22, 1967.

Dalrymple, M.B., "G protein coupled receptor dimers: functional consequences, disease states and drug targets," Pharmacaol. Ther., vol. 118, p. 359-371, 2008.

Dong, C., "Regulation of G protein coupled receptor export trafficking," Biochem. Biophys. Acta, vol. 176, p. 853-870, 2007.

Enan, E., et al., "Deltamethrin-induced thymus atrophy in male Balb/c mice," Biochem. Pharmacol., vol. 51 No. 4, p. 447-454, 1995.

Gilchrist, A., "G-protein-coupled receptor pharmacology: examining the edges between theory and proof," Curr. Opin. Drug Discov. Devel., vol. 10, p. 446-451, 2007.

Grandy, D.K., "Trace amine-associated receptor 1—Family archetype or iconoclast?" Pharmacol. Ther., vol. 116, p. 355-390, 2007.

Han, K.A., et al., "A Novel Octopamine Receptor with Preferential Expression in *Drosophila* Mushroom Bodies," J. Neurosci., vol. 18, p. 3650-3658, 1998.

Jurado-Pueyo, M., "GRK2-dependent desensitization downstream of G proteins," Recept. Signal Transduct. Res., vol. 28, p. 59-70, 2008.

Klaasse, E., "Internalization and desensitization of adenosine receptors," Purinergic Signalling, vol. 4, p. 21-37, 2008.

Ma, L., "Beta-arrestin signaling and regulation of transcription," J. Cell. Sci., vol. 120, p. 213-218, 2007.

Milligan, G., "New aspects of g-protein-coupled receptor signalling and regulation," Trends Endocrinol. Metab., vol. 9, p. 13-19, 1998.

Nakahata, N., "Regulation of G Protein-coupled Receptor Function by Its Binding Proteins," Yakugaku Zasshi, vol. 127, p. 3-14, 2007.

Neitzel, K.L., "Cellular mechanisms that determine selective RGS protein regulation of G protein-coupled receptor signaling," Semin Cell. Dev. Biol., vol. 17, p. 383-389, 2006.

New, D.C., "Molecular mechanisms mediating the G protein-coupled receptor regulation of cell cycle progression," J. Mol. Signaling, vol. 2, p. 2-16, 2007.

Premont, R.T., "Physiological roles of G protein-coupled receptor kinases and arrestins," Annu. Rev Physiol., vol. 69, p. 511-534, 2007.

Sato, M., "Accessory proteins for G proteins; partners in signaling," Annu. Rev. Pharmacol. Toxicol., vol. 46, p. 151-187, 2006.

Saudou, et al., "Cloning and characterization of a *Drosophila* tyramine receptor," The EMBO Journal, vol. 9(11), p. 3611-7, 1990.

Schulte, G., "Novel aspects of G-protein-coupled receptor signalling—different ways to achieve specificity," Acta Physiol., vol. 190, p. 33-38, 2007.

Smrcka, A.V., "G protein beta gamma subunits: Central mediators of G protein-coupled receptor signaling," Cell. Mol. Life Sci., vol. 65, p. 2191-2214, 2008.

Stewart, A.J., "Phospholipase C-eta Enzymes as Putative Protein Kinase C and $Ca^{2+}$ Signalling Components in Neuronal and Neuroendocrine Tissues," Neuroendocrinology, vol. 86, p. 243-248, 2007.

Takeishi, Y., "Role of diacylglycerol kinase in cellular regulatory processes: a new regulator for cariomyocyte hypertrophy," Pharmacol. Ther., vol. 115, p. 352-359, 2007.

Torrecilla, I., "Co-ordinated covalent modification of G-protein coupled receptors," Curr. Pharm. Des., vol. 12, p. 1797-1808, 2006.

Von Nickisch-Rosenegk, et al., "Cloning of biogenic amine receptors from moths (*Bombyx mori* and *Heliothis virescens*)," Insect Biochem. Mol. Biol., vol. 26, p. 817 -827, 1996.

Wolfe, B.L., "Clathrin-Dependent Mechanisms of G Protein-coupled Receptor Endocytosis," Traffic, vol. 8, p. 462-470, 2007.

Xu, Z.Q., "Regulation of G protein-coupled receptor trafficking," Acta Physiol, vol. 190, p. 39-45, 2007.

Yang, W., "Mechanisms of regulation and function of Gprotein-coupled receptor kinases," World J. Gastroenterol, vol. 12, p. 7753-7757, 2006.

Yu, J.H., "Heterotrimeric G protein signaling and RGSs in *Aspergillus nidulans*," J. Microbio., vol. 44, p. 145-154, 2006.

Genbank Accession No. AF343878, "Mamestra brassicae putative octopamine receptor (OAR) mRNA, complete cds.," 2001 [online] [Retrieved on Nov. 19, 2012] Retrieved from: http://ww.ncbi.nlm.nih.gov/nuccore/13173420.

Genbank Accession No. AJ007617, "*Drosophila melanogaster* mRNA for octopamine receptor, splice variant 1B," 1999 [online] [Retrieved on Nov. 19, 2012] Retrieved from: http://www.ncbi.nlm.nih.gov/nuccore/AJ007617.

U.S. Appl. No. 61/043,084, filed Apr. 7, 2008, "Insect Control Methods and Compositions Using Neonicotinoids".

U.S. Appl. No. 61/048,477, filed Apr. 28, 2008, "Pest Control Compositions and Methods".

U.S. Appl. No. 61/070,137, filed Mar. 19, 2008, "Insect and Parasite Control Methods and Compositions".

U.S. Appl. No. 61/087,140, filed Aug. 7, 2008, "Compositions and Methods for Increasing Pesticide Effectiveness".

PCT International Preliminary Report on Patentability in corresponding International application No. PCT/US2009/037733, issued Sep. 21, 2010, 12 pages.

First Office Action of the State Intellectual Property Office, mailed in related Chinese Application No. 200980118165.6, dated Nov. 1, 2011.

\* cited by examiner

```
ATGCCATCGG CAGATCAGAT CCTGTTTGTA AATGTCACCA CAACGGTGGC GGCGGCGGCT CTAACCGCTG CGGCCGCCGT CAGCACCACA
Met Pro Ser Gly Asp Gln Ile Leu Phe Val Asn Val Thr Thr Thr Val Ala Ala Ala Leu Thr Ala Ala Ala Val Ser Thr Thr

AAGTCCGGAA GCGGCAACGC CCGCACGGGC TACACGGGGC CGGATGACGA TGCGGGCATG GGAACGGAGG CGGTGGCTAA CATATCCGGC
Lys Ser Gly Ser Gly Asn Ala Ala Ala Gly Tyr Thr Asp Ser Asp Asp Ala Gly Met Gly Thr Glu Ala Val Ala Asn Ile Ser Gly

TCGCTGGTGG AGGGCCTGAC CACCGTTACC GCGGCATTGA GTACGGCTCA GGCGGACAAG GACTCAGCGC GAGAATGCGA AGGAGCTGTG
Ser Leu Val Glu Gly Leu Thr Thr Val Thr Ala Ala Leu Ser Thr Ala Gln Ala Asp Lys Asp Ser Ala Gly Glu Cys Glu Gly Ala Val

GAGGAGCTGC ATGCCAGCAT CCTGGGCCTC CAGCTGGGTG TGCCCGGAGTG GGAGGCCCTT CTCACCGCCC TGGTTCTCTC GGTCATTATC
Glu Glu Leu His Ala Ser Ile Leu Gly Leu Gln Leu Ala Val Pro Glu Trp Glu Ala Leu Leu Thr Ala Leu Val Leu Ser Val Ile Ile

GTGCTGACCA TCATCGGGAA CATCCTGGTG ATTCTGAGTG TGTTCACCTA CAAGCCGCTG CGCATCGTCC AGAACTTCTT CATAGTTTCG
Val Leu Thr Ile Ile Gly Asn Ile Leu Val Ile Leu Ser Val Phe Thr Tyr Lys Pro Leu Arg Ile Val Gln Asn Phe Phe Ile Val Ser

CTGGCGGTGG CCGATCTCAC GGTGGCCCCTT CTGGTGCTGC CCTTCAACGT GGCTTACTCG ATCCTGGGGC GCTGGGAGTT CGGCATCCAC
Leu Ala Val Ala Asp Leu Thr Val Ala Leu Leu Val Leu Pro Phe Asn Val Ala Tyr Ser Ile Leu Gly Arg Trp Glu Phe Gly Ile His

CTGTGCAAGC TGTGGCTCAC CTGCGACGTG CTGTGCTGCA CTAGCTCCAT CCTGAACCTG TGTCCCATAG CCCTCGACCG GTACTGGGCC
Leu Cys Lys Leu Trp Leu Thr Cys Asp Val Leu Cys Cys Thr Ser Ser Ile Leu Asn Leu Cys Ala Ile Ala Leu Asp Arg Tyr Trp Ala

ATTACGGACC CCATCAACTA TGCCCAGAAG AGGACCGTTG GTCGCGTCCT GCTCCTCATC TCCGGGGTGT GGCTACTTTC GCTGCTGATA
Ile Thr Asp Pro Ile Asn Tyr Ala Gln Lys Arg Thr Val Gly Arg Val Leu Leu Leu Ile Ser Gly Val Trp Leu Leu Ser Leu Leu Ile

AGTAGTCCGC CGTTGATCGG CTGGAACGAC AGTTCACGAG CGCCACGCCC TGCGAGCTGA CCTCGCAGCG AGGCCTACGTG
Ser Ser Pro Pro Leu Ile Gly Trp Asn Asp Ser Ser Arg Ala Thr Pro Cys Glu Leu Thr Ser Gln Arg Gly Tyr Val

ATCTACTCCT CGCTGGGCTC CTTCTTTATT CCGCTGGCCA TCATGACGAT CGTTCTACATC GAGATCTTCG TGGCCACGCG GCGCCGCCTA
Ile Tyr Ser Ser Leu Gly Ser Phe Phe Ile Pro Leu Ala Ile Met Thr Ile Val Tyr Ile Glu Ile Phe Val Ala Thr Arg Arg Arg Leu
```

FIG. 8A

```
AGGGAGGCGAG CCAGGGGCCAA CAAGCTTAAC ACGATCGCTC TGAAGTCCAC TGAGCTCGAG CCGATGGCAA ACTCCTCGCC CGTCGCCGCC
Arg Glu Arg Ala Arg Ala Asn Lys Leu Asn Thr Ile Ala Leu Lys Ser Thr Glu Leu Glu Pro Met Ala Asn Ser Ser Pro Val Ala Ala

TCCAACTCCG GCTCCAAGTC GGGTCTCCTA GCCAGCTGGC TTTGCTGCGG CCCAGTTCG GCCCAGTTCG GATCCAGAAC
Ser Asn Ser Gly Ser Lys Ser Gly Ser Leu Ala Ser Trp Leu Cys Cys Gly Arg Asp Arg Ala Gln Phe Ala Thr Pro Met Ile Gln Asn

GACCAGGAGA GCATCAGCAG TGAAACCCAC CAGCCGCAGG ATTCCTCCAA AGCGGGTCCC CATGGCAACA GCGATCCCCA ACAGCAGCAC
Asp Gln Glu Ser Ile Ser Ser Glu Thr His Gln Pro Gln Asp Ser Ser Lys Ala Gly Pro His Gly Asn Ser Asp Pro Gln Gln His

GTCGTCGTGC TGGTCAAGAA GTCGGCGTCGC GCCAAGACCA AGGACTCCAT TAAGCACGGC AAGACCCGTG GTGGCCAGCA GTCGCAGTCC
Val Val Val Leu Val Lys Lys Ser Arg Arg Ala Lys Thr Lys Asp Ser Ile Lys His Gly Lys Thr Arg Gly Gly Gln Gln Ser Gln Ser

TCGTCCACAT GCGAGCCCCA CGGGGAGCAA CAGCTCTTAC CCGCCGGCGG GGATGGCGGT AGCTGCCAGC CCGGCGGAGG CCACTCTGGA
Ser Ser Thr Cys Glu Pro His Gly Glu Gln Gln Leu Leu Pro Ala Gly Gly Gly Met Ala Val Ser Cys Gln Pro Gly Gly His Ser Gly

GGGCGAAAGT CGGACGCCGA GATCAGCACG GAGAGCGGGA GCGATCCCAA AGGTTGCATA CAGGTCTGCG TGACTCAGGC GGACGAGCAA
Gly Gly Lys Ser Asp Ala Glu Ile Ser Thr Glu Ser Gly Ser Asp Pro Lys Gly Cys Ile Gln Val Cys Val Thr Gln Ala Asp Glu Gln

ACGTCCCTAA AGCTGACCCC GCCGCAATCC TCGACGGGAG TCGCTGCCGT TTCTGTCACT CCGTTGCAGA AGAAGACTAG TGGGGTTAAC
Thr Ser Leu Lys Leu Thr Pro Pro Gln Ser Ser Thr Gly Val Ala Ala Val Ser Val Thr Pro Leu Gln Lys Lys Thr Ser Gly Val Asn

CAGTTCATTG AGGAGAAACA GAAGATCTCG CTTTCCAAGG AGCGGCGAGC GGCTCGCACC CTGGGCATCA TCATGGGCGT GTTCGTCATC
Gln Phe Ile Glu Glu Lys Gln Lys Ile Ser Leu Ser Lys Glu Arg Arg Ala Ala Arg Thr Leu Gly Ile Ile Met Gly Val Phe Val Ile

TGCTGGCTGC CCTTCTTCCT CATGTACGTC ATTCTGCCCT TCTGCCAGAC CTGCTGCCCC ACGAACAAGT TCAAGAACTT CATCACCTGG
Cys Trp Leu Pro Phe Phe Leu Met Tyr Val Ile Leu Pro Phe Cys Gln Thr Cys Cys Pro Thr Asn Lys Phe Lys Asn Phe Ile Thr Trp

CTGGGCTACA TCAACTCGGG CCTGAATCCG GTCATCTACA CCATCTTCAA CCTCGACTAC CGCCGGGCCT TCAAGCGGACT TCTGGGCCTG
Leu Gly Tyr Ile Asn Ser Gly Leu Asn Pro Val Ile Tyr Thr Ile Phe Asn Leu Asp Tyr Arg Arg Ala Phe Lys Arg Leu Leu Gly Leu

AATGA
Asn →
```

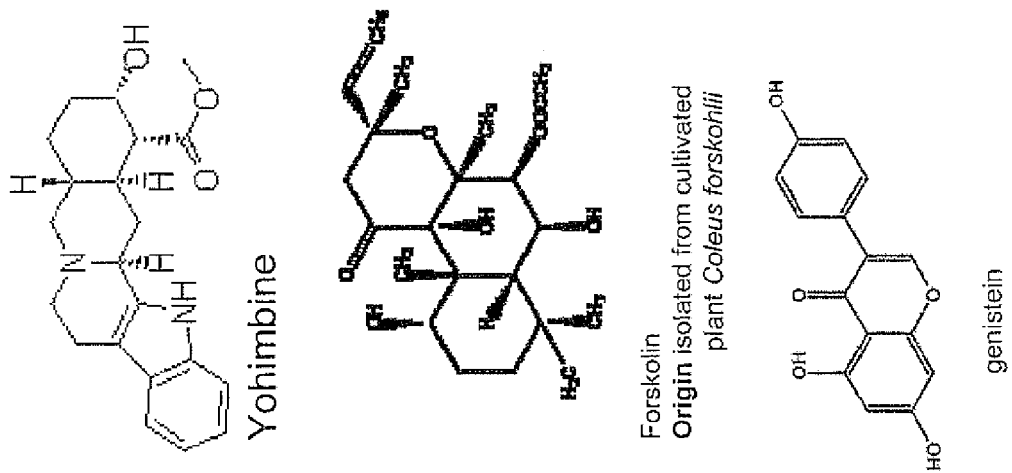
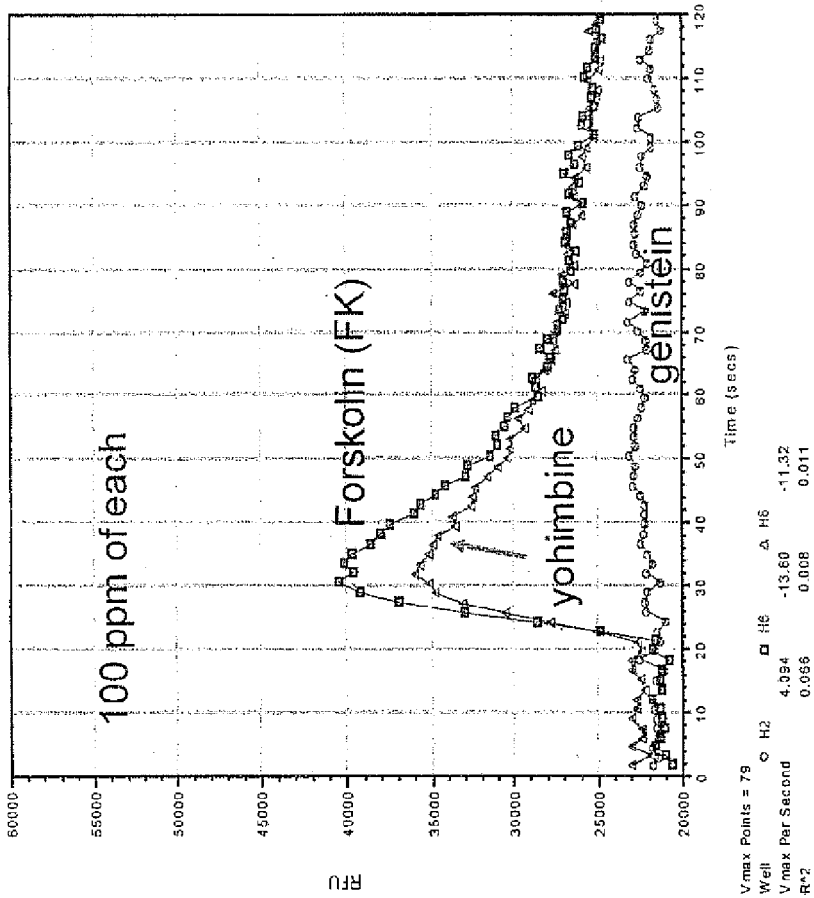
Figure 24

PEST CONTROL COMPOSITIONS AND METHODS

CROSS-REFERENCE TO RELATED APPLICATIONS

The present application is a U.S. National Stage entry under 35 U.S.C. §371 of International Application No. PCT/US2009/037733, filed Mar. 19, 2009, designating the United States of America and published in English on Sep. 24, 2009, which in turn claims priority to U.S. Application No. 61/070,137, filed Mar. 19, 2008, U.S. Application No. 61/043,084, filed Apr. 7, 2008, U.S. Application No. 61/048,477, filed Apr. 28, 2008, and U.S. Application No. 61/087,140, filed Aug. 7, 2008, each of which is incorporated herein by reference in its entirety.

FIELD OF THE INVENTION

The present invention relates to compositions and methods related to controlling insects. The invention also relates to compositions and methods for altering and/or disrupting G protein-coupled receptor signaling and cycling resulting in the disruption of normal biology or behavior in invertebrates.

BACKGROUND OF THE INVENTION

While the first recorded use of chemicals to control pests dates back to 2500 BC, only in the last 60 years has chemical control has been widely used. Early pesticides included hellebore to control body lice, nicotine to control aphids, and pyrithrin to control a wide variety of insects. Lead arsenate was first used in 1892 as an orchard spray, while at the same time it was discovered that a mixture of lime and copper sulphate (Bordeaux mixture) controlled downy mildew, a fungal disease of grapes.

The modern era of chemical pest control commenced during World War II. For example, DDT played a major role in maintaining the health and welfare of soldiers who used it to control body lice and mosquitoes. Further developments of pesticides followed, and with their relatively low cost, ease of use, and effectiveness, they became the primary means of pest control. Protection of crops, produce, animals, and humans over extended periods became possible with corresponding increases in food production and improved standards of living.

Some modern pesticides are sophisticated compounds that are carefully researched to ensure they are effective against target organisms, generally safe to the environment, and can be used without undue hazard to users or consumers. Many of these have been developed to target specific biochemical reactions within the target organism, e.g. an enzyme necessary for photosynthesis within a plant or a hormone required for normal development in an insect. Thus, some modern chemicals are safer, more specific, and friendlier to the environment than the older products they have replaced.

Furthermore, G protein-coupled receptors (GPCRs) form one of the largest families of integral membrane receptors. GPCRs transduce information provided by extracellular stimuli into intracellular second messengers via their coupling to heterotrimeric G proteins and the subsequent regulation of a variety of effector systems. Therapeutic agents often target GPCRs because of their capability to bind ligands, hormones, and drugs with high specificity. Agonist activation of GPCRs also initiates processes that desensitize GPCR responsiveness and their internalization.

Common to most GPCRs is the cyclic process of signaling, desensitization, internalization, resensitization, and recycling to the plasma membrane. This cycle prevents cells from undergoing excessive receptor stimulation or periods of prolonged inactivity. Mechanisms for desensitization of GPCRs include receptor phosphorylation and subsequent endocytosis, which removes the receptor-ligand complex from the cell surface. As a result of this desensitization process, a common limitation of GPCR-targeted compositions is target organism tolerance or resistance, as receptor desensitization can mute their effectiveness.

SUMMARY

The present disclosure relates to embodiments of a composition for controlling a target pest comprising a first agent and a second agent, wherein the first agent has a first activity against the target pest, the second agent has a second activity against the target pest, the composition has a third activity against the target pest, and the third activity reflects a synergistic interaction of the first agent and the second agent.

In a further aspect, the first agent comprises one or more compounds selected from the group consisting of amyl butyrate, trans-anethole, anise star oil, black seed oil, citral, p-cymene, genistein, geraniol, geranyl acetate, isopropyl myristate, d-limonene, linalool, linalyl acetate, lilac flower oil, methyl salicylate, a-pinene, piperonal, piperonyl alcohol, tetrahydrolinalool, thyme oil, thyme oil white, thymol, triethyl citrate, vanillin, and wintergreen oil.

In a further aspect, the first agent is capable of interacting with a receptor in the target pest.

In a further aspect, the receptor is a G protein-coupled receptor.

In a further aspect, the second agent is selected from the group consisting of a pesticide, a fungicide, an herbicide, a nematicide, an insecticide, an acaricide, and a bacteriocide.

In a further aspect, the second agent acts on a molecular target other than the receptor.

In a further aspect, the first agent is capable of interacting with the receptor to trigger, alter, or disrupt a biological function related to the binding of the receptor with the first agent, and the second agent is capable of interacting with a non-receptor molecule or step associated with cycling of the receptor, to disrupt the cycling of the receptor.

In a further aspect, the first activity persists for a first period, the second activity persists for a second period, the third activity persists for a third period, and the third period is longer than either the first period or the second period.

In a further aspect, at least one of the first activity and the second activity is essentially zero.

In a further aspect, the target pest is a species belonging to an animal order selected from the group consisting of Acari, Anoplura, Araneae, Blattaria, Blattodea, Coleoptera, Collembola, Diptera, Grylloptera, Hemiptera, Heteroptera, Homoptera, Hymenoptera, Isopoda, Isoptera, Lepidoptera, Mantodea, Mallophaga, Neuroptera, Odonata, Orthoptera, Psocoptera, Rhabditida, Siphonaptera, Symphyla, Thysanura, and Thysanoptera.

In a further aspect, the second agent is a diamide compound.

In a further aspect, the second agent is a spirocyclic phenyl-substituted tetronic acid pesticide.

In a further aspect, the second agent is selected from the group consisting of fipronil, clothianidin, imidacloprid, abamectin, forskolin, genistein, yohimbine, fluoxastrobin, flubendiamide and spiromesifen.

In a further embodiment, the second agent comprises fipronil.

In a further aspect of this embodiment, the first agent comprises amyl butyrate and anise star oil.

In a further aspect of this embodiment, amyl butyrate is present within a range of 20%-30%, and anise star oil is present within a range of 40%-60%.

In a further aspect of this embodiment, the first agent comprises geraniol, isopropyl myristate, and thyme oil white.

In a further aspect of this embodiment, geraniol is present within a range of 25%-35%, isopropyl myristate is present within a range of 35%-45%, and thyme oil white is present within a range of 25%-35%.

In a further aspect of this embodiment, the first agent comprises p-cymene, linalool, a-pinene, and thymol.

In a further aspect of this embodiment, p-cymene is present within a range of 25%-35%, linalool is present within a range of 5%-10%, a-pinene is present within a range of 2%-5%, and thymol is present within a range of 30%-45%.

In a further aspect of this embodiment, the first agent comprises isopropyl myristate, d-limonene, linalool, piperonal, piperonyl alcohol, tetrahydrolinalool, and vanillin.

In a further aspect of this embodiment, isopropyl myristate is present within a range of 15%-25%, d-limonene is present within a range of 5%-15%, linalool is present within a range of 10%-20%, piperonal is present within a range of 15%-25%, piperonyl alcohol is present within a range of 5%-15%, tetrahydrolinalool is present within a range of 15%-25%, and vanillin is present within a range of 0.5%-5%.

In a further embodiment, the second agent comprises imidacloprid.

In a further aspect of this embodiment, the first agent comprises geraniol, isopropyl myristate, and thyme oil white.

In a further aspect of this embodiment, geraniol is present within a range of 15%-35%, isopropyl myristate is present within a range of 35%-45%, and thyme oil white is present within a range of 25%-45%.

In a further aspect of this embodiment, the first agent comprises wintergreen oil, isopropyl myristate, and thyme oil white.

In a further aspect of this embodiment, wintergreen oil is present within a range of 20%-60%, isopropyl myristate is present within a range of 30%-40%, and thyme oil white is present within a range of 2%-45%.

In a further aspect of this embodiment, the first agent comprises p-cymene, linalool, a-pinene, and thymol.

In a further aspect of this embodiment, p-cymene is present within a range of 25%-35%, linalool is present within a range of 5%-10%, a-pinene is present within a range of 2%-5%, and thymol is present within a range of 30%-45%.

In a further aspect of this embodiment, the first agent comprises d-limonene and thyme oil white.

In a further aspect of this embodiment, the first agent additionally comprises lilac flower oil.

In a further aspect of this embodiment, d-limonene is present within a range of 25%-35%, thyme oil white is present within a range of 25%-35%, and lilac flower oil is present within a range of 35%-50%.

In a further aspect of this embodiment, the first agent additionally comprises wintergreen oil.

In a further aspect of this embodiment, d-limonene is present within a range of 50%-60%, thyme oil white is present within a range of 10%-20%, and wintergreen oil is present within a range of 25%-40%.

In a further embodiment, the second agent comprises abamectin.

In a further aspect of this embodiment, the first agent comprises isopropyl myristate, thyme oil white, and wintergreen oil.

In a further aspect of this embodiment, isopropyl myristate is present within a range of 30%-40%, thyme oil white is present within a range of 15%-25%, and wintergreen oil is present within a range of 40%-50%.

In a further embodiment, the second agent comprises clothianidin.

In a further aspect of this embodiment, the first agent comprises d-limonene, thyme oil white, and lilac flower oil.

In a further aspect of this embodiment, d-limonene is present within a range of 25%-35%, thyme oil white is present within a range of 25%-35%, and lilac flower oil is present within a range of 35%-50%.

In a further embodiment, the second agent comprises yohimbine, forskolin, or genistein.

In a further aspect of this embodiment, the first agent comprises isopropyl myristate and thyme oil white.

In a further aspect of this embodiment, the first agent additionally comprises geraniol.

In a further aspect of this embodiment, geraniol is present within a range of 25%-35%, isopropyl myristate is present within a range of 35%-45%, and thyme oil white is present within a range of 25%-35%.

In a further aspect of this embodiment, the first agent additionally comprises wintergreen oil.

In a further aspect of this embodiment, wintergreen oil is present within a range of 40%-50%, isopropyl myristate is present within a range of 30%-40%, and thyme oil white is present within a range of 15%-25%.

In a further embodiment, the second agent comprises forskolin or genistein, and the first agent comprises t-anethole, p-cymene, linalool, a-pinene, and thymol.

In a further aspect of this embodiment, t-anethole is present within a range of 15%-25%, p-cymene is present within a range of 0.5%-10%, linalool is present within a range of 30%-45%, a-pinene is present within a range of 2%-10%, and thymol is present within a range of 30%-45%.

In a further embodiment, the second agent comprises genistein.

In a further aspect of this embodiment, the first agent comprises anise star oil.

In a further aspect of this embodiment, the first agent additionally comprises amyl butyrate.

In a further aspect of this embodiment, amyl butyrate is present within a range of 20%-30%, and anise star oil is present within a range of 40%-60%.

In a further embodiment, the second agent is an alkaloid.

In a further aspect of this embodiment, the second agent is selected from the group consisting of caffeine, theobromine and theophylline.

In a further embodiment, the second agent is a flavonoid.

In a further aspect of this embodiment, the second agent is selected from the group consisting of epicatechin, hesperidin, kaempferol, naringin, nobiletin, proanthocyanidins, quercetin, resveratrol, rutin, and tangeretin.

In a further embodiment, the second agent is an isoflavone.

In a further aspect of this embodiment, the second agent is selected from the group consisting of daidzein, biochanin A, coumesterol, formononetin, and puerarin.

In a further embodiment, the second agent is a flavone, a flavonol, a flavanone, a 3-hydroxyflavanone, a flavan-3-ol, or an anthocyanidin.

In a further aspect of this embodiment, the second agent is selected from the group consisting of apigenin, luteolin, diosmin, flavoxate, fisetin, isorhamnetin, myricetin, pachypodol, rhamnazin, morin, eriodictyol, hesperetin, homoeriodictyol, naringenin, dihydrokaempferol, dihydroquercetin, catechin, epicatechin, epigallocatechin, cyanidin, delphinidin, malvidin, pelargonidin, peonidin, and petunidin.

In a further embodiment, the second agent is an organosulfide.

In a further aspect of this embodiment, the second agent is selected from the group consisting of allicin, glutathione, indole-3-carbinol, an isothiocyanate, and sulforaphane.

In a further embodiment, the second agent is a phenolic acid.

In a further aspect of this embodiment, the second agent is selected from the group consisting of capsaicin, ellagic acid, gallic acid, rosmarinic acid, and tannic acid.

In a further embodiment, the second agent is a phytosterol.

In a further aspect of this embodiment, the second agent is selected from the group consisting of beta-sitosterol and saponins.

In a further embodiment, the second agent is selected from the group consisting of a damnacanthal, a digoxin and a phytic acid.

In a further embodiment, the target pest is a species belonging to the order Rhabditida.

In a further embodiment, the target pest is a roundworm.

In a further embodiment, the target pest is a species belonging to the order Diptera.

In a further embodiment, the target pest is a species belonging to an order selected from the group consisting of Acari, Diptera, Hemiptera, and Thysanoptera.

In a further embodiment, the target pest is a species belonging to an order selected from the group consisting of Blattaria and Thysanoptera.

A further embodiment provides a method of controlling a target pest, comprising administering an effective amount of a composition in accordance with one of the embodiments described above to the target pest or a substrate associated with the target pest, thereby achieving synergistic pest control.

In a further aspect of this embodiment, the substrate is selected from a group consisting of a crop, a plant, a surface, and a vertebrate animal.

A method for controlling a target pest, comprising applying to the target pest or to a substrate associated with the target pest a composition comprising a first agent and a second agent, wherein the first agent has a first activity against the target pest, the second agent has a second activity against the target pest, the composition has a third activity against the target pest, and the third activity reflects a synergistic interaction of the first agent and the second agent, thereby resulting in synergistic pest control.

A further embodiment provides a method of pest control comprising applying a composition to a target pest or to a substrate associated with a target pest, wherein the composition comprises a first agent comprising at least one receptor ligand and a second agent comprising a pesticide, and wherein the pest control comprises affecting a physiological condition of the pest associated with a function of the pesticide while also affecting a function of the receptor associated with the receptor ligand, thereby resulting in synergistic pest control.

A further embodiment provides a method of pest control comprising the steps of: providing a target pest having at least one target GPCR receptor; contacting the target pest with a composition comprising at least a first agent and a second agent, wherein the first agent is capable of interacting with the target receptor to trigger, disrupt or alter a biological function related to the binding of the target receptor with the first agent, and wherein the second agent is capable of interacting with a non-receptor molecule or step associated with cycling of the target receptor, to disrupt the cycling of the target receptor; wherein the first and second agents in combination cooperate to amplify the disrupted or altered function resulting from the binding of the target receptor by the first agent, resulting in synergistic control of the pest.

Further embodiments of the present invention provide compositions for controlling a target pest including a pest control product and at least one active agent, wherein: the active agent can be capable of interacting with a receptor in the target pest; the pest control product can have a first activity against the target pest when applied without the active agent and the compositions can have a second activity against the target pest; and the second activity can be greater than the first activity. The first and second activities can be quantified by measuring concentration of the pest control product effective to control the target pest, and a concentration corresponding to the first activity can be higher than a concentration corresponding to the second activity. The first and second activities can be quantified by measuring disablement effect of the target pest at a standard concentration of pest control product, and the compositions exhibit a greater disablement effect than the pest control product applied without the active agent. The first activity can persist for a first period, the second activity can persist for a second period, and the second period can be longer than the first period. The active agent can include a synergistic combination of at least two receptor ligands. The second activity can reflect a synergistic interaction of the active agent and the pest control product.

The target pest can be selected from the group consisting of a fungus, a plant, an animal, a moneran, and a protist. The target pest can be an arthropod species, such as, for example, an insect, an arachnid, or an arachnoid. The target pest can be a species belonging to an animal order selected from: Acari, Anoplura, Araneae, Blattodea, Coleoptera, Collembola, Diptera, Grylloptera, Heteroptera, Homoptera, Hymenoptera, Isopoda, Isoptera, Lepidoptera, Mantodea, Mallophaga, Neuroptera, Odonata, Orthoptera, Psocoptera, Siphonaptera, Symphyla, Thysanura, and Thysanoptera.

The pest control product can be a chlorphenoxy compound such as, for example, 2,4-D Amine and/or 2,4D IBE. Likewise, the pest control product can be a carbamate such as, for example, methomyl, carbofuran, carbaryl, BPMC, carbendazim, carbosulfan, captan hydrochloride, and/or cartap. The pest control product can be an organophosphate such as, for example, acephate, malathion, diazinon, chlorpyfiros, fenoxycab, edifenphos, febuconazole, chlorphenapyr, magnesium phosphide, metamidophos, and/or fenitrothion. The pest control product can be an organochlorine such as, for example, DDT, DDE, and/or heptachlorepoxide. The pest control product can be a pyrethroid such as, for example, cypermethrin, cynmethylin+2,4-D IBE, lambdacyhalothrin, dazomet, cyfluthrin, betacypermethrin, pendimethlin, permethrin, deltamethrin, bifenethrin, alphacypermethrin, fenvalerate, propanil, and/or esfenvalerate. The pest control product can be a neonicotinoid such as, for example, thiomethoxam, fipronil, clothianidin, and/or imidacloprid. The pest control product can include at least one of an avermectin, abamectin, spinosad, fluxastrobin, and/or indoxacarb. The pest control product can be a botanical product such as, for example, rotenone, nicotine, caffeine, a pyrethrum, an essential oil, and/or a fixed oil. The pest control product can be a fungicide, a nematicide, an insecticide, an acaricide, and/or a bactericide.

The receptor can be a G protein-coupled receptor (GPCR), such as a GPCR of the insect olfactory cascade, such as, for example, a tyramine receptor, an olfactory receptor Or43a, an olfactory receptor Or83b and/or an octopamine receptor. Binding of the receptor by an ingredient of the compositions can result in a change in intracellular level of cAMP and/or calcium, wherein the change can be sufficient to permit control of the target pest.

Control can include a condition such as, for example, killing, knockdown, repellency, interference with reproduction, interference with feeding, and interference with a stage of a life cycle of the target pest.

Embodiments of the invention also include a crop protected by the compositions disclosed herein.

In addition, embodiments of the invention can include compositions for controlling a target pest including a pest control product and at least one active agent, wherein: the active agent can include a ligand of a GPCR of a target pest, wherein binding of the ligand to the GPCR can cause a change in a level of cAMP or calcium that can permit control of the target pest; the pest control product can have a first activity against the target pest, the active agent can have a second activity against the target pest, and the compositions can have a third activity against the target pest; and the third activity can be greater than the first activity or the second activity. The active agent can include a synergistic combination of at least two GPCR ligands. The third activity can be indicative of synergy between the active agent and the pest control product. In some embodiments, compositions can include at least two active ingredients, wherein at least one active ingredient interacts with a G protein-coupled receptor (GPCR) of the pest and wherein at least one active ingredient does not interact with the GPCR, and wherein the at least two active ingredients in combination have a synergistic pest-control activity. The pest can be an insect and the GPCR can be associated with olfaction, and further the GPCR preferably can be absent from vertebrate animals. The synergistic pest-control activity can have a coefficient of synergy in excess of 1.5. The synergistic pest-control activity can exceed additive effects of the active ingredients, as measured by the Colby calculation of synergy. The GPCR can have a high affinity for the active ingredient in a target organism and the GPCR can be absent or can have a low affinity for the active ingredient in a non-target organism. The non-target organism can be a vertebrate animal. In some embodiments, the target organism can be a plant, an animal, a fungus, a protist, or a moneran, and the non-target organism can be selected from a crop plant, a vertebrate animal, and a non-pest invertebrate.

In some embodiments, the invention provides low-resistance pest-control compositions, including at least a first active ingredient and a second active ingredient, wherein the first active ingredient interacts with a first molecular target under genetic control within a selected pest, and wherein the second active ingredient interacts with a second molecular target under genetic control within the selected pest, and wherein the ingredients in the compositions act together in a complementary manner upon the target pest, and wherein resistance to the compositions in an individual target pest requires two separate genetic lesions divergent from a non-resistant population of the pest. The first and second molecular targets can include two separate molecules encoded or controlled by separate genetic elements. The complementary manner can include an additive effect of each agent acting separately, or the complementary manner can include a synergistic effect as compared with each agent acting separately. The first molecular target can be a GPCR, and the second molecular target is preferably not the same as the first molecular target.

Also provided in some embodiments are pest-control compositions exhibiting high potency against an invertebrate target pest and low toxicity against a vertebrate animal, the compositions including a synergistic combination of active agents, wherein each active agent interacts with a molecular target with high affinity in the target pest and that can be absent form, or present with low affinity, from the vertebrate. The at least one active agent can be a ligand of a selected GPCR, and the at least one active agent is preferably not a ligand of the selected GPCR. The high target potency and low vertebrate toxicity can be expressed as a ratio of LD50 (target) versus LD50 (vertebrate animal), and wherein the ratio can be less than 100:1.

In some embodiments, the invention provides methods of pest control including contacting a target pest with a composition as described herein, resulting in control of the pest. The methods can include applying a composition to a target pest or to a substrate associated with a target pest, wherein the compositions can include a pesticide and an active agent including at least one receptor ligand, and wherein the pest control can include affecting a physiological condition of the pest associated with a function of the pesticide while also affecting a function of the receptor associated with the receptor ligand. The binding of the receptor by an ingredient of the compositions can result in a change in intracellular level of cAMP and/or calcium, and wherein the change can be sufficient to permit control of the target pest. The pesticide can be selected from a chlorphenoxy compound, a carbamate, an organophosphate, an organochlorine, a pyrethroid, a neonicotinoid, a botanical product, a fungicide, a nematicide, and insecticide, and acaracide, a bactericide. and an avermectin. The substrate can be, for example, a crop plant and/or a soil. The target pest can be, for example, a fungus, a plant, an animal, a moneran, or a protist. The use of the compositions can permit an improvement of control of the pest as compared with use of the pesticide alone or the active agent alone. The improvement can include a synergistic interaction of the pest control product with the active agent. The improvement can include an improved result with use of a substantially similar amount of the pest control product. The improved result can be at least one of: increased killing of the target pest; increased interference with reproduction by the target pest; and prolonged effectiveness of the pest control product. The improvement can include a substantially similar result with use of a substantially lower amount of the pest control product and/or the active agent. Use of the compositions permits an agricultural improvement such as, for example, increased crop yield; reduced frequency of application of pest control product; reduced phytotoxicity associated with the pesticide; and reduced cost or increased value associated with at least one environmental factor. The environmental factor can include, for example, air quality, water quality, soil quality, detectable pesticide residue, safety or comfort of workers; and a collateral effect on a non-target organism.

Also provided are methods of developing a compositions for pest control, including: providing a cell line expressing at least one of: a tyramine receptor, an olfactory receptor Or43a, or an olfactory receptor Or83b, wherein binding of a ligand to any of the receptors causes a change in a level of intracellular cAMP or calcium, and the change can be indicative of a potential for invertebrate pest control; contacting the cell with a candidate ligand; detecting a change in the level of cAMP and/or calcium in the cell; identifying the candidate ligand as an active compound for control of an invertebrate pest; and combining the active compound with a pesticide to form a composition for pest control, wherein the pesticide does not bind to a receptor bound by the active compound, and wherein a combined effect of the active compound and the pesticide can include an effect against a target pest that can be greater than the effect of either the active compound alone or the pesticide alone. The compositions further can include a second active compound capable of binding at least one of the receptors. The active compounds can cooperate to cause a synergistic change in the level of cAMP and/or calcium in the cell line and/or in a target pest. The combined effect of the active compound and the pesticide can be synergistic. The combined effect can be determined by at least one condition selected from the group consisting of: killing, knockdown, repellency, interference with reproduction, interference with feeding, and interference with a stage of a life cycle of the target pest.

Also provided are further methods of pest control, including, providing a composition including at a first and a second active ingredient, wherein the first active ingredient interacts with a receptor of a target pest, and wherein the second active ingredient can be a pesticide that does not interact with the receptor of the first active ingredient; and contacting the pest with the compositions, wherein the contacting results in synergistic pest control. The compositions further can include a third active ingredient, wherein the third active ingredient interacts with a receptor of the target pest, and wherein at least the first and third active ingredients in combination synergistically interact to permit control of the target pest. The first and third active ingredients can optionally bind the same receptor; in other embodiments, the first and third active ingredients do not bind the same receptor. The first, second, and third active ingredients in combination can have a synergistic effect that can be greater than the effect of any single ingredient and can be also greater than the synergistic effect of the first and third ingredients in combination. The receptor can be a GPCR such as, for example, a tyramine receptor, an olfactory receptor Or43a, and an olfactory receptor Or83b. The pest control can be associated with a receptor-activated alteration in a level of cAMP and/or calcium within the pest. The alteration can persist for at least about 60 seconds.

Also provided are other methods of pest control, including: providing a composition including at least two active ingredients, wherein at least one active ingredient interacts with a GPCR of a target pest, the composition produces a first level of at least one of intracellular calcium and cyclic AMP in a cell expressing the GPCR on exposure to the cell, and the first level can be higher than a second level produced when the cell can be contacted with any single active ingredient; and contacting the pest with the compositions, wherein the contacting results in synergistic pest control. Other embodiments provide methods for controlling a target pest including use of a pest control compositions, the compositions including a pest control product and at least one active agent, wherein: the active agent can include a ligand of a GPCR of a target pest, wherein binding of the ligand to the GPCR causes a change in a level of cAMP or calcium that permits control of the target pest; the pest control product can have a first activity against the target pest, the active agent can have a second activity against the target pest, and the compositions can have a third activity against the target pest; and the third activity can be greater than the first activity or the second activity. A further method of pest control can include use of a pest control composition, wherein the composition can include at least two active ingredients, wherein at least one active ingredient interacts with a G protein-coupled receptor (GPCR) of the pest and wherein at least one active ingredient does not interact with the GPCR, and wherein the at least two active ingredients in combination have a synergistic pest-control activity. Other methods of pest control can permit low-resistance in a target pest, including administering a pest-control composition, the composition including at least a first active ingredient and a second active ingredient, wherein the first active ingredient interacts with a first molecular target under genetic control within a selected pest, and wherein the second active ingredient interacts with a second molecular target under genetic control within the selected pest, and wherein the ingredients in the composition act together in a complementary manner upon the target pest, and wherein resistance to the composition in an individual target pest requires two separate genetic lesions divergent from a non-resistant population of the pest.

Still other embodiments provide pest control compositions exemplified by the following: in combination, a blend of lilac flower oil (LFO), d-limonene, thyme oil, and further including a pesticide. The pesticide can be, for example, clothianidin. The blend can include 10-80% LFO, 5-60% d-limonene, and 10-80% thyme oil. In other embodiments, the blend can include 20-60% LFO, 10-45% d-limonene, and 20-60% thyme oil. In other embodiments, blend can include 42.6% w/w LFO, 27.35% w/w d-limonene, and 30.08% w/w thyme oil white.

In certain embodiments, the invention can include a method of pest control including the steps of; providing a target pest having at least one target GPCR receptor; contacting the target pest with a composition comprising at least a first active agent and a second active agent, wherein the first active agent is capable of interacting with the target receptor to trigger, disrupt or alter a biological function related to the binding of the target receptor with the first active agent, and wherein the second active agent is capable of interacting with a non-receptor molecule or step associated with cycling of the target receptor, to disrupt the signaling cascade of the target receptor. In some embodiments the active agents in combination can cooperate to amplify the disrupted or altered function resulting from the binding of the target receptor by the first active agent, resulting in control of the pest. In some embodiments of the invention, the composition can include a third active agent, and the third active agent can be capable of interacting with a GPCR receptor in the target pest, and the interaction can be complementary to the action of the first active agent.

In some embodiments, the first and third active agents can interact with the same receptor, or different receptors. In some embodiments the complementarity of the first and third active agents can cause an additive effect of the active agents together as compared with an effect of each active agent separately. In some embodiments the complementarity of the first and third active agents can cause a synergistic effect of the active agents together as compared with an effect of each active agent separately. In some embodiments, receptor cycling can include at least one of receptor sensitization, receptor desensitization, receptor recycling, ligand release, receptor phosphorylation, and receptor dephosphorylation.

Embodiments of the invention can include a pest-control composition that has a first active agent capable of disrupting or altering a function of a receptor in a target pest, and a second active agent capable of disrupting cycling of the receptor, and the second active agent can act to amplify an effect of the first active agent.

Embodiments of the invention can include a method of making a pest control composition with the steps of: providing a target pest having at least one target receptor; contacting the target pest with a composition including at least a first active agent and a second active agent, wherein the first active agent is capable of interacting with the target receptor to disrupt or alter a function related to normal activity of the target receptor, and wherein the second active agent is capable of interacting with a non-receptor molecule or step associated with cycling of the target receptor, to disrupt the cycling of the target receptor. Some embodiments can include measuring the effect of the composition upon the target pest and selecting the at least a first active agent based on the desired properties of the composition. Some embodiments of the invention can include a third active agent, wherein the third active agent can be capable of interacting with a receptor in the target pest, and wherein the interaction can be complementary to the action of the first active agent. In some embodiments, the first and third active agents can interact with a same receptor, or with a different receptor. In some embodiments the complementarity of the first and third active agents can cause an additive effect of the active agents together as compared with an effect of each active agent separately. Likewise, the complementarity of the first and third active agents can cause a synergistic effect of the active agents together as compared with an effect of each active agent separately.

Embodiments of the invention can include a pest-control composition that has an active agent capable of disrupting or altering cycling of a GPCR in a target pest, wherein the active agent acts to amplify an effect of a ligand binding the GPCR. Further, the amplification can result in a prolonged intracellular Ca2+ cascade as compared with the Ca2+ cascade that occurs when the receptor is bound without the presence of the active agent. In some embodiments, the amplification can result in a prolonged perturbation of intracellular cAMP level as compared with the perturbation in cAMP level that occurs when the receptor is bound without the presence of the active agent.

Embodiments of the invention can include a pest-control composition that has an active agent capable of disrupting or altering cycling of a GPCR in a target pest, wherein the active agent acts to attenuate an effect of a ligand binding the GPCR.

Certain embodiments of the invention can include a method of pest control including the steps of: providing a target pest having at least one target GPCR receptor; contacting the target pest with a composition including at least a first active agent and a second active agent, wherein the first active agent can be capable of interacting with the target receptor to trigger, disrupt or alter a biological function related to the binding of the target receptor with the first active agent, and wherein the second active agent can be capable of interacting with a non-receptor molecule or step associated with the biological pathway triggered, disrupted, or altered as a result of the first active agent's interacting with the target receptor; wherein the active agents in combination can cooperate to amplify the disrupted or altered function resulting from the binding of the target receptor by the first active agent, resulting in control of the pest.

In various embodiments, the composition can further include a third active agent, wherein the third active agent can be capable of interacting with a GPCR receptor in the target pest, and wherein the interaction can be complementary to the action of the first active agent. Likewise, the first and third active agents can interact with a same receptor, or with different receptors. Additionally, the complementarity of the first and third active agents can cause an additive effect of the active agents together as compared with an effect of each active agent separately.

BRIEF DESCRIPTION OF THE DRAWINGS

FIG. 8A shows the nucleic acid sequence and the peptide sequence of a Tyramine receptor;

FIG. 8B shows the nucleic acid sequence and the peptide sequence of a Tyramine receptor;

FIG. 24A shows fluorescence intensity curves corresponding to intracellular calcium ion concentrations, with the curve corresponding to the compositions containing 1) yohimbine alone, 2) forskolin alone, and 3) genistein alone.

FIG. 24B shows schematic molecular structures of yohimbine, forskolin and genistein.

DESCRIPTION OF EXEMPLARY EMBODIMENTS

Figure 1:
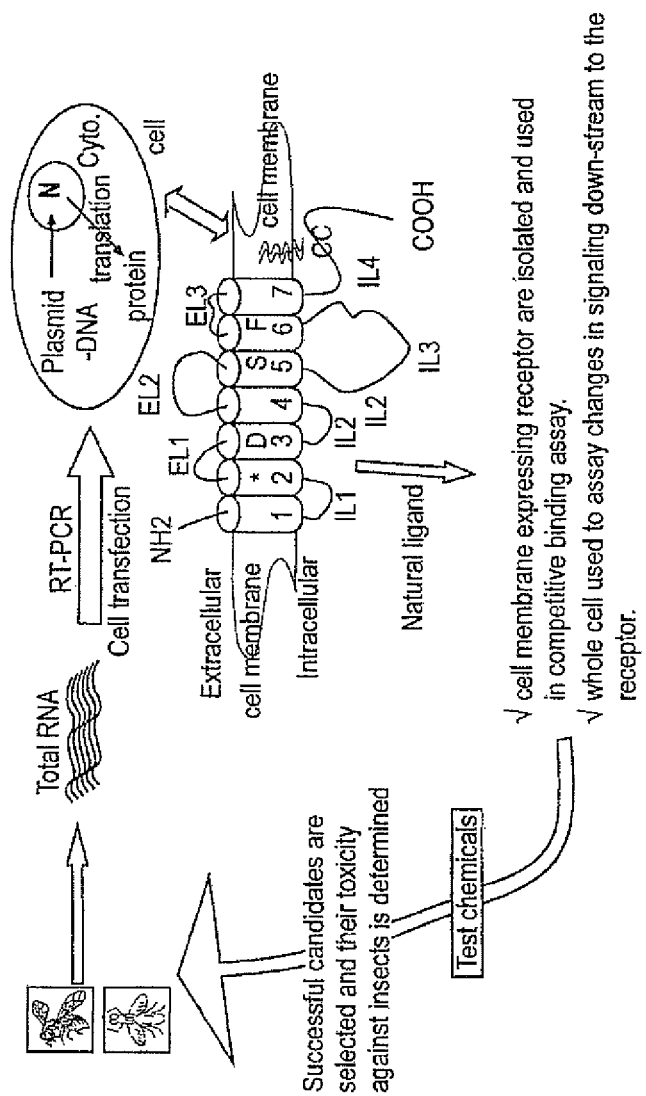
FIG. 1 shows a screening method using a transfected cell lines expressing a receptor of interest, for example, a biogenic amine receptor, such as, a TyR or an octopamine receptor.

Many previously known and commercialized products having sufficient pesticidal activity to be useful also have toxic or deleterious effects on mammals, fish, fowl, or other non-target species. For example, common insecticides such as organophosphorus compounds and carbamates inhibit the activity of acetylcholinesterase in all classes of animals. Chlordimeform and related formamidines are known to act on insect octopamine receptors, but have been removed from the market because of cardiotoxic potential in vertebrates and carcinogenicity in animals and a varied effect on different insects.

However, the deleterious effects of many pesticides can be mitigated by reducing the amount of pesticide that can be applied to a given area to achieve the desired result. This reduction can be achieved by combining the pesticidal compound or product with selected active ingredients. These active ingredients can comprise, for example, plant essential oils, and the like. Combinations of selected active ingredients with selected pesticidal compounds or products can reduce the concentration of pesticide needed to achieve a net efficiency, and extend the useful life of existing synthetic pesticides.

The details of one or more embodiments of the invention are provided. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom.

Embodiments of the invention are directed to methods of screening compositions for pest control potential, compositions for controlling pests, and methods for using these compositions.

As used herein, "pests" can mean any organism whose existence it can be desirable to control. Pests can include, for example, bacteria, cestodes, fungi, insects, nematodes, parasites, plants, and the like.

As used herein, "pesticidal" can mean, for example, antibacterial, antifungal, antiparasitic, herbicidal, insecticidal, and the like.

Furthermore, G protein uncoupling in response to phosphorylation by both second messenger-dependent protein kinases and G protein-coupled receptor kinases (GRKs) leads to GPCR desensitization. GRK-mediated receptor phosphorylation promotes the binding of beta-arrestins, which in addition to uncoupling receptors from heterotrimeric G proteins, also target many GPCRs for internalization in clathrin-coated vesicles. Beta-arrestin proteins play a dual role in regulating GPCR responsiveness by contributing to both receptor desensitization and internalization.

Following desensitization, GPCRs can be resensitized. GPCR sequestration to endosomes is thought to be the mechanism by which GRK-phosphorylated receptors are dephosphorylated and resensitized. The identification of beta-arrestins as GPCR trafficking molecules suggested that beta-arrestins can be determinants for GPCR resensitization. However, other cellular components also play pivotal roles in the de- and re-sensitization (D/R) process, including, for example, GRK, N-ethylmaleimide-sensitive factor (NSF), clathrin adaptor protein (AP-2 protein), protein phosphatases, clathrin, and the like. In addition to these molecules, other moieties such as, for example, endosomes, lysosomes, and the like, also influence the D/R process. These various components of the D/R cycle provide opportunities to disrupt or alter GPCR "availability" to extracellular stimuli, and thus attenuate or intensify the effect of those extracellular stimuli upon target organisms. Attenuation, achieved, for example, by inhibition of the resensitization process, or the like, can limit the effects of extracellular stimuli (such as, for example, UV exposure, toxins, or the like) on the GPCR signaling process. Intensifying a signal cascade, achieved, for example, by inhibition of the desensitization process, or the like, can increase the effects of extracellular stimuli (such as, for example, pharmaceuticals, insecticides, or the like) on the GPCR signaling process.

Components of the GPCR signaling process have been the object of significant study; opportunities and targets for disruption of the signaling process according to the present invention are numerous. Discussions of the components of G-protein signaling are provided in Yu (2006) Heterotrimeric G protein signaling and RGSs in *Aspergillus nidulans*, *J Microbiol* 44:145-154; Dong (2007) Regulation of G protein-coupled receptor export trafficking, *Biochim Biophys Acta* 1768:853-870; Nakahata (2007) Regulation of G Protein-coupled Receptor Function by Its Binding Proteins, *Yakugaku Zasshi* 127:3-14; Yang (2006) Mechanisms of regulation and function of G-protein-coupled receptor kinases, *World J Gastroenterol* 12:7753-7757; Ma (2007) Beta-arrestin signaling and regulation of transcription; *J Cell Sci* 120:213-218; New (2007) Molecular mechanisms mediating the G protein-coupled receptor regulation of cell cycle progression, *J Mol Signaling* 2:2-16; Klasse (2008) Internalization and desensitization of adenosine receptors, *Purinergic Signalling* 4:21-37; Stewart (2007) Phospholipase C-eta Enzymes as Putative Protein Kinase C and Ca2+ Signalling Components in Neuronal and Neuroendocrine Tissues, *Neuroendocrinology* 86:243-248; Xu (2007) Regulation of G protein-coupled receptor trafficking, *Acta Physiol* 190:39-45; Wolfe (2007) Clathrin-Dependent Mechanisms of G Protein-coupled Receptor Endocytosis, *Traffic* 8:462-470; Schulte (2007) Novel aspects of G-protein-coupled receptor signalling—different ways to achieve specificity, *Acta Physiol* 190:33-38; Torrecilla (2006) Co-ordinated covalent modification of G-protein coupled receptors, *Curr Pharm Des* 12:1797-1808; Neitzel (2006) Cellular mechanisms that determine selective RGS protein regulation of G protein-coupled receptor signaling, *Semin Cell Dev Biol* 17:383-389; Sato (2006) Accessory proteins for G proteins; partners in signaling, *Annu Rev Pharmacol Toxicol* 46:151-187; Appert-Collin (2006) Regulation of g protein-coupled receptor signaling by a-kinase anchoring proteins, *Recept Signal Transduct Res* 26:631-46; Premont (2007) Physiological roles of G protein-coupled receptor kinases and arrestins, *Annu Rev Physiol* 69:511-534; Smrcka (2008) G protein beta gamma subunits: Central mediators of G protein-coupled receptor signaling, *Cell Mol Life Sci* 65:2191-2214; Grandy (2007) Trace amine-associated receptor 1—Family archetype or iconoclast?, *Pharmacol Ther* 116:355-390; Gilchrist (2007) G-protein-coupled receptor pharmacology: examining the edges between theory and proof, *Curr Opin Drug Discov Devel* 10:446-451; Takeishi (2007) Role of diacylglycerol kinase in cellular regulatory processes: a new regulator for cariomyocyte hypertrophy, *Pharmacol Ther* 115:352-359; Dalrymple (2008) G protein-coupled receptor dimers: functional consequences, disease states and drug targets, *Pharmacol Ther* 118:359-371; Jurado-Pueyo (2008) GRK2-dependent desensitization downstream of G proteins, *Recept Signal Transduct Res* 28:59-70; Milligan (1998) New aspects of g-protein-coupled receptor signalling and regulation, *Trends Endocrinol Metab* 9:13-19. Each of the foregoing is incorporated by reference in its entirety for its disclosure of the mechanisms and components of GPCR signaling, cycling, regulation, and the like.

Embodiments of the invention can include a method to disrupt or alter GPCR D/R by altering or disrupting the various signal cascades triggered through GPCR action. Certain embodiments can disrupt or alter GPCR D/R in various ways, including, for example, the application of compositions containing active agents such as, for example, essential oils, and the like.

Screening of Compositions

In some embodiments of the invention, the screening method for pest control potential can target a molecule of an insect olfactory receptor protein. In some embodiments of the invention, the screening method for pest control potential can target an insect olfactory receptor protein. The insect olfactory system includes more than 60 identified olfactory receptors. These receptors are generally members of a large family of G protein coupled receptors (GPCRs).

As used herein, a "receptor" is an entity on the cell membrane or within the cell, cytoplasm, or cell nucleus that can bind to a specific molecule (a ligand), such as, for example, a neurotransmitter, hormone, or the like, and initiates the cellular response to the ligand. Ligand-induced changes in the behavior of receptor proteins can result in physiological changes that constitute the biological actions of the ligands.

In accordance with the present disclosure, receptors such as G protein-coupled receptors may be classified on the basis of binding affinity of the receptor to an active ingredient. This may also be expressed as the binding affinity of the active ingredient for the receptor. The binding affinity of an active ingredient for a receptor, or the binding affinity of a receptor for an active ingredient, may be measured in accordance with methods disclosed herein or methods known to those of skill in the art. As used in the present disclosure, a "low" affinity indicates that a high concentration of the active ingredient relative to the receptor is required to maximally occupy the binding site of the receptor and trigger a physiological response, while a "high" affinity indicates that that a low concentration of the active ingredient relative to the receptor is adequate to maximally occupy the binding site of the receptor and trigger a physiological response. A "high" affinity may correspond to, for example, an active ingredient concentration of two or more orders of magnitude less than the concentration of the receptor that is effective to trigger the physiological response, while a "low" affinity may correspond to an active ingredient concentration of one or more orders of magnitude greater than the concentration of the receptor that is effective to trigger the physiological response.

In *Drosophila melanogaster*, the olfactory receptors are located in two pairs of appendages located on the head of the fly. The family of *Drosophila* chemoreceptors includes approximately 62 odorant receptor (Or) and 68 gustatory receptor (Gr) proteins, encoded by families of approximately 60 Or and 60 Gr genes through alternative splicing. Some of these receptor proteins have been functionally characterized, while others have been identified by sequence homology to other sequences but have not been fully characterized. Other insects have similar olfactory receptor proteins.

In certain embodiments, the insect olfactory receptor protein targeted by the screening or insect control method of the invention is the tyramine receptor (TyR). In additional embodiments, the insect olfactory receptor protein is the insect olfactory receptor protein Or83b or Or43a. In additional embodiments, the targeted protein can be any of the insect olfactory protein receptors.

Additionally, other components of the insect olfactory receptor cascade can be targeted using the method of the invention in order to identify useful insect control compounds. Exemplary insect olfactory cascade components that can be targeted by methods of the invention include but are not limited to serotonin receptor, Or22a, Or22b, Gr5a, Gr21a, Gr61a, β-arrestin receptor, GRK2 receptor, and tyramine β-hydroxylase receptor, and the like.

With reference to FIG. 1, an exemplary screening method for identifying effective pest control compositions can make use of one or more transfected cell lines expressing a receptor of interest, for example, a biogenic amine receptor, such as, a TyR or an octopamine receptor.

In some embodiments of the invention, isolated cell membranes expressing the receptor of interest can be used in competitive binding assays. Whole cells can be used to study changes in signaling down-stream to the receptor, in response to treatment with a test composition.

Embodiments of the invention can utilize prokaryotic and eukaryotic cells including, for example, bacterial cells, yeast cells, fungal cells, insect cells, nematode cells, plant cells, animal cells, and the like. Suitable animal cells can include, for example, HEK cells, HeLa cells, COS cells, U20S cells, CHO-K1 cells, various primary mammalian cells, and the like. An animal model expressing one or more conjugates of an arrestin and a marker molecule, for example, throughout its tissues, within a particular organ or tissue type, or the like, can be used.

The potential for insect control activity can be identified by measuring the affinity of the test compositions for the receptor in the cell lines expressing a TyR, Or83b, and/or Or43a. The potential for insect control activity can also be identified by measuring the change in intracellular cAMP and/or $Ca^{2+}$ in the cell lines expressing TyR, Or83b, and/or Or43a following treatment with the test compositions. The gene sequences of the TyR, the Or 83b receptor and the Or 43a receptor have substantial similarity between various insect species. As such, the *Drosophila* Schneider cell lines expressing these receptors can be used to screen for compositions having insect control activity in various insect species.

In some embodiments, a method of selecting a composition for pesticidal use can include the following. A cell expressing a TyR is provided and is contacted with test compounds. The receptor binding affinity of the compounds is measured. At least one parameter selected from the following parameters is measured: intracellular cAMP level, and intracellular $Ca^{2+}$ level. A first compound for the composition is identified, that is capable of altering at least one of the parameters, and that has a high receptor binding affinity for the TyR; and a second compound for the composition is identified, that is capable of altering at least one of the parameters, and that has a low receptor binding affinity for the TyR. A composition is selected that includes the first and second compounds. In some embodiments, a composition is selected that includes the first and second compounds and demonstrates an anti-parasitic effect that exceeds the anti-parasitic effect of any of the compounds when used alone.

In some embodiments of the invention, the cell used can be any cell capable of being transfected with and express a TyR. Examples of cells include, but are not limited to: insect cells, such as *Drosophila* Schneider cells, *Drosophila* Schneider 2 cells (S2 cells), and *Spodoptera frugiperda* cells (e.g., Sf9 or Sf21); or mammalian cells, such as Human Embryonic Kidney cells (HEK-293 cells), African green monkey kidney fibroblast cells (COS-7 cells), HeLa Cells, and Human Keratinocyte cells (HaCaT cells).

The TyrR can be a full-length TyrR, a functional fragment of a TyrR, or a functional variant of a TyrR. A functional fragment of a TyrR is a TyrR in which amino acid residues are deleted as compared to the reference polypeptide, i.e., full-length TyrR, but where the remaining amino acid sequence retains the binding affinity of the reference polypeptide for tyramine. A functional variant of a TyrR is a TyrR with amino acid insertions, amino acid deletions, or conservative amino acid substitutions, that retains the binding affinity of the reference polypeptide for tyramine. A "conservative amino acid substitution" is a substitution of an amino acid residue with a functionally similar residue. Examples of conservative substitutions can include, for example, the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; the substitution of one acidic residue, such as aspartic acid or glutamic acid for another, and the like. A conservative amino acid substitution can also include replacing a residue with a chemically derivatized residue, provided that the resulting polypeptide retains the binding affinity of the reference polypeptide for tyramine. Examples of TyrRs can include, for example: TyrRs, such as, *Drosophila melanogaster* TyrR (GENBANK® accession number (GAN) CAA38565), *Locusta migratoria* TyrR (GAN: ☐25321), TyrRs of other invertebrates, TyrRs of nematodes, and the like.

Exemplary screening methods can include "positive" screening, where, for example, compositions that bind a receptor of interest are selected. Exemplary screening methods can include "negative" screening, where, for example, compositions that bind a receptor of interest are rejected. An exemplary method can include: selecting a composition that binds a TyR. Another exemplary method can include: selecting a composition that binds a TyR and does not bind an octopamine receptor.

In some embodiments of the invention, the efficacy of a test composition can be determined by conducting studies with insects. For example, the efficacy of a test composition for repelling an insect can be studied using controlled experiments wherein insects are exposed to the test composition. In some embodiments, the toxicity of a test composition against an insect can be studied using controlled experiments wherein insects are exposed to the test composition.

Methods of screening compositions for insect control activity are set forth in the following applications, each of which is incorporated in its entirety herein by reference: U.S. application Ser. No. 10/832,022, entitled COMPOSITIONS AND METHODS FOR CONTROLLING INSECTS; U.S. application Ser. No. 11/086,615, entitled COMPOSITIONS AND METHODS FOR CONTROLLING INSECTS RELATED TO THE OCTOPAMINE RECEPTOR; U.S. application Ser. No. 11/365,426, entitled COMPOSITIONS AND METHODS FOR CONTROLLING INSECTS INVOLVING THE TYRAMINE RECEPTOR; and U.S.

application Ser. No. 11/870,385, entitled COMPOSITIONS AND METHODS FOR CONTROLLING INSECTS.

Compositions for Pest Control

Embodiments of the invention can include a composition for controlling pests. Embodiments of the invention that include a composition for controlling pests can include an pest control chemical or product. Embodiments of the invention that include a composition for controlling pests can include an active agent.

In embodiments of the invention that include an active agent, the active agent can be, for example, an agent that can have a biological impact on an insect, such as, for example, a chemical, a compound, or the like. In embodiments of the invention that include an active agent, the active agent can be, for example, one or more plant essential oils, or the like. The plant essential oils, when combined, can have a synergistic effect. Embodiments can also can include a fixed oil, which is typically a non-volatile, non-scented plant oil. Additionally, in some embodiments, these compositions can be made up of generally regarded as safe (GRAS) compounds.

In embodiments of the invention that include at least one pest control chemical, the at least one pest control chemical can be selected from, for example, the pest control chemicals set forth in Table 1, or the like.

TABLE 1

| PEST CONTROL CHEMICALS | |
|---|---|
| Pest Control Chemical | CAS Registry Number |
| ABAMECTIN | 71751-41-2 |
| ACEPHATE | 30560-19-1 |
| ACETAMIPRID | 135410-20-7 |
| ACETOCHLOR | 34256-82-1 |
| ACEQUINOCYL | 57960-19-7 |
| ACIBENZOLAR-S-METHYL | |
| ALACHLOR | 15972-60-8 |
| ALDICARB | 116-06-3 |
| ALDIMORPH | |
| ALLETHRIN | 584-79-2 |
| AMISULBROM | |
| AMITRAZ | 33089-61-1 |
| ANILAZINE | |
| AZACONAZOLE | |
| AZOXYSTROBIN | |
| BIFENTHRIN | 82657-04-3 |
| BENALAXYL | |
| BENDIOCARB | 22781-23-3 |
| BENTHIAVALICARB | |
| BENODANIL | |
| BENOMYL | |
| BIFENTHRIN | 82657-04-3 |
| BINAPACRYL | |
| BIORESMETHRIN | 28434-01-7 |
| BIPHENYL | |
| BITERTANOL | |
| BLASTICIDIN-S | |
| BOSCALID | |
| BROMUCONAZOLE | |
| BUPIRIMATE | |
| CAPTAFOL | |
| CAPTAN | |
| CARBENDAZIM | 1563-66-2 |
| CARBOFURAN | |
| CARBARYL | 63-25-2 |
| CARBENDAZIM | |
| CARBOXIN | |
| CARPROPAMID | |
| CHLORDIMEFORM | 6164-98-3 |
| CHLORFENVINFOS | 470-90-6 |
| CHLORONEB | |
| CHLOROTHALONIL | 1897-45-6 |
| CHLOROXURON | 1982-47-4 |
| CHLORPYRIFOS | 2921-88-2 |

TABLE 1-continued

| PEST CONTROL CHEMICALS | |
|---|---|
| Pest Control Chemical | CAS Registry Number |
| CHLOZOLINATE | |
| CLOTHIANIDIN | |
| COPPER (DIFFERENT SALTS) | |
| COPPER FUNGICIDES | |
| CYAZOFAMID | |
| CYCLOPROPANECARBOXYLIC ACID, 2,2-DIMETHYL-3-(2-METHYL-1-PROPENYL)-, CYANO(3-PHENOXYPHENYL)METHYL ESTER | 39515-40-7 |
| CYFLUFENAMID | |
| CYFLUTHRIN | 68359-37-5 |
| CYHALOFOP BUTYL | 122008-85-9 |
| CYHALOTHRIN | 68085-85-8 |
| CYHALOTHRIN K | 91465-08-6 |
| CYHALOTHRIN (lambda) | 91465-08-6 |
| CYHALOTHRIN GAMMA | 76703-62-3 |
| CYMOXANIL | |
| CYPERMETHRIN | 52315-07-8 |
| CYPROCONAZOLE | |
| CYPRODINIL | |
| CYROMAZINE | 66215-27-8 |
| D-TRANS-ALLETHRIN | 28057-48-9 |
| DELTAMETHRIN (DECA-) | 52918-63-5 |
| DIAFENTHIURON | 80060-09-0 |
| DIAZINON | 333-41-5 |
| DICHLOFENTHION | 97-17-6 |
| DICHLOFLUANID | |
| DICLOCYMET | |
| DICLOMEZINE | |
| DICLORAN | |
| DIFENOCONAZOLE | |
| DIETHOFENCARB | |
| DIFLUBENZURON | 35367-38-5 |
| DIFLUMETORIM | |
| DIFENOCONAZOLE | |
| DIMETHIRIMOL | |
| DIMETHOATE | 60-51-5 |
| DIMETHOMORPH | |
| DIMOXYSTROBIN | |
| DINICONAZOLE | |
| DINOCAP | |
| DISULFOTON | 298-04-4 |
| DITHIANON | |
| DODEMORPH | |
| DODINE | |
| EDFINPHOS | |
| ENDOSULFAN | 115-29-7 |
| ENESTROBIN | |
| EPOXICONAZOLE | |
| ESFENVALERATE | 66230-04-4 |
| ETHABOXAM | |
| ETHIRIMOL | |
| ETRIDIAZOLE | |
| FAMOXADONE | |
| FENBUCONAZOLE | |
| FENFURAM | |
| FENITROTHION | 122-14-5 |
| FENOXYCARB | 72490-01-8 |
| ENPROPATHRIN | 39515-41-8 |
| FENAMIDONE | |
| FENARIMOL | |
| FENHEXAMID | |
| FENOXANIL | |
| FENPICLONIL | |
| FENPROPIDIN | |
| FENPROPIMORPH | |
| FENTIN ACETATE | |
| FENTIN CHLORIDE | |
| FENTIN HYDROXIDE | |
| FENVALERATE | 51630-58-1 |
| FERBAM | |
| FERIMZONE | |
| FIPRONIL | 120068-37-3 |
| FLUAZINAM | |
| FLUBENDIAMIDE | 272451-65-7 |

TABLE 1-continued

PEST CONTROL CHEMICALS

| Pest Control Chemical | CAS Registry Number |
|---|---|
| FLUDIOXONIL | |
| FLUMORPH | |
| FLUSILAZOLE | |
| FLUSULFAMIDE | |
| FLUTRIAFOL | |
| FLUOPICOLIDE | |
| FLUOXASTROBIN | |
| FLUQUINCONAZOLE | |
| FLUTOLANIL | |
| FOSETYL-AL | |
| FOLPET | |
| FTHALIDE | |
| FUBERIDAZOLE | |
| FURAMETPYR | |
| FURALAXYL | |
| GUAZATINE | |
| HEXACONAZOLE | 67485-29-4 |
| HYDRAMETHYLNON | |
| HYMEXAZOLE | |
| IMAZALIL | |
| IMIBENCONAZOLE | 105827-78-9 |
| IMIDACLOPRID | |
| IMINOCTADINE | |
| INDOXACARB | |
| IODOCARB | |
| IPCONAZOLE | |
| IPROBENFOS (IBP) | |
| IPRODINE | |
| ISOPROTHIOLANE | |
| ISOTIANIL | |
| KASUGAMYCIN | |
| KRESOXIM-METHYL | |
| LAMBDA-CYHALOTHRIN | 91465-08-6 |
| LUFENURON | 103055-07-8 |
| MALATHION | 121-75-5 |
| MANCOZEB | |
| MANDIPROPAMID | |
| MANEB | |
| MEPANIPYRIM | |
| MEPRONIL | |
| METALAXYL | |
| METALAXYL-M (=MEFENOXAM) | |
| METCONAZOLE | |
| METHIDATHION | 950-37-8 |
| METHAMIDAPHOS (O,S-Dimethylphosphoramidothiolate) | 10265-92-6 |
| METHASULFOCARB | |
| METHOMYL | 16752-77-5 |
| METHYL PARATHION | 298-00-0 |
| METIRAM | |
| METOMINOSTROBIN | |
| METRAFENONE | |
| MINERAL OILS, ORGANIC OILS, POTASSIUM BICARBONATE, MATERIAL OF BIOLOGICAL ORIGIN | |
| MYCLOBUTANIL | |
| NAFTIFINE | |
| NALED | 300-76-5 |
| NUARIMOL | |
| OCTHILINONE | |
| OFURACE | |
| ORYSASTROBIN | |
| OXADIXYL | |
| OXAMYL | 23135-22-0 |
| OXOLINIC ACID | |
| OXPOCONAZOLE | |
| OXYCARBOXIN | |
| OXYDEMETON METHYL | 301-12-2 |
| OXYTETRACYCLINE | |
| PEFURAZOATE | |
| PENCONAZOLE | |
| PENCYCURON | |
| PENTHIOPYRAD | |
| PERMETHRIN | 52645-53-1 |
| PHENOTHRIN | 26002-80-2 |
| PHOPHOROUS ACID AND SALTS | |
| PHORATE | 52645-53-1 |
| PHOSMET | 298-02-2 |
| PICOXYSTROBIN | |
| PIPERALIN | |
| POLYOXIN | |
| PRALLETHRIN (ETOC) | 23031-36-9 |
| PROBENAZOLE (ALSO ANTIBACTERIAL AND ANTIFUNGAL ACTIVITY) | |
| PROCHLORAZ | |
| PROCYMIDONE | |
| PROFENOFOS | 41198-08-7 |
| PROPAMOCARB | |
| PROPICONAZOLE | |
| PROPINEB | |
| PROQUINAZID | |
| PROTHIOCARB | |
| PROTHIOCONAZOLE | |
| PYRACLOSTROBIN | |
| PYRAZOPHOS | |
| PYRETHRUM | 8003-34-7 |
| PYRIBUTICARB | |
| PYRIFENOX | |
| PYRIMETHANIL | |
| PYRIBENCARB | |
| PYROQUILON | |
| QUINTOZENE (PCNB) | |
| QUINOXYFEN | |
| RESMETHRIN | 10453-86-8 |
| SILITHIOFAM | |
| SIMECONAZOLE | |
| SPINOSAD | 131929-60-7 |
| SPIROMESIFEN | 283594-90-1 |
| SPIROXAMINE | |
| STREPTOMYCIN | |
| SULPHUR | |
| TEBUCONAZOLE | |
| TEBUFENOZIDE | 112410-23-8 |
| TECLOFTHALAM (BACTERICIDE) | |
| TECNAZENE (TCNB) | |
| TEFLUTHRIN | 79538-32-2 |
| TERBINAFINE | |
| TETRACONAZOLE | |
| THIABENDAZOLE | |
| TIADINIL | |
| THIFLUZAMIDE | |
| THIOCYCLAM | 31895-21-3 |
| THIODICARB | 59669-26-0 |
| THIOPHANATE | |
| THIOPHANATE-METHYL | |
| THIAMETHOXAM | 153719-23-4 |
| THIRAM | |
| TOLCLOFOS-METHYL | |
| TOLYFLUANID | |
| TRALOMETHRIN | 66841-25-6 |
| TRIADIMEFON | |
| TRIADIMENOL | |
| TRIAZOXIDE | |
| TRICYCLAZOLE | |
| TRIDEMORPH | |
| TRIFLOXYSTROBIN | |
| TRIFLUMIZOLE | |
| TRIFORINE | |
| TRITICONAZOLE | |
| VALIDAMYCIN | |
| VALIPHENAL | |
| VINCLOZOLIN | |
| N,N-DIETHYL-3-METHYLBENZAMIDE (DEET) | 134-62-3 |
| ZINEB | |
| ZIRAM | |
| ZOXAMIDE | |

Embodiments of the invention can include compounds such as, for example, abamectin, allethrin, citronella oil, IR3535® (3-[N-butyl-N-acetyl]-aminopropionic acid ethyl ester), methyl nonyl ketone, metofluthrin, neem oil, nepetalactone, oil of lemon eucalyptus, permethrin, picaridin, p-menthane 3,8 diol, and the like.

Figure 2:
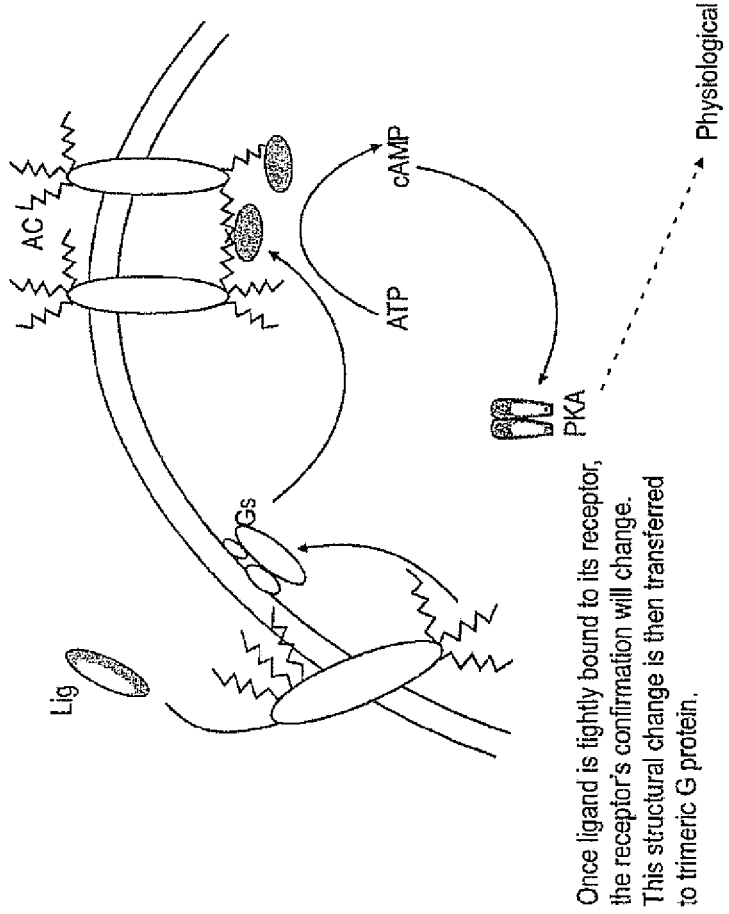
FIG. 2 shows the binding of a ligand to a biogenic amine receptor, resulting in downstream signaling affecting certain physiological responses.
Figure 3:
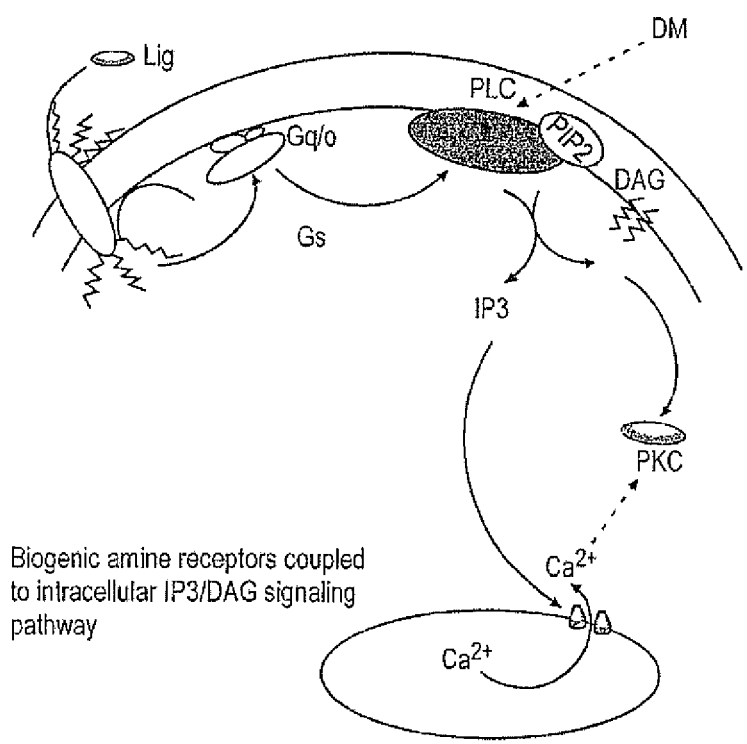
FIG. 3 shows an insect control chemical, deltamethrin (DM), affecting downstream signaling.

Embodiments of the present invention can include at least one insect control chemical, and at least one compound of a plant origin, or at least one blend of compounds of a plant origin. With reference to FIG. 2, compounds of plant origin, such as plant essential oils, can bind certain biogenic amine receptors, resulting in downstream signaling affecting certain physiological responses. With reference to FIG. 3, insect control chemicals, such as deltamethrin (DM), can also affect downstream signaling. As depicted in FIGS. 2 and 3, the compounds or blends of plant origin and the insect control chemicals activate signaling in different manners.

In embodiments that include an insect control chemical, the insect control chemical can include, for example, any insect control chemical from the classes listed in the following table:

TABLE 2

CLASSIFICATION OF INSECT CONTROL COMPOSITIONS

| Group | Subgroup | Primary target site of action | Chemical subgroup or exemplifying active ingredient | Active ingredients |
|---|---|---|---|---|
| 1* | 1A | Acetylcholine esterase inhibitors | Carbamates | Aldicarb<br>Bendiocarb<br>Carbaryl<br>Carbofuran<br>Methiocarb<br>Methomyl<br>Oxamyl<br>Propoxur<br>Thiodicarb |
|  | 1B |  | Organophosphates | Acephate<br>Azinphos-methyl<br>Chlorpyrifos<br>Chlorpyrifos-methyl<br>Coumaphos<br>Diazinon<br>Dichlorvos<br>Dicrotophos<br>Dimethoate<br>Disulfoton<br>Ethoprop<br>Fenamiphos<br>Fenthion<br>Isofenphos<br>Malathion<br>Methamidophos<br>Methidathion<br>Methyl parathion<br>Naled<br>Oxydemeton-methyl<br>Phorate<br>Profenofos<br>Propetamphos<br>Temephos<br>Terbufos<br>Tetrachlorvinphos<br>Trichlorfon |
| 2* | 2A | GABA-gated chloride channel antagonists | Cyclodiene organochlorines | Endosulfan<br>Lindane |
|  | 2B |  | Fipronil (phenylpyrazoles) | Fipronil |
| 3 |  | Sodium channel modulators | Pyrethroids | Allethrin<br>d-cis-trans Allethrin<br>d-trans Allethrin<br>Bifenthrin<br>Bioallethrin S-cyclopentenyl<br>Cyfluthrin<br>Beta-Cyfluthrin<br>Cypermethrin<br>zeta-Cypermethrin<br>Cyphenothrin [(1R)-trans-isomers]<br>Deltamethrin<br>Esfenvalerate<br>Fenpropathrin<br>Fenvalerate<br>Imiprothrin<br>Permethrin |

TABLE 2-continued

CLASSIFICATION OF INSECT CONTROL COMPOSITIONS

| Group | Subgroup | Primary target site of action | Chemical subgroup or exemplifying active ingredient | Active ingredients |
|---|---|---|---|---|
| | | | | Phenothrin [(1R)-trans-isomer] Prallethrin Resmethrin Tefluthrin Tetramethrin Tralomethrin |
| | | | Pyrethrins | Pyrethrins (pyrethrum) |
| | | | Methoxychlor | Methoxychlor |
| 4* | 4A | Nicotinic acetylcholine receptor agonists/antagonists | Neonicotinoids | Acetamiprid Imidacloprid Thiamethoxam |
| | 4B | | Nicotine | Nicotine |
| 6 | | Chloride channel activators | Avermectins, Milbemycins | Abamectin |
| 7* | 7A | Juvenile hormone mimics | Juvenile hormone analogues | Hydroprene Kinoprene Methoprene |
| | 7B | | Fenoxycarb | Fenoxycarb |
| 8* | 8A | Compounds of unknown or non-specific mode of action (fumigants) | Methyl bromide | Methyl bromide and other alkyl halides |
| | 8B | | Chloropicrin | Chloropicrin |
| | 8C | | Sulfuryl fluoride | Sulfuryl fluoride |
| 9* | 9A | Compounds of unknown or non-specific mode of action (selective feeding blockers) | Cryolite | Cryolite |
| 10* | 10A | Compounds of unknown or non-specific mode of action (mite growth inhibitors) | Clofentezine Hexythiazox | Clofentezine Hexythiazox |
| | 10B | | Etoxazole | Etoxazole |
| 11* | 11A1 | Microbial disruptors of insect midgut membranes (includes transgenic crops expressing *B. t.* toxins) | B.t. var. *israelensis* | B.t. var. *israelinsis* |
| | 11B1 | | B.t. var. *aizawai* | B.t. var. *aizawai* |
| | 11B2 | | B.t. var. *kurstaki* | B.t. var. *kurstaki* |
| 12* | 12B | Inhibitors of oxidative phosphorylation, disruptors of ATP formation (inhibitors of ATP synthase) | Organotin miticides | Fentutatin oxide |
| | 12C | | Propargite | Propargite |
| 15 | | Inhibitors of chitin biosynthesis, type 0, Leptdopteran | Benzoylureas | Diflubenzuron Hexaflumuron Novaluron |
| 17 | | Moulting disruptor, Dipteran | Cyromazine | Cyromazine |
| 18* | 18A | Ecdysone agonists/moulting disruptors | Diacylhydrazines | Halofenozide Methoxyfenozide Tebufenozide |
| | 18B | | Azadirachtin | Azadirachtin |
| 19 | | Octopaminergic agonists | Amitraz | Amitraz |
| 20* | 20A | Mitochondrial complex III electron transport inhibitors (Coupling site II) | Hydramethylnon | Hydramethylnon |
| 21 | | Mitochondrial complex I electron transport inhibitors | METI acaricides, Rotenone | Rotenone |
| 22 | | Voltage-dependent sodium channel blockers | Indoxacarb | Indoxacarb |
| 24* | 24A | Mitochondrial complex IV electron transport inhibitors | Aluminum phosphide | Aluminum phosphide |
| | 24C | | Phosphine | Phosphine |
| 25 | | Neuronal inhibitors (unknown mode of action) | Bifenazate | Bifenazate |
| 27* | 27A | Synergists | P450 monooxygenase inhibitors | Piperonyl butoxide |
| UN | UNC | Compounds with unknown mode of action** | Dicofol | Dicofol |
| | UND | | Pyridalyl | Pyridalyl |
| NS | NSA | Miscellaneous non-specific (multi-site) inhibitors† | Borax | Borax |

In some embodiments of the invention, the insect control chemical can include at least one of, for example, an organophosphate compound, a carbamate compound, a carbazate compound, a neonicotinoid compound, an organochlorine compound, an organotin compound, an oxadiazine compound, a pyridazinone compound, a pyrethroid, a tetrazine compound, or the like.

In embodiments of the invention that include at least one organophosphate compound, the organophosphate compound can be, for example, azinphos-methyl, chlorpyrifos, diazinon, dimethoate, methidathion, phosmet, or the like.

In embodiments of the invention that include at least one carbamate compound, the carbamate compound can be, for example, methomyl, oxamyl, carbaryl, formetanate, hexythiazox, or the like.

In embodiments of the invention that include at least one carbazate compound, the carbazate compound can be, for example, bifenazate, or the like.

In embodiments of the invention that include at least one neonicotinoid compound, the neonicotinoid compound can be acetamiprid, imidacloprid, thiacloprid, thiomethoxam, or the like.

In embodiments of the invention that include at least one organochlorine compound, the organochlorine compound can be, for example, endosulfan, dicofil, or the like.

In embodiments of the invention that include at least one organotin compound, the organotin compound can be, for example, hexakis, or the like.

In embodiments of the invention that include at least one oxadiazine compound, the oxadiazine compound can be, for example, indoxacarb, or the like.

In embodiments of the invention that include at least one pyridazinone compound, the pyridazinone compound can be, for example, pyridaben, or the like.

In embodiments of the invention that include at least one pyrethroid, the pyrethroid can be, for example, esfenvalerate, fenpropathrin, permethrin, or the like.

In embodiments of the invention that include at least one tetrazine compound, the tetrazine compound can be, for example, clofentezine, or the like.

Embodiments of the invention can include at least one insect control product; and at least one compound of a plant origin, or at least one blend of compounds of a plant origin. The at least one insect control product can be selected from, for example, the insect control products set forth in Table 4, or the like.

TABLE 3

INSECT CONTROL PRODUCTS

| Brand Name | Generic name | Classification |
|---|---|---|
| ARCHER 50 WP | NICLOSAMIDE | |
| 2,4-D AMINE 6 LBS/USG | 2,4-D AMINE | CHLOROPHENOXY COMPOUND |
| 2,4-D AMINE 3.34 LBS/USG | 2,4-D AMINE | CHLOROPHENOXY COMPOUND |
| 2,4-D AMINE EC | 2,4-D AMINE | CHLOROPHENOXY COMPOUND |
| 2,4-D ESTER | 2,4-D IBE | CHLOROPHENOXY COMPOUND |
| 2,4-D ESTER | 2,4-D IBE | CHLOROPHENOXY COMPOUND |
| 2,4-D ESTER | 2,4-D IBE | CHLOROPHENOXY COMPOUND |
| 2,4-D ESTER | 2,4-D IBE | CHLOROPHENOXY COMPOUND |
| 2,4-D ESTER | 2,4-D IBE | CHLOROPHENOXY COMPOUND |
| 2,4-D GRANULES | 2,4-D IBE | CHLOROPHENOXY COMPOUND |
| 2,4-D GRANULES | 2,4-D IBE | CHLOROPHENOXY COMPOUND |
| 5 Star GENERAL | ISOPROTHIOLANE | |
| ABATE 500 E | TEBUFENOZIDE | |
| ABATE SG | TEMEPHOS | |
| Access 2,4-d ESTER | 2,4-D IBE | CHLOROPHENOXY COMPOUND |
| ACETAM 75 SP | ACEPHATE | ORGANOPHOSPHATE |
| ACROBAT 50 WP | DIMETHOMORPH | |
| ACROBAT MZ | DIMETHOMORPH + MANCOZEB | |
| ACTARA 25 WG | THIABENDAZOLE + 0-PHENOL | |
| ACTELLIC 25 EC | PIPEROPHOS + 2,4-D IBE | |
| ACTIVO 22 SC | ANILOFOS + ETHOYSULFRON | |
| ADER 5 EC | CYPERMETHRIN | PYRETHROID |
| ADMIRE 5 WP | IMAZAQUIN | |
| ADVANCE EC | BUTACHLOR + PROPANIL | MISCELLANEOUS |
| ADVANTAGE 5 G | CARBOFURAN | CARBAMATE |
| ADVANTAGE 5 G | CARBOFURAN | CARBAMATE |
| AFALON 50 WP | LINDANE | |
| AGRI MEK 1.8 EC | AVERMECTIN | CHLORIDE CHANNEL ACTIVATOR |
| AGRICOTE MZ 80 WP | MANCOZEB | DITHIOCARBAMATE |
| AGRISOL A-150 K | POLYOXYETHYLENE DODECYL ETHER | |
| AGRISOL A-150K | POLYOXYETHYLENE SORBITAN FATTY ACIDS | |
| AGRO CYPERMETHRIN 5 EC | CYPERMETHRIN | PYRETHROID |
| AGROPOINT CARTAP 50 SP | CARTAP HYDROCHLORIDE | |
| AGROZEB 80 WP | MANCOZEB | DITHIOCARBAMATE |
| AL-100 TS | SETHOXYDIM | |

TABLE 3-continued

INSECT CONTROL PRODUCTS

| Brand Name | Generic name | Classification |
|---|---|---|
| ALAKDAN 300 | BPMC + CHLOPYRIFOS | |
| ALIETTE 80 WP | FOSETHYL-AL | |
| ALIETTE 800 WG | FOSETHYL-AL | |
| ALMIX 20 WP | METRIBUZIN | |
| AMBUSH 5 EC | CYPERMETHRIN | PYRETHROID |
| AMDRO ANT BAIT | HEXYTHIAZOX | |
| AMETREX 80 WP | AMETRYNE | MISCELLANEOUS |
| AMETREX 80 WP | AMETRYNE | MISCELLANEOUS |
| AMETRYNE 80 WP | AMETRYNE | MISCELLANEOUS |
| AMISTAR 25 SC | AZOXYSTROBIN | |
| AMMO 5 EC | CYPERMETHRIN | PYRETHROID |
| AMWAY APSA 80 | ALKYL ARYL ALKOXYLATE + TALL OIL FATTY AC | |
| ANCOM BUTACHLOR 60 EC | BUTACHLOR | MISCELLANEOUS |
| ANCOM CYPERMETHRIN 5 EC | CYPERMETHRIN | PYRETHROID |
| ANTRACOL 70 WG | PROPICONAZOLE | |
| ANTRACOL 70 WP | PROPINEB | |
| ANVIL 5 SC | HALOXYFOP-R-METHYL ESTER | |
| APACHE 10 G | CADUSAFOS | |
| APACHE 100 ME | CADUSAFOS | |
| APACHE 100 ME | CADUSAFOS | |
| APPLAUD 10 WP | BUPROFESIN | |
| APRON 35 SD | MCPA | |
| AQUADIN 25 EC | NICLOSAMIDE | |
| AQUADIN 70 WP | NICLOSAMIDE | |
| ARGOLD 10 EC | CINMETHYLIN | |
| ARGOLD PLUS | CYNMETHYLIN + 2,4-DIBE | PYRETHROID |
| ARIES SUPER METHRIN 5 EC | CYPERMETHRIN | PYRETHROID |
| ARMOR | THIOPHANATE METHYL | |
| ARMURE 300 EC | DIFECONAZOLE + PROPICONAZOLE | |
| ARNIS 2.5 EC | LAMBDACYHALOTHRIN | PYRETHROID |
| ARRIVO 5 EC | CYPERMETHRIN | PYRETHROID |
| ARROW 5 EC | CYPERMETHRIN | PYRETHROID |
| ASCEND 50 SC | FIPRONIL | |
| ASSET 48 SL | GLYPHOSATE MONOETHALONAMINE SALT | |
| ASSURE II EC | PYRIMETHANIL | |
| ATABRON 5 E | CHLORFLUAZURON | |
| ATRAMET COMBI 80 WP | AMETRYNE + ATRAZINE | MISCELLANEOUS |
| ATRAZINE 80 WP | ATRAZINE | MISCELLANEOUS |
| ATTACK 5R | CYPERMETHRIN | PYRETHROID |
| ATTAIN M-80 | MALATHION | ORGANOPHOSPHATE |
| AVANTEC EC | BUTACHLOR + PROPANIL | MISCELLANEOUS |
| AVID | AVERMECTIN | CHLORIDE CHANNEL ACTIVATOR |
| AX 5 EC | CYPERMETHRIN | PYRETHROID |
| BALEAR 500 SC | CHLOROTHALONIL | CHLORONITRILE |
| BANKIT | AZOXYSTROBIN | |
| BANKO 720 SC | CHLOROTHALONIL | MISCELLANEOUS |
| BANKO 720 SC | CHLOROTHALONIL | MISCELLANEOUS |
| BANKO 75 WP | CHLOROTHALONIL | MISCELLANEOUS |
| BANNER 60 EC | BUTACHLOR | MISCELLANEOUS |
| BANOLE OIL | PARAFFIN OIL | |
| BANOLE OIL 60 | PARAFFINIC MINERAL OIL | |
| BASAGRAN 48 EC | BENTAZONE | |
| BASAMID G | DAZOMET | PYRETHROID |
| BASTA 15 SL | GIBBERRELIC ACID | |
| BASUDIN 40 WP | DIAZINON | ORGANOPHOSPHATE |
| BASUDIN 400 EC | DIAZINON | ORGANOPHOSPHATE |
| BASUDIN 600 EC | DIAZINON | ORGANOPHOSPHATE |
| BAVISTIN 50 DF | CARBARYL | CARBAMATE |
| BAYCOR 300 EC | BITERTANOL | |
| BAYLETON 25 WP | THIOPHANATE METHYL | |
| BAYLUSCIDE 250 EC | NICLOSAMIDE | |

TABLE 3-continued

INSECT CONTROL PRODUCTS

| Brand Name | Generic name | Classification |
|---|---|---|
| BAYLUSCIDE 50 WP | NICLOSAMIDE ETHANOLAMINE SALT | |
| BAYLUSCIDE 70 WP | NICLOSAMIDE ETHANOLAMINE SALT | |
| BAYONET 6% PELLETS | METALDEHYDE | |
| BAYTHROID 0125 EC | CYFLUTHRIN | Pyrethroid |
| BAYTHROID 050 EC | CYFLUTHRIN | Pyrethroid |
| BAZZOKA | CHLORPYFIROS + BPMC | Organophosphate + Carbamate |
| BELEREX TABLET | GIBBERRELIC ACID | |
| BELORAN 400 SL | BENZOXONIUM CHLORIDE | |
| BENLATE 50 WP/OD | BENOMYL | |
| BENSUL 10 WP | BENSULFURON METHYL | |
| BERDUGO 50 WP | NICLOSAMIDE ETHANOLAMINE SALT | |
| BERELEX TABLET | GENERIC NAME | |
| BIDA 2.5 EC | LAMBACYHALOTHRIN | PYRETHROID |
| BIFLEX 10 TC | BIFENTHRIN | |
| BIFLEX 10 TC | BIFENTHRIN | |
| BIFLEX 2.5 TC | BIFENTHRIN | |
| BIFLEX TC | BIFENTHRIN | |
| BIOACT WG | PACLOBUTRAZOL | |
| BIODAN 3 G | CARBUFORAN | CARBAMATE |
| BIOZEB | MANCOZEB | DITHIOCARBAMATE |
| BIOZEB 80 WP | MANCOZEB | DITHIOCARBAMATE |
| BLADE 60 EC | BUTACHLOR | MISCELLANEOUS |
| BLINK 275 EC | CHLORPYFIROS + CYPERMETHRIN | ORGANOPHOSPHATE |
| BLOCKADE 480 SL | BENTAZONE | |
| BLUE COP 770 WP | COPPER HYDROXIDE | MISCELLANEOUS |
| BOLT 50 SP | CARTAP | CARBAMATE |
| BOOST 500 SC | ACIBENZOLAR-S-METHYL | |
| BOXER 5 EC | CYPERMETHRIN | PYRETHROID |
| BRAVO 720 FLO | CHLOROTHALONIL | MISCELLANEOUS |
| BREAK-THRU | POLYCARBOXYLIC ACID | |
| BRODAN 31.5 EC | CHLORPYFIROS + BPMC | Organophosphate + Carbamate |
| BROMO GAS | METHOMYL | |
| BRONCHO | GLYPHOSATE AMMONIUM SALT | |
| BUGBUSTER 5 EC | CYPERMETHRIN | PYRETHROID |
| BULLDOZER 50 WP | NICLOSAMIDE | |
| BULLET 5 EC | CYPERMETHRIN | PYRETHROID |
| BULL'S EYE INSECTICIDE | CYPERMETHRIN | PYRETHROID |
| BUMPER 25 EC | PROPICONAZOLE | |
| BURNDOWN 160 AS | GLYPHOSATE DI-AMMONIUM SALT | |
| BURNDOWN 160 AS | GLYPHOSATE IPA | |
| BUSHWHACK 5 EC | CYPERMETHRIN | PYRETHROID |
| BUTACHLOR 600 EC | BUTACHLOR | MISCELLANEOUS |
| BUTATAF 60 E | BUTACHLOR | MISCELLANEOUS |
| CALIBER 70 WP | NICLOSAMIDE | |
| CALIBER 70 WP | NICLOSAMIDE | |
| CALIXIN 75 EC | TRICLOPYR | |
| CAPTAN 50 WP | CAPTAN | MISCELLANEOUS |
| CAPTAN 50 WP | CAPTAN | MISCELLANEOUS |
| CAPTURE 5 EC | CYPERMETHRIN | PYRETHROID |
| CARANCHO 2.5 EC | ETHOFENPROX | |
| CARBARYL 85 S | CARBARYL | CARBAMATE |
| CARVIL 50 EC | BPMC | CARBAMATE |
| CASCADE 10 WDC | FLUFENOXURON | |
| CELCURE A(P) WOOD PRESERVE | COPPER, CHROME, ARSENIC (CCA) | |
| CHAKU 2.5 EC | LAMBDACYHALOTHRIN | |
| CHAMP DP | COPPER HYDROXIDE | COPPER |
| CHAMPION WP | CUPRIC HYDROXIDE | COPPER |
| CHESS 25 WP | PROPINEB | |
| CHESS 50 WG | PYMETROZINE | |
| CHIX 2.5 EC | BETACYPERMETHRIN | PYRETHROID |
| CHLORMITE TC | CHLOROPYFIROS | ORGANOPHOSPHATE |

TABLE 3-continued

INSECT CONTROL PRODUCTS

| Brand Name | Generic name | Classification |
|---|---|---|
| CHOPPER 85 S | CARBARYL | CARBAMATE |
| CITRUS LUSTER 213 | THIABENDAZOLE | |
| CIVIL 75 WP | CHLOROTHALONIL | MISCELLANEOUS |
| CLEANFIELD EC | BUTACHLOR + PROPANIL | MISCELLANEOUS |
| CLEAR OUT 41 | GLYPHOSPATE IPA | |
| CLEAR OUT 41 PLUS | GLYPHOSPHATE IPA | |
| CLINCHER 100 EC | CYHALOFOP BUTYL | |
| COBRA 20 EC | CHLORPYFIROS | ORGANOPHOSPHATE |
| COMBAT 5 EC | CYPERMETHRIN | PYRETHROID |
| COMMAND 3 ME | CLOMAZONE | |
| COMMAND 3 ME | CLOMAZONE | |
| COMMAND PLUS 600 EC | CLOMAZONE + PROPANIL | |
| COMPETE 75 SP | ACEPHATE | ORGANOPHOSPHATE |
| COMPRO 600 EC | CLOMAZONE + PROPANIL | |
| CONFIDOR 100 SL | IMIDACLOPRID | |
| CONFIDOR 200 SL | IMIDACLOPRID | |
| CONTRAZINE 80 WP | ATRAZINE | MISCELLANEOUS |
| CONTRAZINE 80 WP | ATRAZINE | MISCELLANEOUS |
| CONTROL 250 EC | NICLOSAMIDE | |
| CONTROL 70 WP | NICLOSAMIDE ETHANOLAMINE SALT | |
| CORSAIR 5 EC | PENDIMETHLIN | PYRETHROID |
| CORSAIR 5 EC | PERMETHRIN | PYRETHROID |
| COSAVET DF | SULFUR | |
| COTRIN 5 EC | CYPERMETHRIN | PYRETHROID |
| COTRIN 5 EC | CYPERMETHRIN | PYRETHROID |
| COUNTER 10 G | TEMEPHOS | |
| COZEB 80 WP | MANCOZEB | DITHIOCARBAMATE |
| CRUSHER 250 EC | NICLOSAMIDE | |
| CRUSHER 50 WP | NICLOSAMIDE ETHANOLAMINE SALT | |
| CRUSHER 70 WP | NICLOSAMIDE | |
| CULTAR 25 SC | OXYFLUORFEN | |
| CUPRAVIT OB 21 | COPPER OXYCHLORIDE | COPPER |
| CURZATE M FUNGICIDE | MANCOZEB | DITHIOCARBAMATE |
| CYBEST 5 EC | CYPERMETHRIN | PYRETHROID |
| CYCLONE 5 EC | CYPERMETHRIN | PYRETHROID |
| CYMBUSH 5 EC | CYPERMETHRIN | PYRETHROID |
| CYPER-5 | CYPERMETHRIN | PYRETHROID |
| CYPERMETHRIN 5 EC | CYPERMETHRIN | PYRETHROID |
| CYPERTHRIN 5 EC | CYPERMETHRIN | PYRETHROID |
| CYPEX 50 EC | CYPERMETHRIN | PYRETHROID |
| CYPRO 5 EC | CYPERMETHRIN | PYRETHROID |
| CYREN 300 EC | CHLORPYFIROS | ORGANOPHOSPHATE |
| DACINOL 2787 50 WP | CHLOROTHALONIL | MISCELLANEOUS |
| DACINOL 2787 75 WP | CHLOROTHALONIL | MISCELLANEOUS |
| DACONIL 720 SC | CHLOROTHALONIL | MISCELLANEOUS |
| DEADBOL | NICLOSAMIDE | |
| DECIDE 2.5 EC | DELTAMETHRIN | PYRETHROID |
| DECIS 1% SC | DELTAMETHRIN | PYRETHROID |
| DECIS 2.5 EC | DELTAMETHRIN | PYRETHROID |
| DECIS M 2.5 EC | DELTAMETHRIN | PYRETHROID |
| DECIS R | DELTAMETHRIN | PYRETHROID |
| DECIS TAB | DELTAMETHRIN | PYRETHROID |
| DEFENSA 5 EC | CYPERMETHRIN | PYRETHROID |
| DEGESCH MAGTOXIN | LUFENURON | |
| DEGESCH PLATES/STRIPS | MAGNESSIUM PHOSPHIDE | |
| DEGESH PHOSTOXIN | ALUMINUM PHOSPHIDE | RODENTICIDE |
| DELMARK 2.5 EC | DELTAMETHRIN | PYRETHROID |
| DETIA GAS EX-B | ALUMINUM PHOSPHIDE | RODENTICIDE |
| DETIA GAS EX-T | ALUMINUM PHOSPHIDE | RODENTICIDE |
| DETIA PHOSPHINE PELLETS | ALUMINUM PHOSPHIDE | RODENTICIDE |
| DIACARB 50 EC | BPMC | CARBAMATE |
| DIAFURAN 10 G | CARBOFURAN | CARBAMATE |
| DIAFURAN 3 G | CARBOFURAN | CARBAMATE |
| DIAFURAN 5 G | CARBOFURAN | CARBAMATE |
| DIAGRAN 5 G | DIAZINON | ORGANOPHOSPHATE |
| DIAGRAN 5 G | DIAZINON | ORGANOPHOSPHATE |

TABLE 3-continued

INSECT CONTROL PRODUCTS

| Brand Name | Generic name | Classification |
|---|---|---|
| DIAZINON 40 EC | DIAZINON | ORGANOPHOSPHATE |
| DIAZINON 60 EC | DIAZINON | ORGANOPHOSPHATE |
| DIAZINON 60 EC | DIAZINON | ORGANOPHOSPHATE |
| DIAZINON 60 EC | DIAZINON | ORGANOPHOSPHATE |
| DIAZINON 600 EC | DIAZINON | ORGANOPHOSPHATE |
| DIAZOL 40 EC | DIAZINON | ORGANOPHOSPHATE |
| DIAZOL 40 EC | DIAZINON | ORGANOPHOSPHATE |
| DIAZOL 60 EC | DIAZINON | ORGANOPHOSPHATE |
| DIAZOL 60 EC | DIAZINON | ORGANOPHOSPHATE |
| DICARE 37.5 WG | DIAFENTHIURON + FENOXYCAB | ORGANOPHOSPHATE |
| DICARZOL 20 SP | FORMETHANATE HCL | |
| DIMO 50 SP | CARTAP HYDROCHLORIDE | |
| DIPEL WP | *BACILLUS THURINGIENSIS* | PLANT ORIGIN |
| DIPTEREX 95 SP | TRIBUTYLPOLYGLYCO ETHER | |
| DIREK 800 | BUTACHLOR + SAFENER | |
| DITHANE F-448 | MANCOZEB | DITHIOCARBAMATE |
| DITHANE F-448 | MANCOZEB | DITHIOCARBAMATE |
| DITHANE M-45 | MANCOZEB | DITHIOCARBAMATE |
| DITHANE M-45 | MANCOZEB | DITHIOCARBAMATE |
| DITHANE M-45 WP | MANCOZEB | DITHIOCARBAMATE |
| DITHANE OS 600 | MANCOZEB | DITHIOCARBAMATE |
| DITHANE OS-600 | MANCOZEB | DITHIOCARBAMATE |
| DIUREX 80 WP | DIURON | UREA |
| DIUREX 80 WP | DIURON | UREA |
| DIURON 80 WP | DIURON | UREA |
| DIURON 80 WP | DIURON | UREA |
| DIURON 80 WP | DIURON | UREA |
| DMA 3.34 LBS/USG | 2,4-D AMINE | CHLOROPHENOXY COMPOUND |
| DRAGO 60 WP | FLUFENACET | |
| DREXEL DIURON 80 DF | DIURON | UREA |
| DREXEL MALATHION 57 EC | MALATHION | ORGANOPHOSPHATE |
| DREXEL SULFA 80 W | SULFUR | |
| DURSBAN | CHLORPYRIFOS | ORGANOPHOSPHATE |
| DYNAMEC | AVERMECTIN | CHLORIDE CHANNEL ACTIVATOR |
| EASY 5 EC | CYPERMETHRIN | PYRETHROID |
| ELTRA 200 SC | CARBOFURAN | CARBAMATE |
| EQUATION PRO 52.5 DF | CYMOXANIL + FAMOXADONE | |
| ERASER 70 EC | BUTACHLOR + PROPANIL | MISCELLANEOUS |
| ETHREL 10 SL | ETHEPHON | |
| ETHREL PGR 48% | ETHEPHON | |
| ETROFOLAN 50 WP | ISAZOFOS | |
| EXPERT 20 EC | CHLORPYFIROS | ORGANOPHOSPHATE |
| EXTREME 50 SP | CARTAP HYDROCHLORIDE | |
| FASTAC 15 WDG | ALPHACYPERMETHRIN | PYRETHROID |
| FASTAC 250 SC | ALPHACYPERMETHRIN | PYRETHROID |
| FASTAC R | ALPHACYPERMETHRIN + BPMC | PYRETHROID + CARBAMATE |
| FENOM D 225 EC | DIAZINON + CYPERMETHRIN | Organophosphate + Pyrethroid |
| FLASH 5 EC | CYPERMETHRIN | PYRETHROID |
| FLIP 500 WP | NICLOSAMIDE | |
| FLIP 700 WP | NICLOSAMIDE ETHANOLAMINE SALT | |
| FOLICUR 250 EC | SULPHUR | |
| FOLICUR 430 SC | TEBUCONAZOLE | |
| FORWARD 700 EC | BUTACHLOR + PROPANIL | MISCELLANEOUS |
| FROWNCIDE 50 SC | FLUAZINAM | |
| FRUITONE CPA | CHLOROPHENOXY PROPIONIC ACID | |
| FUJI-ONE 40 EC | ISOPROCARB | |
| FUMITOXIN | ALUMINUM PHOSPHIDE | RODENTICIDE |
| FUNGAFLOR 50 L | HYDRAMETHYLNON | |
| FUNGAFLOR 75 SP | IMAZALIL | |

TABLE 3-continued

INSECT CONTROL PRODUCTS

| Brand Name | Generic name | Classification |
|---|---|---|
| FUNGITOX 70 WP | THIOPHANATE METHYL | |
| FUNGURAN-OH | COPPER HYDROXIDE | MISCELLANEOUS |
| FURADAN 10G | CARBARYL | CARBAMATE |
| FURADAN 3 G | CARBENDAZIM | CARBAMATE |
| FURADAN 3G | CARBOFURAN | CARBAMATE |
| FURADAN 5 G | CARBARYL | CARBAMATE |
| FURADAN 5 G | CARBOFURAN | CARBAMATE |
| FURUDAN 10 G | CARBOSULFAN | CARBAMATE |
| FURUDAN 3 G | CARBOSULFAN | CARBAMATE |
| FURUDAN 5 G | CARBUFORAN | CARBAMATE |
| GALLANT SUPER | HALOSULFURON METHYL | |
| GARLON 4 | TRICHLOROFON | |
| GAROTE EC | CHLORPYRIFOS + BPMC | Organophosphate + Carbamate |
| GAS 250 EC | NICLOSAMIDE | |
| GAUCHO 70 WS | IMIDACLOPRID | |
| GEM 2,4-D AMINE | 2,4-D AMINE | CHLOROPHENOXY COMPOUND |
| GEM 2,4-D ESTER | 2,4-D IBE | CHLOROPHENOXY COMPOUND |
| GEM ATRAZINE | ATRAZINE | MISCELLANEOUS |
| GEM MALATHION 57 EC | MALATHION | ORGANOPHOSPHATE |
| GEMTRAK 50 SP | CARTAP HYDROCHLORIDE | |
| GESAPAX 500 FW | AMETRYNE | MISCELLANEOUS |
| GESAPAX 80 WP | AMETRYNE | MISCELLANEOUS |
| GESAPAX COMBI 80 WP | AMETRYNE + ATRAZINE | MISCELLANEOUS |
| GESAPRIM 80 WP | ATRAZINE | MISCELLANEOUS |
| GLADIATOR 75 WDG | CHLORPYRIFOS | ORGANOPHOSPHATE |
| GLYPHOMAX | GLYPHOSATE IPA | |
| GOAL 24 EC | OXADIAZON | |
| GOAL 24 EC | OXYFLOURFEN | |
| GRAMOXONE 20 AS | PARAFINIC MINERAL OIL | |
| GRASSEDGE | THIOBENCARB | |
| GRASSEDGE 800 EC | THIOBENCARB + 2,4-D | |
| GUARDIAN 5 EC | CYPERMETHRIN | PYRETHROID |
| HALT | *BACILLUS THURINGIENSIS* | PLANT ORIGIN |
| HEDONAL LIQ. SL 400 | 2,4-D AMINE | CHLOROPHENOXY COMPOUND |
| HERBADOX 33 EC | PENDIMETHALIN | |
| HERBIMAX | PIRIMIPHOS METHYL | |
| HERCULES 20 EC | TRIADIMEFON | |
| HI-CONFIL F 75 WP | CHLOROTHALONIL | MISCELLANEOUS |
| HIDROCOB 77 WP | COPPER HYDROXIDE | MISCELLANEOUS |
| HINOSAN 300 EC | EDIFENPHOS | Organophosphate |
| HINOSAN 50 EC | EDIFENPHOS | Organophosphate |
| HI-PER 5 EC | CYPERMETHRIN | PYRETHROID |
| HIT 250 EC | NICLOSAMIDE | |
| HIT WP | NICLOSAMIDE | |
| HOESTICK | TRIAZOPHOS | |
| HOPCIDE 50 EC | BPMC | CARBAMATE |
| HOPCIN 50 EC | BPMC | CARBAMATE |
| HOPKILL 50 EC | BPMC | CARBAMATE |
| HOSTATHION 20 EC | TRIAZOPHOS | |
| HYDROX 77 WP | COPPER HYDROXIDE | COPPER |
| HYDROXIDE SUPER 77 WP | COPER HYDROXIDE | COPPER |
| HYDROXIDE SUPER 77 WP | COPPER HYDROXIDE | COPPER |
| HYTOX 50 WP | MICP | |
| HYVAR X WEEDKILLER | BROMACIL | |
| IMAGE 1.5 LC | IMAZALIL | |
| IMPACT 2.5 EC | DELTAMETHRIN | PYRETHROID |
| INDAR 2F | FENBUCONAZOLE | ORGANOPHOSPHATE |
| INDAR 2F | FENBUCONAZOLE | ORGANOPHOSPHATE |
| INSECT PRO 50 SP | CARTAP HYDOCLORIDE | |
| INSECT PRO 50 SP | CARTAP HYDOCLORIDE | |
| INSTAR | CARTAP HYDROCHLORIDE | |
| INVEST 10 WP | CYCLOSULFAMURON | |

TABLE 3-continued

INSECT CONTROL PRODUCTS

| Brand Name | Generic name | Classification |
|---|---|---|
| IVA DIURON 80 WP | DIURON | MISCELLANEOUS |
| IVA PYRITILINE 20 PE M/B | CHLORPYFIROS | ORGANOPHOSPHATE |
| IVAZEB 80 WP | MANCOZEB | DITHIOCARBAMATE |
| KARATE 2.5 EC | LAMBDACYHALOTHRIN | PYRETHROID |
| KARATE w/ ZEON TECHNOLOGY | LAMBDACYHALOTHRIN | PYRETHROID |
| KARET 40 | MANEB W/ ZINC | |
| KARMEX WEEDKILLER | DIURON | MISCELLANEOUS |
| KHOLUSCIDE 70 WP | NICLOSAMIDE ETHANOLAMINE SALT | |
| KICK 25 EC | NICLOSAMIDE | |
| KICK 70 WP | NICLOSAMIDE | |
| KILLER 5 EC | CYPERMETHRIN | PYRETHROID |
| KILPES 3 EC | FENVALERATE | PYRETHROID |
| KING 5 EC | CYPERMETHRIN | PYRETHROID |
| KITAL ATRAZINE | ATRAZINE | MISCELLANEOUS |
| KITAL MANCOZEB | MANCOZEB | DITHIOCARBAMATE |
| KITAL STRYKER 5 EC | CYPERMETHRIN | PYRETHROID |
| KLEEN UP 480 AS | GLYPHOSATE IPA | |
| KLEN UP 480 AS | GLYPHOSATE IPA | |
| KLERAT WITH BITREX | BRODIFACOUM | COUMARIN |
| KLIK 700 EC | BUTACHLOR + PROPANIL | MISCELLANEOUS |
| KNOCK OUT 5 EC | CYPERMETHRIN | PYRETHROID |
| KOCIDE 101 | CUPRIC HYDROXIDE | MISCELLANEOUS |
| KOCIDE DF | CUPRIC HYDROXIDE | MISCELLANEOUS |
| KOCIDE DF 2000 | COPPER HYDROXIDE | MISCELLANEOUS |
| KOP-HYDROXIDE 50 WP | COPPER HYDROXIDE | MISCELLANEOUS |
| KOTETSU 10 SC | CHLORPHENAPYR | ORGANOPHOSPHATE |
| KRISS EC | LAMBDACYHALOTHRIN | PYRETHROID |
| KUHZAK 25 EC | NICLOSAMIDE | |
| KUHZAK 70 WP | NICLOSAMIDE | |
| KUMULUS DF | ELEMENTAL SULFUR | |
| LANNATE 40 SP | METHIOCARB | |
| LARVIN 350 FS | THIOBENCARB + 2,4-DIBE | |
| LATRON B-1956 | PHENTHOATE + BPMC | |
| LEAD CORP. 2,4-D AMINE | 2,4-D AMINE | CHLOROPHENOXY COMPOUND |
| LEADCORP CARTAP | CARTAP HYDROCHLORIDE | |
| LEADCORP MALATHION 57 EC | MALATHION | ORGANOPHOSPHATE |
| LEADMARK 3 EC | FENVALERATE | PYRETHROID |
| LEADONIL 500 SC | CHLOROTHALONIL | MISCELLANEOUS |
| LEADREX TC | CHLORPYFIROS | ORGANOPHOSPHATE |
| LEADTHREL 480 SL | ETHEPON | |
| LEBAYCID 50 EC | FENTHION | |
| LECSPRO 44 WP | FENTRAZAMIDE + PROPANIL | PYRETHROID |
| LENTREK TC | CHLORPYRIFOS | ORGANOPHOSPHATE |
| LENTREK TC | CHLORPYRIFOS | ORGANOPHOSPHATE |
| LINDAFOR 75 F | LAMBDACYHALOTHRIN | ORGANOCHLORINE |
| LONDAX WP | BENSULFURON METHYL | |
| LORSBAN 3E | CHLORPYRIFOS | ORGANOPHOSPHATE |
| LORSBAN 40 EC | CHLORPYRIFOS | ORGANOPHOSPHATE |
| LUTENSOL A8 | ALKYL POLYETHELENE GLYSOL ETHER | |
| LUV 2,4-D ESTER | 2,4-D IBE | CHLOROPHENOXY COMPOUND |
| LUV MALATHION 57 EC | MALATHION | ORGANOPHOSPHATE |
| MACHETE 5 G | BUTACHLOR | MISCELLANEOUS |
| MACHETE EC | BUTACHLOR | MISCELLANEOUS |
| MACHETE EXPRESS | BUTACHLOR | MISCELLANEOUS |
| MACHO | BUTACHLOR | MISCELLANEOUS |
| MAGIK 5% EC | CYPERMETHRIN | PYRETHROID |
| MAGNUM 5 EC | CYPERMETHRIN | PYRETHROID |
| MAITHREL 10 PGR | ETHEPON | |
| MAITHREL 48 PGR | ETHEPON | |
| MALATHION 57 E PREMIUM | MAGNESSIUM PHOSPHIDE | ORGANOPHOSPHATE |

TABLE 3-continued

INSECT CONTROL PRODUCTS

| Brand Name | Generic name | Classification |
|---|---|---|
| MALATHION 57 EC | MALATHION | ORGANOPHOSPHATE |
| MALATHION 57 EC | MALATHION | ORGANOPHOSPHATE |
| MANAGER 80 WP | MANCOZEB | DITHIOCARBAMATE |
| MANZATE 200 FUNGICIDE | MANCOZEB | DITHIOCARBAMATE |
| MANZATE 75 DF | MANCOZEB | DITHIOCARBAMATE |
| MANZEB 80 WP | MIPC | |
| MARSBYL 85 WP | CARBARYL | CARBAMATE |
| MARVEL 5 EC | CYPERMETHRIN | PYRETHROID |
| MASO 70 WP | NICLOSAMIDE | |
| MASTER 2.5 EC | LAMBDACYHALOTHRIN | PYRETHROID |
| MASTRA DIURON 80 WP | DIURON | MISCELLANEOUS |
| MATADOR 60 SC | METAMIDOPHOS | ORGANOPHOSPHATE |
| MATCH 050 EC | LINURON | UREA |
| MATON 5 EC | CYPERMETHRIN | PYRETHROID |
| MEBROM | METHYL BROMIDE + CHLOROPICRIN | |
| MEGARIFOS 20 EC | CHLORPYFIROS | ORGANOPHOSPHATE |
| MEGATHRIN 5 EC | CYPERMETHRIN | PYRETHROID |
| MELODY DUO | IPRODIONE | |
| MESUROL 50 WP | METHAMIDOPHOS | |
| META BAIT | METALDEHYDE | |
| META BAIT 6% PELLETS | METALAXYL-m + MANCOZEB | |
| METABROM | METHYL BROMIDE + CHLOROPICRIN | |
| MICROTHIOL DF | SPINOSAD | |
| MIMIC 20 F | TEBUCONAZOLE | |
| MIMIC 20 F | TEBUFENOZIDE | |
| MINER 50 SP | CARTAP HYDROCHLORIDE | |
| MIPCIN 50 WP | METSULFURON METHYL + CHLORIMURON ETH | |
| MIRACLE AMINE | 2,4-D AMINE | CHLOROPHENOXY COMPOUND |
| MIRAL 3 G | IPROVALICARB + PROPINEB | |
| MOCAP 10 G | ETHOPROP | |
| MODEL 5 EC | CYPERMETHRIN | PYRETHROID |
| MOLUXIDE 250 EC | NICLOSAMIDE | |
| MOSPHILAN 3 EC | ACETAMIPRID | |
| NABU-S | QUIZALOFOP-P-ETHYL | |
| NEMACUR 10 G | PERMETHRIN + Zn | |
| NEMACUR 400 EC | PHENAMIPHOS | |
| NEMATHORIN 10 G | FOZTHIAZATE | |
| NET 50 WP | NICLOSAMIDE ETHANOLAMINE SALT | |
| NICLOS M | NICLOSAMIDE | |
| NISSORUN 5 EC | HEXAFLUMURON | |
| NOBLITE 60 WG | FENAMIDONE + MANCOZEB | |
| NOMINEE 100 SC | BISPYRIBAC SODIUM | |
| NOMINEE 100 SC | BISPYRIBAC SODIUM | |
| NORDOX 50 WP | COPPER OXIDE | COPPER |
| NURELLE D | CHLORPYFIROS + CYPERMETHRIN | ORGANOPHOSPHATE |
| NUVACRON 300 SCW | Mn—Zn ETHYLENE BISDITHIOCARBAMATE | |
| NYDREL 100 | ETHEPHON | |
| NYDREL 480 | ETHEPHON | |
| OCHO 5 WP | CARBARYL | CARBAMATE |
| OMEGA 45 EC | PRETILACHLOR + FENCLORIM | |
| ONECIDE 15 EC | FLUAZIFOP-P-BUTYL | |
| ORTHENE/ACETAM 75 SP | ACEPHATE | ORGANOPHOSPHATE |
| ORTHENE 75 SP | ACEPHATE | ORGANOPHOSPHATE |
| OXYCHLOR 85 WP | COPPER OXYCHLORIDE | |
| PADAN 50 SP | CAPTAN HYDROCHLORIDE | CARBAMATE |
| PADAN 50 SP | CARTAP HYDROCHLORIDE | |
| PARAFUNGUS 80 WP | MANCOZEB | DITHIOCARBAMATE |
| PARAKUHOL 250 EC | NICLOSAMIDE | |
| PARAPEST D 400 EC | DIAZINON | ORGANOPHOSPHATE |

TABLE 3-continued

INSECT CONTROL PRODUCTS

| Brand Name | Generic name | Classification |
|---|---|---|
| PARAULOD 300 EC | CHLORPYFIROS | ORGANOPHOSPHATE |
| PARTNER 40 DF | CARFENTRAZONE-ETHYL | |
| PARTNER 40 DF | CARFENTRAZONE-ETHYL | |
| PASSPORT 500 SC | CHLOROTHALONIL | MISCELLANEOUS |
| PENNANT | PHENAMIPHOS | |
| PERFEK 31.5 EC | CHLORPYRIFOS + BPMC | Organophosphate + Carbamate |
| PERFEKTHION 40 EC | DIMETHOATE | |
| PERMIT 10 WP | GLYSOPHATE IPA | |
| PESTMASTER | CYPERMETHRIN | PYRETHROID |
| PILARICH 500 G/L FP | CHLOROTHALONIL | MISCELLANEOUS |
| PILARZEB 80 WP | MANCOZEB | DITHIOCARBAMATE |
| PIPSET 35 WP | CINOSULFURON + PIPEROPHOS | |
| PISTOL 50 WP | NICLOSAMIDE ETHANOLAMINE | |
| PISTOL 50 WP | NICLOSAMIDE ETHANOLAMINE SALT | |
| PLANTERS MALATHION 57 EC | MALATHION | ORGANOPHOSPHATE |
| POLIDO 2.5 EC | ETHOFENPROX | |
| PORSANAIL | METALDEHYDE | |
| POSSE 200 SC | CARBOSULFAN | CARBAMATE |
| POWER | GLYPHOSATE IPA | |
| POWER SUPRATECH | GLYPHOSATE DI-AMMONIUM SALT | |
| PREDATOR EC | CHLORPYFIROS | ORGANOPHOSPHATE |
| PREDATOR PLUS | CHLORPYFIROS + CYPERMETHRIN | ORGANOPHOSPHATE |
| PREKILL 330 | PARAQUAT DICHLORIDE | |
| PREMISE 200 SC | IMIDACLOPRID | |
| PREMIUM 5 EC | CYPERMETHRIN | PYRETHROID |
| PREVENT 77 WP | COPPER HYDROXIDE | COPPER |
| PREVICUR-N | PROFENOFOS | |
| PROCIN 25 WP | BUFROFESIN | |
| PROCURE 50 WP | BENOMYL | |
| PROPLANT | PROPAMOCARB | |
| PROVADO SUPRA 050 EC | IMIDACLOPRID | |
| PROVIN 85 WP | CARBARYL | CARBAMATE |
| PUNISH 5.5 EC | CYPERMETHRIN | PYRETHROID |
| PYRITILENE 20 PE M/B | CHLOPYFIROS | ORGANOPHOSPHATE |
| PYTOX 10 EC | PERMETHRIN | PYRETHROID |
| QUICKPHOS (ROUND TAB) | ALUMINUM PHOSPHIDE | RODENTICIDE |
| RACUMIN DUST | COUMATETRALYL | |
| RADISSON MANCOZEB 80 WP | MANCOZEB | DITHIOCARBAMATE |
| RADOR 262.5 EC | CHLORPYFIROS + BETACYFLUTHRIN | Organophosphate + Pyrethroid |
| RAFT 800 WG | NICLOSAMIDE ETHANOLAMINE SALT | |
| RAPIDO 5 EC | CYPERMETHRIN | PYRETHROID |
| RATKIL ZINC PHOSPHIDE80% BAIT | WARFARIN | |
| RATOXIN P | TRISILOXANE ALKOXYLATE + ALLYL ETHOXYLA | |
| RECRUIT II | HEXACONAZOLE | |
| REDEEM 80 WP | MANCOZEB | DITHIOCARBAMATE |
| RED-OUT 80 WP | MANCOZEB | DITHIOCARBAMATE |
| REGENT 0.3 GR | FIPRONIL | |
| REV 800 WP | MANCOZEB | DITHIOCARBAMATE |
| RICESTAR EC | FENOXAPROP P-ETHYL | |
| RIDOMIL GOLD MZ 68 WP | METALAXYL + MANCOZEB | |
| RIDOMIL MZ 58 WP | METALAXYL | |
| RILOF 500 EC | PICLORAM + 2,4-D | |
| RIPCORD 2.5 EC | CYPERMETHRIN | PYRETHROID |
| ROBODAX 25 EC | NICLOSAMIDE | |
| ROGUE EC | BUTACHLOR + 2,4-D | |
| RONSTAR 25 EC | OXADIARGYL | |

TABLE 3-continued

INSECT CONTROL PRODUCTS

| Brand Name | Generic name | Classification |
|---|---|---|
| RONSTAR 2G | OXADIAZON | |
| ROUND-UP BIOSORB | GLYPHOSATE ISOPROPYLAMINE SALT | |
| ROUNDUP EW | GLYPHOSATE IPA | |
| ROUND-UP MAX | GLUFOSINATE AMMONIUM | |
| ROVER | CHLOROTHALONIL | MISCELLANEOUS |
| ROVRAL 50 WP | INDOXACARB | |
| ROVRAL AQUAFLO 50 SC | IPRODIONE | |
| ROYAL CARTAP | CARTAP | CARBAMATE |
| ROYANIL 75 WP | CHLOROTHALONIL | MISCELLANEOUS |
| SABEDONG 5 EC | CYPERMETHRIN | PYRETHROID |
| SAMURAI 60EC | BUTACHLOR | MISCELLANEOUS |
| SANAFURAN 3 G | CARBOSULFAN | CARBAMATE |
| SANAZOLE 250 EC | PROPICONAZOLE | |
| SAPROL EC | TRIFLUMIZOLE | |
| SATURN 60 EC | THIAMETOXAM | |
| SATURN D | THIOBENCARB + 2,4-D | |
| SATURN S | THIOBENCARB | THIOCARBAMATE |
| SAVIOR 80 WP | MANCOZEB | DITHIOCARBAMATE |
| SCOPE 70 WP | THIOPHANATE METHYL | |
| SCORE 250 EC | DIFENOCONAZOLE | |
| SELECRON 500 EC | PROCHLORAZ MN | |
| SELECT 120 EC | CLETHODIM | |
| SELECT 120 EC | CLETHODIM | |
| SENCOR 70 WP | METHYL BROMIDE + CHLOROPICRIN | |
| SENTINEL 75 WP | CHLOROTHALONIL | MISCELLANEOUS |
| SERVWEL 2,4-D AMINE | 2,4-D AMINE | CHLOROPHENOXY COMPOUND |
| SERVWEL MALATHION 57 EC | MALATHION | ORGANOPHOSPHATE |
| SERVWEL MANCOZEB 80 WP | MANCOZEB | DITHIOCARBAMATE |
| SERVWEL TKO 50 EC | CYPERMETHRIN | PYRETHROID |
| SERVWEL 2,4-D GRANULES | 2,4-D IBE | CHLOROPHENOXY COMPOUND |
| SEVIN 50 WP | CARBUFORAN | CARBAMATE |
| SEVIN 85 WP | CARBUFORAN | CARBAMATE |
| SHERPA 5 EC | CYPERMETHRIN | PYRETHROID |
| SHIELD | CHLOROTHALONIL | MISCELLANEOUS |
| SHOTGUN M | MANCOZEB | DITHIOCARBAMATE |
| SICO 250 EC | DIFENOCONAZOLE | |
| SIGA 300 EC | CHLORPYRIFOS | ORGANOPHOSPHATE |
| SIGANEX 600 SC | PYMETROZINE | |
| SIGMA | GLYPHOSPHATE IPA | |
| SILWET 408 | TRISILOXANE ALKOXYLATE + ALLYL ETHOXYLA | |
| SILWET 408 | TRIFORINE | |
| SLASH | GLYPHOSATE IPA | |
| SMART 480 | GLYPHOSATE IPA | |
| SMART 480 | GLYPHOSATE IPA | |
| SMASH 5 EC | CYPERMETHRIN | PYRETHROID |
| SNAIL CHAMP 25 EC | NICLOSAMIDE | |
| SNAIL OUT 50 WP | NICLOSAMIDE | |
| SNAILKIL 6% P | METALDEHYDE | |
| SNIPER 5 EC | CYPERMETHRIN | PYRETHROID |
| SOFIT 300 EC | POLYOXYETHYLENE SORBITANT FATTY ACIDS + | |
| SOLIGNUM BROWN | PERMETHRIN | PYRETHROID |
| SOLIGNUM COLORLESS | PERMETHRIN | PYRETHROID |
| SOLNET 500 EC | PRETILACHLOR | |
| SONIC 60 EC | BUTACHLOR | MISCELLANEOUS |
| SPECTRA 5 EC | CYPERMETHRIN | PYRETHROID |
| SPEED 25 EC | MONOCROTOPHOS | |
| SPEED 50 WP | NICLOSAMIDE | |
| SPEEDEX | POLYETHER:POLYMETHYLSILOXANE COPOLYME | |
| STAM LV-10 | PROPAMOCARB HCL | |
| STAR 5 EC | CYPERMETHRIN | PYRETHROID |

TABLE 3-continued

INSECT CONTROL PRODUCTS

| Brand Name | Generic name | Classification |
|---|---|---|
| STEADFAST TC | ALPHACYPERMETHRIN | PYRETHROID |
| STEWARD WDG | IMIDACLOPRID + CYFLUTHRIN | |
| STIMUKIL FLY BAIT | METHOMYL | |
| STINGRAY 5.625 | DELTAMETHRIN + BUPROFEZIN | |
| STIX 480 EC | CARBUFORAN | CARBAMATE |
| STOP 6% PELLETS | METALDEHYDE | |
| STORM WAX W/ BITREX | FLOCOUMAFEN | |
| SUCCESS NATURALYTE 25 SC | SORBITAN MONOOLATE(SB), POLYOXYETHYL | |
| SUMI-ALPHA 2.5 EC | ESFENVALERATE | PYRETHROID |
| SUMI-ALPHA 2.5 EC | ESFENVALERATE | PYRETHROID |
| SUMI-ALPHA 2.5 EC | ESFENVALERATE | PYRETHROID |
| SUMICIDIN | FENVALERATE | PYRETHROID |
| SUMICIDIN 3 EC | FENVALERATE | PYRETHROID |
| SUMICIDIN 3 EC | FENVALERATE | PYRETHROID |
| SUMI-EIGHT | DINICONAZOLE | |
| SUMITHION 40 WDP | FENITROTHION | ORGANOPHOSPHATE |
| SUMITHION 50 EC | FENITROTHION | ORGANOPHOSPHATE |
| SUMITHION 50 EC | FENITHROTHION | ORGANOPHOSPHATE |
| SUMITHION 50 EC | FENITROTHION | ORGANOPHOSPHATE |
| SUNRICE 15 WDG | ETHOXYSULFURON | |
| SUNSPRAY 8N | *PAECILOMYCES LILACINUS* STRAIN 251 | |
| SUPER BLUE 85 WP | COPPER OXYCHLORIDE | COPPER |
| SUPREME 5 EC | CYPERMETHRIN | PYRETHROID |
| SUPREMO EC | BPMC + CHLORPYFIROS | |
| SURE 250 EC | NICLOSAMIDE | |
| SUREKILL 70 WP | NICLOSAMIDE | |
| SURFACTANT A-100 | POLYETHER-POLYMETHYLSILOXANE COPOLYM | |
| SURFACTANT A-100 | POLYOXYETHYLENE DODECYL ETHER | |
| SURFIX | BETA PINENE POLYMER | |
| SWEEP | THIOPHANATE METHYL | |
| SWIPE 25 EC | NICLOSAMIDE | |
| SWIPE 50 WP | NICLOSAMIDE | |
| TAMARON 600 SL | METALDEHYDE | |
| TAMEX 360 EC | BUTRALIN | |
| TARGET 2.5 EC | NICLOSAMIDE | |
| TARGET 25 EC | NICLOSAMIDE | |
| TECTO 45 FW | TETRAMETHYLTHIURAM DISULPHIDE | |
| TEGA 075 EC | TRIDEMORPH | |
| TELONE II | DICHCHLOROPROPENE | |
| TERMEX 48 EC | CHLORPYFIROS | ORGANOPHOSPHATE |
| TERMIDOR 2.5 EC | FIPRONIL | |
| TERMINATOR 2.5 EC | LAMBDACYHALOTHRIN | PYRETHROID |
| TERMITE-X | CHLORPYFIROS | ORGANOPHOSPHATE |
| TERRAGUARD 48 EC | CHLORPYFIROS | ORGANOPHOSPHATE |
| THESIS 2.5 EC | DELTAMETHRIN | PYRETHROID |
| THIRAM 80 WG | TETRAMETHYLTHIURAM DISULPHIDE | |
| THYLATE 80 WG | TERBUFOS | |
| TIGER 25 SC | NICLOSAMIDE | |
| TILT 250 EC | PROPANIL | |
| TIMBER GUARD CLEAR | PERMETHRIN + Zn | |
| TIMBER GUARD MEDIUM BROWN | PERMETHRIN | PYRETHROID |
| TOP 70 WP | THIOPHANATE METHYL | |
| TOPNOTCH | THIODICARB | |
| TOPSIN-M 70 WP | THIOPHANATE METHYL | |
| TOPSTAR 60 EC | OXADIARGYL | |
| TORDON 101 MIXTURE | PHTHALIC GLYCEROLALKYL | |
| TORNADO 60 EC | BUTACHLOR + PROPANIL | MISCELLANEOUS |
| TORNADO 60 EC | BUTACHLOR + PROPANIL | MISCELLANEOUS |

TABLE 3-continued

INSECT CONTROL PRODUCTS

| Brand Name | Generic name | Classification |
|---|---|---|
| TORO | BUTACHLOR + PROPANIL | MISCELLANEOUS |
| TORPEDO 5 EC | CYPERMETHRIN | PYRETHROID |
| TRAMEX COMBI 80 WP | AMETRYNE + ATRAZINE | MISCELLANEOUS |
| TRANZEB 455 FC | MANCOZEB | DITHIOCARBAMATE |
| TRANZEB 80 WP | MANCOZEB | DITHIOCARBAMATE |
| TRAP 70 WP | NICLOSAMIDE | |
| TREBON 10 EC | ETHOFENPROX | |
| TREBON 10 EC | ETHOFENPROX | |
| TREBON 10 EW | ETHOFENPROX | |
| TREFIC 20 WP | ETHOFENPROX | |
| TRIFMINE 30 WP | TRIFLOXYSTROBIN | |
| TRIGARD 75 WP | CYROMAZINE | |
| TRIM 50 WP | LINURON | |
| TRINEB 80 WP | MANCOZEB + CYMOXANIL | |
| TRIO 50 WP | PROCHLORAZ | |
| TRIPLEX 50 EC | CYPERMETHRIN | PYRETHROID |
| TROJAN 31.5 EC | CHLORPYFIROS + BPMC | |
| TWISTER 70 EC | BUTACHLOR + PROPANIL | MISCELLANEOUS |
| TWISTER EC | BUTACHLOR + PROPANIL | MISCELLANEOUS |
| ULTIMO EC 200 | NICLOSAMIDE | |
| ULTIMO EC 225 | NICLOSAMIDE | |
| UPROOT 60 EC | BUTACHLOR | MISCELLANEOUS |
| VECTRON 10 EW | ETHOFENPROX | |
| VECTRON 20 WP | ETHOFENPROX | |
| VEGETOX 50 SP | CARTAP | CARBAMATE |
| VERTIMEC | AVERMECTIN | CHLORIDE CHANNEL ACTIVATOR |
| VEXTER 300 EC | CHLORPYFIROS | ORGANOPHOSPHATE |
| VINDEX PLUS | PHENTHOATE | |
| VISOCOL 50 WP | NICLOSAMIDE | |
| VITAL BLUE 85 WP | COPPER OXYCHLORIDE | COPPER |
| VITIGRAN BLUE 58 WP | COPPER OXYCHLORIDE | COPPER |
| VITIGRAN BLUE 58 WP | COPPER OXYCHLORIDE | COPPER |
| VONDOZEB 42 SC | MANCOZEB | DITHIOCARBAMATE |
| VONDOZEB 75 DF | MANCOZEB | DITHIOCARBAMATE |
| VONDOZEB L | MANEB | |
| VONDOZEB PLUS | MANCOZEB | DITHIOCARBAMATE |
| WALLOP 70 WP | NICLOSAMIDE | |
| WARRIOR 31.5 | CHLORPYRIFOS + BPMC | ORGANOPHOSPHATE + CARBAMATE |
| WAZARY 10 FL | FENVALERATE | PYRETHROID |
| WAZARY 10 FL | FENVALERATE | PYRETHROID |
| WEAPON 5 EC | CYPERMETHRIN | PYRETHROID |
| WEDKILL 2,4-D | 2,4-D IBE | CHLOROPHENOXY COMPOUND |
| WEEDER 60 EC | BUTACHLOR | MISCELLANEOUS |
| WEEDTROL 40 EC | 2,4-D IBE | CHLOROPHENOXY COMPOUND |
| WEISER ATRAZINE 80 WP | ATRAZINE | 1,3,5-TRIAZINE |
| WEISSER ATRAZINE 80 WP | ATRAZINE | 1,3,5-TRIAZINE |
| WEISSER CYPERMETHRIN 5 EC | CYPERMETHRIN | PYRETHROID |
| WHIP-S 120 EW | FENOXAPROP P-ETHYL | |
| WHIP-S 75 EW | FENOXAPROP P-ETHYL | |
| WINNER 5 EC | CYPERMETHRIN | PYRETHROID |
| WIPER5 EC | CYPERMETHRIN | PYRETHROID |
| WOLMAN CCA-C | COPPER, CHROME, ARSENIC (CCA) | |
| XENTARI WDG | *BACILLUS THURINGIENSIS* | PLANT ORIGIN |
| X-PHOS 20 EC | CHLORPYFIROS | ORGANOPHOSPHATE |
| X-PHOS 40 EC | CHLORPYFIROS | ORGANOPHOSPHATE |
| X-RAT 1% P | WARFARIN | |
| XTRAGRO 10 LS | ETHEPHON | |
| XTRAGRO 240 PGR | ETHEPHON | |
| XTRAGRO 480 PGR | ETHEPHON | |
| ZACARB 85 WP | CARBARYL | CARBAMATE |
| ZACK 50 WP | MIPC | |
| ZECTRIC 6% PELLETS | METALDEHYDE | |
| ZEPHYR | AVERMECTIN | CHLORIDE CHANNEL ACTIVATOR |

TABLE 3-continued

INSECT CONTROL PRODUCTS

| Brand Name | Generic name | Classification |
| --- | --- | --- |
| ZINC PHOSPHIDE 80 DP | ZINC PHOSPHIDE | |
| ZOOM 5 EC | CYPERMETHRIN | PYRETHROID |

Embodiments of the invention can include at least one biologically-based insecticide, such as, for example, abamectin, proteins and/or spores derived from *Bacillus thuriniensis*, spinosad, or the like.

Embodiments of the invention can include at least one insect growth regulator, such as, for example, etoxazol, methoxyfenozide, pyriproxyfen, or the like.

Embodiments of the invention can include at least one oil, such as, for example, "Superior oil," highly-refined oils, and the like.

Embodiments of the invention can include at least one pheromone, such as, for example, Codling moth pheromone, Oriental fruit moth pheromone, and the like.

Embodiments of the invention can include a herbicidal chemical or product. In some embodiments, these herbicidal chemicals can include, for example, amide herbicides, anilide herbicides, arylalanine herbicides, chloroacetanilide herbicides, sulfonanilide herbicides, sulfonamide herbicides, thioamide herbicides, antibiotic herbicides, aromatic acid herbicides, benzoic acid herbicides, pyrimidinyloxybenzoic acid herbicides, pyrimidinylthiobenzoic acid herbicides, phthalic acid herbicides, picolinic acid herbicides, quinolinecarboxylic acid herbicides, arsenical herbicides, benzoylcyclohexanedione herbicides, benzofuranyl alkylsulfonate herbicides, benzothiazole herbicides, carbamate herbicides, carbanilate herbicides, cyclohexene oxime herbicides, cyclopropylisoxazole herbicides, dicarboximide herbicides, dinitroaniline herbicides, dinitrophenol herbicides, diphenyl ether herbicides, nitrophenyl ether herbicides, dithiocarbamate herbicides, halogenated aliphatic herbicides, imidazolinone herbicides, inorganic herbicides, nitrile herbicides, organophosphorus herbicides, oxadiazolone herbicides, phenoxy herbicides, phenoxyacetic herbicides, phenoxybutyric herbicides, phenoxypropionic herbicides, aryloxyphenoxypropionic herbicides, phenylenediamine herbicides, pyrazole herbicides, benzoylpyrazole herbicides, phenylpyrazole herbicides, pyridazine herbicides, pyridazinone herbicides, pyridine herbicides, pyrimidinediamine herbicides, quaternary ammonium herbicides, thiocarbamate herbicides, thiocarbonate herbicides, thiourea herbicides, triazine herbicides, chlorotriazine herbicides, methoxytriazine herbicides, methylthiotriazine herbicides, triazinone herbicides, triazole herbicides, triazolopyrimidine herbicides, uracil herbicides, urea herbicides, phenylurea herbicides, sulfonylurea herbicides, pyrimidinylsulfonylurea herbicides, triazinylsulfonylurea herbicides, thiadiazolylurea herbicides, unclassified herbicides, and the like.

Embodiments of the invention can include a fungicidal chemical or product. In some embodiments, these fungicidal chemicals can include, for example, aliphatic nitrogen fungicides, amide fungicides, acylamino acid fungicides, anilide fungicides, benzanilide fungicides, furanilide fungicides sulfonanilide fungicides, benzamide fungicides, furamide fungicides, phenylsulfamide fungicides, sulfonamide fungicides, valinamide fungicides, antibiotic fungicides, strobilurin fungicides, aromatic fungicides, benzimidazole fungicides, benzimidazole precursor fungicides, benzothiazole fungicides, bridged diphenyl fungicides, carbamate fungicides, benzimidazolylcarbamate fungicides, carbanilate fungicides, conazole fungicides, copper fungicides, dicarboximide fungicides, dichlorophenyl dicarboximide fungicides, phthalimide fungicides, dinitrophenol fungicides, dithiocarbamate fungicides, imidazole fungicides, inorganic fungicides, mercury fungicides, morpholine fungicides, organophosphorus fungicides, organotin fungicides, oxathin fungicides, oxazole fungicides, polysulfide fungicides, pyrazole fungicides, pyridine fungicides, pyrimidine fungicides, pyrrole fungicides, quinoline fungicides, quinone fungicides, quinoxaline fungicides, thiazole fungicides, thiazolidine fungicides, thiocarbamate fungicides, thiophene fungicides, triazine fungicides, triazole fungicides, urea fungicides, unclassified fungicides, and the like.

In embodiments of the invention that include at least one compound or chemical of a plant origin, the at least one compound or chemical of a plant origin can include, for example, any of the compounds or chemicals listed in table 4, or the like:

TABLE 4

COMPOUNDS OF PLANT ORIGIN

| | | | |
| --- | --- | --- | --- |
| T-ANETHOLE | CORN OIL | LILAC FLOWER | PIPERONAL |
| ALLYL SULFIDE | B-COSTOL | OIL (LFO) | PIPERONYL |
| ALLYL TRISULFIDE | CRYPTONE | LIME OIL | PIPERONYL |
| ALLYL-DISULFIDE | CUMIN OIL | D-LIMONENE | ACETATE |
| ARTEMISIA | CURZERENONE | LINALOOL | PIPERONYL |
| ALCOHOL ACETATE | P-CYMENE | LINALYL | ALCOHOL |
| BENZALDEHYDE | DAVANONE | ACETATE | PIPERONYL |
| BENZOIC ACID | DIALLYL | LINALYL | AMINE |
| BENZYL ACETATE | TETRASULFIDE | ANTHRANILATE | PRENAL |
| BENZYL ALCOHOL | DIETHYL | LINDESTRENE | PULEGONE |
| BERGAMOTENE | PHTHALATE | LINDENOL | QUININE |
| B-BISABOLENE | DIHYDROPYROCURZERENONE | LINSEED OIL | ROSEMARY OIL |
| BISABOLENE OXIDE | DIHYDROTAGENTONE | METHYL-ALLYL- | SABINENE |
| A-BISABOLOL | BETA-ELEMENE | TRISULFIDE | SABINYL |
| BISABOLOL OXIDE | GAMMA- | MENTHOL | ACETATE |
| BISOBOLOL OXIDE B | ELEMENE | MENTHONE | SAFFLOWER OIL |
| BORNYL ACETATE | ELMOL | 2-METHOXY | A-SANTALENE |

TABLE 4-continued

COMPOUNDS OF PLANT ORIGIN

| | | | |
|---|---|---|---|
| B-BOURBONENE | ESTRAGOLE | FURANODIENE | SANTALOL |
| BLACK SEED OIL (BSO) | 2-ETHYL-2-HEXEN-1-OL | MENTHYL ACETATE | SATIVEN A-SELINENE |
| A-CADINOL | EUGENOL | METHYL | SESAME OIL |
| CAMPHENE | EUGENOL | CINNAMATE | B-SESQUPHELANDRENE |
| A-CAMPHOLENE | ACETATE | METHYL CITRATE | SILICONE FLUID |
| A-CAMPHOLENE ALDEHYDE | A-FARNESENE (Z,E)-A-FARNESENE | METHYL DI-HYDROJASMONATE | SODIUM LAURYL SULFATE |
| CAMPHOR | E-B-FARNESENE | MENTHYL SALICYLATE | SOYBEAN OIL |
| CARVACROL | FENCHONE | MINERAL OIL | SPATHULENOL |
| D-CARVONE | FURANODIENE | MUSK AMBRETTE | TAGETONE |
| L-CARVONE | A-1,3-DIENE | MYRCENE | TANGERINE OIL |
| CARYOPHYLLENE OXIDE | FURANOEUDESM A-1,4-DIENE | MYRTENAL NERALDIMETHYL | A-TERPINENE TERPINENE 900 |
| TRANS-CARYOPHYLLENE | FURANO GERMACRA | ACETATE NEROLIDOL | A-TERPINEOL A-TERPINOLENE |
| CASTOR OIL | 1,10(15)-DIENE-6-ONE | NONANONE | GAMMA-TERPINEOL |
| CEDAR OIL CHAMAZULENE | FURANOSESQUITERPENE | GAMMA-NONALACTONE | A-TERPINYL |
| 1,8-CINEOLE | GARLIC OIL | OIL OF | ACETATE |
| CINNAMALDEHYDE | GERANIOL | PENNYROYAL | 2-TERT-BUTYL-P-QUINONE |
| CINNAMYL ALCOHOL | GERANIOL ACETATE | OLIVE OIL ORANGE SWEET | A-THUJONE |
| CINNAMON OIL | GERANIAL | OIL | THYME OIL |
| CITRAL A | GERMACRENE D | 1-OCTANOL | THYMOL |
| CITRAL B | GERMACRENE B | E OCIMENONE | THYMYL METHYL |
| ISOPROPYL CITRATE | GRAPEFRUIT OIL A-GURJUNENE | Z OCIMENONE 3-OCTANONE | ETHER GAMMA-UNDECALACTONE |
| CITRONELLAL | A-HUMULENE | OCIMENE | VALERIC |
| CITRONELLA OIL | A-IONONE | OCTYL ACETATE | ANHYDRIDE |
| CITRONELLOL | B-IONONE | PEANUT OIL | VANILLIN |
| CITRONELLYL ACETATE | ISOBORNEOL | PERILLYL ALCOHOL | TRANS-VERBENOL |
| CITRONELLYL FORMATE | ISOFURANOGERM ACRENE | PEPPERMINT OIL A-PHELLANDRENE | CIS-VERBENOL VERBENONE |
| CLOVE OIL | ISO-MENTHONE | B-PHELLANDRENE | WHITE MINERAL |
| A-COPAENE | ISO-PULEGONE | PHENETHYL | OIL |
| CORNMINT OIL | JASMONE LECITHIN LEMON OIL LEMON GRASS OIL | PROPRIONATE PHENYL ACETALDEHYDE A-PINENE B-PINENE PINE OIL TRANS-PINOCARVEOL | YOMOGI ALCOHOL ZINGIBERENE |

Additional compounds and chemicals of a plant origin that can be used in accordance with embodiments of the present invention are set forth in the following applications, each of which is incorporated in its entirety herein by reference: U.S. application Ser. No. 10/832,022, entitled COMPOSITIONS AND METHODS FOR CONTROLLING INSECTS; U.S. application Ser. No. 11/086,615, entitled COMPOSITIONS AND METHODS FOR CONTROLLING INSECTS RELATED TO THE OCTOPAMINE RECEPTOR; U.S. application Ser. No. 11/365,426, entitled COMPOSITIONS AND METHODS FOR CONTROLLING INSECTS INVOLVING THE TYRAMINE RECEPTOR; and U.S. application Ser. No. 11/870,385, entitled COMPOSITIONS AND METHODS FOR CONTROLLING INSECTS.

In certain embodiments, it can be desirable to include a naturally-occurring version or a synthetic version of a compound. For example, in certain embodiments it can be desirable to include a synthetic lime oil that can be obtained commercially. In certain exemplary compositions, it can be desirable to include a compound that is designated as meeting Food Chemical Codex (FCC), for example, Geraniol Fine FCC or Tetrahydrolinalool FCC, which compounds can also be obtained commercially.

In embodiments of the invention that include at least one blend of compounds of a plant origin, the compounds of plant origin can be tested for their precise chemical composition using, for example, High-Pressure Liquid Chromatography (HPLC), Mass Spectrometry (MS), gas chromatography, or the like.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "substantially," as used herein, means at least about 80%, preferably at least about 90%, more preferably at least about 99%, for example at least about 99.9%. In some embodiments, the term "substantially" can mean completely, or about 100%.

In embodiments of the invention that include at least one blend of compounds of a plant origin, the at least one blend of compounds can include at least two compounds. For example, in an exemplary embodiment, the at least one blend of compounds can include LFO and Black Seed Oil (BSO).

Other exemplary embodiments include the blends of compounds set forth on pages 71-120 of WIPO Publication No. WO/2008/088827, published on Jul. 24, 2008.

In certain embodiments wherein the composition includes LFO, one or more of the following compounds can be substituted for the LFO: Tetrahydrolinalool, Ethyl Linalool, Heliotropine, Hedion, Hercolyn D, and Triethyl Citrate. In certain embodiments wherein the composition includes LFO, a blend of the following compounds can be substituted for the LFO: Isopropyl myristate, Tetrahydrolinalool FCC, Linalool, Geraniol Fine FCC, Piperonal (aldehyde), and Vanillin.

In certain embodiments wherein the composition includes LFO, a blend of the following compounds can be substituted for the LFO: Isopropyl myristate, Tetrahydrolinalool, Linalool, Geraniol, Piperonal (aldehyde), Vanillin, Methyl Salicylate, and D-limonene.

In certain embodiments wherein the composition includes BSO, one or more of the following compounds can be substituted for the BSO: alpha-thujene: alpha-pinene; beta-pinene; p-cymene; limonene; and tert-butyl-p-benzoquinone.

In certain exemplary embodiments wherein the composition includes Thyme Oil, one or more of the following compounds can be substituted for the Thyme Oil: thymol, α-thujone; α-pinene, camphene, β-pinene, p-cymene, α-terpinene, linalool, borneol, β-caryophyllene, and carvacrol.

Compounds used to prepare the exemplary compositions of the present invention can be obtained from commercial sources.

In some embodiments of the compositions, it can be desirable to include compounds each having a purity of about 60%, 65%, 70%, 75%, 80%, 85%, 90%, or 95%. For example, in some embodiments of the compositions that include geraniol, it can be desirable to include a geraniol that is at least about 60%, 85% or 95% pure. In some embodiments, it can be desirable to include a specific type of geraniol. For example, in some embodiments, the compositions can include: geraniol 60, geraniol 85, or geraniol 95. When geraniol is obtained as geraniol 60, geraniol 85, or geraniol 95, then forty percent, fifteen percent, or five percent of the oil can be Nerol. Nerol is a monoterpene ($C_{10}H_{18}O$), that can be extracted from attar of roses, oil of orange blossoms and oil of lavender.

Embodiments of the present invention can include art-recognised ingredients normally used in such formulations. These ingredients can include, for example, antifoaming agents, anti-microbial agents, anti-oxidants, anti-redeposition agents, bleaches, colorants, emulsifiers, enzymes, fats, fluorescent materials, fungicides, hydrotropes, moisturisers, optical brighteners, perfume carriers, perfume, preservatives, proteins, silicones, soil release agents, solubilisers, sugar derivatives, sun screens, surfactants, vitamins waxes, and the like.

In certain embodiments, embodiments of the present invention can also contain other adjuvants or modifiers such as one or more therapeutically or cosmetically active ingredients. Exemplary therapeutic or cosmetically active ingredients useful in the compositions of the invention can include, for example, fungicides, sunscreening agents, sunblocking agents, vitamins, tanning agents, plant extracts, anti-inflammatory agents, anti-oxidants, radical scavenging agents, retinoids, alpha-hydroxy acids, emollients, antiseptics, antibiotics, antibacterial agents, antihistamines, and the like, and can be present in an amount effective for achieving the therapeutic or cosmetic result desired.

In some embodiments, compositions of this invention can include one or more materials that can function as an antioxidant, such as reducing agents and free radical scavengers. Suitable materials that can function as an antioxidant can include, for example: acetyl cysteine, ascorbic acid, t-butyl hydroquinone, cysteine, diamylhydroquinone, erythorbic acid, ferulic acid, hydroquinone, p-hydroxyanisole, hydroxylamine sulfate, magnesium ascorbate, magnesium ascorbyl phosphate, octocrylene, phloroglucinol, potassium ascorbyl tocopheryl phosphate, potassium sulfite, rutin, sodium ascorbate, sodium sulfite, sodium thloglycolate, thiodiglycol, thiodiglycolamide, thioglycolic acid, thiosalicylic acid, tocopherol, tocopheryl acetate, tocopheryl linoleate, tris (nonylphenyl)phosphite, and the like.

Embodiments of the invention can also include one or more materials that can function as a chelating agent to complex with metallic ions. This action can help to inactivate the metallic ions for the purpose of preventing their adverse effects on the stability or appearance of a formulated composition. Chelating agents suitable for use in an embodiment of this invention can include, for example, aminotrimethylene phosphonic acid, beta-alanine diacetic acid, calcium disodium EDTA, citric acid, cyclodextrin, cyclohexanediamine tetraacetic acid, diammonium citrate, diammonium EDTA, dipotassium EDTA, disodium azacycloheptane diphosphonate, disodium EDTA, disodium pyrophosphate, EDTA (ethylene diamine tetra acetic acid), gluconic acid, HEDTA (hydroxyethyl ethylene diamine triacetic acid), methyl cyclodextrin, pentapotassium triphosphate, pentasodium aminotrimethylene phosphonate, pentasodium triphosphate, pentetic acid, phytic acid, potassium citrate, potassium gluconate, sodium citrate, sodium diethylenetriamine pentamethylene phosphonate, sodium dihydroxyethylglycinate, sodium gluconate, sodium metaphosphate, sodium metasilicate, sodium phytate, triethanolamine ("TEA")-EDTA, TEA-polyphosphate, tetrahydroxypropyl ethylenediamine, tetrapotassium pyrophosphate, tetrasodium EDTA, tetrasodium pyrophosphate, tripotassium EDTA, trisodium EDTA, trisodium HEDTA, trisodium phosphate, and the like.

Embodiments of the invention can also include one or more materials that can function as a humectant. A humectant is added to a composition to retard moisture loss during use, which effect is accomplished, in general, by the presence therein of hygroscopic materials.

In some embodiments, each compound can make up between about 1% to about 99%, by weight (wt/wt %) or by volume (vol/vol %), of the composition. For example, one composition of the present invention comprises about 2% alpha-Pinene and about 98% D-limonene. As used herein, percent amounts, by weight or by volume, of compounds are to be understood as referring to relative amounts of the compounds. As such, for example, a composition including 7% linalool, 35% thymol, 4% alpha-pinene, 30% para-cymene, and 24% soy bean oil (vol/vol %) can be said to include a ratio of 7 to 35 to 4 to 30 to 24 linalool, thymol, alpha-pinene, para-cymene, and soy bean oil, respectively (by volume). As such, if one compound is removed from the composition, or additional compounds or other ingredients are added to the composition, it is contemplated that the remaining compounds can be provided in the same relative amounts. For example, if soy bean oil were removed from the exemplary composition, the resulting composition would include 7 to 35 to 4 to 40 linalool, thymol, alpha-pinene, and para-cymene, respectively (by volume). This resulting composition would include 9.21% linalool, 46.05% thymol, 5.26% alpha-pinene, and 39.48% para-cymene (vol/vol %). For another example, if safflower oil were added to the original composition to yield a final composition containing 40% (vol/vol) safflower oil, then the resulting composition would include 4.2% linalool, 21% thymol, 2.4% alpha-pinene, 18% para-cymene, 14.4% soy bean oil, and 40% safflower oil (vol/vol %). One having ordinary skill in the art would understand that volume percentages are easily converted to weight percentages based the known or measured specific gravity of the substance.

Surprisingly, by combining certain insect control chemicals, and compounds or blends of the present invention, insect control activity of the resulting compositions can be enhanced, i.e., a synergistic effect on insect control activity is achieved when a certain chemical or chemicals, and a certain compound or compounds are combined. In other words, the compositions including certain combinations of at least one chemical, and at least one compound or at least one blend of compounds can have an enhanced ability to control insects, as compared to each of the chemicals or compounds taken alone.

In embodiments of the present invention, "synergy" can refer to any substantial enhancement, in a combination of at least two ingredients, of a measurable effect, when compared with the effect of one active ingredient alone, or when compared with the effect of the complete combination minus at least one ingredient. Synergy is a specific feature of a combination of ingredients, and is above any background level of enhancement that would be due solely to, e.g., additive effects of any random combination of ingredients. Effects include but are not limited to: repellant effect of the composition; pesticidal effect of the composition; perturbation of a cell message or cell signal such as, e.g., calcium, cyclic-AMP, and the like; and diminution of activity or downstream effects of a molecular target.

In various embodiments, a substantial enhancement can be expressed as a coefficient of synergy, wherein the coefficient is a ratio of the measured effect of the complete blend, divided by the effect of a comparison composition, typically a single ingredient or a subset of ingredients found in the complete blend. In some embodiments, the synergy coefficient can be adjusted for differences in concentration of the complete blend and the comparison composition.

Synergy coefficients can be calculated as follows. An activity ratio (R) can be calculated by dividing the % effect of the composition ($A_B$) by the % effect of the comparison composition ($X_n$), as follows:

$$R = A_B/X_n \qquad \text{Formula 1}$$

A concentration adjustment factor (F) can be calculated based on the concentration ($C_n$), i.e., % (wt/wt) or % (vol/vol), of the comparison composition in the composition, as follows:

$$F = 100/C_n \qquad \text{Formula 2}$$

The synergy coefficient (S) can then be calculated by multiplying the activity ratio (R) and the concentration adjustment factor (F), as follows:

$$S = (R)(F) \qquad \text{Formula 3}$$

As such, the synergy coefficient (S) can also by calculated, as follows:

$$S = [(A_B/X_n)(100)]/C_n \qquad \text{Formula 4}$$

In Formula 4, $A_B$ is expressed as % effect of the blend, $X_n$ is expressed as % effect of the comparison composition ($X_n$), and $C_n$ is expressed as % (wt/wt) or % (vol/vol) concentration of the comparison composition in the blend.

In some embodiments of the invention, a coefficient of synergy of 1.1, 1.2, 1.3, 1.4, or 1.5 can be substantial and commercially desirable. In other embodiments, the coefficient of synergy can be from about 1.6 to about 5, including but not limited to 1.8, 2.0, 2.5, 3.0, 3.5, 4.0, and 4.5. In other embodiments, the coefficient of synergy can be from about 5 to 50, including but not limited to 10, 15, 20, 25, 30, 35, 40, and 45. In other embodiments, the coefficient of synergy can be from about 50 to about 500, or more, including but not limited to 50, 75, 100, 125, 150, 200, 250, 300, 350, 400, and 450. Any coefficient of synergy above 500 is also contemplated within embodiments of the present invention.

Given that a broad range of synergies can be found in various embodiments of the invention, it is expressly noted that a coefficient of synergy can be described as being "greater than" a given number and therefore not necessarily limited to being within the bounds of a range having a lower and an upper numerical limit. Likewise, in some embodiments of the invention, certain low synergy coefficients, or lower ends of ranges, are expressly excluded. Accordingly, in some embodiments, synergy can be expressed as being "greater than" a given number that constitutes a lower limit of synergy for such an embodiment. For example, in some embodiments, the synergy coefficient is equal to or greater than 25; in such an embodiment, all synergy coefficients below 25, even though substantial, are expressly excluded.

Compositions containing combinations of certain chemicals and compounds can be tested for synergistic effect on insect control activity by comparing the effect of a particular combination of at least one chemical, and at least one compound or at least one blend of compounds, to the effect of the individual chemical(s) and compound(s). Additional information related to making a synergy determination can be found in the Examples set forth in this document.

Exemplary methods that can be used to determine the synergistic effect of a particular composition are set forth in the following applications, each of which is incorporated in its entirety herein by reference: U.S. application Ser. No. 10/832,022, entitled COMPOSITIONS AND METHODS FOR CONTROLLING INSECTS; U.S. application Ser. No. 11/086,615, entitled COMPOSITIONS AND METHODS FOR CONTROLLING INSECTS RELATED TO THE OCTOPAMINE RECEPTOR; U.S. application Ser. No. 11/365,426, entitled COMPOSITIONS AND METHODS FOR CONTROLLING INSECTS INVOLVING THE TYRAMINE RECEPTOR; and U.S. application Ser. No. 11/870,385, entitled COMPOSITIONS AND METHODS FOR CONTROLLING INSECTS.

In some embodiments, synergy or synergistic effect associated with a composition can be determined using calculations similar to those described in Colby, S. R., "Calculating synergistic and antagonistic responses of herbicide combinations," *Weeds* (1967) 15:1, pp. 20-22, which is incorporated herein by this reference. In this regard, the following formula can be used to express an expected % effect (E) of a composition including two compounds, Compound X and Compound Y:

$$E = X + Y - (X*Y/100) \qquad \text{Formula 5}$$

In Formula 5, X is the measured actual % effect of Compound X in the composition, and Y is the measured actual % effect of Compound Y of the composition. The expected % effect (E) of the composition is then compared to a measured actual % effect (A) of the composition. If the actual % effect (A) that is measured differs from the expected % effect (E) as calculated by the formula, then the difference is due to an interaction of the compounds. Thus, the composition has synergy (a positive interaction of the compounds) when A>E. Further, there is a negative interaction (antagonism) when A<E.

Formula 5 can be extended to account for any number of compounds in a composition; however it becomes more complex as it is expanded, as is illustrated by the following formula for a composition including three compounds, Compound X, Compound Y, and Compound Z:

$$E = X+Y+Z-((XY+XZ+YZ)/100)+(X*Y*Z/10000) \quad \text{Formula 6}$$

An easy-to-use formula that accommodates compositions with any number of compounds can be provided by modifying Formulas 5 and 6. Such a modification of the formula will now be described. When using Formulas 5 and 6, an untreated control value (untreated with composition or compound) is set at 100%, e.g., if the effect being measured is the amount of target parasites killed, the control value would be set at 100% survival of target parasite. In this regard, if treatment with Compound A results in 80% killing of a target parasite, then the treatment with Compound A can be said to result in a 20% survival, or 20% of the control value. The relationship between values expressed as a percent effect and values expressed as a percent-of-control are set forth in the following formulas, where E' is the expected % of control of the composition, $X_n$ is the measured actual % effect of an individual compound (Compound $X_n$) of the composition, $X_n'$ is the % of control of an individual compound of the composition, and A' is the actual measured % of control of the of the composition.

$$E = 100 - E' \quad \text{Formula 7}$$

$$X_n = 100 - X_n' \quad \text{Formula 8}$$

$$A = 100 - A' \quad \text{Formula 9}$$

By substituting the percent-of-control values for the percent effect values of Formulas 5 and 6, and making modifications to accommodate any number (n) of compounds, the following formula is provided for calculating the expected % of control (E') of the composition:

$$E' \left( \prod_{i=1}^{n} X_i' \right) \div 100^{n-1} \quad \text{Formula 10}$$

According to Formula 10, the expected % of control (E') for the composition is calculated by dividing the product of the measured actual % of control values ($X_n'$) for each compound of the composition by $100^{n-1}$. The expected % of control (E') of the composition is then compared to the measured actual % of control (A') of the composition. If the actual % of control (A') that is measured differs from the expected % of control (E') as calculated by the Formula 10, then the difference is due to an interaction of the compounds. Thus, the composition has synergy (a positive interaction of the compounds) when A'<E'. Further, there is a negative interaction (antagonism) when A'>E'.

Compositions containing two or more compounds in certain ratios or relative amounts can be tested for a synergistic effect by comparing the pesticidal effect of a particular composition of compounds to the pesticidal effect of a component the composition.

Furthermore, embodiments of the invention can include a method for screening a composition for indirect GPCR desensitization inhibitory activity. In certain embodiments of the invention, an indication that the test composition has indirect GPCR desensitization inhibitory activity can be apparent when a test composition has GPCR desensitization inhibitory activity with respect to different GPCRs. In certain embodiments, an indication that the test composition has indirect GPCR desensitization inhibitory activity can be apparent when GPCR cycling is inhibited without the composition binding the receptor itself. In certain embodiments of the invention, indications of desensitization can include a reduced response to extracellular stimuli, such as, for example, a reduction in GPCR recycling from the plasma membrane to the cell's interior and back to the plasma membrane, or the like. Another indication can be an altered period for the GPCR regulated activation of the $Ca^{2+}$ cascade or the cAMP levels in the organism.

Embodiments of the invention can include a method for screening a composition for indirect GPCR resensitization inhibitory activity. In certain embodiments of the invention, an indication that the test composition has indirect GPCR resensitization inhibitory activity can be apparent when a test composition has GPCR resensitization inhibitory activity with respect to different GPCRs. In certain embodiments, an indication that the test composition has indirect GPCR resensitization inhibitory activity can be apparent when GPCR cycling is inhibited without the composition binding the receptor itself. In certain embodiments of the invention, indications of resensitization can include a reduced response to extracellular stimuli, such as, for example, a reduction in GPCR recycling from the plasma membrane to the cell's interior and back to the plasma membrane, or the like, or a recovery to normal or static level of $Ca^{2+}$ or cAMP.

Embodiments of the invention can include a method for screening a composition for non-specific GPCR desensitization inhibitory activity. The method can include screening a test composition for GPCR desensitization inhibitory activity against two or more different GPCRs. In certain embodiments of the invention, an indication that the test composition has non-receptor-specific GPCR desensitization inhibitory activity can be apparent when a test composition has GPCR desensitization inhibitory activity with respect to each of the two or more different GPCRs. In certain embodiments of the invention, indications of desensitization inhibitory activity can include a reduced response to extracellular stimuli, such as, for example, a reduction in GPCR recycling from the plasma membrane to the cell's interior and back to the plasma membrane, or the like. Another indication can be an altered period for the GPCR regulated activation of the $Ca^{2+}$ cascade or the cAMP levels in the organism.

Embodiments of the invention can include a method for screening a composition for non-specific GPCR resensitization inhibitory activity. The method can include screening a test composition for GPCR resensitization inhibitory activity against two or more different GPCRs. In certain embodiments of the invention, an indication that the test composition has non-receptor-specific GPCR resensitization inhibitory activity can be apparent when a test composition has GPCR resensitization inhibitory activity with respect to each of the two or more different GPCRs. In certain embodiments of the invention, indications of resensitization inhibition can include a reduced response to extracellular stimuli, such as, for example, a reduction in GPCR recycling from the plasma membrane to the cell's interior and back to the plasma membrane, or the like. Another indication can be an altered period for the GPCR regulated activation of the $Ca^{2+}$ cascade or the cAMP levels in the organism.

In an embodiment of the invention, one cell can be used to screen a test composition for indirect GPCR desensitization inhibitory activity. In such an embodiment, the cell can express two or more GPCRs that are different from each other such that a detection method can be used for determining whether there is an indication that a test composition has GPCR desensitization inhibitory activity with respect to each of the different GPCRs.

In some embodiments of the invention, a multi-well format can be used to screen a test composition for indirect GPCR desensitization inhibitory activity. In some embodiments, each well of the plate can contain at least one cell that includes a GPCR, and the assay can include adding a compound in an amount known to activate that GPCR, and thus affect intracellular $Ca^{2+}$ levels, to each well. In some embodiments, at least one test compound can also be added to each well. In some embodiments, $Ca^{2+}$ level can be tested at various time points after adding the at least one test compound. In certain embodiments, time points used for testing intracellular $Ca^{2+}$ level can extend beyond the time points where an increase in $Ca^{2+}$ level can be seen without the presence of the at least one test compound. In some embodiments, methods of the invention can identify compounds that prolong agonist effect on GPCRs. In some embodiments of the invention, cAMP levels can be evaluated to gauge the effect of the at least one test compound on GPCR response.

In some embodiments of the invention, a multi-well format can be used to screen a test composition for indirect GPCR desensitization inhibitory activity. In some embodiments, each well of the plate can contain at least one cell that includes a GPCR, and the assay can include adding a compound in an amount less than that required to activate that GPCR, and thus affect intracellular $Ca^{2+}$ levels, to each well. In some embodiments, at least one test compound can also be added to each well. In some embodiments, $Ca^{2+}$ level can be tested at various time points after adding the at least one test compound. In certain embodiments, time points used for testing intracellular Ca level can extend beyond the time points where an increase in Ca level can not be seen without the presence of the at least one test compound. In some embodiments, methods of the invention can identify compounds that enhance agonist effect on GPCRs. In some embodiments of the invention, cAMP levels can be evaluated to gauge the effect of the at least one test compound on GPCR response.

In some embodiments of the invention, a cell used in the method can also include at least one conjugate comprising a marker molecule and a protein associated with the GPCR desensitization pathway of one or more of the GPCRs that are being evaluated. The conjugate can indicate, through the use of the marker molecule, GPCR desensitization inhibitory activity of a test composition with respect to each of the GPCRs that are being used to screen the test composition. The conjugate can comprise, for example, an arrestin protein and a marker molecule, a GPCR and a marker molecule, or the like. In one embodiment, the cell can comprise a conjugate of an arrestin protein and a marker molecule as well as a conjugate of a GPCR and a marker molecule.

In some embodiments of the invention, two or more different GPCRs that require agonist for desensitization, or are constitutively desensitized, can be used. In general, such methods can comprise exposing the cell to, for example, a test composition, to an agonist for the first GPCR (when the first GPCR requires agonist for desensitization), and to an agonist for the second GPCR (when the second GPCR requires agonist for desensitization), or the like, then determining whether the composition has GPCR desensitization inhibitory activity with respect to the first GPCR and with respect to the second GPCR. In such embodiments, an indication of GPCR desensitization inhibitory activity with respect to the first GPCR and an indication of GPCR desensitization inhibitory activity with respect to the second GPCR can be distinguished by using, for example, a different conjugate for the determination of GPCR desensitization inhibitory activity of the compositions with respect to the different GPCRs, or the like. For example, a cell can include a first conjugate comprising a first GPCR and a first marker molecule and a second conjugate comprising a second GPCR and a second marker molecule. In such an embodiment, it can be possible to expose the cell to the test composition, the agonist for the first GPCR (if needed for desensitization), and the agonist for the second GPCR (if needed for desensitization) simultaneously or non-simultaneously, and determine whether the composition has GPCR desensitization inhibitory activity with respect to the first GPCR and the second GPCR.

Detection for each of the items/events discussed above can be conducted, for example, at one point in time, over a period of time, at two or more points in time for comparison (e.g., before and after exposure to a test composition), or the like. An indication of GPCR desensitization inhibitory activity can be determined by, for example, detecting one or more of the items or events discussed above in a cell exposed to the test composition and comparing the results to those obtained by detecting for the same item or event in a control cell, by comparing the results to a predetermined value, or the like.

Embodiments of the invention can utilize prokaryotic and eukaryotic cells including, for example, bacterial cells, yeast cells, fungal cells, insect cells, nematode cells, plant cells, animal cells, and the like. Suitable animal cells can include, for example, HEK cells, HeLa cells, COS cells, U20S cells, CHO-K1 cells, various primary mammalian cells, and the like. An animal model expressing one or more conjugates of an arrestin and a marker molecule, for example, throughout its tissues, within a particular organ or tissue type, or the like, can be used.

Embodiments of the invention can utilize at least one cell that expresses, for example, a known GPCR, a variety of known GPCRs, an unknown GPCR, a variety of unknown GPCRs, a modified GPCR, a variety of modified GPCRs, and the like. The at least one cell can, for example, naturally express the GPCRs, can be genetically engineered to express the GPCRs at varying levels of expression, can be genetically engineered to inducibly express the GPCRs, or the like.

In certain embodiments of the invention, the at least one cell can comprise one or more conjugates of a marker molecule and a protein associated with the GPCR desensitization pathway. For example, one or more of the cells can comprise a conjugate of an arrestin protein and a marker molecule, or a conjugate of a GPCR and a marker molecule, or the like.

For certain embodiments of the invention, marker molecules that can be used as a conjugate can include, for example, molecules that are detectable by spectroscopic, photochemical, radioactivity, biochemical, immunochemical, colorimetric, electrical, and optical means, including, for example, bioluminescence, phosphorescence, fluorescence, and the like. Marker molecules can be, for example, biologically compatible molecules, and the like. Suitable marker molecules can include, for example, radioisotopes, epitope tags, affinity labels, enzymes, fluorescent groups, chemiluminescent groups, and the like. In some embodiments of the invention, the marker molecules are optically detectable, including, for example, optically detectable proteins, such that they can be excited chemically, mechanically, electrically, or radioactively to emit fluorescence, phosphorescence, or bioluminescence. Optically detectable marker molecules can include, for example, beta-galactosidase, firefly luciferase, bacterial luciferase, fluorescein, Texas Red, horseradish peroxidase, alkaline phosphatase, rhodamine-conjugated antibody, and the like. In other embodiments, the optically detectable marker molecules can be inherently fluorescent molecules, such as fluorescent proteins, including, for example, Green Fluorescent Protein (GFP), and the like.

In certain embodiments of the invention, all forms of arrestin, both naturally occurring and engineered variants, including, for example, visual arrestin, beta-arrestin 1, beta-arrestin 2, and the like, can be used. Confocal microscopy can be used to identify such protein-protein interaction and also to study the trafficking of the protein complex.

In some embodiments, the cell can be transfected with DNA so that the conjugate of arrestin and a marker molecule can be produced within the cell.

GPCRs used in embodiments of the invention can also be conjugated with a marker molecule. In some embodiments, the carboxyl-terminus of the GPCR can be conjugated with a marker molecule. A carboxyl-terminal tail conjugated or attached to a marker molecule can be used in a carboxyl-terminal tail exchange to provide a modified GPCR.

In some embodiments of the invention, the GPCRs can be antibody-labeled, for example with an antibody conjugated to an immunofluorescence molecule, or the like, or the GPCRs can be conjugated with, for example, a luminescent donor or the like. In some embodiments, the GPCRs can be conjugated with, for example luciferase, *Renilla* luciferase, or the like.

Embodiments of the invention can be used to evaluate the effect of a test compound on GPCR R/D by measuring intracellular second messenger generation. Intracellular effectors can include, for example, cAMP, cyclic GMP, calcium, phosphatidylinositol, a hydrogen ion, an ion transport molecule, and the like. Additionally, enzymes such as, for example, adenylyl cyclase, phosphodiesterase, phospholipase C, protein kinase, phospholipase $A_2$, and the like, can be measured to gauge the effects of test compounds on GPCR R/D.

Controlling Pests

Embodiments of the invention can be used to control insect species belonging to orders Acari, Anoplura, Araneae, Blattodea, Coleoptera, Collembola, Diptera, Grylloptera, Heteroptera, Homoptera, Hymenoptera, Isopoda, Isoptera, Lepidoptera, Mantodea, Mallophaga, Neuroptera, Odonata, Orthoptera, Psocoptera, Siphonaptera, Symphyla, Thysanura, and Thysanoptera.

Embodiments of the present invention can be used to control, for example, the insects set forth on pages 123-195 of WIPO Publication No. WO/2008/088827, published on Jul. 24, 2008.

For purposes of simplicity, the term "insect" shall be used through out this application; however, it should be understood that the term "insect" refers, not only to insects, but also to arachnids, larvae, and like invertebrates. Also for purposes of this application, the term "insect control" shall refer to having a repellant effect, a pesticidal effect, or both.

"Target pest" refers to the organism that is the subject of the insect control effort.

"Repellant effect" is an effect wherein more insects are repelled away from a host or area that has been treated with the composition than a control host or area that has not been treated with the composition. In some embodiments, repellant effect is an effect wherein at least about 75% of insects are repelled away from a host or area that has been treated with the composition. In some embodiments, repellant effect is an effect wherein at least about 90% of insects are repelled away from a host or area that has been treated with the composition.

"Pesticidal effect" is an effect wherein treatment with a composition causes at least about 1% of the insects to die. In this regard, an $LC_1$ to $LC_{100}$ (lethal concentration) or an $LD_1$ to $LD_{100}$ (lethal dose) of a composition will cause a pesticidal effect. In some embodiments, the pesticidal effect is an effect wherein treatment with a composition causes at least about 5% of the exposed insects to die. In some embodiments, the pesticidal effect is an effect wherein treatment with a composition causes at least about 10% of the exposed insects to die. In some embodiments, the pesticidal effect is an effect wherein treatment with a composition causes at least about 25% of the insects to die. In some embodiments the pesticidal effect is an effect wherein treatment with a composition causes at least about 50% of the exposed insects to die. In some embodiments the pesticidal effect is an effect wherein treatment with a composition causes at least about 75% of the exposed insects to die. In some embodiments the pesticidal effect is an effect wherein treatment with a composition causes at least about 90% of the exposed insects to die.

"Disablement" is an effect wherein insects are mobility-impaired such that their mobility is reduced as compared to insects that have not been exposed to the composition. In some embodiments, disablement is an effect wherein at least about 75% of insects are mobility-impaired such that their mobility is reduced as compared to insects that have not been exposed to the composition. In some embodiments, disablement is an effect wherein at least about 90% of insects are mobility-impaired such that their mobility is reduced as compared to insects that have not been exposed to the composition. In some embodiments, disablement can be caused by a disabling effect at the cellular or whole-organism level.

Embodiments of the invention can be used to control parasites. As used herein, the term "parasite" includes parasites, such as but not limited to, protozoa, including intestinal protozoa, tissue protozoa, and blood protozoa. Examples of intestinal protozoa include, but are not limited to: *Entamoeba hystolytica, Giardia lamblia, Cryptosporidium muris,* and *Cryptosporidium parvum*. Examples of tissue protozoa include, but are not limited to: *Trypanosomatida gambiense, Trypanosomatida rhodesiense, Trypanosomatida crusi, Leishmania mexicana, Leishmania braziliensis, Leishmania tropica, Leishmania donovani, Toxoplasma gondii,* and *Trichomonas vaginalis*. Examples of blood protozoa include, but are not limited to *Plasmodium vivax, Plasmodium ovale, Plasmodium malariae,* and *Plasmodium falciparum*. *Histomonas meleagridis* is yet another example of a protozoan parasite.

As used herein, the term "parasite" further includes, but is not limited to: helminthes or parasitic worms, including nematodes (round worms) and platyhelminthes (flat worms). Examples of nematodes include, but are not limited to: animal and plant nematodes of the adenophorea class, such as the intestinal nematode *Trichuris trichiura* (whipworm) and the plant nematode *Trichodorus obtusus* (stubby-root nematode); intestinal nematodes of the secementea class, such as *Ascaris lumbricoides, Enterobius vermicularis* (pinworm), *Ancylostoma duodenale* (hookworm), *Necator americanus* (hookworm), and *Strongyloides stercoralis*; and tissue nematodes of the secementea class, such as *Wuchereria bancrofti* (Filaria bancrofti) and *Dracunculus medinensis* (Guinea worm). Examples of plathyeminthes include, but are not limited to: Trematodes (flukes), including blood flukes, such as *Schistosoma mansoni* (intestinal Schistosomiasis), *Schisto-*

*soma haematobium*, and *Schistosoma japonicum*; liver flukes, such as *Fasciola hepatica*, and *Fasciola gigantica*; intestinal flukes, such as *Heterophyes heterophyes*; and lung flukes such as *Paragonimus westermani*. Examples of platheminthes further include, but are not limited to: Cestodes (tapeworms), including *Taenia solium, Taenia saginata, Hymenolepis nana*, and *Echinococcus granulosus*.

Furthermore, the term "parasite" further includes, but is not limited to those organisms and classes of organisms set forth on pages 196-205 of WIPO Publication No. WO/2008/088827, published on Jul. 24, 2008, or the like.

Embodiments of the invention can be used to prevent or treat the parasite hosts set forth on pages 205-232 of WIPO Publication No. WO/2008/088827, published on Jul. 24, 2008, or the like.

Embodiments of the invention can be used to treat crops in order to limit or prevent insect infestation. The types of crops that can be treated can include, for example, those listed on pages 232-239 of WIPO Publication No. WO/2008/088827, published on Jul. 24, 2008, or the like.

In certain embodiments of the invention, an area can be treated with a composition of the present invention, for example, by using a spray formulation, such as an aerosol or a pump spray, or a burning formulation, such as a candle or a piece of incense containing the composition, or the like. In certain embodiments of the invention, an area can be treated, for example, via aerial delivery, by truck-mounted equipment, or the like. Of course, various treatment methods can be used without departing from the spirit and scope of the present invention. For example, compositions can be comprised in household products, for example, hard surface cleaners, and the like.

An exemplary dispenser of a system of the present invention can deliver an pest control composition to the atmosphere in a continuous manner over a period of time. The exemplary dispenser can include a reservoir for holding a pest control composition, and a wick for drawing the composition from the reservoir and releasing the insect control composition into the atmosphere. The reservoir can be constructed from a material that is impermeable to the pest control composition, for example, appropriate glass, ceramic, or polymeric materials can be used. The reservoir can include an aperture, which can be sealed or unsealed, as desired. When the exemplary system of the present invention is not in use, the aperture can be sealed to prevent the release of the pest control composition into the atmosphere. It may be desirable, for example, to seal the aperture when the exemplary system is being stored or transported. When the system is in use, the aperture is unsealed, such that the wick can draw the pest control composition from the reservoir, and release the control composition through the aperture into the atmosphere.

In certain embodiments of the invention, the rate of release of the composition can be controlled, for example, by making adjustments to the wick of the dispenser. For example, the surface area of the wick that is exposed to the atmosphere can be altered. Generally, the greater the exposed surface area, the greater the rate of release of the pest control composition. In this regard, in certain embodiments, the dispenser can include multiple wicks and the reservoir can include multiple apertures through which the insect control composition can be released into the atmosphere. As another example, the wick can be constructed from a particular material that draws the pest control composition from the reservoir and releases it into the environment at a desired rate, such as, for example, a wick made of wood, a wick made of a synthetic fiber, or the like.

Another exemplary dispenser of a system of the present invention can deliver an insect control composition to a desired area. The dispenser can include a sealed pouch that can be constructed from a material that is impermeable to the insect control composition, for example, a metallic foil, a polymeric material, or the like. The pouch can define a volume for holding the insect control composition. The composition can be provided in a material disposed within the volume of the pouch, for example, a sponge, a cloth saturated with the material, or the like. When it becomes desirable to place the exemplary system into use, the pouch can be unsealed, exposing the composition for release into the atmosphere or for application to a desired area.

In certain embodiments the insect control composition is provided in a saturated cloth within the pouch, which can be used to apply the control composition a desired area. For example, a desired area can be an animal, such as a human, a domestic animal, surfaces within a dwelling, an outdoor living area, or the like.

In certain embodiments, the dispenser can further include a hook, allowing the pouch and exposed control composition to be hung in a desired location, such as in a closet or a pantry.

In certain embodiments, a method of the present invention can deliver insect an control composition to a desired area. In certain embodiments, a dispenser used with the method can be constructed from a substantially planar, integral piece of material, having a first side that is coated with control composition, and a second side that is not coated with control composition. The integral piece of material can be folded and sealed such that the side coated with the control composition is contained within the volume defined by the sealed pouch. When the pouch is unsealed, the side that is coated with control composition is exposed. The substantially planar piece of material can be placed in a desired location to deliver control composition to the atmosphere, or to crawling insects that walk across the material.

Another exemplary dispenser of a system of the present invention can deliver an insect control composition to a desired area. The control composition can be incorporated into an appropriate material. In certain embodiments, the composition-containing material can be a material that is capable of controlling the release rate of the control composition, i.e., controlled-release material, allowing the control composition to be released into the atmosphere at a desired rate that can be adjusted by providing controlled-release material having appropriate specifications. The controlled-release material can be constructed from an appropriate polymer. In other embodiments the composition-containing material does not allow the control composition to be released into the atmosphere, but rather retains the control composition. An optional casing that is impermeable to the insect control composition can be provided to hold the composition-containing material until the system is ready for use. When the system is ready for use, the casing can be peeled away, exposing the composition-containing material. The composition-containing material can be placed in a desired location to deliver control composition to crawling insects that walk across the material, or to deliver the control composition to the atmosphere when a controlled-release material is used, e.g., control flying insects.

In certain embodiments, the composition-containing material can have a substantially planar design, appropriate for positioning adjacent a mattress for controlling bed bugs, e.g., *Cimex lectularius*. A substantially planar design can also be used, for example, as or with a picnic table cloth. In certain embodiments, the composition-containing material can be used as ground cover for a garden bed or adjacent crop plants to control weeds. In certain embodiments, the composition-containing material can take the shape of a bag, and could be used for trash collection, while controlling insect commonly attracted to household garbage or other trash.

Another exemplary dispenser of a system of the present invention can be a substantially dry sheet containing the control composition, which control composition can be applied to a desired location upon exposing the cloth to water or an aqueous liquid, e.g., perspiration. In certain embodiments, the dry sheet containing the control composition can dissolve into a cream or gel when exposed to water or an aqueous liquid, which can then be applied to a desired area. For example, a desired area can be an animal, such as a human, a domestic animal, or another animal.

The following references are incorporated herein by this reference: U.S. Pat. No. 6,610,254 to Furner et al., issued Aug. 26, 2003, entitled "Dual Function Dispenser," U.S. Pat. No. 6,360,477 to Flashinski et al., issued Mar. 26, 2002, entitled "Insect Control Pouch," U.S. Pat. No. 5,980,931 to Fowler et al., issued Nov. 9, 1999, entitled "Cleansing Products Having a Substantially Dry Substrate," U.S. Pat. No. 4,320,113 to Kydonieus, issued Mar. 16, 1982, entitled "Process for Controlling Cockroaches and Other Crawling Insects," U.S. Pat. No. 4,943,435 to Baker et al., issued Jul. 24, 1990, entitled "Prolonged Activity Nicotine Patch," United States Patent Publication No. 2004/0185080 to Hojo, et al, entitled "Sustained Release Dispenser Comprising Two or More Sex Pheromone Substances and a Pest Control Method," PCT Publication No. WO/2006/061803 to Firmenich, et al, entitled "A Device for Dispensing a Volatile Liquid and Method for its Activation," and PCT Publication No. WO/2004/006968 to Firmenich, et al., entitled "A Device for Dispensing Active Volatile Liquid."

Treatment can include, for example, use of a oil-based formulation, a water-based formulation, a residual formulation, and the like. In some embodiments, combinations of formulations can be employed to achieve the benefits of different formulation types.

Embodiments of the invention can result in agricultural improvements, such as, for example, increased crop yield, reduced frequency of application of pest control product, reduced phytotoxicity associated with the pesticide, reduced cost or increased value associated with at least one environmental factor, and the like.

In embodiments of the invention that can reduce the cost of, or increase the value associated with at least one environmental factor, the environmental factor can include, for example, air quality, water quality, soil quality, detectable pesticide residue, safety or comfort of workers, collateral effect on a non-target organism, and the like.

Embodiments of the present invention can be used to control pests by either treating a host directly, or treating an area where the host will be located. For purposes of this application, host is defined as a plant, human or other animal. The host can be treated, for example, directly by using a cream or spray formulation, that can be applied externally or topically, when appropriate in light of the specific composition being used, e.g., to the skin of a human. A composition can be applied to the host, for example, in the case of a human, using formulations of a variety of personal products or cosmetics for use on the skin or hair. For example, any of the following can be used, when appropriate in light of the specific composition being used: fragrances, colorants, pigments, dyes, colognes, skin creams, skin lotions, deodorants, talcs, bath oils, soaps, shampoos, hair conditioners and styling agents.

The present invention is further illustrated by the following examples.

EXAMPLES

Test compositions are provided, including a first agent comprising a blend selected from Table 5 (below) and a second agent comprising a pest control chemical or a synergist.

TABLE 5

| | | | | |
|---|---|---|---|---|
| | | BLENDS | | |
| | Compounds | CAS Registry Number | low % | high % |
| Blend 1 | LFO | | 4 | 30 |
| | D-Limonene | 5989-27-5 | 8 | 99 |
| | Thyme Oil White | 8007-46-3 | 0.1 | 20 |
| | Blend 65 | | 8 | 99 |
| Blend 2 | D-Limonene | 5989-27-5 | 9 | 99 |
| | Thyme Oil White | 8007-46-3 | 0.1 | 20 |
| | Linalool Coeur | 78-70-6 | 0.1 | 4 |
| | Tetrahydrolinalool | 78-69-3 | 0.1 | 5 |
| | Vanillin | 121-33-5 | 0.06 | 0.3 |
| | Isopropyl myristate | 110-27-0 | 0.1 | 5 |
| | Piperonal (aldehyde) [Heliotropine] | 120-57-0 | 0.1 | 5 |
| | Blend 66 | | 8 | 99 |
| | Geraniol Fine FCC | 106-24-1 | 0.1 | 4 |
| | Triethyl Citrate | 77-93-0 | 0.1 | 5 |
| Blend 3 | D-Limonene | 5989-27-5 | 45 | 99 |
| | Thyme Oil White | 8007-46-3 | 0.1 | 10 |
| | Blend 66 | | 5 | 30 |
| | Blend 63 | | 0.1 | 10 |
| Blend 4 | LFO | | 30 | 99 |
| | BSO | 977017-84-7 | 15 | 99 |
| Blend 5 | BSO | 977017-84-7 | 15 | 99 |
| | Linalool Coeur | 78-70-6 | 6 | 40 |
| | Tetrahydrolinalool | 78-69-3 | 8 | 45 |
| | Vanillin | 121-33-5 | 0.1 | 5 |
| | Isopropyl myristate | 110-27-0 | 10 | 55 |
| | Piperonal (aldehyde) [Heliotropine] | 120-57-0 | 0.1 | 20 |
| | Geraniol Fine FCC | 106-24-1 | 0.1 | 25 |

TABLE 5-continued

BLENDS

| | Compounds | CAS Registry Number | low % | high % |
|---|---|---|---|---|
| Blend 6 | D-Limonene | 5989-27-5 | 0.1 | 25 |
| | BSO | 977017-84-7 | 15 | 85 |
| | Linalool Coeur | 78-70-6 | 0.1 | 25 |
| | Tetrahydrolinalool | 78-69-3 | 0.1 | 25 |
| | Vanillin | 121-33-5 | 0.1 | 3 |
| | Isopropyl myristate | 110-27-0 | 0.1 | 30 |
| | Piperonal (aldehyde) [Heliotropine] | 120-57-0 | 0.1 | 10 |
| | Geraniol Fine FCC | 106-24-1 | 0.1 | 15 |
| | Methyl Salicylate 98% Nat | 119-36-8 | 8 | 70 |
| Blend 7 | Thyme Oil White | 8007-46-3 | 15 | 90 |
| | Wintergreen Oil | 68917-75-9 | 15 | 99 |
| | Vanillin | 121-33-5 | 0.1 | 4 |
| | Isopropyl myristate | 110-27-0 | 20 | 99 |
| Blend 8 | D-Limonene | 5989-27-5 | 20 | 99 |
| | Thyme Oil White | 8007-46-3 | 0.1 | 25 |
| | Wintergreen Oil | 68917-75-9 | 25 | 99 |
| Blend 9 | LFO | | 6 | 40 |
| | D-Limonene | 5989-27-5 | 25 | 99 |
| | Thyme Oil White | 8007-46-3 | 5 | 30 |
| | Linalool Coeur | 78-70-6 | 0.1 | 3 |
| | Citral | 5392-40-5 | 0.1 | 20 |
| | gamma-terpinene | 99-85-4 | 0.1 | 20 |
| | Alpha-Pinene, 98% | 80-56-8 | 0.1 | 5 |
| | alpha-Terpineol | 98-55-5 | 0.1 | 15 |
| | Terpinolene | 586-62-9 | 0.1 | 15 |
| | Para-Cymene | 99-87-6 | 0.1 | 5 |
| | Linalyl Acetate | 115-95-7 | 0.1 | 6 |
| | Beta Pinene | 127-91-3 | 0.1 | 6 |
| | Camphor Dextro | 464-49-3 | 0.05 | 0.3 |
| | Terpinene 4 OL | 562-74-3 | 0.05 | 0.3 |
| | Alpha Terpinene | 99-86-5 | 0.1 | 6 |
| | Borneol L | 507-70-0 | 0.1 | 3 |
| | Camphene | 79-92-5 | 0.1 | 2 |
| | Decanal | 112-31-2 | 0.06 | 0.3 |
| | Dodecanal | 112-54-9 | 0.06 | 0.3 |
| | Fenchol Alpha | 512-13-0 | 0.005 | 0.1 |
| | Geranyl Acetate | 105-87-3 | 0.06 | 0.3 |
| | Isoborneol | 124-76-5 | 0.08 | 1 |
| | 2-Methyl 1,3-cyclohexadiene | 30640-46-1, 1888-90-0 | 0.08 | 1 |
| | Myrcene | 123-35-3 | 0.1 | 3 |
| | Nonanal | 124-19-6 | 0.005 | 0.08 |
| | Octanal | 124-13-0 | 0.005 | 0.2 |
| | Tocopherol Gamma (TENOX ®) | 54-28-4 | 0.005 | 0.08 |
| Blend 10 | D-Limonene | 5989-27-5 | 0.1 | 25 |
| | Thyme Oil White | 8007-46-3 | 0.1 | 25 |
| | Blend 65 | | 40 | 99 |
| | Linalool Coeur | 78-70-6 | 0.1 | 6 |
| | Tetrahydrolinalool | 78-69-3 | 0.1 | 8 |
| | Vanillin | 121-33-5 | 0.08 | 0.6 |
| | Isopropyl myristate | 110-27-0 | 0.1 | 8 |
| | Piperonal (aldehyde) [Heliotropine] | 120-57-0 | 0.1 | 8 |
| | Geraniol Fine FCC | 106-24-1 | 0.1 | 4 |
| | Triethyl Citrate | 77-93-0 | 0.1 | 8 |
| Blend 11 | Thyme Oil White | 8007-46-3 | 3 | 65 |
| | Wintergreen Oil | 68917-75-9 | 15 | 99 |
| | Isopropyl myristate | 110-27-0 | 20 | 99 |
| Blend 12 | D-Limonene | 5989-27-5 | 5 | 30 |
| | Linalool Coeur | 78-70-6 | 8 | 40 |
| | Tetrahydrolinalool | 78-69-3 | 15 | 99 |
| | Vanillin | 121-33-5 | 0.1 | 8 |
| | Isopropyl myristate | 110-27-0 | 15 | 85 |
| | Piperonal (aldehyde)[Heliotropine] | 120-57-0 | 5 | 30 |
| | Geraniol Fine FCC | 106-24-1 | 5 | 30 |
| Blend 13 | D-Limonene | 5989-27-5 | 5 | 30 |
| | Geraniol Fine FCC | 106-24-1 | 5 | 30 |
| | Blend 62 | | 50 | 99 |
| Blend 14 | D-Limonene | 5989-27-5 | 5 | 30 |
| | Blend 72 | | 55 | 99 |
| Blend 15 | D-Limonene | 5989-27-5 | 5 | 30 |
| | Linalool Coeur | 78-70-6 | 10 | 55 |
| | Tetrahydrolinalool | 78-69-3 | 10 | 65 |
| | Vanillin | 121-33-5 | 0.1 | 4 |
| | Isopropyl myristate | 110-27-0 | 10 | 60 |

TABLE 5-continued

BLENDS

| | Compounds | CAS Registry Number | low % | high % |
|---|---|---|---|---|
| | Piperonal (aldehyde)[Heliotropine] | 120-57-0 | 10 | 65 |
| | Piperonyl Alcohol | 495-76-1 | 0.1 | 25 |
| Blend 16 | D-Limonene | 5989-27-5 | 5 | 30 |
| | BSO | 977017-84-7 | 15 | 80 |
| | Linalool Coeur | 78-70-6 | 5 | 30 |
| | Tetrahydrolinalool | 78-69-3 | 6 | 35 |
| | Vanillin | 121-33-5 | 0.1 | 4 |
| | Mineral Oil White (USP) | 8042-47-5 | 8 | 45 |
| | Isopropyl myristate | 110-27-0 | 8 | 45 |
| | Piperonal (aldehyde)[Heliotropine] | 120-57-0 | 0.1 | 15 |
| | Geraniol Fine FCC | 106-24-1 | 0.1 | 20 |
| Blend 17 | D-Limonene | 5989-27-5 | 10 | 99 |
| | Linalool Coeur | 78-70-6 | 0.1 | 10 |
| | Tetrahydrolinalool | 78-69-3 | 0.1 | 10 |
| | Vanillin | 121-33-5 | 0.08 | 0.6 |
| | Isopropyl myristate | 110-27-0 | 0.1 | 10 |
| | Piperonal (aldehyde)[Heliotropine] | 120-57-0 | 0.1 | 10 |
| | Piperonyl Alcohol | 495-76-1 | 0.1 | 5 |
| | Blend 66 | | 10 | 99 |
| Blend 18 | Linalool Coeur | 78-70-6 | 0.1 | 15 |
| | Tetrahydrolinalool | 78-69-3 | 0.1 | 20 |
| | Vanillin | 121-33-5 | 0.1 | 2 |
| | Isopropyl myristate | 110-27-0 | 0.1 | 20 |
| | Piperonal (aldehyde)[Heliotropine] | 120-57-0 | 0.1 | 20 |
| | Piperonyl Alcohol | 495-76-1 | 0.1 | 10 |
| | Blend 66 | | 40 | 99 |
| Blend 19 | LFO | | 20 | 99 |
| | D-Limonene | 5989-27-5 | 15 | 85 |
| | Thyme Oil White | 8007-46-3 | 15 | 90 |
| Blend 20 | D-Limonene | 5989-27-5 | 15 | 85 |
| | Thyme Oil White | 8007-46-3 | 15 | 95 |
| | Blend 63 | | 20 | 99 |
| Blend 21 | D-Limonene | 5989-27-5 | 15 | 85 |
| | Thyme Oil White | 8007-46-3 | 15 | 90 |
| | Linalool Coeur | 78-70-6 | 0.1 | 15 |
| | Tetrahydrolinalool | 78-69-3 | 0.1 | 25 |
| | Vanillin | 121-33-5 | 0.1 | 2 |
| | Isopropyl myristate | 110-27-0 | 0.1 | 25 |
| | Piperonal (aldehyde)[Heliotropine] | 120-57-0 | 0.1 | 25 |
| | Geraniol Fine FCC | 106-24-1 | 0.1 | 10 |
| | Triethyl Citrate | 77-93-0 | 0.1 | 25 |
| Blend 22 | Phenyl Ethyl Propionate | | 20 | 99 |
| | Methyl Salicylate | | 20 | 99 |
| | Blend 43 | | 15 | 85 |
| Blend 23 | D-Limonene | 5989-27-5 | 0.1 | 10 |
| | Thyme Oil White | 8007-46-3 | 0.1 | 15 |
| | Benzyl Alcohol | 100-51-6 | 8 | 50 |
| | Isopar M | 64742-47-8 | 10 | 65 |
| | Water | 7732-18-5 | 25 | 99 |
| | Blend 63 | | 0.1 | 15 |
| | Stock 10% SLS Solution | | 0.1 | 10 |
| Blend 24 | D-Limonene | 5989-27-5 | 0.1 | 10 |
| | Thyme Oil White | 8007-46-3 | 0.1 | 15 |
| | Linalool Coeur | 78-70-6 | 0.1 | 3 |
| | Tetrahydrolinalool | 78-69-3 | 0.1 | 4 |
| | Vanillin | 121-33-5 | 0.05 | 0.3 |
| | Isopropyl myristate | 110-27-0 | 0.1 | 4 |
| | Piperonal (aldehyde)[Heliotropine] | 120-57-0 | 0.1 | 4 |
| | Geraniol Fine FCC | 106-24-1 | 0.1 | 2 |
| | Triethyl Citrate | 77-93-0 | 0.1 | 4 |
| | Benzyl Alcohol | 100-51-6 | 8 | 50 |
| | Isopar M | 64742-47-8 | 10 | 65 |
| | Water | 7732-18-5 | 25 | 99 |
| | Stock 10% SLS Solution | | 0.1 | 10 |
| Blend 25 | D-Limonene | 5989-27-5 | 6 | 40 |
| | Thyme Oil White | 8007-46-3 | 8 | 45 |
| | Benzyl Alcohol | 100-51-6 | 30 | 99 |
| | Blend 63 | | 10 | 55 |
| Blend 26 | LFO | | 0.1 | 25 |
| | D-Limonene | 5989-27-5 | 8 | 99 |
| | Thyme Oil White | 8007-46-3 | 0.1 | 20 |
| | Blend 66 | | 8 | 99 |
| Blend 27 | Linalool Coeur | 78-70-6 | 0.1 | 20 |
| | Soy Bean Oil | 8016-70-4 | 10 | 70 |
| | Thymol (crystal) | 89-83-8 | 20 | 99 |

TABLE 5-continued

BLENDS

| | Compounds | CAS Registry Number | low % | high % |
|---|---|---|---|---|
| | Alpha-Pinene, 98% | 80-56-8 | 0.1 | 10 |
| | Para-Cymene | 99-87-6 | 15 | 85 |
| Blend 28 | Linalool Coeur | 78-70-6 | 0.1 | 25 |
| | Thymol (crystal) | 89-83-8 | 25 | 99 |
| | Alpha-Pinene, 98% | 80-56-8 | 0.1 | 15 |
| | Para-Cymene | 99-87-6 | 20 | 99 |
| Blend 29 | D-Limonene | 5989-27-5 | 0.1 | 25 |
| | Thyme Oil White | 8007-46-3 | 0.1 | 30 |
| | Blend 65 | | 35 | 99 |
| | Linalool Coeur | 78-70-6 | 0.1 | 8 |
| | Tetrahydrolinalool | 78-69-3 | 0.1 | 10 |
| | Vanillin | 121-33-5 | 0.08 | 1 |
| | Isopropyl myristate | 110-27-0 | 0.1 | 10 |
| | Piperonal (aldehyde)[Heliotropine] | 120-57-0 | 0.1 | 5 |
| | Geraniol Fine FCC | 106-24-1 | 0.1 | 5 |
| Blend 30 | D-Limonene | 5989-27-5 | 15 | 85 |
| | Thyme Oil White | 8007-46-3 | 0.1 | 15 |
| | Methyl Salicylate | | 35 | 99 |
| Blend 31 | Thyme Oil White | 8007-46-3 | 0.1 | 5 |
| | Wintergreen Oil | 68917-75-9 | 0.1 | 8 |
| | Isopropyl myristate | 110-27-0 | 0.1 | 6 |
| | Span 80 | 1338-43-8 | 0.1 | 2 |
| | Isopar M | 64742-47-8 | 8 | 45 |
| | Water | 7732-18-5 | 40 | 99 |
| | Bifenthrin | 83657-04-3 | 0.005 | 0.2 |
| Blend 32 | Castor Oil hydrogenated - PEO40 | | 30 | 99 |
| | Lemon Grass Oil - India | | 10 | 70 |
| | Blend 1 | | 10 | 70 |
| Blend 33 | LFO | | 8 | 50 |
| | D-Limonene | 5989-27-5 | 35 | 99 |
| | Thyme Oil White | 8007-46-3 | 6 | 35 |
| | BSO | 977017-84-7 | 0.1 | 15 |
| Blend 34 | D-Limonene | 5989-27-5 | 0.1 | 25 |
| | Thyme Oil White | 8007-46-3 | 0.1 | 30 |
| | Blend 65 | | 30 | 99 |
| | Linalool Coeur | 78-70-6 | 0.1 | 5 |
| | Tetrahydrolinalool | 78-69-3 | 0.1 | 8 |
| | Vanillin | 121-33-5 | 0.06 | 0.5 |
| | Isopropyl myristate | 110-27-0 | 0.1 | 8 |
| | Piperonal (aldehyde)[Heliotropine] | 120-57-0 | 0.1 | 8 |
| | Geraniol Fine FCC | 106-24-1 | 0.1 | 4 |
| | Triethyl Citrate | 77-93-0 | 0.1 | 8 |
| | Isopar M | 64742-47-8 | 8 | 40 |
| Blend 35 | Isopropyl myristate | 110-27-0 | 20 | 99 |
| | Wintergreen Oil | | 25 | 99 |
| | Blend 68 | | 10 | 60 |
| Blend 36 | Wintergreen Oil | 68917-75-9 | 25 | 99 |
| | Isopropyl myristate | 110-27-0 | 20 | 99 |
| | Thyme Oil Red | 8007-46-3 | 10 | 60 |
| Blend 37 | Wintergreen Oil | 68917-75-9 | 25 | 99 |
| | Vanillin | 121-33-5 | 0.06 | 0.3 |
| | Isopropyl myristate | 110-27-0 | 20 | 99 |
| | Thyme Oil Red | 8007-46-3 | 10 | 60 |
| Blend 38 | Thyme Oil White | 8007-46-3 | 15 | 95 |
| | Isopropyl myristate | 110-27-0 | 25 | 99 |
| | Geraniol Fine FCC | 106-24-1 | 10 | 70 |
| Blend 39 | Isopropyl myristate | 110-27-0 | 25 | 99 |
| | Geraniol Fine FCC | 106-24-1 | 10 | 70 |
| | Thyme Oil White | 8007-46-3 | 20 | 99 |
| Blend 40 | Orange Terpenes | 68647-72-3 | 0.1 | 25 |
| | Blend 68 | | 0.1 | 30 |
| | Blend 69 | | 35 | 99 |
| | Blend 71 | | 6 | 40 |
| Blend 41 | Linalool Coeur | 78-70-6 | 10 | 70 |
| | Amyl Butyrate | 540-18-1 | 10 | 70 |
| | Anise Star Oil | | 30 | 99 |
| Blend 42 | Thyme Oil White | 8007-46-3 | 15 | 75 |
| | Amyl Butyrate | 540-18-1 | 10 | 70 |
| | Anise Star Oil | | 30 | 99 |
| Blend 43 | Tetrahydrolinalool | 78-69-3 | 10 | 70 |
| | Vanillin | 121-33-5 | 0.1 | 4 |
| | Hercolyn D | 8050-15-5 | 0.1 | 15 |
| | Isopropyl myristate | 110-27-0 | 8 | 45 |
| | Piperonal (aldehyde)[Heliotropine] | 120-57-0 | 0.1 | 25 |
| | Ethyl Linalool | 10339-55-6 | 10 | 70 |

TABLE 5-continued

| | BLENDS | | | |
|---|---|---|---|---|
| | Compounds | CAS Registry Number | low % | high % |
| | Hedione | 24851-98-7 | 0.1 | 20 |
| | Triethyl Citrate | 77-93-0 | 5 | 30 |
| | Dipropylene glycol (DPG) | 246-770-3 | 0.1 | 25 |
| Blend 44 | Blend 63 | | 25 | 99 |
| | Thyme Oil White | | 30 | 99 |
| Blend 45 | Linalool coeur | 78-70-6 | 0.1 | 20 |
| | Tetrahydrolinalool | 78-69-3 | 0.1 | 25 |
| | Vanillin | 121-33-5 | 0.1 | 2 |
| | Isopropyl myristate | 110-27-0 | 0.1 | 30 |
| | Piperonal (aldehyde)[Heliotropine] | 120-57-0 | 0.1 | 30 |
| | Geraniol Fine FCC | 106-24-1 | 0.1 | 15 |
| | Triethyl citrate | 77-93-0 | 0.1 | 30 |
| | Thyme Oil White | | 30 | 99 |
| Blend 46 | Phenyl Ethyl Propionate | | 10 | 55 |
| | Benzyl Alcohol | 100-51-6 | 30 | 99 |
| | Methyl Salicylate | | 10 | 55 |
| | Blend 43 | | 8 | 40 |
| Blend 47 | Thyme Oil White | 8007-46-3 | 15 | 75 |
| | Amyl Butyrate | 540-18-1 | 10 | 70 |
| | Anise Star Oil | | 30 | 99 |
| | Genistein | | 0.005 | 0.1 |
| Blend 48 | Linalool coeur | 78-70-6 | 10 | 70 |
| | Amyl Butyrate | 540-18-1 | 10 | 70 |
| | Anise Star Oil | | 30 | 99 |
| | Thyme Oil White | | 0.005 | 0.1 |
| Blend 49 | LFO | | 10 | 70 |
| | BSO | 977017-84-7 | 10 | 70 |
| | Benzyl Alcohol | 100-51-6 | 30 | 99 |
| Blend 50 | Isopropyl myristate | 110-27-0 | 10 | 70 |
| | Wintergreen oil | | 15 | 90 |
| | Thyme oil white | | 8 | 40 |
| | Myristicin | | 15 | 99 |
| Blend 51 | Isopropyl myristate | 110-27-0 | 15 | 80 |
| | Wintergreen oil | | 15 | 95 |
| | Isopropyl alcohol | 67-63-0 | 0.1 | 10 |
| | Thyme oil white | | 8 | 40 |
| | Myristicin | | 15 | 75 |
| Blend 52 | Isopropyl myristate | 110-27-0 | 20 | 99 |
| | Wintergreen oil | | 25 | 99 |
| | Thyme oil white | | 10 | 60 |
| | Genistein | | 0.001 | 0.1 |
| Blend 53 | Isopropyl myristate | 110-27-0 | 20 | 99 |
| | Wintergreen oil | | 20 | 99 |
| | Isopropyl alcohol | 67-63-0 | 5 | 30 |
| | Thyme oil white | | 8 | 50 |
| | Genistein | | 0.001 | 0.1 |
| Blend 54 | Isopropyl myristate | 110-27-0 | 10 | 70 |
| | Wintergreen oil | | 15 | 90 |
| | Thyme oil white | | 8 | 40 |
| | Genistein | | 0.001 | 0.1 |
| | Myristicin | | 15 | 99 |
| Blend 55 | Mineral oil white | 8042-47-5 | 20 | 99 |
| | Wintergreen oil | | 25 | 99 |
| | Thyme oil white | | 10 | 60 |
| Blend 56 | Mineral oil white | 8042-47-5 | 10 | 50 |
| | Wintergreen oil | | 10 | 65 |
| | Thyme oil white | | 5 | 30 |
| | Benzaldehyde | | 30 | 99 |
| Blend 57 | Mineral oil white | 8042-47-5 | 10 | 55 |
| | Wintergreen oil | | 10 | 65 |
| | Thyme oil white | | 5 | 30 |
| | Genistein | | 15 | 75 |
| | Benzaldehyde | | 15 | 80 |
| Blend 58 | Linalool Coeur | 78-70-6 | 4 | 65 |
| | Thymol (crystal) | 89-83-8 | 20 | 99 |
| | Alpha-Pinene, 98% | 80-56-8 | 1 | 10 |
| | Para-Cymene | 99-87-6 | 1 | 55 |
| | Trans-Anethole | 4180-23-8 | 10 | 55 |
| Blend 59 | Linalool Coeur | 78-70-6 | 0.1 | 30 |
| | Thymol (crystal) | 89-83-8 | 25 | 99 |
| | Alpha-Pinene, 98% | 80-56-8 | 0.1 | 30 |
| | Para-Cymene | 99-87-6 | 15 | 99 |
| Blend 60 | Soy Bean Oil | 8016-70-4 | 15 | 75 |
| | Alpha-Pinene, 98% | 80-56-8 | 0.1 | 10 |
| | Para-Cymene | 99-87-6 | 15 | 85 |

TABLE 5-continued

| | | | | |
|---|---|---|---|---|
| | Compounds | CAS Registry Number | low % | high % |
| | Linalyl Acetate | 115-95-7 | 0.1 | 20 |
| | Thymol acetate | 528-79-0 | 20 | 99 |
| Blend 61 | Alpha-Pinene, 98% | 80-56-8 | 0.1 | 30 |
| | Para-Cymene | 99-87-6 | 10 | 55 |
| | Linalyl Acetate | 115-95-7 | 10 | 70 |
| | Thymol acetate | 528-79-0 | 30 | 99 |
| Blend 62 | Linalool Coeur | 78-70-6 | 10 | 60 |
| | Tetrahydrolinalool | 78-69-3 | 10 | 70 |
| | Vanillin | 121-33-5 | 0.1 | 8 |
| | Isopropyl myristate | 110-27-0 | 15 | 90 |
| | Piperonal (aldehyde)[Heliotropine] | 120-57-0 | 5 | 30 |
| | Geraniol Fine FCC | 106-24-1 | 8 | 40 |
| Blend 63 | Linalool Coeur | 78-70-6 | 8 | 40 |
| | Tetrahydrolinalool | 78-69-3 | 10 | 55 |
| | Vanillin | 121-33-5 | 0.1 | 4 |
| | Isopropyl myristate | 110-27-0 | 10 | 55 |
| | Piperonal (aldehyde)[Heliotropine] | 120-57-0 | 10 | 55 |
| | Geraniol Fine FCC | 106-24-1 | 5 | 30 |
| | Triethyl Citrate | 77-93-0 | 10 | 55 |
| Blend 64 | Linalool Coeur | 78-70-6 | 10 | 60 |
| | Tetrahydrolinalool | 78-69-3 | 10 | 70 |
| | Vanillin | 121-33-5 | 0.1 | 4 |
| | Isopropyl myristate | 110-27-0 | 10 | 70 |
| | Piperonal (aldehyde)[Heliotropine] | 120-57-0 | 10 | 70 |
| | Piperonyl Alcohol | 495-76-1 | 0.1 | 30 |
| Blend 65 | D-Limonene | 5989-27-5 | 25 | 99 |
| | Linalool Coeur | 78-70-6 | 0.1 | 4 |
| | Citral | 5392-40-5 | 5 | 30 |
| | gamma-terpinene | 99-85-4 | 5 | 30 |
| | Alpha-Pinene, 98% | 80-56-8 | 0.1 | 6 |
| | alpha-Terpineol | 98-55-5 | 0.1 | 20 |
| | Terpinolene | 586-62-9 | 0.1 | 20 |
| | Para-Cymene | 99-87-6 | 0.1 | 5 |
| | Linalyl Acetate | 115-95-7 | 0.1 | 8 |
| | Beta Pinene | 127-91-3 | 0.1 | 10 |
| | Camphor Dextro | 464-49-3 | 0.06 | 0.3 |
| | Terpinene 4 OL | 562-74-3 | 0.06 | 0.3 |
| | Alpha Terpinene | 99-86-5 | 0.1 | 10 |
| | Borneol L | 507-70-0 | 0.1 | 5 |
| | Camphene | 79-92-5 | 0.1 | 2 |
| | Decanal | 112-31-2 | 0.08 | 0.6 |
| | Dodecanal | 112-54-9 | 0.06 | 0.3 |
| | Fenchol Alpha | 512-13-0 | 0.001 | 0.1 |
| | Geranyl Acetate | 105-87-3 | 0.08 | 0.6 |
| | Isoborneol | 124-76-5 | 0.1 | 2 |
| | 2-Methyl 1,3-cyclohexadiene | 30640-46-1, 1888-90-0 | 0.1 | 2 |
| | Myrcene | 123-35-3 | 0.1 | 4 |
| | Nonanal | 124-19-6 | 0.001 | 0.1 |
| | Octanal | 124-13-0 | 0.05 | 0.2 |
| | Tocopherol Gamma (TENOX ®) | 54-28-4 | 0.001 | 0.1 |
| Blend 66 | D-Limonene | 5989-27-5 | 30 | 99 |
| | Linalool Coeur | 78-70-6 | 0.1 | 5 |
| | gamma-terpinene | 99-85-4 | 6 | 40 |
| | Alpha-Pinene, 98% | 80-56-8 | 0.1 | 8 |
| | Terpinolene | 586-62-9 | 0.1 | 25 |
| | Para-Cymene | 99-87-6 | 0.1 | 6 |
| | Linalyl Acetate | 115-95-7 | 0.1 | 10 |
| | Beta Pinene | 127-91-3 | 0.1 | 10 |
| | Camphor Dextro | 464-49-3 | 0.1 | 10 |
| | Terpinene 4 OL | 562-74-3 | 0.06 | 0.3 |
| | Alpha Terpinene | 99-86-5 | 0.08 | 0.6 |
| | Borneol L | 507-70-0 | 0.1 | 5 |
| | Camphene | 79-92-5 | 0.1 | 3 |
| | Decanal | 112-31-2 | 0.08 | 0.6 |
| | Dodecanal | 112-54-9 | 0.08 | 0.6 |
| | Fenchol Alpha | 512-13-0 | 0.001 | 0.1 |
| | Geranyl Acetate | 105-87-3 | 0.08 | 0.6 |
| | Isoborneol | 124-76-5 | 0.1 | 2 |
| | 2-Methyl 1,3-cyclohexadiene | 30640-46-1, 1888-90-0 | 0.1 | 2 |
| | Myrcene | 123-35-3 | 0.1 | 5 |
| | Nonanal | 124-19-6 | 0.001 | 0.2 |
| | Octanal | 124-13-0 | 0.05 | 0.3 |
| | Tocopherol Gamma (TENOX ®) | 54-28-4 | 0.001 | 0.2 |

TABLE 5-continued

BLENDS

| | Compounds | CAS Registry Number | low % | high % |
|---|---|---|---|---|
| Blend 67 | D-Limonene | 5989-27-5 | 20 | 99 |
| | Linalool Coeur | 78-70-6 | 5 | 30 |
| | Alpha-Pinene, 98% | 80-56-8 | 0.1 | 15 |
| | Terpinolene | 586-62-9 | 5 | 30 |
| | Para-Cymene | 99-87-6 | 5 | 30 |
| | Linalyl Acetate | 115-95-7 | 0.1 | 15 |
| | Beta Pinene | 127-91-3 | 0.1 | 15 |
| | Alpha Terpinene | 99-86-5 | 0.1 | 15 |
| | Camphene | 79-92-5 | 0.1 | 20 |
| | Myrcene | 123-35-3 | 0.1 | 30 |
| Blend 68 | D-Limonene | 5989-27-5 | 0.08 | 1 |
| | Thyme Oil Red | 8007-46-3 | 0.1 | 4 |
| | Thymol (crystal) | 89-83-8 | 30 | 99 |
| | alpha-Terpineol | 98-55-5 | 0.1 | 6 |
| | Para-Cymene | 99-87-6 | 10 | 60 |
| | Linalyl Acetate | 115-95-7 | 0.1 | 5 |
| | Caryophyllene-B | 87-44-5 | 0.1 | 10 |
| | Borneol L | 507-70-0 | 0.1 | 6 |
| | Myrcene | 123-35-3 | 0.1 | 4 |
| | Tea Tree Oil | | 0.1 | 6 |
| | Cypress Oil | | 0.1 | 10 |
| | Peppermint Terpenes | 8006-90-4 | 0.1 | 30 |
| | Linalool 90 | | 0.1 | 10 |
| Blend 69 | D-Limonene | 5989-27-5 | 30 | 99 |
| | Citral | 5392-40-5 | 0.1 | 25 |
| | gamma-terpinene | 99-85-4 | 5 | 30 |
| | Alpha-Pinene, 98% | 80-56-8 | 0.1 | 5 |
| | alpha-Terpineol | 98-55-5 | 0.1 | 15 |
| | Terpinolene | 586-62-9 | 0.1 | 20 |
| | Lime Distilled Oil | | 0.06 | 0.3 |
| | Lime Expressed Oil | | 0.06 | 0.3 |
| | Linalyl Acetate | 115-95-7 | 0.1 | 6 |
| | Caryophyllene-B | 87-44-5 | 0.06 | 0.3 |
| | Beta Pinene | 127-91-3 | 0.1 | 8 |
| | Terpinene 4 OL | 562-74-3 | 0.005 | 0.2 |
| | Alpha Terpinene | 99-86-5 | 0.1 | 6 |
| | Borneol L | 507-70-0 | 0.1 | 5 |
| | Camphene | 79-92-5 | 0.1 | 2 |
| | Geranyl Acetate | 105-87-3 | 0.08 | 0.6 |
| | Isoborneol | 124-76-5 | 0.06 | 0.3 |
| | Linalool 90 | | 0.1 | 3 |
| | Camphor Gum | | 0.005 | 0.2 |
| | Aldehyde C-10 | | 0.005 | 0.2 |
| | Aldehyde C-12 | | 0.06 | 0.3 |
| Blend 70 | Eugenol | 97-53-0 | 0.003 | 0.1 |
| | Eucalyptol (1,8 Cineole) | | 0.05 | 0.3 |
| | Methyl Salicylate | | 60 | 99.9 |
| | Linalool 90 | | 0.05 | 0.3 |
| | Ethyl Salicylate | | 0.05 | 0.3 |
| Blend 71 | Tetrahydrolinalool | 78-69-3 | 6 | 35 |
| | Hercolyn D | 8050-15-5 | 0.1 | 25 |
| | Isopropyl myristate | 110-27-0 | 0.1 | 20 |
| | Piperonal (aldehyde)[Heliotropine] | 120-57-0 | 5 | 30 |
| | Ethyl Linalool | 10339-55-6 | 5 | 30 |
| | Triethyl Citrate | 77-93-0 | 0.1 | 30 |
| | Dipropylene glycol (DPG) | 246-770-3 | 5 | 30 |
| | Cinnamic Alcohol | 104-54-1 | 0.1 | 5 |
| | Eugenol | 97-53-0 | 0.1 | 5 |
| | Phenyl Ethyl Alcohol | 60-12-8 | 10 | 65 |
| | Iso Eugenol | | 0.08 | 1 |
| | Methyl Dihydrojasmonate | | 5 | 30 |
| Blend 72 | Linalool Coeur | 78-70-6 | 8 | 40 |
| | Tetrahydrolinalool | 78-69-3 | 10 | 70 |
| | Vanillin | 121-33-5 | 0.1 | 8 |
| | Isopropyl myristate | 110-27-0 | 15 | 85 |
| | Piperonal (aldehyde)[Heliotropine] | 120-57-0 | 5 | 30 |
| | Piperonyl Alcohol | 495-76-1 | 5 | 30 |
| | Geraniol Fine FCC | 106-24-1 | 5 | 30 |
| Blend 73 | Blend 11 | | 50 | 99 |
| | Stock 10% SLS Solution | | 5 | 30 |
| Blend 74 | Polyglycerol-4-oleate | 9007-48-1 | 0.1 | 3 |
| | Lecithin | 8002-43-5 | 0.08 | 0.6 |
| | Water | 7732-18-5 | 5 | 30 |
| | Blend 11 | | 50 | 99 |

TABLE 5-continued

| | BLENDS | | | |
|---|---|---|---|---|
| | Compounds | CAS Registry Number | low % | high % |
| Blend 75 | Potassium Sorbate | 590-00-1 or 24634-61-5 | 0.1 | 4 |
| | Xanthan Gum | 11138-66-2 | 0.08 | 1 |
| | Water | 7732-18-5 | 45 | 99 |
| | Blend 74 | | 10 | 50 |
| Blend 76 | Potassium Sorbate | 590-00-1 or 24634-61-5 | 0.1 | 2 |
| | Polyglycerol-4-oleate | 9007-48-1 | 0.1 | 2 |
| | Xanthan Gum | 11138-66-2 | 0.08 | 1 |
| | Lecithin | 8002-43-5 | 0.06 | 0.3 |
| | Water | 7732-18-5 | 20 | 99 |
| | Blend 11 | | 15 | 99 |
| Blend 77 | Thyme Oil White | 8007-46-3 | 0.1 | 25 |
| | Wintergreen Oil | 68917-75-9 | 2 | 55 |
| | Isopropyl myristate | 110-27-0 | 1 | 40 |
| | Potassium Sorbate | 590-00-1 or 24634-61-5 | 0.06 | 0.3 |
| | Polyglycerol-4-oleate | 9007-48-1 | 0.1 | 2 |
| | Xanthan Gum | 11138-66-2 | 0.08 | 1 |
| | Lecithin | 8002-43-5 | 0.06 | 0.3 |
| | Water | 7732-18-5 | 20 | 99 |
| Blend 78 | Polyglycerol-4-oleate | 9007-48-1 | 0.1 | 3 |
| | Lecithin | 8002-43-5 | 0.08 | 0.6 |
| | Water | 7732-18-5 | 5 | 30 |
| | Blend 11 | | 50 | 99 |
| Blend 79 | Water | 7732-18-5 | 0.1 | 20 |
| | Blend 74 | | 40 | 99 |
| | Stock 2.5% Xanthan-1% Ksorbate | | 6 | 40 |
| Blend 80 | Water | 7732-18-5 | 0.1 | 10 |
| | Blend 78 | | 45 | 99 |
| | Stock 2.5% Xanthan-1% Ksorbate | | 6 | 40 |
| Blend 81 | Potassium Sorbate | 590-00-1 or 24634-61-5 | 0.1 | 4 |
| | Xanthan Gum | 11138-66-2 | 0.08 | 1 |
| | Water | 7732-18-5 | 45 | 99 |
| | Blend 78 | | 10 | 50 |
| Blend 82 | Blend 1 | | 0.1 | 8 |
| | Water | | 60 | 99 |
| Blend 83 | Polyglycerol-4-oleate | 9007-48-1 | 0.1 | 3 |
| | Lecithin | 8002-43-5 | 0.08 | 0.6 |
| | Water | 7732-18-5 | 5 | 30 |
| | Blend 11 | | 50 | 99 |
| Blend 84 | Potassium Sorbate | 590-00-1 or 24634-61-5 | 0.1 | 4 |
| | Xanthan Gum | 11138-66-2 | 0.08 | 1 |
| | Water | 7732-18-5 | 45 | 99 |
| | Blend 83 | | 10 | 50 |
| Blend 85 | *Citronella* Oil | 106-22-9 | 0.08 | 0.6 |
| | Carbopol 940 | [9003-01-4] | 0.08 | 0.6 |
| | BHT (butylated hydroxytoluene) | 128-37-0 | 0.06 | 0.3 |
| | Water | 7732-18-5 | 30 | 99 |
| | Emulsifying Wax | 67762-27-0, 9005-67-8 | 8 | 40 |
| | Light Liquid Paraffin | 8012-95-1 | 0.1 | 10 |
| | White Soft Paraffin | [8009-03-8] | 0.1 | 25 |
| | Sodium Metabisulphate | [7681-57-4] | 0.08 | 1 |
| | Propylene Glycol | [57-55-6] | 0.1 | 6 |
| | Methyl Paraben | [99-76-3] | 0.08 | 0.6 |
| | Propyl Paraben | [94-13-3] | 0.005 | 0.2 |
| | Cresmer RH40 hydrogenated castor oil | [61791-12-6] | 0.1 | 15 |
| | Triethanolamine | [102-71-6] | 0.08 | 0.6 |
| | Vitamin E Acetate | [58-95-7] | 0.002 | 0.08 |
| | Disodium EDTA | [139-33-3] | 0.005 | 0.2 |
| | Blend 1 | | 0.1 | 15 |
| Blend 86 | Span 80 | 1338-43-8 | 0.005 | 0.2 |
| | Sodium Benzoate | 532-32-1 | 0.08 | 0.6 |
| | Isopar M | 64742-47-8 | 15 | 85 |
| | A46 Propellant | | 8 | 45 |
| | Water | 7732-18-5 | 25 | 99 |
| | Isopropyl alcohol | 67-63-0 | 0.1 | 5 |
| | Blend 8 | | 6 | 40 |
| Blend 87 | Isopar M | 64742-47-8 | 30 | 99 |
| | A46 Propellant | | 20 | 99 |

TABLE 5-continued

BLENDS

| | Compounds | CAS Registry Number | low % | high % |
|---|---|---|---|---|
| | Isopropyl alcohol | 67-63-0 | 0.1 | 10 |
| | Blend 25 | | 0.1 | 20 |
| Blend 88 | Isopar M | 64742-47-8 | 30 | 99 |
| | A46 Propellant | | 20 | 99 |
| | Bifenthrin | 83657-04-3 | 0.005 | 0.2 |
| | Isopropyl alcohol | 67-63-0 | 0.1 | 10 |
| | Blend 25 | | 0.1 | 20 |
| Blend 89 | Isopar M | 64742-47-8 | 30 | 99 |
| | A46 Propellant | | 20 | 99 |
| | Blend 20 | | 0.1 | 20 |
| Blend 90 | Potassium Sorbate | 590-00-1 or 24634-61-5 | 0.06 | 0.3 |
| | Polyglycerol-4-oleate | 9007-48-1 | 0.08 | 0.6 |
| | Xanthan Gum | 11138-66-2 | 0.08 | 0.6 |
| | Lecithin | 8002-43-5 | 0.003 | 0.1 |
| | Water | 7732-18-5 | 45 | 99 |
| | Isopropyl alcohol | 67-63-0 | 0.1 | 8 |
| | Blend 35 | | 8 | 45 |
| Blend 91 | Potassium Sorbate | 590-00-1 or 24634-61-5 | 0.06 | 0.3 |
| | Polyglycerol-4-oleate | 9007-48-1 | 0.08 | 0.6 |
| | Xanthan Gum | 11138-66-2 | 0.08 | 1 |
| | Lecithin | 8002-43-5 | 0.003 | 0.1 |
| | Water | 7732-18-5 | 50 | 99 |
| | Blend 35 | | 8 | 40 |
| Blend 92 | Isopropyl myristate | 110-27-0 | 0.1 | 10 |
| | Geraniol Fine FCC | 106-24-1 | 0.1 | 8 |
| | Potassium Sorbate | 590-00-1 or 24634-61-5 | 0.06 | 0.3 |
| | Polyglycerol-4-oleate | 9007-48-1 | 0.1 | 2 |
| | Xanthan Gum | 11138-66-2 | 0.08 | 1 |
| | Lecithin | 8002-43-5 | 0.05 | 0.2 |
| | Water | 7732-18-5 | 50 | 99 |
| | Blend 68 | | 0.1 | 10 |
| | Isopropyl alcohol | 67-63-0 | 0.1 | 8 |
| Blend 93 | Wintergreen Oil | 68917-75-9 | 0.1 | 15 |
| | Isopropyl myristate | 110-27-0 | 0.1 | 10 |
| | Thyme Oil Red | 8007-46-3 | 0.1 | 6 |
| | Stock 0.3% SLS-0.1% Xanthan Soln | | 55 | 99 |
| Blend 94 | Stock 0.3% SLS & 0.1% Xanthan Soln | | 60 | 99 |
| | Blend 38 | | 0.1 | 15 |
| Blend 95 | Lecithin, Soya | 8030-76-0 | 0.08 | 0.6 |
| | Polyglycerol-4-oleate | 9007-48-1 | 0.1 | 3 |
| | Water | 7732-18-5 | 5 | 30 |
| | Blend 11 | | 50 | 99 |
| Blend 96 | Thyme Oil White | 8007-46-3 | 20 | 99 |
| | Isopropyl myristate | 110-27-0 | 15 | 95 |
| | Lecithin, Soya | 8030-76-0 | 0.08 | 0.6 |
| | Polyglycerol-4-oleate | 9007-48-1 | 0.1 | 3 |
| | Water | 7732-18-5 | 5 | 30 |
| | Wintergreen Oil | | 10 | 65 |
| Blend 97 | Lecithin, Soya | 8030-76-0 | 0.06 | 0.3 |
| | Polyglycerol-4-oleate | 9007-48-1 | 0.1 | 3 |
| | Water | 7732-18-5 | 5 | 30 |
| | Blend 7 | | 50 | 99 |
| Blend 98 | Thyme Oil White | 8007-46-3 | 10 | 55 |
| | Wintergreen Oil | 68917-75-9 | 20 | 99 |
| | Vanillin | 121-33-5 | 0.1 | 4 |
| | Isopropyl myristate | 110-27-0 | 15 | 90 |
| | Lecithin, Soya | 8030-76-0 | 0.06 | 0.3 |
| | Polyglycerol-4-oleate | 9007-48-1 | 0.1 | 3 |
| | Water | 7732-18-5 | 5 | 30 |
| Blend 99 | Polyglycerol-4-oleate | 9007-48-1 | 0.1 | 6 |
| | Water | 7732-18-5 | 0.1 | 25 |
| | Blend 11 | | 50 | 99 |
| Blend 100 | Thyme Oil White | 8007-46-3 | 20 | 99 |
| | Isopropyl myristate | 110-27-0 | 15 | 95 |
| | Polyglycerol-4-oleate | 9007-48-1 | 0.1 | 6 |
| | Water | 7732-18-5 | 0.1 | 25 |
| | Wintergreen Oil | | 10 | 65 |
| Blend 101 | Potassium Sorbate | 590-00-1 or 24634-61-5 | 0.06 | 0.3 |
| | Polyglycerol-4-oleate | 9007-48-1 | 0.1 | 6 |
| | Xanthan Gum | 11138-66-2 | 0.08 | 1 |

TABLE 5-continued

| | | | BLENDS | |
|---|---|---|---|---|
| | Compounds | CAS Registry Number | low % | high % |
| | Water | 7732-18-5 | 50 | 99 |
| | Blend 97 | | 6 | 35 |
| Blend 102 | D-Limonene | 5989-27-5 | 0.1 | 15 |
| | Thyme Oil White | 8007-46-3 | 0.1 | 5 |
| | Lecithin, Soya | 8030-76-0 | 0.001 | 0.04 |
| | Potassium Sorbate | 590-00-1 or 24634-61-5 | 0.06 | 0.3 |
| | Polyglycerol-4-oleate | 9007-48-1 | 0.1 | 6 |
| | Xanthan Gum | 11138-66-2 | 0.08 | 1 |
| | Water | 7732-18-5 | 50 | 99 |
| | Wintergreen Oil | | 0.1 | 10 |
| Blend 103 | Potassium Sorbate | 590-00-1 or 24634-61-5 | 0.06 | 0.3 |
| | Xanthan Gum | 11138-66-2 | 0.08 | 1 |
| | Water | 7732-18-5 | 50 | 99 |
| | Blend 95 | | 6 | 35 |
| Blend 104 | Thyme Oil White | 8007-46-3 | 0.1 | 10 |
| | Isopropyl myristate | 110-27-0 | 0.1 | 10 |
| | Lecithin, Soya | 8030-76-0 | 0.002 | 0.08 |
| | Potassium Sorbate | 590-00-1 or 24634-61-5 | 0.06 | 0.3 |
| | Polyglycerol-4-oleate | 9007-48-1 | 0.06 | 0.3 |
| | Xanthan Gum | 11138-66-2 | 0.08 | 1 |
| | Water | 7732-18-5 | 55 | 99 |
| | Wintergreen Oil | | 0.1 | 8 |
| Blend 105 | Potassium Sorbate | 590-00-1 or 24634-61-5 | 0.06 | 0.3 |
| | Xanthan Gum | 11138-66-2 | 0.08 | 1 |
| | Water | 7732-18-5 | 50 | 99 |
| | Blend 99 | | 6 | 35 |
| Blend 106 | Thyme Oil White | 8007-46-3 | 0.1 | 10 |
| | Wintergreen Oil | 68917-75-9 | 0.1 | 8 |
| | Isopropyl myristate | 110-27-0 | 0.1 | 10 |
| | Potassium Sorbate | 590-00-1 or 24634-61-5 | 0.06 | 0.3 |
| | Polyglycerol-4-oleate | 9007-48-1 | 0.08 | 0.6 |
| | Xanthan Gum | 11138-66-2 | 0.08 | 1 |
| | Water | 7732-18-5 | 55 | 99 |
| Blend 107 | Potassium Sorbate | 590-00-1 or 24634-61-5 | 0.1 | 4 |
| | Xanthan Gum | 11138-66-2 | 0.1 | 8 |
| | Water | 7732-18-5 | 60 | 99 |
| Blend 108 | Sodium Benzoate | 532-32-1 | 0.1 | 6 |
| | Water | 7732-18-5 | 60 | 99 |
| Blend 109 | Span 80 | 1338-43-8 | 0.1 | 4 |
| | Tween 80 | | 0.1 | 5 |
| | Isopar M | 64742-47-8 | 8 | 40 |
| | Water | 7732-18-5 | 35 | 99 |
| | Blend 8 | | 0.1 | 10 |
| | 2% Sodium Benzoate | | 6 | 35 |
| Blend 110 | D-Limonene | 5989-27-5 | 0.1 | 5 |
| | Thyme Oil White | 8007-46-3 | 0.1 | 2 |
| | Wintergreen Oil | 68917-75-9 | 0.1 | 3 |
| | Span 80 | 1338-43-8 | 0.1 | 4 |
| | Tween 80 | | 0.1 | 5 |
| | Sodium Benzoate | 532-32-1 | 0.08 | 0.6 |
| | Isopar M | 64742-47-8 | 8 | 40 |
| | Water | 7732-18-5 | 40 | 99 |
| Blend 111 | Propellent A70 | | 10 | 65 |
| | Blend 109 | | 45 | 99 |
| Blend 112 | D-Limonene | 5989-27-5 | 0.1 | 5 |
| | Thyme Oil White | 8007-46-3 | 0.08 | 1 |
| | Wintergreen Oil | 68917-75-9 | 0.1 | 3 |
| | Span 80 | 1338-43-8 | 0.1 | 3 |
| | Tween 80 | | 0.1 | 5 |
| | Sodium Benzoate | 532-32-1 | 0.08 | 0.6 |
| | Isopar M | 64742-47-8 | 6 | 35 |
| | Water | 7732-18-5 | 35 | 99 |
| | Propellent A70 | | 10 | 65 |
| Blend 113 | Sodium Lauryl Sulfate | 151-21-3 | 5 | 30 |
| | Water | 7732-18-5 | 55 | 99 |
| Blend 114 | Sodium Lauryl Sulfate | 151-21-3 | 0.08 | 1 |
| | Xanthan Gum | 11138-66-2 | 0.06 | 0.3 |
| | Water | 7732-18-5 | 60 | 99.9 |

TABLE 5-continued

BLENDS

| | Compounds | CAS Registry Number | low % | high % |
|---|---|---|---|---|
| Blend 115 | *Citronella* Oil | 106-22-9 | 0.08 | 0.6 |
| | Carbopol 940 | [9003-01-4] | 0.08 | 0.6 |
| | BHT (butylated hydroxytoluene) | 128-37-0 | 0.06 | 0.3 |
| | Water | 7732-18-5 | 30 | 99 |
| | Emulsifying Wax | 67762-27-0, 9005-67-8 | 8 | 40 |
| | Light Liquid Paraffin | 8012-95-1 | 0.1 | 10 |
| | White Soft Paraffin | [8009-03-8] | 0.1 | 25 |
| | Sodium Metabisulphate | [7681-57-4] | 0.08 | 1 |
| | Propylene Glycol | [57-55-6] | 0.1 | 6 |
| | Cresmer RH40 hydrogenated castor oil | [61791-12-6] | 0.1 | 15 |
| | Triethanolamine | [102-71-6] | 0.08 | 0.6 |
| | Vitamin E Acetate | [58-95-7] | 0.002 | 0.08 |
| | Disodium EDTA | [139-33-3] | 0.005 | 0.2 |
| | Blend 1 | | 0.1 | 15 |
| Blend 116 | Water | 7732-18-5 | 20 | 99 |
| | Blend 75 | | 35 | 99 |
| Blend 117 | D-Limonene | 5989-27-5 | 0.1 | 10 |
| | Thyme Oil White | 8007-46-3 | 0.1 | 15 |
| | Benzyl Alcohol | 100-51-6 | 8 | 50 |
| | Isopar M | 64742-47-8 | 10 | 65 |
| | Water | 7732-18-5 | 25 | 99 |
| | Bifenthrin | 83657-04-3 | 0.005 | 0.2 |
| | Blend 63 | | 0.1 | 15 |
| | Stock 10% SLS Solution | | 0.1 | 10 |
| Blend 118 | Thyme Oil White | 8007-46-3 | 0.1 | 2 |
| | Wintergreen Oil | 68917-75-9 | 0.1 | 3 |
| | Isopropyl myristate | 110-27-0 | 0.1 | 3 |
| | Sodium Lauryl Sulfate | 151-21-3 | 0.002 | 0.08 |
| | Water | 7732-18-5 | 60 | 99 |
| Blend 119 | Thyme Oil White | 8007-46-3 | 0.1 | 4 |
| | Wintergreen Oil | 68917-75-9 | 0.1 | 8 |
| | Isopropyl myristate | 110-27-0 | 0.1 | 5 |
| | AgSorb clay carrier | | 60 | 99 |
| Blend 120 | Thyme Oil White | 8007-46-3 | 0.1 | 4 |
| | Wintergreen Oil | 68917-75-9 | 0.1 | 8 |
| | Isopropyl myristate | 110-27-0 | 0.1 | 5 |
| | DG Lite | | 60 | 99 |
| Blend 121 | D-Limonene | 5989-27-5 | 15 | 75 |
| | Thyme Oil White | 8007-46-3 | 0.1 | 4 |
| | Linalool Coeur | 78-70-6 | 0.08 | 0.6 |
| | Tetrahydrolinalool | 78-69-3 | 0.08 | 0.6 |
| | Vanillin | 121-33-5 | 0.002 | 0.08 |
| | Isopropyl myristate | 110-27-0 | 0.08 | 0.6 |
| | Piperonal (aldehyde) [Heliotropine] | 120-57-0 | 0.08 | 0.6 |
| | Blend 66 | | 0.1 | 10 |
| | Geraniol 60 | 106-24-1 | 0.06 | 0.3 |
| | Triethyl Citrate | 77-93-0 | 0.08 | 0.6 |
| | Water | 7732-18-5 | 35 | 99 |
| | Stock 10% SLS Solution | | 0.1 | 10 |
| Blend 122 | Miracle Gro (Sterile) | | 60 | 99 |
| | Blend 11 | | 0.1 | 15 |
| Blend 123 | Thyme Oil White | 8007-46-3 | 15 | 75 |
| | Amyl Butyrate | 540-18-1 | 15 | 75 |
| | Anise Star Oil | | 30 | 99 |
| | Genistein | | 0.001 | 0.1 |
| Blend 124 | Linalool Coeur | | 0.1 | 20 |
| | Tetrahydrolinalool | | 0.1 | 25 |
| | Vanillin | | 0.1 | 2 |
| | Isopropyl myristate | | 0.1 | 30 |
| | Piperonal (aldehyde) [Heliotropine] | | 0.1 | 30 |
| | Geraniol Fine FCC | | 0.1 | 15 |
| | Triethyl Citrate | | 0.1 | 30 |
| | Thyme Oil White | | 30 | 99 |
| Blend 125 | D-Limonene | 5989-27-5 | 5 | 30 |
| | Linalool Coeur | 78-70-6 | 8 | 40 |
| | Tetrahydrolinalool | 78-69-3 | 15 | 75 |
| | Vanillin | 121-33-5 | 0.1 | 8 |
| | Isopropyl myristate | 110-27-0 | 15 | 85 |
| | Piperonal (aldehyde) | 120-57-0 | 5 | 30 |
| | Geraniol 60 | | 5 | 30 |
| Blend 126 | D-Limonene | 5989-27-5 | 45 | 99 |
| | Thyme Oil White | 8007-46-3 | 0.1 | 10 |
| | Linalool Coeur | 78-70-6 | 0.1 | 2 |

TABLE 5-continued

| BLENDS | | | |
|---|---|---|---|
| Compounds | CAS Registry Number | low % | high % |
| Tetrahydrolinalool | 78-69-3 | 0.1 | 3 |
| Vanillin | 121-33-5 | 0.005 | 0.2 |
| Isopropyl myristate | 110-27-0 | 0.1 | 3 |
| Piperonal (aldehyde) [Heliotropine] | 120-57-0 | 0.1 | 3 |
| Blend 66 | | 5 | 30 |
| Geraniol 60 | | 0.1 | 2 |
| Triethyl Citrate | 77-93-0 | 0.1 | 3 |

The foregoing Table 5 provides exemplary combinations of ingredients for useful blends in accordance with the invention. In many cases a particular ingredient is listed very specifically such as, for example, with reference to a CAS number and/or particular modifiers of the basic name of the ingredient. Such specific listings are non-limiting examples of types of ingredients, and similar ingredients (such as, for example, with different CAS numbers and/or variant forms of the type of ingredient) can be substituted within the scope of certain embodiments of the invention.

The foregoing Table 5 also provides an examplary range of amounts of each ingredient expressed as a weight/weight percentage of the listed blend. The exemplary range for each ingredient in each blend is provided as a number in the fourth column indicating a value at the low end of such exemplary range, and in the fifth column indicating a value at the high end of such exemplary range. The provided ranges are exemplary; other useful ranges exist and are expressly within the scope of certain embodiments on the invention. Namely, other high and low amounts defining other useful ranges and/or amounts of the listed ingredients, can include 1%, 2%, 5%, 10%, 15%, 20%, 25%, 40%, 50%, 60%, 75%, 85%, 95%, 110%, 125%, 150%, 175%, 200%, 250%, 300%, 400%, 500%, 750%, 900%, or 1000% of the amount listed as the low amount and/or the high amount, with the caveat that the relative percentage of any given ingredient cannot exceed 99.99% of the total blend of ingredients.

Furthermore, other blends useful in accordance with the present invention are shown in the following table.

TABLE 6

| Ingredients | Exemplified form | % Range 1 | | % Range 2 | | % Range 3 | | % Range 4 | | Exemplified % (w/w) |
|---|---|---|---|---|---|---|---|---|---|---|
| Example 1 - Ingredient Family 1 | | | | | | | | | | |
| Linalool | Linalool Coeur | 0.66% | 19.80% | 3.30% | 9.90% | 4.95% | 8.25% | 5.94% | 7.26% | 6.60% |
| Base Oil | Soy Bean Oil | 2.40% | 72.00% | 12.00% | 36.00% | 18.00% | 30.00% | 21.60% | 26.40% | 24.00% |
| Thymol | Thymol (crystal) | 3.72% | 99.00% | 18.60% | 55.80% | 27.90% | 46.50% | 33.48% | 40.92% | 37.20% |
| Pinene | Alpha-Pinene, 98% | 0.38% | 11.40% | 1.90% | 5.70% | 2.85% | 4.75% | 3.42% | 4.18% | 3.80% |
| Cymene | Para-Cymene | 2.84% | 85.17% | 14.20% | 42.59% | 21.29% | 35.49% | 25.55% | 31.23% | 28.39% |
| Example 2 - Ingredient Family 2 | | | | | | | | | | |
| Thyme Oil | Thyme Oil White | 2.06% | 61.80% | 10.30% | 30.90% | 15.45% | 25.75% | 18.54% | 22.66% | 20.60% |
| Wintergreen Oil | Wintergreen Oil | 4.51% | 99.00% | 22.55% | 67.65% | 33.83% | 56.38% | 40.59% | 49.61% | 45.10% |
| Isopropyl myristate | Isopropyl myristate | 3.43% | 99.00% | 17.15% | 51.45% | 25.73% | 42.88% | 30.87% | 37.73% | 34.30% |
| Example 3 - Ingredient Family 3 | | | | | | | | | | |
| Thyme Oil | Thyme Oil White | 2.48% | 74.25% | 12.38% | 37.13% | 18.56% | 30.94% | 22.28% | 27.23% | 24.75% |
| Amyl Butyrate | Amyl Butyrate | 2.30% | 69.12% | 11.52% | 34.56% | 17.28% | 28.80% | 20.74% | 25.34% | 23.04% |
| Anise Star Oil | Anise Star Oil | 5.22% | 99.00% | 26.11% | 78.32% | 39.16% | 65.26% | 46.99% | 57.43% | 52.21% |
| Example 4 - Ingredient Family 4 | | | | | | | | | | |
| Thyme Oil | Thyme Oil White | 2.48% | 74.25% | 12.38% | 37.13% | 18.56% | 30.94% | 22.28% | 27.23% | 24.75% |
| Amyl Butyrate | Amyl Butyrate | 2.30% | 69.12% | 11.52% | 34.56% | 17.28% | 28.80% | 20.74% | 25.34% | 23.04% |
| Anise Star Oil | Anise Star Oil | 5.22% | 99.00% | 26.10% | 78.30% | 39.15% | 65.25% | 46.98% | 57.42% | 52.20% |
| Isoflavone | Genistein | 0.001% | 5.00% | 0.005% | 0.02% | 0.008% | 0.012% | 0.009% | 0.011% | 0.01% |
| Example 5 - Ingredient Family 5 | | | | | | | | | | |
| Thyme Oil | Thyme Oil White | 2.05% | 61.50% | 10.25% | 30.75% | 15.38% | 25.63% | 18.45% | 22.55% | 20.50% |
| Wintergreen Oil | Wintergreen Oil | 4.50% | 99.00% | 22.50% | 67.50% | 33.75% | 56.25% | 40.50% | 49.50% | 45.00% |
| Vanillin | Vanillin | 0.11% | 5.00% | 0.55% | 1.65% | 0.83% | 1.38% | 0.99% | 1.21% | 1.10% |
| Isopropyl myristate | Isopropyl myristate | 3.34% | 99.00% | 16.70% | 50.10% | 25.05% | 41.75% | 30.06% | 36.74% | 33.40% |
| Example 6 - Ingredient Family 6 | | | | | | | | | | |
| Limonene | D-Limonene | 5.63% | 99.00% | 28.15% | 84.45% | 42.23% | 70.38% | 50.67% | 61.93% | 56.30% |
| Thyme Oil | Thyme Oil White | 1.24% | 37.14% | 6.19% | 18.57% | 9.29% | 15.48% | 11.14% | 13.62% | 12.38% |
| Wintergreen Oil | Wintergreen Oil | 3.13% | 93.96% | 15.66% | 46.98% | 23.49% | 39.15% | 28.19% | 34.45% | 31.32% |
| Example 7 - Ingredient Family 7 | | | | | | | | | | |
| Potassium Sorbate | Potassium Sorbate | 0.10% | 5.00% | 0.50% | 1.50% | 0.75% | 1.25% | 0.90% | 1.10% | 1.00% |
| Xanthan Gum | Xanthan Gum | 0.03% | 5.00% | 0.14% | 0.42% | 0.21% | 0.35% | 0.25% | 0.31% | 0.28% |
| Water | Water | 8.18% | 99.00% | 40.91% | 99.00% | 61.37% | 99.00% | 73.64% | 90.00% | 81.82% |
| Blend 74 | Blend 74 | 1.69% | 50.7% | 8.45% | 25.35% | 12.68% | 21.13% | 15.21% | 18.59% | 16.90% |

TABLE 6-continued

| Ingredients | Exemplified form | % Range 1 | | % Range 2 | | % Range 3 | | % Range 4 | | Exemplified % (w/w) |
|---|---|---|---|---|---|---|---|---|---|---|
| Example 8 - Ingredient Family 8 | | | | | | | | | | |
| Isopropyl myristate | Isopropyl myristate | 4.84% | 99.00% | 24.18% | 72.53% | 36.26% | 60.44% | 43.52% | 53.19% | 48.35% |
| Geraniol | Geraniol Fine FCC | 1.50% | 44.94% | 7.49% | 22.47% | 11.24% | 18.73% | 13.48% | 16.48% | 14.98% |
| Thyme Oil | Thyme Oil White | 3.67% | 99.00% | 18.34% | 55.01% | 27.50% | 45.84% | 33.00% | 40.34% | 36.67% |
| Example 9 - Ingredient Family 9 | | | | | | | | | | |
| Limonene | D-Limonene | 0.99% | 29.70% | 4.95% | 14.85% | 7.43% | 12.38% | 8.91% | 10.89% | 9.90% |
| Linalool | Linalool Coeur | 1.41% | 42.42% | 7.07% | 21.21% | 10.61% | 17.68% | 12.73% | 15.55% | 14.14% |
| Tetrahydrolinalool | Tetrahydrolinalool | 2.43% | 72.87% | 12.15% | 36.44% | 18.22% | 30.36% | 21.86% | 26.72% | 24.29% |
| Vanillin | Vanillin | 0.25% | 7.44% | 1.24% | 3.72% | 1.86% | 3.10% | 2.23% | 2.73% | 2.48% |
| Isopropyl myristate | Isopropyl myristate | 2.89% | 86.76% | 14.46% | 43.38% | 21.69% | 36.15% | 26.03% | 31.81% | 28.92% |
| Piperonal | Piperonal (aldehyde) | 1.00% | 29.91% | 4.99% | 14.96% | 7.48% | 12.46% | 8.97% | 10.97% | 9.97% |
| Geraniol | Geraniol Fine FCC | 1.03% | 30.90% | 5.15% | 15.45% | 7.73% | 12.88% | 9.27% | 11.33% | 10.30% |
| Example 10 - Ingredient Family 10 | | | | | | | | | | |
| Limonene | D-Limonene | 2.85% | 85.38% | 14.23% | 42.69% | 21.35% | 35.58% | 25.61% | 31.31% | 28.46% |
| Thyme Oil | Thyme Oil White | 3.13% | 93.87% | 15.65% | 46.94% | 23.47% | 39.11% | 28.16% | 34.42% | 31.29% |
| Blend 63 | Blend 63 | 4.03% | 99.00% | 20.13% | 60.38% | 30.19% | 50.31% | 36.23% | 44.28% | 40.25% |
| Example 11 - Ingredient Family 11 | | | | | | | | | | |
| Limonene | D-Limonene | 0.96% | 28.89% | 4.82% | 14.45% | 7.22% | 12.04% | 8.67% | 10.59% | 9.63% |
| BSD | BSD | 2.67% | 79.98% | 13.33% | 39.99% | 20.00% | 33.33% | 23.99% | 29.33% | 26.66% |
| Linalool | Linalool Coeur | 0.98% | 29.46% | 4.91% | 14.73% | 7.37% | 12.28% | 8.84% | 10.80% | 9.82% |
| Tetrahydrolinalool | Tetrahydrolinalool | 1.18% | 35.43% | 5.91% | 17.72% | 8.86% | 14.76% | 10.63% | 12.99% | 11.81% |
| Vanillin | Vanillin | 0.12% | 5.00% | 0.60% | 1.80% | 0.90% | 1.50% | 1.08% | 1.32% | 1.20% |
| Base oil | Mineral Oil White USP | 1.50% | 44.91% | 7.49% | 22.46% | 11.23% | 18.71% | 13.47% | 16.47% | 14.97% |
| Isopropyl myristate | Isopropyl myristate | 1.45% | 43.62% | 7.27% | 21.81% | 10.91% | 18.18% | 13.09% | 15.99% | 14.54% |
| Piperonal | Piperonal (aldehyde) | 0.49% | 14.55% | 2.43% | 7.28% | 3.64% | 6.06% | 4.37% | 5.34% | 4.85% |
| Geraniol | Geraniol Fine FCC | 0.65% | 19.53% | 3.26% | 9.77% | 4.88% | 8.14% | 5.86% | 7.16% | 6.51% |
| Example 12 - Ingredient Family 12 | | | | | | | | | | |
| Thyme Oil | Thyme Oil White | 4.19% | 99.00% | 20.93% | 62.79% | 31.40% | 52.33% | 37.67% | 46.05% | 41.86% |
| Isopropyl myristate | Isopropyl myristate | 3.83% | 99.00% | 19.17% | 57.51% | 28.76% | 47.93% | 34.51% | 42.17% | 38.34% |
| Geraniol | Geraniol Fine FCC | 1.98% | 59.40% | 9.90% | 29.70% | 14.85% | 24.75% | 17.82% | 21.78% | 19.80% |
| Example 13 - Ingredient Family 13 | | | | | | | | | | |
| Linalool | Linalool Coeur | 2.34% | 70.14% | 11.69% | 35.07% | 17.54% | 29.23% | 21.04% | 25.72% | 23.38% |
| Amyl Butyrate | Amyl Butyrate | 2.35% | 70.38% | 11.73% | 35.19% | 17.60% | 29.33% | 21.11% | 25.81% | 23.46% |
| Anise Star Oil | Anise Star Oil | 5.32% | 99.00% | 26.58% | 79.74% | 39.87% | 66.45% | 47.84% | 58.48% | 53.16% |
| Example 14 - Ingredient Family 14 | | | | | | | | | | |
| Linalool | Linalool Coeur | 3.74% | 99.00% | 18.72% | 56.16% | 28.08% | 46.80% | 33.70% | 41.18% | 37.44% |
| Thymol | Thymol | 3.67% | 99.00% | 18.36% | 55.08% | 27.54% | 45.90% | 33.05% | 40.39% | 36.72% |
| Pinene | Alpha-pinene, 98% | 0.47% | 13.98% | 2.33% | 6.99% | 3.50% | 5.83% | 4.19% | 5.13% | 4.66% |
| Cymene | Para-Cymene | 0.19% | 5.61% | 0.94% | 2.81% | 1.40% | 2.34% | 1.68% | 2.06% | 1.87% |
| Anethole | Trans-Anethole | 1.93% | 57.93% | 9.66% | 28.97% | 14.48% | 24.14% | 17.38% | 21.24% | 19.31% |
| Example 15 - Ingredient Family 15 | | | | | | | | | | |
| Limonene | D-Limonene | 2.74% | 82.05% | 13.68% | 41.03% | 20.51% | 34.19% | 24.62% | 30.09% | 27.35% |
| Thyme Oil | Thyme Oil White | 3.01% | 90.24% | 15.04% | 45.12% | 22.56% | 37.60% | 27.07% | 33.09% | 30.08% |
| Lilac Flower Oil | Lilac Flower Oil | 4.26% | 99.00% | 21.30% | 63.90% | 31.95% | 53.25% | 38.34% | 46.86% | 42.57% |
| Example 16 - Ingredient Family 16 | | | | | | | | | | |
| Thyme Oil | Thyme Oil White | 3.82% | 99.00% | 19.11% | 57.32% | 28.66% | 47.76% | 34.39% | 42.03% | 38.21% |
| Wintergreen Oil | Wintergreen Oil | 2.48% | 74.37% | 12.40% | 37.19% | 18.59% | 30.99% | 22.31% | 27.27% | 24.79% |
| Isopropyl Myristate | Isopropyl Myristate | 3.59% | 99.00% | 17.95% | 53.84% | 26.92% | 44.86% | 32.30% | 39.48% | 35.89% |
| vanillin | Vanillin | 0.11% | 5.00% | 0.56% | 1.67% | 0.83% | 1.39% | 1.00% | 1.22% | 1.11% |
| Example 17 - Ingredient Family 17 | | | | | | | | | | |
| Wintergreen Oil | Wintergreen Oil | 2.48% | 74.46% | 12.41% | 37.23% | 18.62% | 31.03% | 22.34% | 27.30% | 24.82% |
| Isopropyl Myristate | Isopropyl Myristate | 3.59% | 99.00% | 17.97% | 53.91% | 26.96% | 44.93% | 32.35% | 39.53% | 35.94% |
| Thyme Oil | Thyme Oil White | 3.92% | 99.00% | 19.62% | 58.86% | 29.43% | 49.05% | 35.32% | 43.16% | 39.24% |
| Example 18 - Ingredient Family 18 | | | | | | | | | | |
| Thyme Oil | Thyme Oil White | 0.46% | 13.8% | 2.30% | 6.90% | 3.45% | 5.75% | 4.14% | 5.06% | 4.60% |
| Wintergreen Oil | Wintergreen Oil | 5.78% | 99.00% | 28.90% | 86.70% | 43.35% | 72.25% | 52.02% | 63.58% | 57.80% |
| Isopropyl Myristate | Isopropyl Myristate | 3.76% | 99.00% | 18.80% | 56.40% | 28.20% | 47.00% | 33.84% | 41.36% | 37.60% |
| Example 19 - Ingredient Family 19 | | | | | | | | | | |
| Thyme Oil | Thyme Oil White | 3.16% | 94.71% | 15.79% | 47.36% | 23.68% | 39.46% | 28.41% | 34.73% | 31.57% |
| Isopropyl myristate | Isopropyl myristate | 3.86% | 99.00% | 19.28% | 57.84% | 28.92% | 48.20% | 34.70% | 42.42% | 38.56% |
| Wintergreen Oil | Wintergreen Oil | 2.99% | 89.61% | 14.94% | 44.81% | 22.40% | 37.34% | 26.88% | 32.86% | 29.87% |

TABLE 6-continued

| Ingredients | Exemplified form | % Range 1 | | % Range 2 | | % Range 3 | | % Range 4 | | Exemplified % (w/w) |
|---|---|---|---|---|---|---|---|---|---|---|
| Example 20 - Ingredient Family 20 | | | | | | | | | | |
| Thyme Oil | Thyme Oil White | 2.06% | 61.80% | 10.30% | 30.90% | 15.45% | 25.75% | 18.54% | 22.66% | 20.60% |
| Isopropyl myristate | Isopropyl myristate | 3.43% | 99.00% | 17.15% | 51.45% | 25.73% | 42.88% | 30.87% | 37.73% | 34.30% |
| Geraniol | Geraniol Fine FCC | 4.51% | 99.00% | 22.55% | 67.65% | 33.83% | 56.38% | 40.59% | 49.61% | 45.10% |
| Example 21 - Ingredient Family 21 | | | | | | | | | | |
| Thyme Oil | Thyme Oil White | 1.24% | 37.14% | 6.19% | 18.57% | 9.29% | 15.48% | 11.14% | 13.62% | 12.38% |
| Wintergreen Oil | Wintergreen Oil | 3.13% | 93.96% | 15.66% | 46.98% | 23.49% | 39.15% | 28.19% | 34.45% | 31.32% |
| Limonene | D-Limonene | 5.63% | 99.00% | 28.15% | 84.45% | 42.23% | 70.38% | 50.67% | 61.93% | 56.30% |
| Example 22 - Ingredient Family 22 | | | | | | | | | | |
| LFO | LFO | 5.01% | 99.00% | 25.07% | 75.20% | 37.60% | 62.66% | 45.12% | 55.14% | 50.13% |
| BSO (Black Seed Oil) | BSO | 4.99% | 99.00% | 24.94% | 74.81% | 37.40% | 62.34% | 44.88% | 54.86% | 49.87% |
| Example 23 - Ingredient Family 23 | | | | | | | | | | |
| LFO | LFO | 8.01% | 99.00% | 40.05% | 99.00% | 60.07% | 99.00% | 72.08% | 88.10% | 80.09% |
| BSO (Black Seed Oil) | BSO | 1.99% | 59.73% | 9.96% | 29.87% | 14.93% | 24.89% | 17.92% | 21.90% | 19.91% |

Example 1

Pesticidal Effect on *Culex quinquefasciatus*

The effect of compositions, and their individual ingredients, on the mortality of insects is tested. Multiple plexiglass chambers are used. A treatment chamber is provided for each composition and ingredient that is tested, and the chambers are sprayed (aerosol spray) evenly on all surfaces with the composition or ingredient being tested. A control chamber is provided that is not treated.

Southern house mosquitoes, *Culex quinquefasciatus*, are obtained as test organisms. Multiple laboratory-cultured, sucrose-fed female mosquitoes aged about 2-5 days are released into the glass chambers prior to the spraying of aerosol. The discharge rate (gm/second) of each can of aerosol to be tested is predetermined. Based on the dosage required, an estimated time of spray of aerosol is discharged into the glass chamber.

Knockdown of mosquitoes is observed at indicated intervals up to about 20 minutes. After about 20 minutes, all mosquitoes are collected and placed in cylindrical polyethylene containers with 10% sucrose pads. Mortality is observed 4 hours post-treatment. The mortality value is based on a combination of dead and moribund mosquitoes over the total number of mosquitoes initially released.

The data from an exemplary study is shown in Table 7. The study tested: (1) a composition comprising Pyrethrum and Blend 4; (2) Pyrethrum; (3) BSO; and (4) LFO (IFF Inc., Hazlet, N.J.). The percent mortality of the mosquitoes treated with the composition was 100%, compared to 60% for BSO alone, 80% for LFO alone, 90% for Pyrethrum alone, and 0% for the non-treated control. Blend 4 is exemplified in Ingredient Family 23 in Table 6.

TABLE 7

| | Mosquitoes | | |
|---|---|---|---|
| | # Added to Chamber | # Dead after 4 hours | % Mortality |
| Control | 50 | 0 | 0% |
| BSO | 50 | 30 | 60% |
| LFO | 50 | 40 | 80% |
| Pyrethrum | 50 | 45 | 90% |

TABLE 7-continued

| | Mosquitoes | | |
|---|---|---|---|
| | # Added to Chamber | # Dead after 4 hours | % Mortality |
| Composition (Pyrethrum and Blend 4) | 50 | 50 | 100% |

Example 2

Synergistic Compositions as Indicated by TyR Binding Inhibition

When the chemical(s) and compound(s) are combined to provide the compositions of the present invention, there is a synergistic effect. The efficacy for insect control and the synergistic effect of compositions can be predicted and demonstrated in a variety of manners, for example, a competition binding assay can be used. With reference to Table 8, the percent TyrR binding inhibition affected by the following agents was determined using a competition binding assay: the natural ligand, Tyramine (TA); Blend 7 (exemplified in Ingredient Family 5 of Table 6); Blend 12 (exemplified in Ingredient Family 9 of Table 6); DM; Pyrethrum; 90:1 Blend 7+DM; 9:1 Blend 7+Pyrethrum; 90:1 Blend 12+DM; and 9:1 Blend 12+Pyrethrum.

TABLE 8

| Agent | % TyrR Binding Inhibition |
|---|---|
| Tyramine (TA) | 75 |
| Blend 7 | 30 |
| Blend 12 | 60 |
| DM | 10 |
| Pyrethrum | 5 |
| 90:1 Blend 7 + DM | 50 |
| 9:1 Blend 7 + Pyrethrum | 60 |
| 90:1 Blend 12 + DM | 60 |
| 9:1 Blend 12 + Pyrethrum | 60 |

One example of an synergistic effect shown by this study is as follows: the insect control chemical, Pyrethrum, only has a 5% TyrR binding inhibition, and Blend 7 only has a 30% TyrR binding inhibition; however, when Pyrethrum and Blend 7 are combined, the TyrR binding inhibition increases to 60%, approaching that of the natural ligand.

Example 3

Pesticidal Effect Against *Blattella germanica*

With reference to Table 9, the pesticidal effect against *Blattella germanica* (German cockroaches) was determined for DM, Blend 12 (exemplified in Ingredient Family 9 of Table 6), and the composition including deltamethrin (DM) and Blend 12. Treatment with DM alone resulted in an average knock down (KD) of the insects in 120 sec, and 100% killing of the insects in 15 minutes. Treatment with Blend 12 alone resulted in an average KD of the insects in 20 sec, and 100% killing of the insects in 5 minutes. A synergistic effect was shown for the combination treatment that resulted in an average KD of the insects in 5 sec, and 100% killing of the insects in 55 seconds. The composition including Blend 12 and DM was shown to be effective and was shown to have a synergistic effect. Additionally, the above-described methods, including competition receptor binding assays, assessments of changes in cAMP, and assessments of changes in $Ca^{2+}$, are confirmed to be effective at predicting and demonstrating the synergistic effect of and the efficacy of the composition.

TABLE 9

Efficacy of DM and Blend 12 against German cockroaches

| Chemicals | Bioactivity | |
|---|---|---|
| | KD | 100% Kill |
| DM (0.037 mg/cm$^2$) (17 ptl of 16.99% formulated DM) | 120 sec | 15 min |
| Blend 12 (1.9 mg/cm$^2$) | 20 sec | 5 min |
| Composition (1.9 mg/cm$^2$) (1 part DM:9 parts Blend 12 (v/v)) | 5 sec | 55 sec |

Example 4

Pesticidal Effect Against *Aedes aegypti*

Figure 4A:
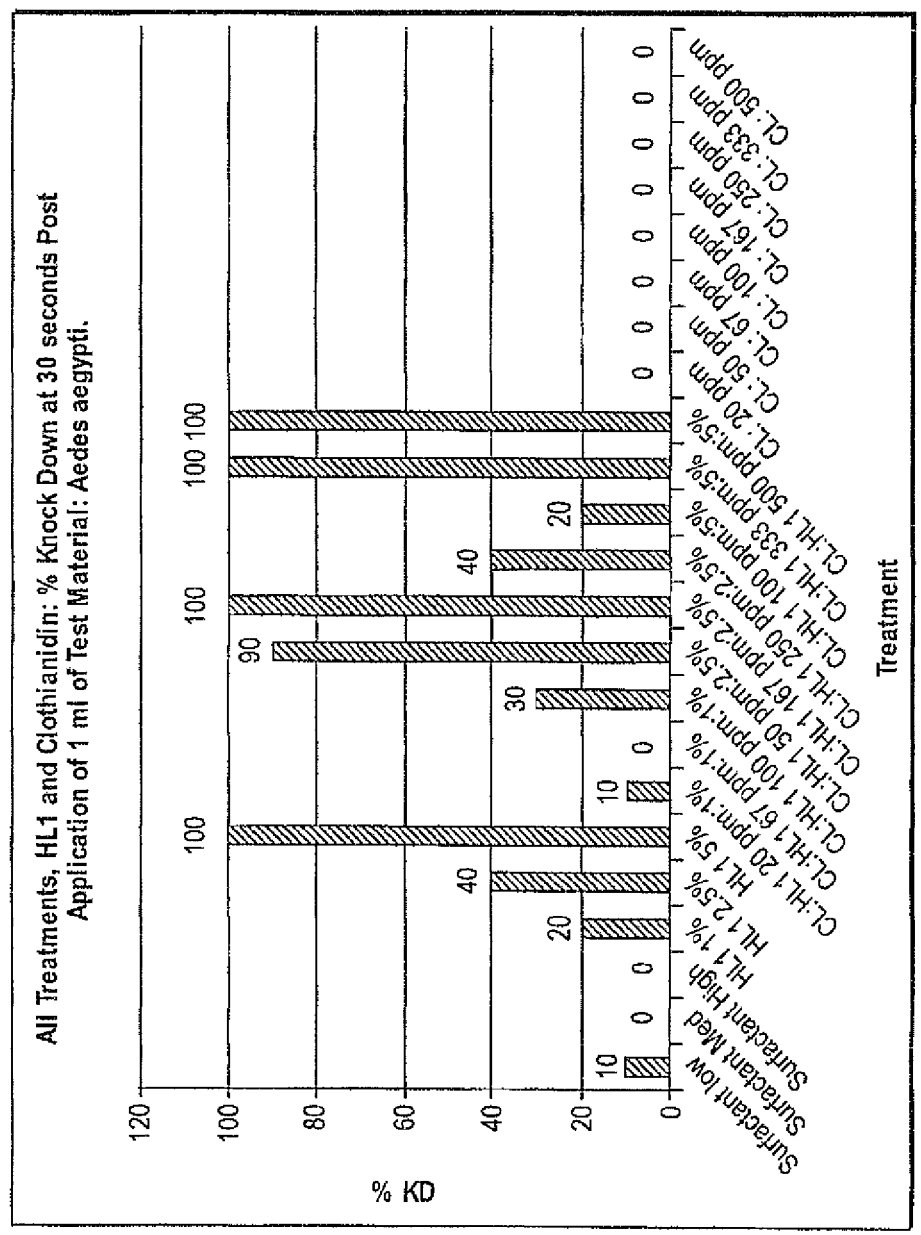
FIG. 4A shows a pesticidal effect against *Aedes aegypti* caused by 1) a test composition; 2) clothianidin; and 3) a combination of a test composition and clothianidin.

With reference to FIG. 4A, the pesticidal effect against *Aedes aegypti* was determined for Blend 19 (labeled "HL1", exemplified in Ingredient Family 15 in Table 6) and the composition including clothianidin (CL) and Blend 19. Treatment with CL alone at 500 ppm resulted in no KD of the target insect, however treatment with CL at 167 ppm combined with 2.5% Blend 19 resulted in 100% KD. The composition including Blend 19 and CL was shown to be effective and was shown to have a synergistic effect.

Figure 4B:
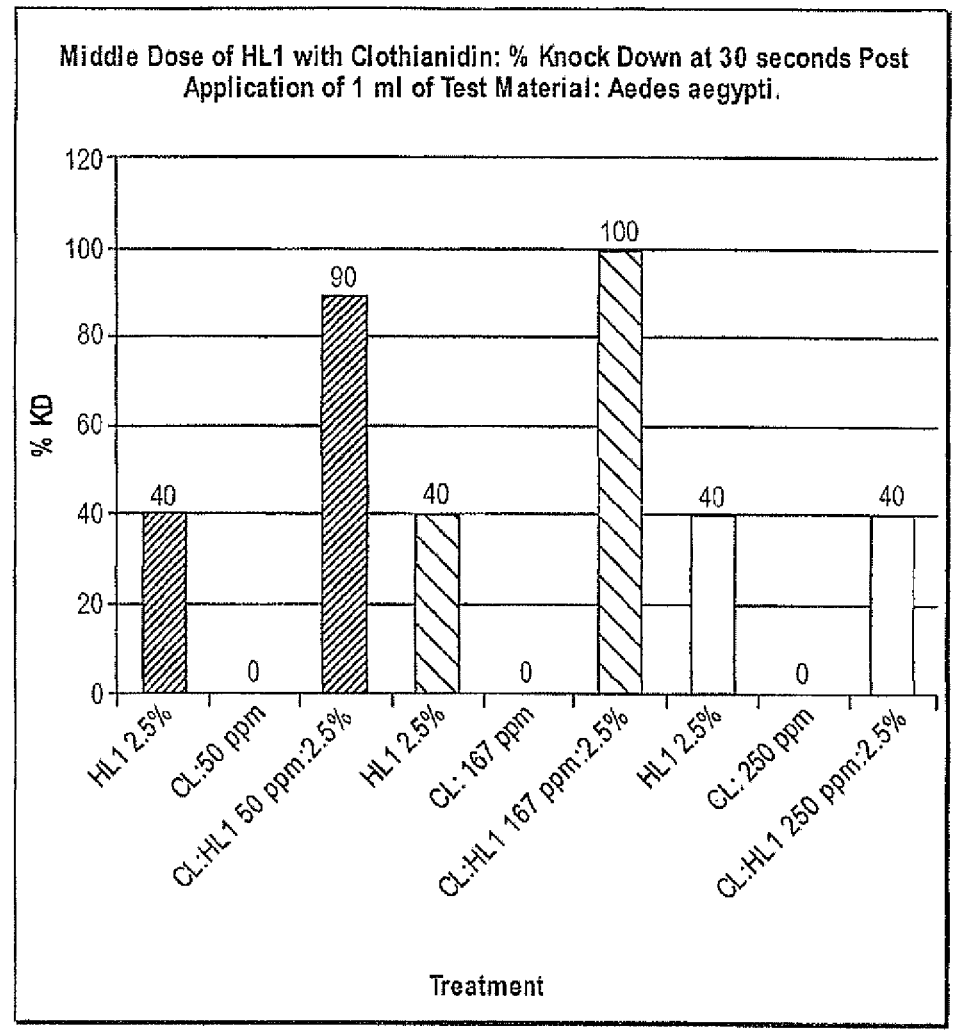
FIG. 4B shows a pesticidal effect against *Aedes aegypti* caused by 1) a test composition; 2) clothianidin; and 3) a combination of a test composition and clothianidin.

Similarly, with reference to FIG. 4B, the pesticidal effect against *Aedes aegypti* was determined for Blend 19 (labeled "HL1") and the composition including CL and Blend 19. Treatment with CL alone at 250 ppm resulted in no KD of the target insect, however treatment with CL at 167 ppm combined with 2.5% Blend 19 resulted in 100% KD. The composition including Blend 19 and CL was shown to be effective and was shown to have a synergistic effect.

Figure 4C:
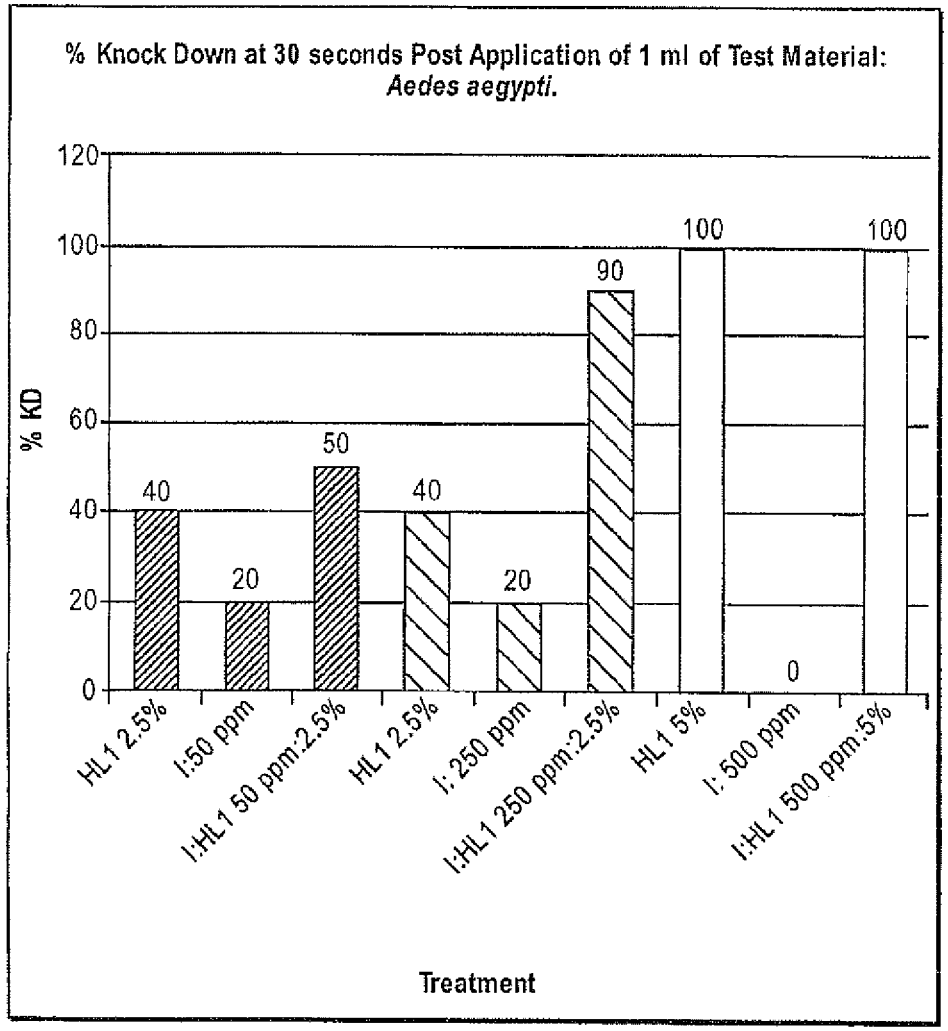
FIG. 4C shows a pesticidal effect against *Aedes aegypti* caused by 1) a test composition; 2) imidacloprid; and 3) a combination of a test composition and imidacloprid.

Similarly, with reference to FIG. 4C, the pesticidal effect against *Aedes aegypti* was determined for Blend 19 (labeled "HL1") and the composition including Imidacloprid and Blend 19. Treatment with Imidacloprid alone at 250 ppm resulted in 20% KD of the target insect at 30 seconds post-treatment, while treatment with 2.5% Blend 19 alone resulted in 40% KD of the target insect at 30 seconds post-treatment. However treatment with Imidacloprid at 250 ppm combined with 2.5% Blend 19 resulted in 90% KD at 30 seconds post-treatment. The composition including Blend 19 and CL was shown to be effective and was shown to have a synergistic effect.

Figure 4D:
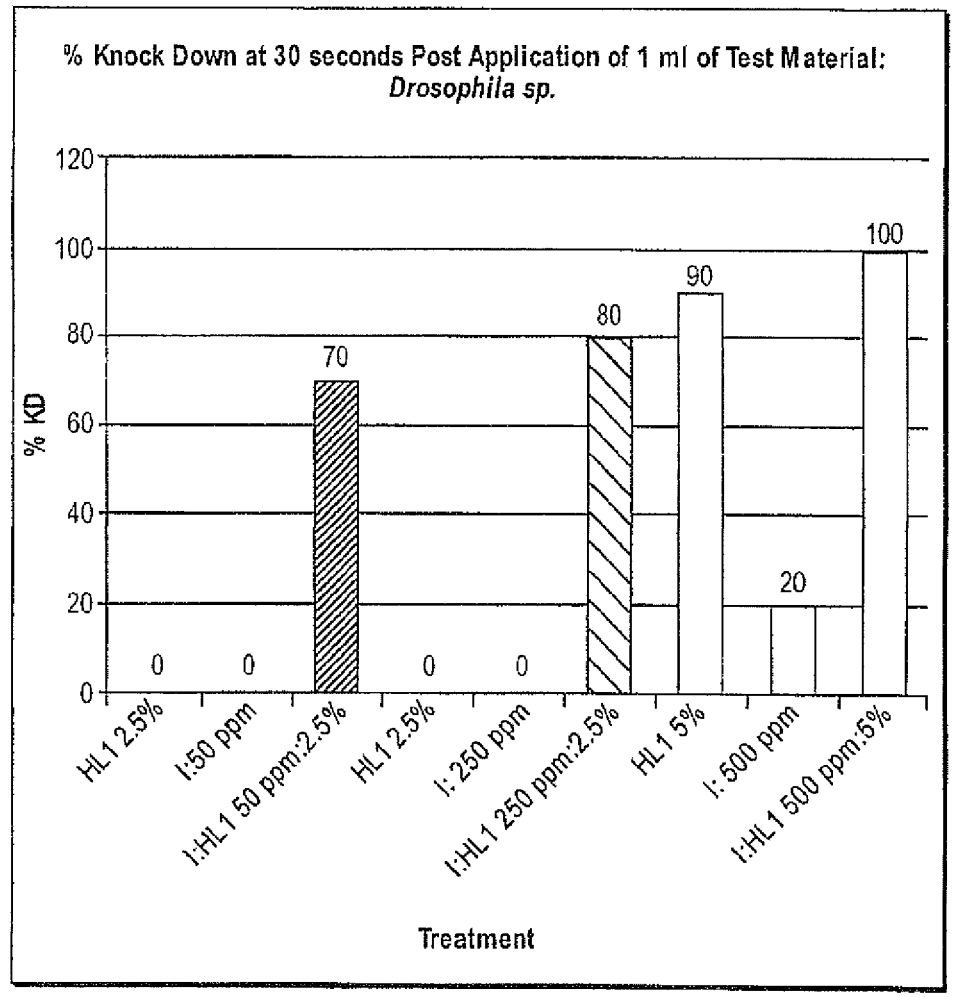
FIG. 4D shows a pesticidal effect against *Drosophila* sp. caused by 1) a test composition; 2) imidacloprid; and 3) a combination of a test composition and imidacloprid.

Similarly, with reference to FIG. 4D, the pesticidal effect against *Drosophila* sp. was determined for Blend 19 (labeled "HL1") and the composition including Imidacloprid and Blend 19. Treatment with Imidacloprid alone at 50 ppm resulted in 0% KD of the target insect at 30 seconds post-treatment, while treatment with 2.5% Blend 19 alone also resulted in 0% KD of the target insect at 30 seconds post-treatment. However treatment with Imidacloprid at 50 ppm combined with 2.5% Blend 19 resulted in 70% KD at 30 seconds post-treatment. The composition including Blend 19 and CL was shown to be effective and was shown to have a synergistic effect.

Example 5

Pesticidal Effect Against *Aedes aegypti*

Figure 5:
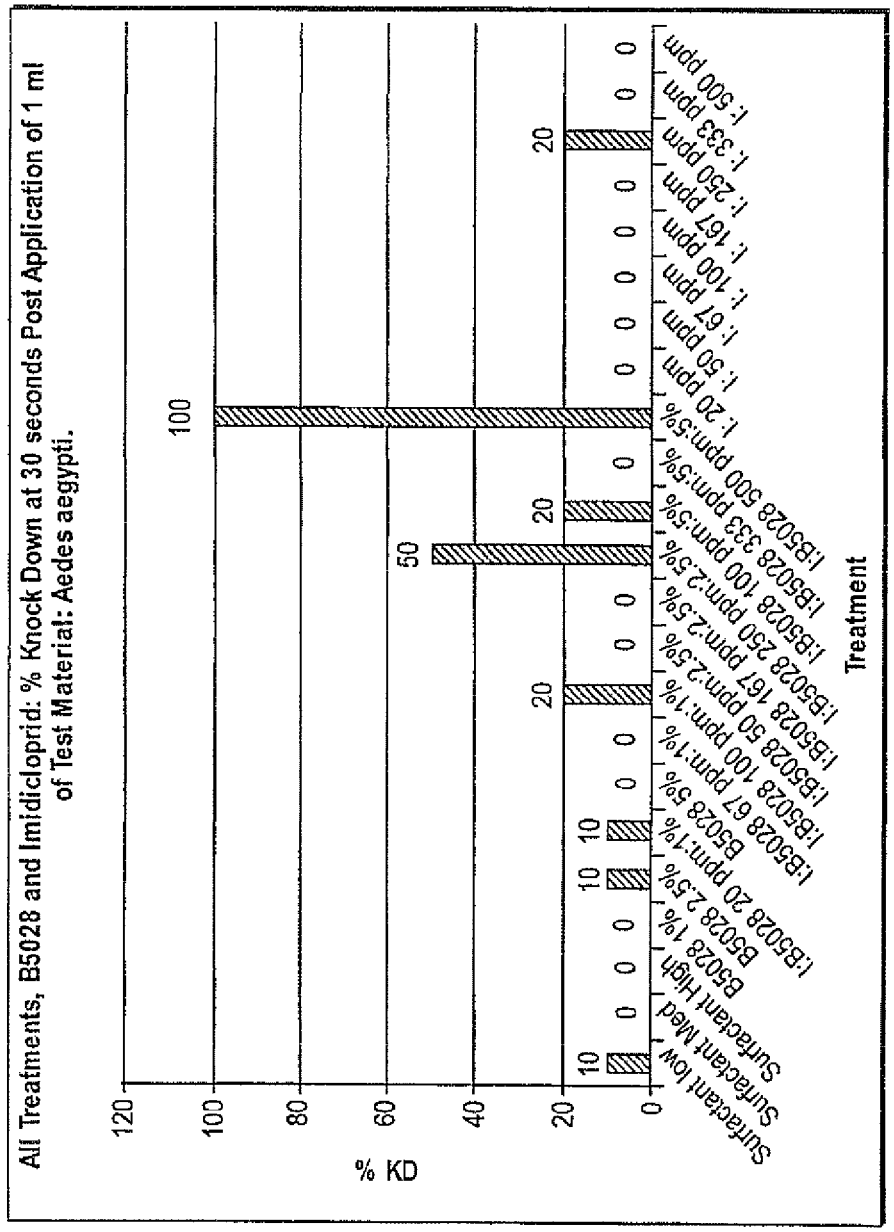
FIG. 5 shows a pesticidal effect against *Aedes aegypti* caused by 1) a test composition; 2) imidacloprid; and 3) a combination of a test composition and imidacloprid.

With reference to FIG. 5, the pesticidal effect against *Aedes aegypti* was determined for Blend 11 (labeled "B5028", exemplified in Ingredient Family 2 in Table 6) and the composition including Imidacloprid (labeled "I") and B5028. Treatment with Imidacloprid alone at 500 ppm resulted in no KD of the target insect, and treatment with B5028 at 5% showed 10% KD of the target. However treatment with Imidacloprid at 500 ppm combined with B5028 at 5% resulted in 100% KD. The composition including B5028 and imidacloprid was shown to be effective and was shown to have a synergistic effect.

Example 6

Comparison of Pesticidal Effects

Similarly, with reference to Table 10, the pesticidal effect against German cockroaches was determined for deltamethrin (DM), Blend 7 (exemplified in Ingredient Family 5 of Table 6), and the composition including DM and Blend 7. Treatment with DM alone resulted in an average KD of the insects in 140 sec, and 100% killing of the insects in 12 minutes. Treatment with Blend 7 alone resulted in an average KD of the insects in 10 sec, and 100% killing of the insects in 45 seconds. A synergistic effect was shown for the combination treatment that results in an average KD of the insects in 5 sec, and 100% killing of the insects in 17 seconds. The composition including Blend 7 and DM was shown to be effective and was shown to have a synergistic effect. The above-described methods, including competition receptor binding assays, assessments of changes in cAMP, and assessments of changes in $Ca^{2+}$, were confirmed to be effective at predicting and demonstrating the synergistic effect of and the efficacy of the composition.

TABLE 10

Efficacy of DM and Blend 7 against German cockroaches

| Chemicals | Bioactivity | |
|---|---|---|
| | KD | 100% Kill |
| DM (0.037 mg/cm$^2$) (17 µl of 16.99% formulated DM) | 140 sec | 12 min |
| Blend 7 (3.8 mg/cm$^2$) | 10 sec | 45 sec |

TABLE 10-continued

Efficacy of DM and Blend 7 against German cockroaches

| Chemicals | Bioactivity | |
|---|---|---|
| | KD | 100% Kill |
| Composition (3.8 mg/cm$^2$) (1 part DM:99 parts Blend 7 (v/v)) | 5 sec | 17 sec |

Example 7

Comparison of Pesticidal Effects

With reference to Table 11, the pesticidal effect against Darkling Beetles was determined for Pyrethrum, Blend 12 (exemplified in Ingredient Family 9 of Table 6), and the composition including Pyrethrum and Blend 12.

TABLE 11

Efficacy of Pyrethrum and Blend 12 against Darkling Beetles

| | % Mortality after Application by direct spray to Darkling Beetle | | | |
|---|---|---|---|---|
| Test Material | Day 1 | Day 4 | Day 8 | Day 12 |
| Vehicle Control (Water) | 0 ± 0% | 0 ± 0% | 5 ± 7% | 5 ± 7% |
| 4% Blend 12 | 15 ± 5% | 40 ± 13% | 55 ± 10% | 80 ± 0% |
| 4% Pyrethrum | 0 ± 0% | 10 ± 10% | 20 ± 19% | 30 ± 28% |
| 2% Blend 12 and 2% Pyrethrum | 25 ± 13% | 45 ± 17% | 80 ± 14% | 100 ± 0%** |

Values displayed are the mean plus or minus the standard deviation for 4 replicates of 10 insects each, except vehicle control-(2 replicates of 10 insects each).
**Significantly greater than all other values for mortality (P < 0.001, 2 tail student t Test)

The synergistic effect can be altered by changing the specific combinations of ingredients or changing the specific ratios of ingredients.

Example 8

Pesticidal Effect Against *Periplaneta americana*

Figure 6A:
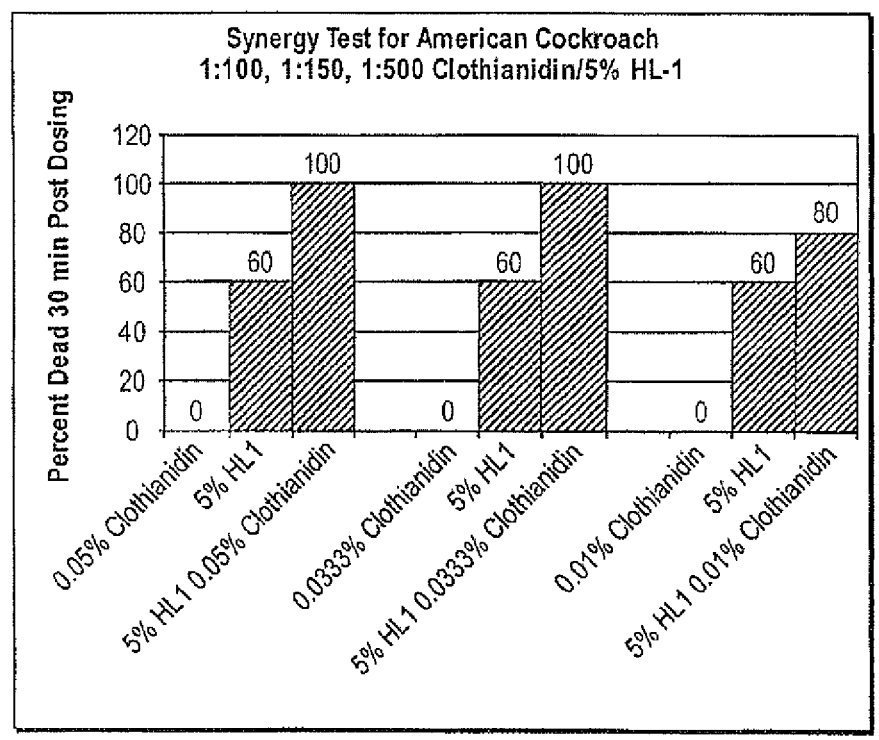
FIG. 6A shows a pesticidal effect against *Periplaneta americana* caused by 1) a test composition; 2) clothianidin; and 3) a combination of a test composition and clothianidin.

With reference to FIG. 6A, the pesticidal effect against *Periplaneta americana* was determined for Blend 19 (labeled "HL1", exemplified in Ingredient Family 15 in Table 6) and the composition including clothianidin (CL) and Blend 19. Treatment with CL alone at 0.05% resulted in no mortality of the target insect at 30 minutes post-treatment, while treatment with Blend 19 at 5% resulted in 60% target mortality 30 minutes post-treatment. However treatment with CL at 0.05% combined with 5% Blend 19 resulted in 100% mortality 30 minutes post-treatment. The composition including Blend 19 and CL was shown to be effective and was shown to have a synergistic effect.

Figure 6B:
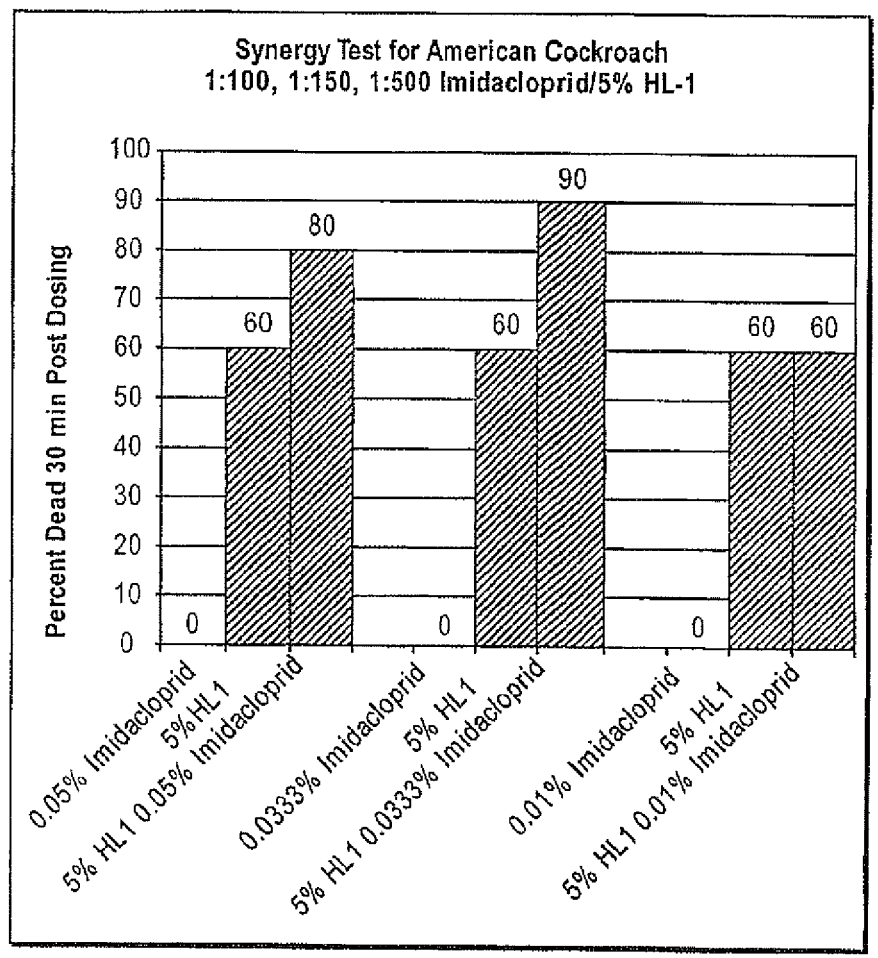
FIG. 6B shows a pesticidal effect against *Periplaneta americana* caused by 1) a test composition; 2) imidacloprid; and 3) a combination of a test composition and imidacloprid.

With reference to FIG. 6B, the pesticidal effect against *Periplaneta americana* was determined for Blend 19 (labeled "HL1") and the composition including Imidacloprid and Blend 19. Treatment with Imidacloprid alone (at 0.05%, 0.033%, and 0.01%) resulted in no mortality of the target insect at 30 minutes post-treatment, while treatment with Blend 19 at 5% resulted in 60% target mortality 30 minutes post-treatment. However treatment with Imidacloprid at 0.033% combined with 5% Blend 19 resulted in 90% mortality 30 minutes post-treatment. The composition including Blend 19 and Imidacloprid was shown to be effective and was shown to have a synergistic effect.

Example 9

Pesticidal Effect Against Bed Bugs

Figure 7:
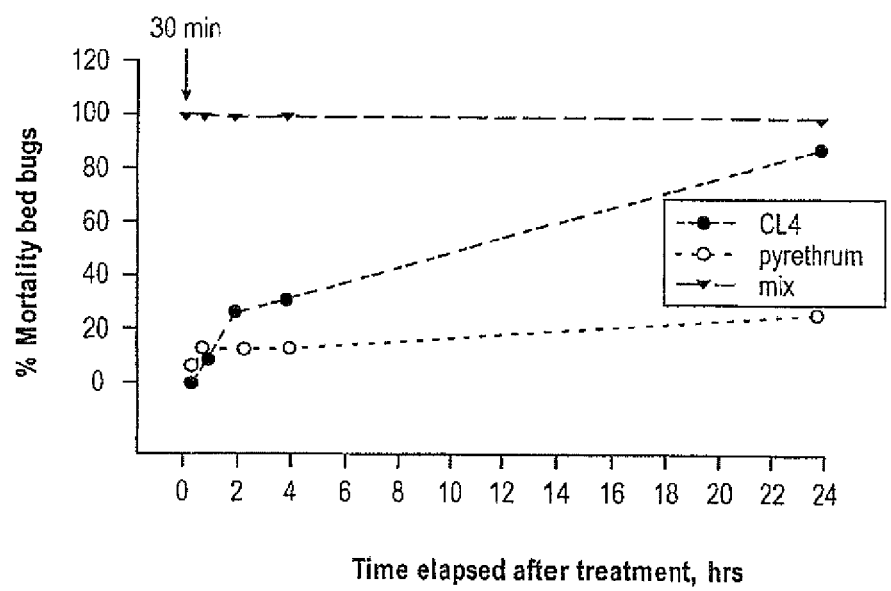
FIG. 7 shows a pesticidal effect against bed bugs caused by 1) a test composition; 2) pyrethrum; and 3) a combination of a test composition and pyrethrum.

Turning now to FIG. 7 showing the pesticidal effect against bed bugs expressed as percent mortality as a function of time, the 1:1 ratio composition was shown to have a synergistic effect, when compared to the pesticidal effect of Blend 12 (labeled as "CL-4", exemplified in Ingredient Family 9 in Table 6) or Pyrethrum alone. The pyrethrum alone did not achieve higher than about 30% mortality, and Blend 12 alone did not achieve higher than about 80% mortality. However, the 1:1 ratio composition including Blend 12 and Pyrethrum resulted in 100% mortality, as early as about 30 minutes after treatment, and had a residual effect lasting up to about 24 hours after treatment.

Example 10

Pesticidal Effects of a Combination of Blend 11 with Imidacloprid Against Thrips Thrips were exposed to three different groups of compositions. Both knockdown (KD) and mortality were measured at indicated time intervals. Knockdown of target pests is measured in a plexilglass chamber at indicated intervals. Mortality of target pests is measured in cylindrical polyethylene containers with 10% sucrose pads. The mortality value is based on a combination of dead and moribund pests over the total number of pests initially released. The KD and mortality measurements were made at 5 minutes, 30 minutes, 1 hour, 2 hours, 4 hours and 24 hours post treatment.

Figure 9:
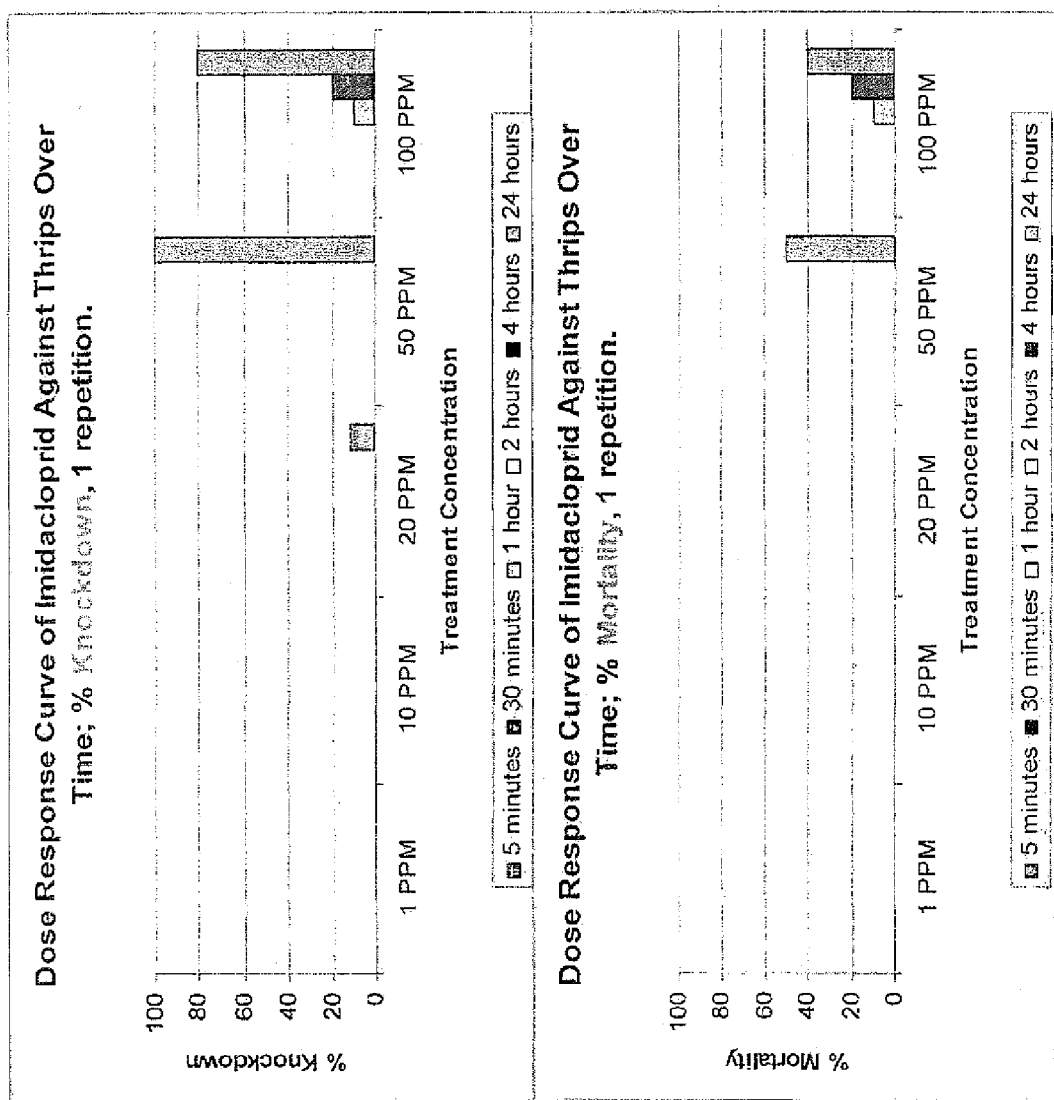
FIG. 9 shows dose dependent pesticidal effects (knockdown and mortality) of imidacloprid against thrips over time.

With reference to FIG. 9, the first group of compositions contained imidacloprid at 1 ppm, 10 ppm, 20 ppm, 50 ppm and 100 ppm. Treatment with imidacloprid alone at 1 ppm or 10 ppm resulted in no KD of the thrips till the end of the experiment at 24 hours post treatment. Treatment with imidacloprid alone at 20 ppm resulted in 12% KD of the thrips at 24 hours post treatment. Treatment with imidacloprid alone at 50 ppm resulted in 100% KD of the thrips at 24 hours post treatment. Treatment with imidacloprid alone at 100 ppm resulted in 10%, 20% and 80% KD of the thrips at 2 hours, 4 hours and 24 hours post treatment, respectively. Moreover, treatment with imidacloprid alone at 1 ppm, 10 ppm or 20 ppm resulted in no mortality of the thrips till the end of the experiment at 24 hours post treatment. Treatment with imidacloprid alone at 50 ppm resulted in 50% mortality of the thrips at 24 hours post treatment. Treatment with imidacloprid alone at 100 ppm resulted in 10%, 20% and 40% mortality of the thrips at 2 hours, 4 hours and 24 hours post treatment, respectively.

The composition of Blend 11 is exemplified in Ingredient Family 17 in Table 6.

With reference to FIG. 10A, the second group of compositions contained Blend 11 at 0.01%, 0.1%, 0.2%, 0.5% and 1% by volume. Treatment with Blend 11 alone at 0.1% by volume resulted in no KD of the thrips till the end of the experiment at 24 hours post treatment. Treatment with Blend 11 alone at 0.01%, 0.2%, 0.5% and 1% by volume resulted in 12%, 20%, 36% and 50% KD of the thrips at 24 hours post-treatment, respectively. Moreover, as shown in FIG. 10B, treatment with Blend 11 alone at 0.1% by volume resulted in no mortality of the thrips till the end of the experiment at 24 hours post treatment. Treatment with Blend 11 alone at 0.01%, 0.2%, 0.5% and 1% by volume resulted in 12%, 20%, 36% and 37% mortality of the thrips at 24 hours post treatment, respectively.

Figure 11:
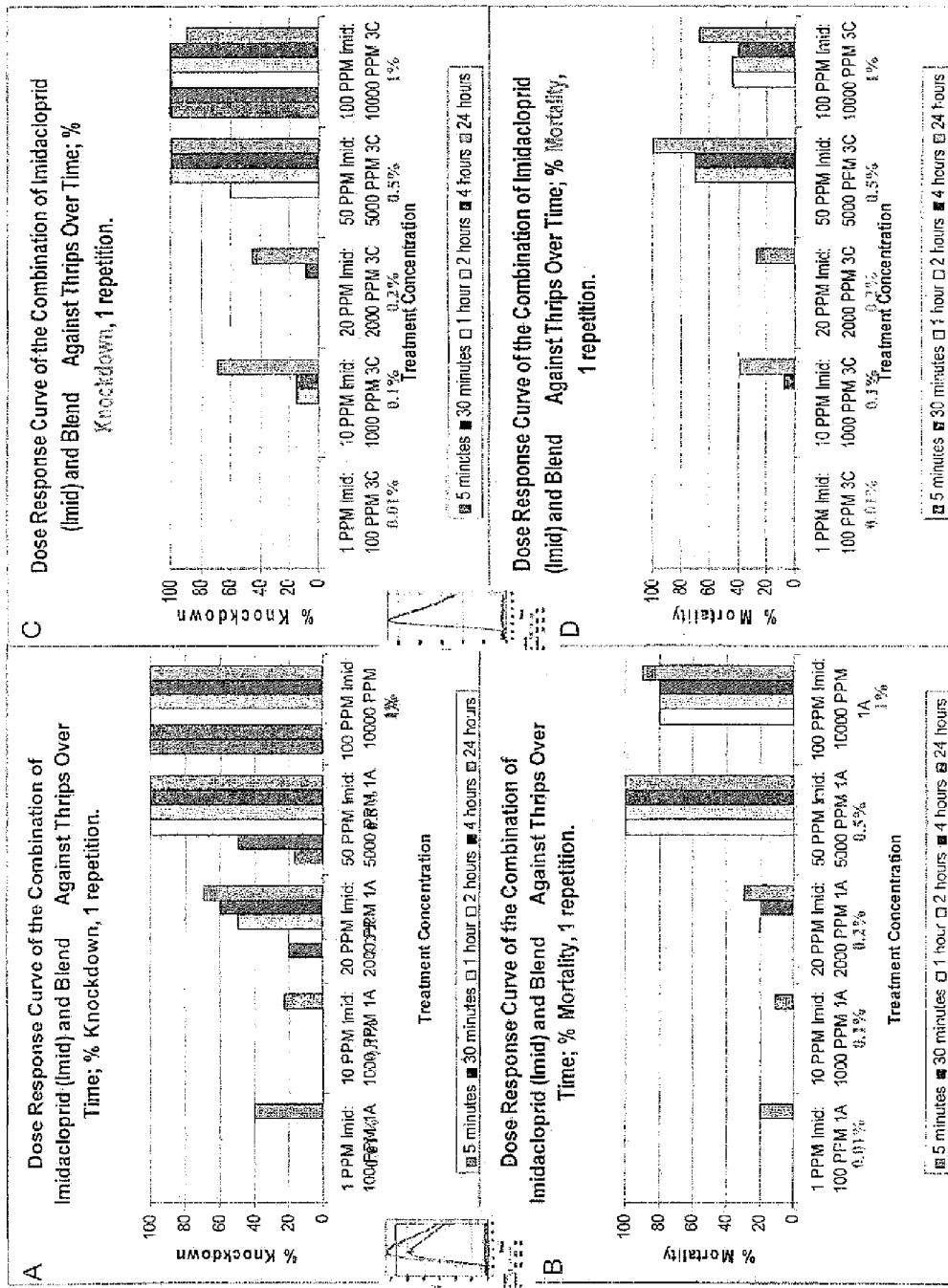
FIG. 11A shows shows a dose dependent pesticidal effect (knockdown) against thrips caused by a composition containing the mixture of Blend 11 and imidacloprid.
FIG. 11B shows shows a dose dependent pesticidal effect (mortality) against thrips caused by a composition containing the mixture of Blend 11 and imidacloprid.
FIG. 11C shows a dose dependent pesticidal effect (knockdown) against thrips caused by a composition containing the mixture of Blend 8 and imidacloprid.
FIG. 11D shows shows a dose dependent pesticidal effect (mortality) against thrips caused by a composition containing the mixture of Blend 8 and imidacloprid.

With reference to FIGS. 11A and B, the third group of compositions contained a mixture of Blend 11 and imidacloprid at 100:1 by volume. The concentration of Blend 11 was 0.01%, 0.1%, 0.2%, 0.5% and 1% by volume, respectively.

As shown in FIG. 11A, treatment with the composition with the mixture of Blend 11 at 0.01% and 0.1% by volume and imidacloprid resulted in 40% and 22% KD of the thrips at 24 hours post-treatment, respectively. Treatment with the composition with the mixture of Blend 11 at 0.2% by volume and imidacloprid resulted in 20%, 20%, 50%, 60% and 70% KD of the thrips at 30 minutes, 1 hours, 2 hours, 4 hours and 24 hours post treatment, respectively. Treatment with the composition with the mixture of Blend 11 at 0.5% by volume and imidacloprid resulted in 18% and 50% KD of the thrips at 5 minutes and 30 minutes post treatment, respectively, and 100% KD between 1 hour and 24 hours post treatment, respectively. Treatment with the composition with the mixture of Blend 11 at 1% by volume and imidacloprid resulted in 100% KD between 5 minutes and 24 hours post treatment. Moreover, as shown in FIG. 11B, treatment with the composition with the mixture of Blend 11 at 0.01% and 0.1% by volume and imidacloprid resulted in 20% and 10% mortality of the thrips at 24 hours post-treatment, respectively. Treatment with the composition with the mixture of Blend 11 at 0.2% by volume and imidacloprid resulted in 20% and 30% mortality of the thrips at 4 hours and 24 hours post-treatment, respectively. Treatment with the composition with the mixture of Blend 11 at 0.5% by volume and imidacloprid resulted in 100% mortality of the thrips between 1 hour and 24 hours post treatment. Treatment with the composition with the mixture of Blend 11 at 1% by volume and imidacloprid resulted in 80% mortality of the thrips between 1 hours and 4 hours post treatment, and 90% mortality at 24 hours post treatment.

These results demonstrate that the combination of imidacloprid and Blend 11 is effective and has a synergistic effect.

Example 11

Pesticidal Effects of a Combination of Blend 8 with Imidacloprid Against Thrips

Thrips were exposed to three different groups of compositions. Both knockdown (KD) and mortality were measured as described in Example 10 at 5 minutes, 30 minutes, 1 hour, 2 hours, 4 hours and 24 hours post treatment. The composition of Blend 8 is exemplified in Ingredient Family 21 in Table 6.

With reference to FIG. 9, the first group of compositions contained imidacloprid at 1 ppm, 10 ppm, 20 ppm, 50 ppm and 100 ppm, as discussed in Example 10.

With reference to FIG. 10C, the second group of compositions contained Blend 8 at 0.01%, 0.1%, 0.2%, 0.5% and 1% by volume. Treatment with Blend 8 alone at 0.2% by volume resulted in 20% KD of the thrips at 24 hours post-treatment. Treatment with Blend 8 alone at 0.01%, 0.1%, 0.5% and 1% by volume resulted in no KD of the thrips till the end of the experiment at 24 hours post treatment, respectively. Moreover, as shown in FIG. 10D treatment with Blend 8 alone at all concentrations tested resulted in no mortality of the thrips till the end of the experiment at 24 hours post treatment.

With reference to FIGS. 11C and D, the third group of compositions contained a mixture of Blend 8 and imidacloprid at 100:1 by volume. The concentration of Blend 8 was 0.01%, 0.1%, 0.2%, 0.5% and 1% by volume, respectively.

As shown in FIG. 11C, treatment with the composition with the mixture of Blend 8 at 0.01% by volume and imidacloprid resulted in no KD of the thrips till the end of the experiment at 24 hours post treatment. Treatment with the composition with the mixture of Blend 8 at 0.1% by volume and imidacloprid resulted in 17%, 17% and 70% KD of the thrips at 2 hours, 4 hours and 24 hours post treatment, respectively. Treatment with the composition with the mixture of Blend 8 at 0.2% by volume and imidacloprid resulted in 8% and 43% KD of the thrips at 4 hours and 24 hours post treatment, respectively. Treatment with the composition with the mixture of Blend 8 at 0.5% by volume and imidacloprid resulted in 60% KD of the thrips at 1 hour post treatment, and 100% KD between 2 hours and 24 hours post treatment, respectively. Treatment with the composition with the mixture of Blend 8 at 1% by volume and imidacloprid resulted in 100% KD between 5 minutes and 4 hours post treatment, respectively, and 90% KD at 24 hours post treatment. Moreover, as shown in FIG. 11D treatment with the composition with the mixture of Blend 8 at 0.01% by volume and imidacloprid resulted in no mortality of the thrips till the end of the experiment at 24 hours post treatment. Treatment with the composition with the mixture of Blend 8 at 0.1% by volume and imidacloprid resulted in 8% and 40% mortality of the thrips at 4 hours and 24 hours post treatment, respectively. Treatment with the composition with the mixture of Blend 8 at 0.2% by volume and imidacloprid resulted in 28% mortality of the thrips at 24 hours post treatment. Treatment with the composition with the mixture of Blend 8 at 0.5% by volume and imidacloprid resulted in 70%, 70% and 100% mortality of the thrips at 2 hours, 4 hours and 24 hours post treatment, respectively. Treatment with the composition with the mixture of Blend 8 at 1% by volume and imidacloprid resulted in 44%, 44%, 40% and 68% mortality of the thrips at 1 hour, 2 hours, 4 hours and 24 hours post treatment, respectively.

These results demonstrate that the combination of imidacloprid and Blend 8 is effective and has a synergistic effect.

Example 12

Pesticidal Effects of a Combination of Blend 38 with Imidacloprid Against Thrips Thrips were exposed to three different groups of compositions. Both knockdown (KD) and mortality were measured as described in Example 10 at 1 hour, 2 hours, 4 hours and 24 hours post treatment. Blend 38 (label "B5049" and "TT 1A") is exemplified in Ingredient Family 12 in Table 6.

Figure 12:
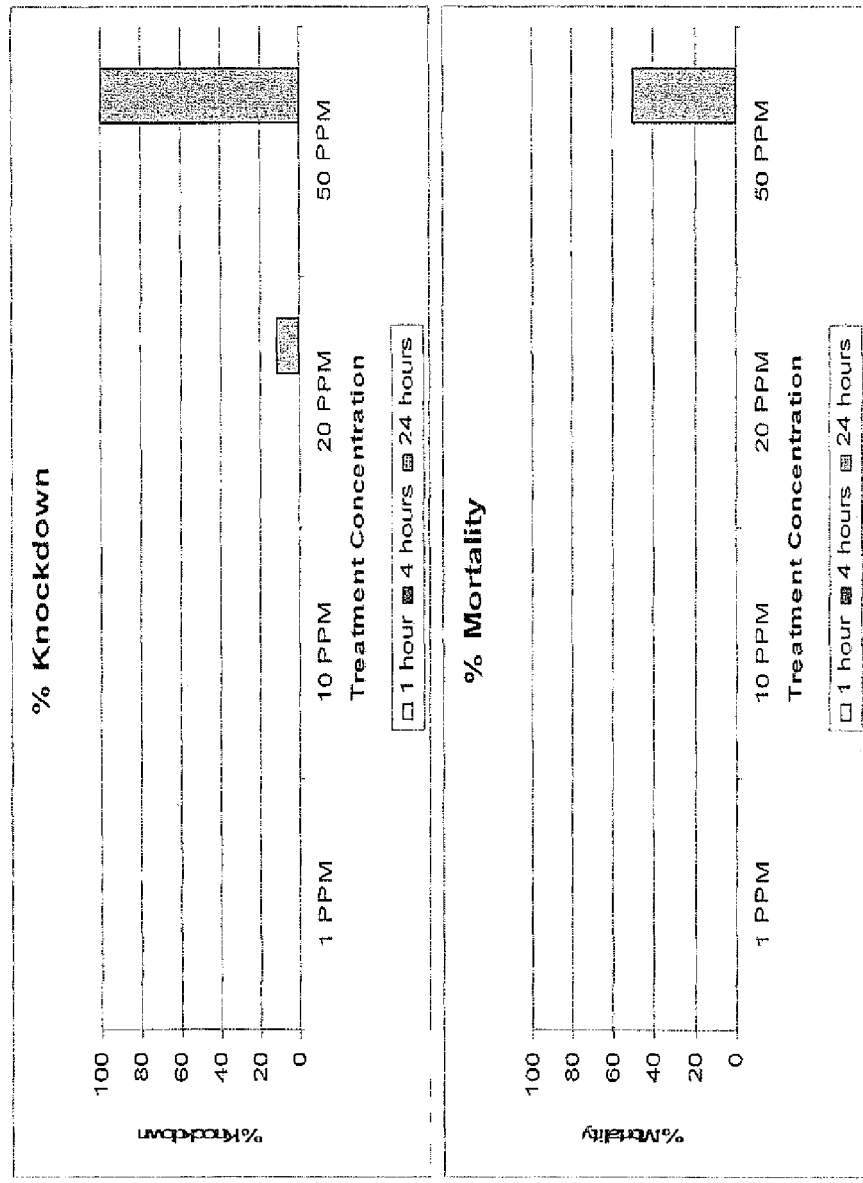
FIG. 12 shows dose dependent pesticidal effects (knockdown and mortality) of imidacloprid against thrips over time.

With reference to FIG. 12, the first group of compositions contained imidacloprid at 1 ppm, 10 ppm, 20 ppm, and 50 ppm. Treatment with imidacloprid alone at 1 ppm or 10 ppm resulted in no KD of the thrips till the end of the experiment at 24 hours post treatment. Treatment with imidacloprid alone at 20 ppm resulted in 12% KD of the thrips at 24 hours post treatment. Treatment with imidacloprid alone at 50 ppm resulted in 100% KD of the thrips at 24 hours post treatment. Moreover, treatment with imidacloprid alone at 1 ppm, 10 ppm or 20 ppm resulted in no mortality of the thrips till the end of the experiment at 24 hours post treatment. Treatment with imidacloprid alone at 50 ppm resulted in 50% mortality of the thrips at 24 hours post treatment.

Figure 13:
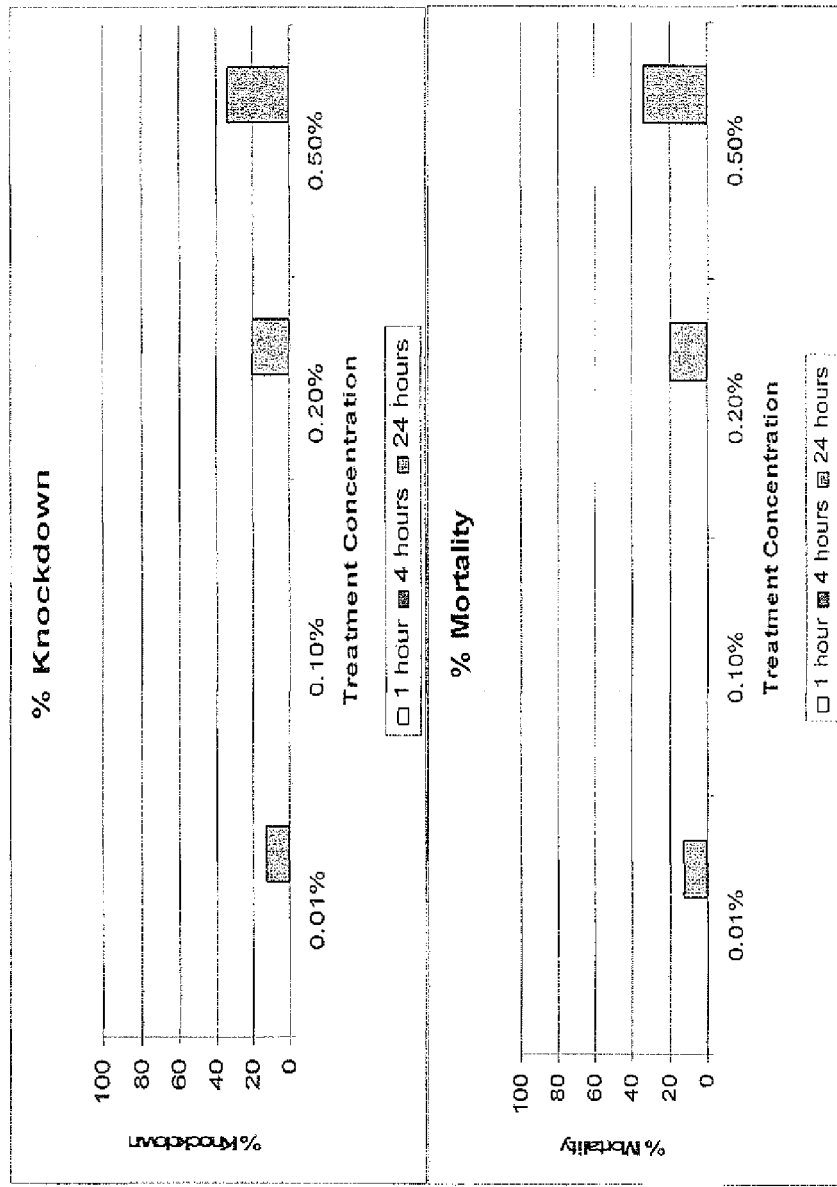
FIG. 13 shows dose dependent pesticidal effects (knockdown and mortality) of Blend 38 (labeled "B5049") against thrips over time.

With reference to FIG. 13, the second group of compositions contained Blend 38 (labeled "B5049") at 0.01%, 0.10%, 0.20%, and 0.50% by volume. Treatment with Blend 38 alone at 0.10% by volume resulted in no KD of the thrips till the end of the experiment at 24 hours post treatment. Treatment with Blend 38 alone at 0.01%, 0.20% and 0.50% by volume resulted in 12%, 20% and 37% KD of the thrips at 24 hours post treatment, respectively. Moreover, treatment with Blend 38 alone at 0.10% by volume resulted in no mortality of the thrips till the end of the experiment at 24 hours post treatment. Treatment with Blend 38 alone at 0.01%, 0.20% and 0.50% by volume resulted in 12%, 20% and 37% mortality of the thrips at 24 hours post treatment, respectively.

Figure 14:
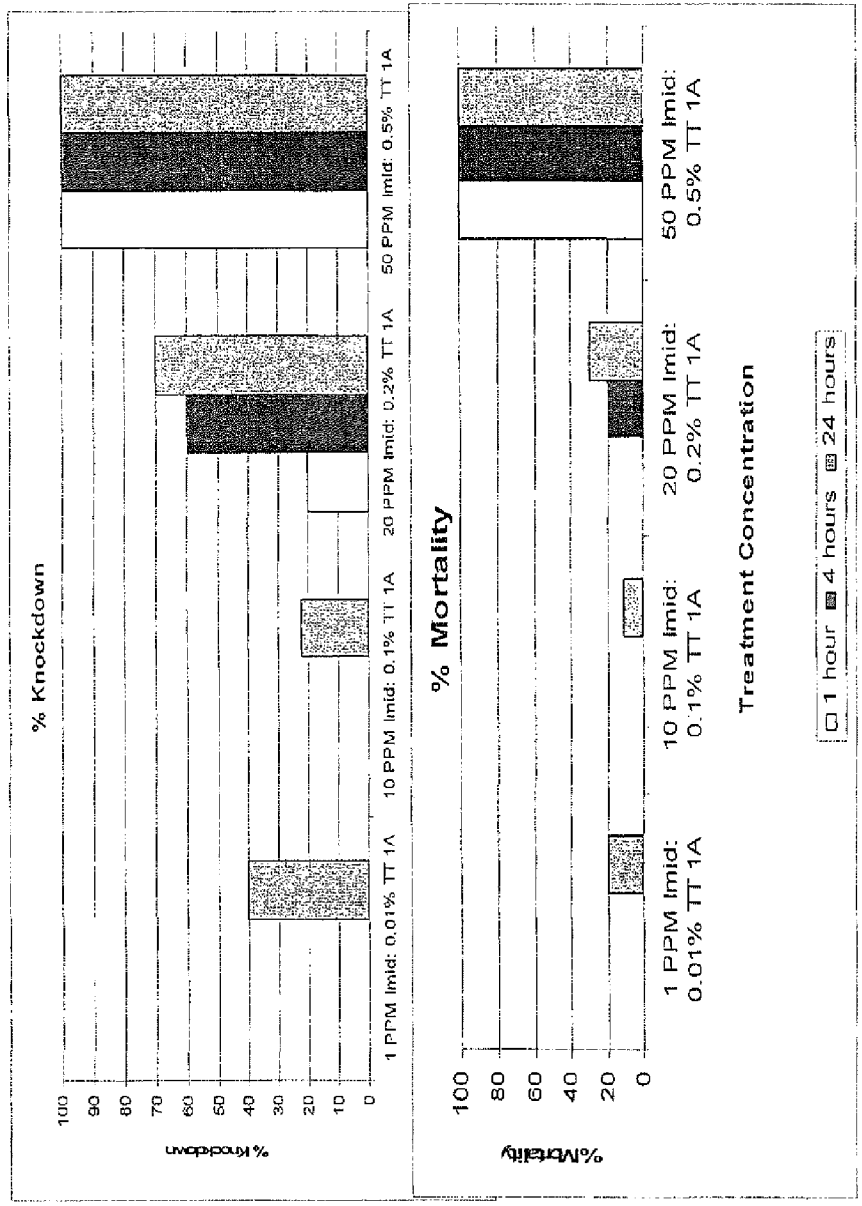
FIG. 14 shows dose dependent pesticidal effects (knockdown and mortality) against thrips over time caused by a composition containing the mixture of imidacloprid and Blend 38 (labeled "B5049" and "TT 1A").

With reference to FIG. 14, the third group of compositions contained a mixture of Blend 38 (label "B5049" and "TT 1A") and imidacloprid at 100:1 by volume. The concentration of Blend 38 was 0.01%, 0.1%, 0.2%, and 0.5% by volume, respectively. The KD and mortality measurements were done at 1 hour, 4 hours and 24 hours post treatment.

As shown in FIG. 14, treatment with the composition with the mixture of Blend 38 (label "B5049" and "TT 1A") at 0.01% by volume and imidacloprid resulted in 40% KD of the thrips at 24 hours post treatment. Treatment with the composition with the mixture of Blend 38 at 0.1% by volume and imidacloprid resulted in 22% KD of the thrips at 24 hours post treatment. Treatment with the composition with the mixture of Blend 38 at 0.2% by volume and imidacloprid resulted in 20%, 60% and 70% KD of the thrips at 1 hour, 4 hours and 24 hours post treatment, respectively. Treatment with the composition with the mixture of Blend 38 at 0.5% by volume and imidacloprid resulted in 100% KD of the thrips between 1 hour and 24 hours post treatment, respectively. Moreover, treatment with the composition with the mixture of Blend 38 at 0.01% by volume and imidacloprid resulted in 20% mortality of the thrips at 24 hours post treatment. Treatment with the composition with the mixture of Blend 38 at 0.1% by volume and imidacloprid resulted in 11% mortality of the thrips at 24 hours post treatment. Treatment with the composition with the mixture of Blend 38 at 0.2% by volume and imidacloprid resulted in 20% and 30% mortality of the thrips at 4 hours and 24 hours post treatment, respectively. Treatment with the composition with the mixture of Blend 38 at 0.5% by volume and imidacloprid resulted in 100% mortality of the thrips between 1 hour and 24 hours post treatment, respectively.

These results demonstrate that the combination of imidacloprid and Blend 38 is effective and has a synergistic effect.

Example 13

Pesitcideal Effect Against Adult Green Peach Aphids

Adult green peach aphids were observed and counted on the plants in a greenhouse. Then different compositions were sprayed directly onto the plants with aphids. Three days after the composition was applied, aphids were counted again to evaluate the pesticidal effects of the composition.

Figure 15:
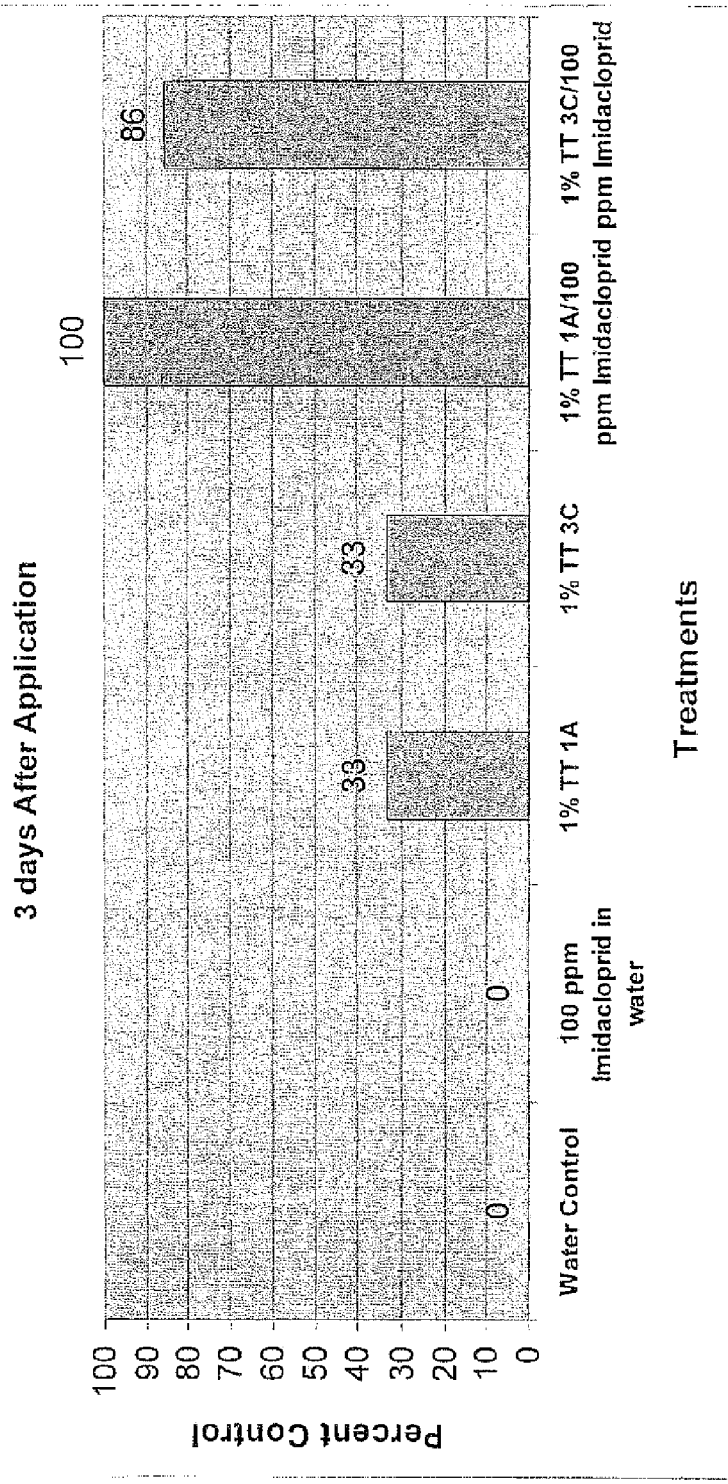
FIG. 15 shows dose dependent pesticidal effect against thrips over time caused by 1) water control or imidacloprid diluted in water; 2) a test composition; and 3) a combination of a test composition and imidacloprid. The test compositions are Blend 38 (labeled "B5049" and "TT 1A") and Blend 39 (labeled "B5053" and "TT 3C").

With reference to FIG. 15, water and imidacloprid in water at 100 ppm were used as control. No changes in aphid numbers were observed in these two groups.

With reference to FIG. 15, treatment with Blend 38 (label "B5049" and "TT 1A", exemplified in Ingredient Family 12 in Table 6) alone at 1% by volume resulted in 33% decrease in aphid number on the plants (33 Percent Control as shown in FIG. 15). Treatment with Blend 39 (label "B5053" and "TT 3C", exemplified in Ingredient Family 8 in Table 6) alone at 1% by volume also resulted in 33% decrease in aphid number on the plants (33 Percent Control as shown in FIG. 15).

With reference to FIG. 15, treatment with the composition containing the mixture of Blend 38 (labeled "B5049" and "TT 1A") at 1% by volume and 100 ppm imidacloprid resulted in complete elimination of aphids on the plants (100 Percent Control as shown in FIG. 15). Treatment with Blend 39 (labeled "B5053" and "TT 3C", exemplified in Ingredient Family 8 in Table 6) at 1% by volume resulted in 86% decrease in aphid number on the plants (86 Percent Control as shown in FIG. 15).

These results demonstrate that imidacloprid and Blends 38 and 39 are effective and have synergistic effects.

Example 14

Pesticidal Effect Against *C. Elegans*

*C. elegans* were exposed to two different groups of compositions before the mortality of *C. elegans* was measured.

With reference to Table 12, the first group of compositions contained Blend 27 alone at LC50 and applied to *C. elegans*. The treatment killed 50% *C. elegans*. The second group of composition contained Blend 27 (exemplified in Ingredient Family 1 in Table 6) at LC50 combined with fipronil at 5 ppm and applied to *C. elegans*. The treatment killed 93% *C. elegans*. The result demonstrates that fipronil and Blend 27 are effective and have synergistic effects.

Blends listed in Table 12, alone and in combination with fipronil, were tested in the same fashion.

TABLE 12

Pesticidal Effects of Blends with and without Fipronil

| | Exemplified in Table 6 | LC50 | Fipronil Concentration by Volume | Kill % C elegans | |
|---|---|---|---|---|---|
| | | | | w/o Fipronil | w Fipronil |
| Blend 27 | Ingredient Family 1 | 150 ppm | 5 ppm | 50% | 93% |
| Blend 39 | Ingredient Family 8 | 424 ppm | 5 ppm | 43% | 77% |
| Blend 42 | Ingredient Family 3 | 269 ppm | 5 ppm | 48% | 100% |
| Blend 12 | Ingredient Family 9 | 519 ppm | 5 ppm | 50% | 85% |

The results demonstrate that the combinations of fipronil and these blends are effective and have synergistic effects.

Example 15

Pesticidal Effect Against *Drosophila*

*Drosophila* were exposed to two different groups of compositions before the mortality of *drosophila* was measured.

With reference to Table 13, the first group of compositions contained Blend 39 (exemplified in Ingredient Family 8 in Table 6) alone at LD50 and applied to *drosophila*. The treatment killed 50% *drosophila*. The second group of compositions contained Blend 39 at LD50 combined with fipronil at 5 ppm and applied to *drosophila*. The treatment killed 95% *drosophila*. The result demonstrates that the combination of fipronil and Blend 39 is effective and has a synergistic effect.

Blends listed in Table 13, alone and in combination with fipronil, were tested in the same fashion.

TABLE 13

Pesticidal Effects of Blends with and without Fipronil

|  | Exemplified in Table 6 | LD50 | Fipronil Concentration by Volume | Kill % C elegans w/o Fipronil | w Fipronil |
|---|---|---|---|---|---|
| Blend 39 | Ingredient Family 8 | 75 ppm | 5 ppm | 50% | 95% |
| Blend 42 | Ingredient Family 3 | 46 ppm | 5 ppm | 41% | 100% |

These results demonstrate that these combinations of fipronil and the blends are effective and have synergistic effects.

Example 16

Pesticidal Effect Against Drosphila melanogaster

With reference to Table 14, the pesticidal effect against drosphila melanogaster was determined for Blend 19 and the composition including fipnoril and Blend 19. The composition of Blend 19 is also exemplified in Ingredient Family 15 of Table 6. Each composition was tested on 30 drosphila melanogaster by spraying directly onto the flies. Treatment with acetone as control at 0.5 µl/fly killed 2 flies, fipnoril alone at 20 ppm killed 12 flies, and Blend 19 alone at 0.5 µg/fly killed 10 flies. However, treatment with fipronil at 20 ppm combined with Blend 19 at 0.5 µg/fly killed all of the 30 flies. The composition including Blend 19 and fipronil was shown to be effective and was shown to have a synergistic effect.

TABLE 14

Toxicity of Blend 19 with and without Fipronil against Drosphila Melanogaster

| Chemical | Dose (amount/fly) | # of Flies Killed |
|---|---|---|
| Control (acetone) | 0.5 µl | 2/30 |
| Fipronil | 20 ppm | 12/30 |
| Blend 19 | 0.5 µg | 10/30 |
| Blend 19 + Fipronil | 0.5 µg Blend 19 + 20 ppm fipronil | 30/30 |

Example 17

Preparation of Stably Transfected Schneider Cell Lines with Tyramine Receptor (TyrR)

A. PCR Amplification and Subcloning Drosophila melanogaster Tyramine Receptor.

Tyramine receptor is amplified from Drosophila melanogaster head cDNA phage library GH that is obtained through the Berkeley Drosophila Genome Project (Baumann, A., 1999, Drosophila melanogaster mRNA for octopamine receptor, splice variant 1B NCBI direct submission, Accession AJ007617). The nucleic acid sequence and the peptide sequence of TyrR are set forth in FIGS. 8A and 8B. Phage DNA is purified from this library using a liquid culture lysate. (Baxter, et al., 1999, Insect Biochem Mol Biol 29, 461-467). Briefly, oligonucleotides that are used to amplify the open reading frame of the Drosophila tyramine receptor (TyrR) (Han, et al., 1998, J Neurosci 18, 3650-3658; von Nickisch-Rosenegk, et al., 1996. Insect Biochem Mol Biol 26, 817-827) consist of the 5' oligonucleotide: 5' gccgaattcgccaccAT-GCCATCGGCAGATCAGATCCTG 3' and 3' oligonucleotide: 5' taatctagaTCAATTCAGGCCCA-GAAGTCGCTTG 3'. Capitalized letters match the tyramine receptor sequence. An added Kozak sequence (Grosmaitre, X., Jacquin-Joly, E., 2001 Mamestra brassicae putative octopamine receptor (OAR) mRNA, complete cds. NCBI direct submission, Accession AF43878) is indicated by underlined nucleotides. The 5' oligonucleotide also contains an EcoR I site and the 3' oligonucleotide a Xba I site. The PCR is performed using Vent polymerase (New England Biolabs) with the following conditions: about 95° C., about 5 min for about 1 cycle; about 95° C., about 30 sec; and about 70° C., about 90 sec for about 40 cycles and about 70° C., about 10 min for about 1 cycle.

The PCR product is digested with EcoR I and Xba I, subcloned into pcDNA 3 (Invitrogen) and sequenced on both strands by automated DNA sequencing (Vanderbilt Cancer Center). When this open reading frame is translated to protein, it is found to correctly match the published tyramine receptor sequence (Saudou, et al., The EMBO Journal vol 9 no 1, 6-617). For expression in Drosophila Schneider cells, the TyrR ORF is excised from pcDNA3 and inserted into pAC5.1/V5-His(B) [pAc5(B)] using the Eco RI and Xba I restriction sites.

For transfection, Drosophila Schneider cells are stably transfected with pAc5(B)-TyrR ORF using the calcium phosphate-DNA coprecipitation protocol as described by Invitrogen Drosophila Expression System (DES) manual. The precipitation protocol is the same for either transient or stable transfection except for the use of an antibiotic resistant plasmid for stable transfection. At least about ten clones of stably transfected cells are selected and separately propagated. Stable clones expressing the receptors are selected by whole cell binding/uptake using $^3$H-tyramine. For this assay, cells are washed and collected in insect saline (170 mM NaCl, 6 mM KCl, 2 mM NaHCO$_3$, 17 mM glucose, 6 mM NaH$_2$PO$_4$, 2 mM CaCl$_2$, and 4 mM MgCl$_2$). About 3 million cells in about 1 mL insect saline are incubated with about 4 nM $^3$H-tyramine at about 23° C. for about 5 minutes. Cells are centrifuged for about 30 seconds and the binding solution is aspirated. The cell pellets are washed with about 500 µL insect saline and the cells are resuspended and transferred to scintillation fluid. Nonspecific binding is determined by including about 50 µM unlabeled-tyramine in the reaction. Binding is quantified counting radioactivity using a using a Liquid Scintillation β-counter (Beckman, Model LS1801).

B. Selection of Clones Having the Highest Level of Functionally Active Tyramine Receptor Protein.

Tyramine receptor binding/uptake is performed to determine which of the transfected clones have the highest levels of functionally active tyramine receptor protein. There are about 10 clonal lines for tyramine receptor and about 2 pAc (B) for control. $^3$H-tyramine (about 4 nM/reaction) is used as a tracer, with and without about 50 µM unlabeled tyramine as a specific competitor. For this assay, cells are grown in plates and are collected in about 3 ml of medium for cell counting and the number of cells is adjusted to about 3×10$^6$ cells/ml. About two pAcB clones are used in parallel as controls. About 1 ml cell suspension is used per reaction. Based on specific binding, about 3 clones express a high level of active tyramine receptor protein. The clone having the highest specific tyramine receptor binding (about 90%), is selected for further studies. The selected clone is propagated and stored in liquid nitrogen. Aliquot of the selected clone are grown for whole cell binding and for plasma membrane preparation for kinetic and screening studies. The control pAcB does not demonstrate any specific binding for the tyramine receptor.

C. Efficacy of Schneider Cells Transfected with Tyramine Receptor for Screening Compositions for Tyramine Receptor Interaction.

Cells transfected with the tyramine receptor (about $1 \times 10^6$ cells/ml) are cultured in each well of a multi-well plate. About 24 hours after plating the cells, the medium is withdrawn and replaced with about 1 ml insect saline (about 23C). Different concentrations of $^3$H-tyramine (about 0.1-10 nM) are added with and without about 10 µM unlabeled tyramine and incubated at room temperature (RT). After about a 20 minute incubation, the reaction is stopped by rapid aspiration of the saline and at least one wash with about 2 ml insect saline (about 23C). Cells are solubilized in about 300 µl 0.3M NaOH for about 20 min at RT. Solubilized cells are transferred into about 4 ml Liquid Scintillation Solution (LSS) and vigorously vortexed for about 30 sec before counting the radioactivity using a Liquid Scintillation β-counter (Beckman, Model LS1801) (LSC).

Receptor specific binding data is expressed as fmol specific binding per $1 \times 10^6$ cells and measured as a function of $^3$H-tyramine concentration. Specific binding values are calculated as the difference between values in the absence of and values in the presence of about 10 µM unlabeled tyramine. The maximum specific binding occurs at about 5 nM $^3$H-tyramine. Untransfected cells do not respond to tyramine at concentrations as high as about 100 µM.

To study the kinetics of the tyramine receptor in stably transfected cells with pAcB-TyrR, crude membrane fractions are prepared from the transfected cells and used to calculate the equilibrium dissociation constant ($K_d$), Maximum Binding Capacity ($B_{max}$), equilibrium inhibitor dissociation constant ($K_i$) and $EC_{50}$ (effective concentration at which binding is inhibited by 50%). A preliminary study to determine the optimum concentration of membrane protein for receptor binding activity is performed. In this study, different concentrations of protein (about 10-50 µg/reaction) are incubated in about 1 ml binding buffer (50 mM Tris, pH 7.4, 5 mM $MgCl_2$ and 2 mM ascorbic acid). The reaction is initiated by the addition of about 5 nM $^3$H-tyramine with and without about 10 µM unlabeled tyramine. After about 1 hr incubation at room temperature, reactions are terminated by filtration through GF/C filters (VWR), which have been previously soaked in about 0.3% polyethyleneimine (PEI). The filters are washed one time with about 4 ml ice cold Tris buffer and air dried before the retained radioactivity is measured using LSC. Binding data is analyzed by curve fitting (GraphPad software, Prism). The data demonstrates no differences between about 10, 20, 30 and 50 µg protein/reaction in tyramine receptor specific binding. Therefore, about 10 µg protein/reaction is used.

To determine $B_{max}$ and $K_d$ values for tyramine receptor (TyrR) in membranes expressing TyrR, saturation binding experiments are performed. Briefly, about 10 µg protein is incubated with $^3$H-tyramine at a range of concentrations (about 0.2-20 nM). Binding data is analyzed by curve fitting (GraphPad software, Prism) and the $K_d$ for tyramine binding to its receptor is determined.

To determine the affinities of several ligands for TyrR, increasing concentration of several compounds are tested for their ability to inhibit binding of about 2 nM $^3$H-tyramine. For both saturation and inhibition assays total and non-specific binding is determined in the absence and presence of about 10 µM unlabeled-tyramine, respectively. Receptor binding reactions are incubated for about 1 hour at room temperature (RT) in restricted light. Reactions are terminated by filtration through GF/C filters (VWR), which have been previously soaked in about 0.3% polyethyleneimine (PEI). The filters are washed one time with about 4 ml ice cold Tris buffer and air dried before retained radioactivity is measured using LSC. Binding data is analyzed by curve fitting (GraphPad software, Prism).

In a saturation binding curve of $^3$H-tyramine ($^3$H-TA) to membranes prepared from Schneider cells expressing tyramine receptor, $^3$H-tyramine has a high affinity to tyramine receptor in the stably transfected cells with pAcB-TyrR with $K_d$ determined to be about 1.257 nM and $B_{max}$ determined to be about 0.679 pmol/mg protein.

In inhibition binding of $^3$H-tyramine ($^3$H-TA) to membranes prepared from Schneider cells expressing tyramine receptor in the presence and absence of various concentrations of unlabeled tyramine (TA), the $EC_{50}$ and the $K_i$ for tyramine against its receptor in Schneider cells expressing tyramine receptor are about 0.331 µM and 0.127 µM, respectively.

In order to determine the pharmacological profile of tyramine receptor (TyrR), the ability of a number of putative *Drosophila* neurotransmitters to displace $^3$H-tyramine ($^3$H-TA) binding from membranes expressing tyramine receptor is tested. In inhibition binding of $^3$H-Tyramine to membranes prepared from Schneider cells expressing tyramine receptor in the presence and absence of different concentrations of unlabeled ligands (including Tyramine (TA), Octopamine (OA), Dopamine (DA), and Serotonin (SE)), tyramine displays the highest affinity ($K_i$ of about 0.127 µM, $EC_{50}$ of about 0.305 µM) for the *Drosophila* TyrR. Octopamine, dopamine and serotonin were less efficient than tyramine at displacing $^3$H-tyramine binding.

With respect to the $K_i$ and $EC_{50}$ of the ligands, the rank order of potency is as follows: tyramine>octopamine>dopamine>serotonin, showing the likelihood that the stably transfected Schneider cells are expressing a functionally active tyramine receptor.

As such, Schneider cells expressing tyramine receptor are effective as a model for studies and screening for compositions that interact with the tyramine receptor.

Example 18

In vitro Calcium Mobilization Measurement

Intracellular calcium ion concentrations ($[Ca^{2+}]_i$) are measured by using the acetoxymethyl (AM) ester of the fluorescent indicator fura-2 (Enan, et al., Biochem. Pharmacol. vol 51, 447-454). Cells expressing the tyramine receptor are grown under standard conditions. A cell suspension is prepared in assay buffer (140 mM NaCl, 10 mM HEPES, 10 mM glucose, 5 mM KCl, 1 mM $CaCl_2$, 1 mM $MgCl_2$) and the cell number is adjusted to about $2 \times 10^6$ cells per ml. Briefly, about 1.0 ml cell suspension (about $2 \times 10^6$ cells) is incubated with about 5 µM fura 2/AM for about 30 min at about 28° C. After incubation, the cells are pelleted at about 3700 rpm for about 10 sec at room temperature and then resuspended in about 1.5 ml assay buffer. $[Ca^{2+}]_i$ changes are analyzed in a spectrofluorometer in the presence and absence of test chemicals. Excitation wave lengths are about 340 nm (generated by $Ca^{2+}$-bound fura-2) and about 380 nm (corresponding to $Ca^{2+}$-free fura-2). The fluorescence intensity is monitored at an emission wave length of about 510 nm. No absorbance of fluorescence artifacts are observed with any of the compounds used. The ratio of about 340/380 nm is calculated and plotted as a function of time.

Example 19

In vitro Cyclic AMP (cAMP) Measurement

Cells are grown on dishes and the media changed the day before the treatment. When cells are approximately 95% confluent, media is aspirated and the cells are washed one time with about 5 mL of about 27° C. insect saline (170 mM NaCl, 6.0 mM KCl, 2.0 mM NaHCO$_3$, 17.0 mM glucose, 6.0 mM NaH2PO$_4$, 2.0 mM CaCl$_2$, 4.0 mM MgCl$_2$; pH 7.0). About 20 mL of insect saline is added, and cells are harvested by gentle scraping. An aliquot of the cells is counted by hemocytometer, and the cells are then centrifuged for about 5 minutes at about 1000 RPM. Cells are resuspended to give about 3×10$^6$ cells per mL. IBMX is added to about 200 .mu.M. Then about 1 mL of cell suspension is aliquoted for treatment. Forskolin (cAMP inducing agent), tyramine or different composition candidates are added, and the cells are incubated at about 27° C. for about 10 minutes.

Treated cells are centrifuged at about 13000 g for about 10 seconds. The solution is aspirated and about 1 mL of about −20° C. 70% ethanol is added. The cell pellet is disrupted by vortexing and the samples placed at about −20° C. overnight. Following the ethanol extraction, cellular debris is pelleted by centrifugation at about 13000 g for about 5 minutes. The supernatant is transferred to a tube and lyophilized to dryness in a rotary speed-vac. The resulting extract is resuspended in about 100 .mu.L TE and used for the cAMP assay.

The cAMP assay is based on competition binding between endogenous cAMP and $^3$H-cAMP to a cAMP binding protein. The $^3$H-cAMP Biotrak system (Amersham Biosciences) is used for this assay as per the manufacturer's instructions. Briefly, about 50 .mu.L of the cellular extract is incubated with about 50 .mu.L $^3$H-cAMP and about 100 .mu.L cAMP binding protein in an ice bath for about 2-4 hours. Charcoal (about 100 .mu.L) is then added and the solution centrifuged for about 3 minutes at about 4.degree. C. About 200 .mu.L of the reaction mixture is removed and levels of .sup.3H-cAMP are determined by scintillation counting. Levels of endogenous cAMP from the cells are calculated using a standard curve with cold cAMP ranging from about 0 to 16 pmol per reaction.

Example 20

Synergistic Effects of a Combination of a Blend and Imidacloprid on In vitro Calcium Mobilization A Schneider cell line was produced that expressed a cell-surface tyramine receptor of *Drosophila melanogaster*, as described above. Cells of this line were exposed to three different compositions. The first composition contained imidacloprid at 20 ppm. The second solution contained Blend 19 at 0.01% by volume. The third composition contained a mixture of imidacloprid at 20 ppm and Blend 19 at 0.01% by volume. The results of this procedure are shown in FIG. 16A as fluorescence intensity curves corresponding to intracellular calcium ion concentrations.

Figure 16:
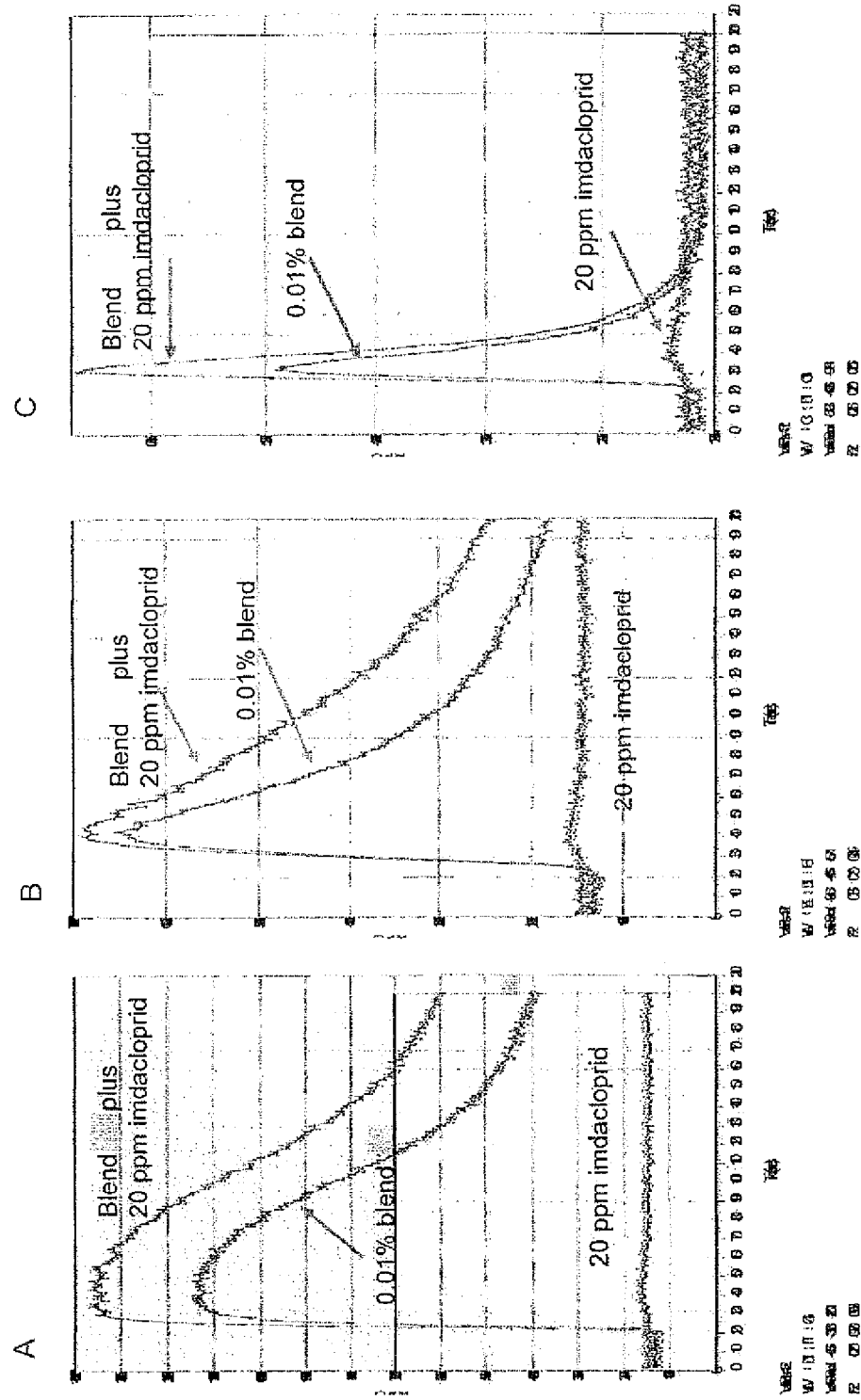
FIG. 16A shows fluorescence intensity curves corresponding to intracellular calcium ion concentrations, with the curve corresponding to the compositions containing 1) imidacloprid alone, 2) Blend 19 alone, and 3) the mixture of imidacloprid and Blend 19.
FIG. 16B shows fluorescence intensity curves corresponding to intracellular calcium ion concentrations, with the curve corresponding to the compositions containing 1) imidacloprid alone, 2) Blend 27 alone, and 3) the mixture of imidacloprid and Blend 27.
FIG. 16C shows fluorescence intensity curves corresponding to intracellular calcium ion concentrations, with the curve corresponding to the compositions containing 1) imidacloprid alone, 2) Blend 75 alone, and 3) the mixture of imidacloprid and Blend 75.

As shown in FIG. 16A, the composition containing the mixture of imidacloprid and Blend 19 exhibited (1) a much higher peak intensity, (2) a higher $V_{max}$ per second, and (3) a higher intensity at each time point between 30 second and 120 seconds (end of the calcium measurement) than the compositions containing either of the ingredients alone. This demonstrates that imidacloprid and Blend 19 act synergistically in this cell system to affect intracellular calcium ion concentrations.

Blends listed in the Table 15, alone and in combination with imidacloprid, were tested in the same fashion.

TABLE 15

Figure 17:
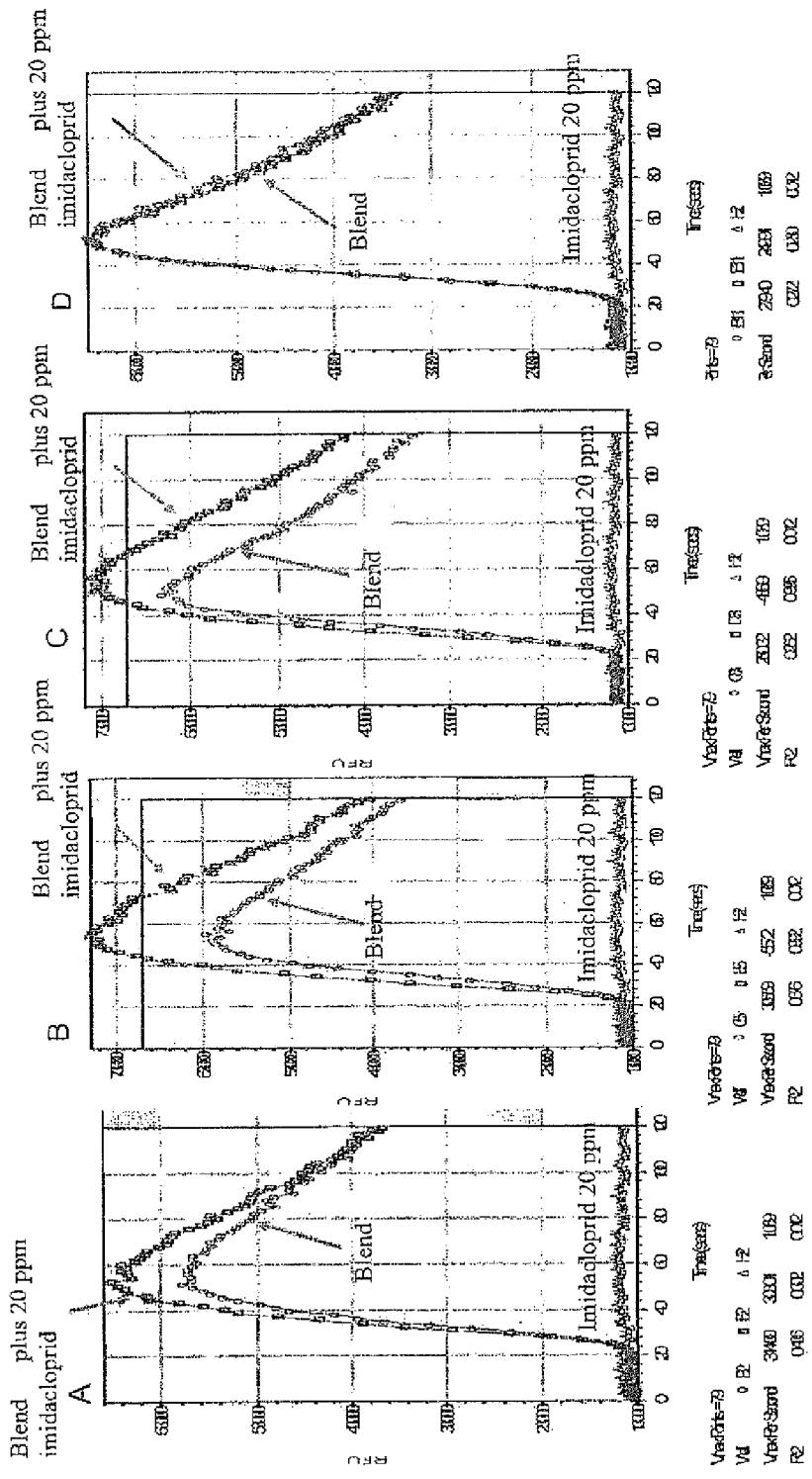
FIG. 17A shows fluorescence intensity curves corresponding to intracellular calcium ion concentrations, with the curve corresponding to the compositions containing 1) imidacloprid alone, 2) Blend 7 alone, and 3) the mixture of imidacloprid and Blend 7.
FIG. 17B shows fluorescence intensity curves corresponding to intracellular calcium ion concentrations, with the curve corresponding to the compositions containing 1) imidacloprid alone, 2) Blend 15 alone, and 3) the mixture of imidacloprid and Blend 15.
FIG. 17C shows fluorescence intensity curves corresponding to intracellular calcium ion concentrations, with the curve corresponding to the compositions containing 1) imidacloprid alone, 2) Blend 11 alone, and 3) the mixture of imidacloprid and Blend 11.
FIG. 17D shows fluorescence intensity curves corresponding to intracellular calcium ion concentrations, with the curve corresponding to the compositions containing 1) imidacloprid alone, 2) Blend 11 alone, and 3) the mixture of imidacloprid and Blend 11.
Figure 18:
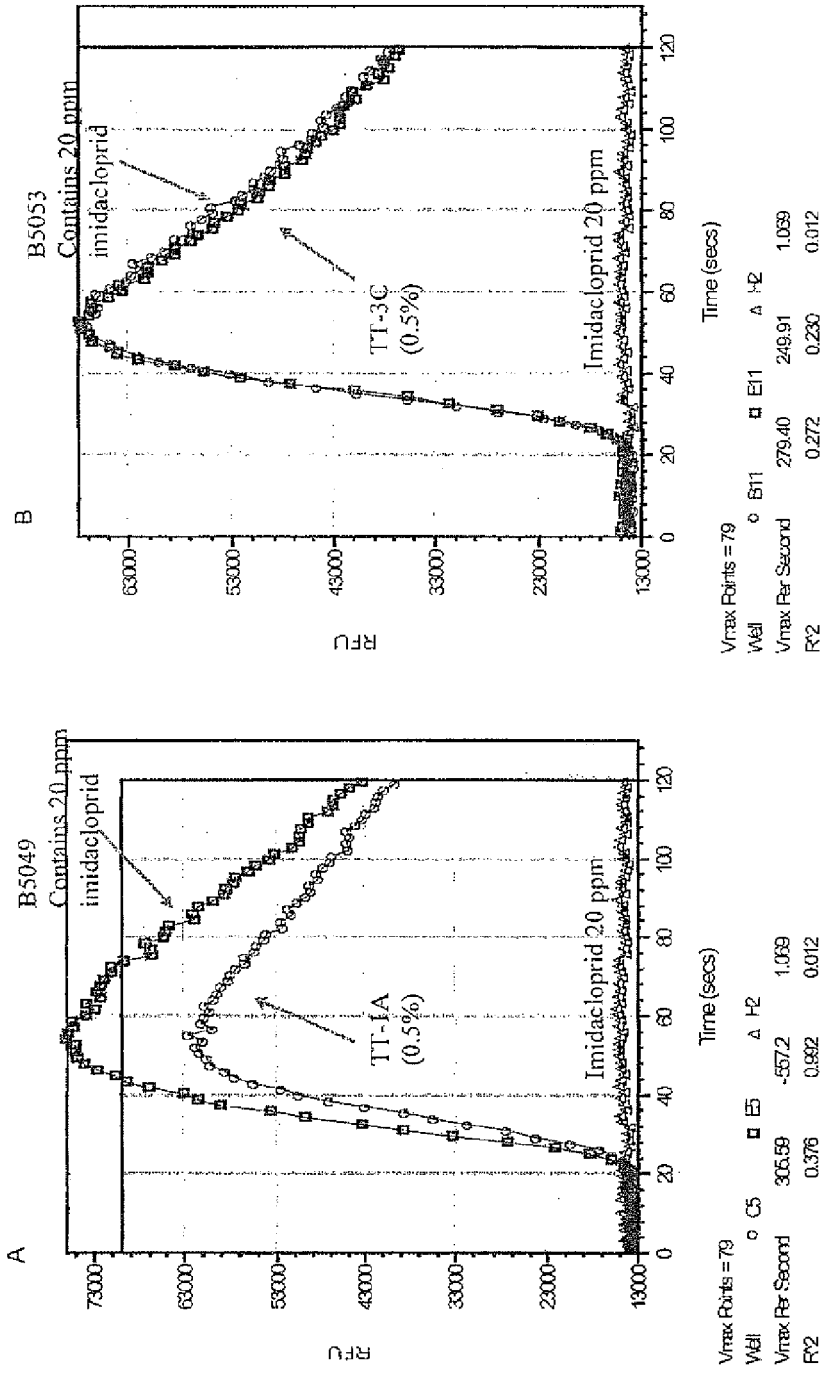
FIG. 18A shows fluorescence intensity curves corresponding to intracellular calcium ion concentrations, with the curve corresponding to the compositions containing 1) imidacloprid alone, 2) Blend 38 alone, and 3) the mixture of imidacloprid and Blend 38. Blend 38 is labeled as "B5049".
FIG. 18B shows fluorescence intensity curves corresponding to intracellular calcium ion concentrations, with the curve corresponding to the compositions containing 1) imidacloprid alone, 2) Blend 39 alone, and 3) the mixture of imidacloprid and Blend 39. Blend 39 is labeled as "B5053".

|  | Exemplified in Table 6 | Blend Concentration by Volume | Imidacloprid Concentration by volume | Results Shown |
|---|---|---|---|---|
| Blend 19 | Ingredient Family 15 | 0.01% | 20 ppm | FIG. 16A |
| Blend 27 | Ingredient Family 1 | 0.01% | 20 ppm | FIG. 16B |
| Blend 75 | Ingredient Family 7 | 0.01% | 20 ppm | FIG. 16C |
| Blend 7 | Ingredient Family 16 | 0.5% | 20 ppm | FIG. 17A |
| Blend 11 | Ingredient Family 17 | 0.5% | 20 ppm | FIG. 17B |
| Blend 11 | Ingredient Family 18 | 0.5% | 20 ppm | FIG. 17C |
| Blend 38 | Ingredient Family 12 | 0.5% | 20 ppm | FIG. 18A |

Blend 75 used in this example is exemplified in Ingredient Family 7, and contains (wt/wt) 1.00% potassium sorbate, 0.28% xanthan gum, 81.82% water, 0.04% D-limonene, 0.17% thyme oil white, 8.62% thymol (crystal), 0.33% alpha-terpineol, 3.37% para-cymene, 0.25% linalyl acetate, 0.67% Caryophyllene-B, 0.33% Borneol L, 0.16% myrcene, 0.33% tea tree oil, 0.48% cypress oil, 1.64% peppermint terpenes, and 0.52% linalool 90.

Synergistic effects were observed for all the compositions containing the mixture of imidacloprid and each blend shown in Table 15. The results are shown in FIGS. 16A-C, 17A-C and 18A.

These combinations of ingredients, when applied to a pest expressing the tyramine receptor, also act synergistically to control the pest.

Example 21

Synergistic Effects of a Combination of a Blend and Fipronil on In vitro Calcium Mobilization A Schneider cell line was produced that expressed a cell-surface tyramine receptor of *Drosophila melanogaster*, as described above. Cells of this line were exposed to three different compositions. The first composition contained fipronil at 20 ppm. The second solution contained Blend 19 at 0.1% by volume. The third composition contained a mixture of fipronil at 20 ppm and Blend 19 at 0.1% by volume. Blend 19 is exemplified in Ingredient Family 15 in Table 6. The results of this procedure are shown in FIG. 19 as fluorescence intensity curves corresponding to intracellular calcium ion concentrations.

Figure 19:
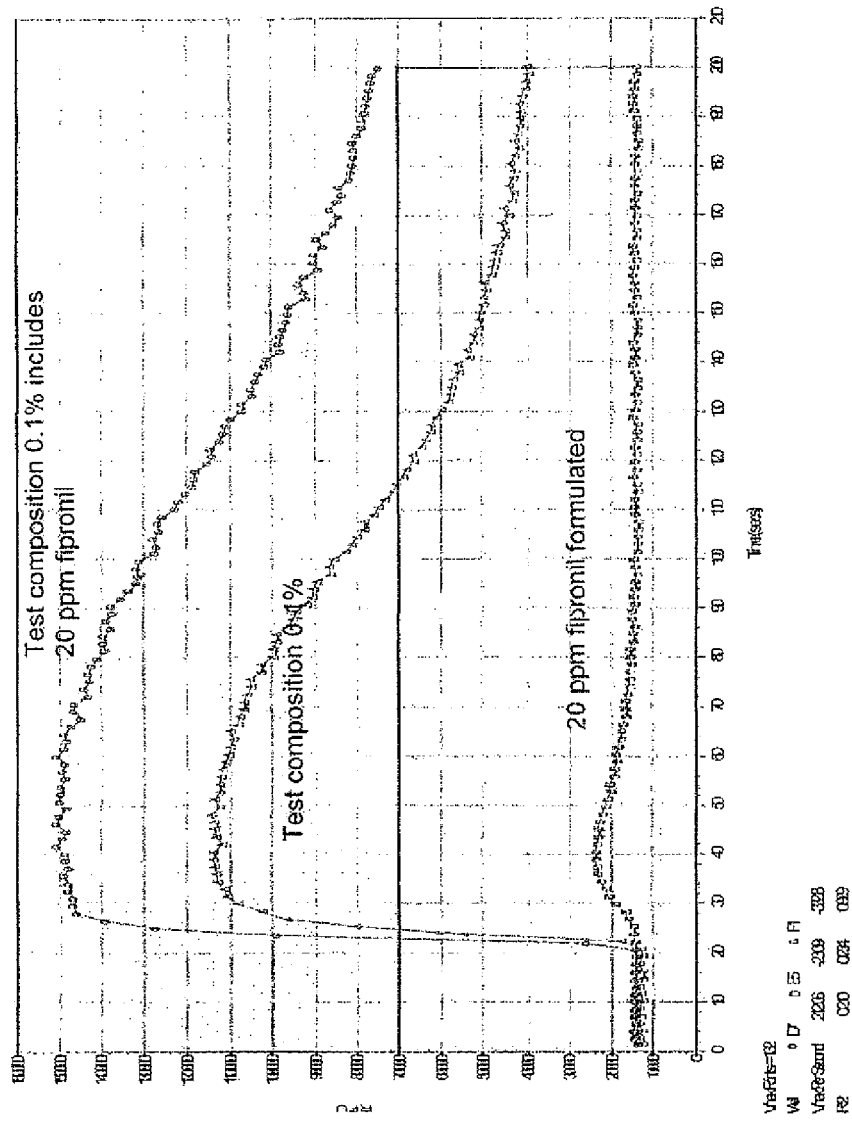
FIG. 19 shows fluorescence intensity curves corresponding to intracellular calcium ion concentrations, with the curve corresponding to the compositions containing 1) fipronil alone, 2) a test composition alone, and 3) the mixture of fipronil and the test composition. The test composition is Blend 19.

As shown in FIG. 19, the composition containing the mixture of fipronil and Blend 19 exhibited (1) a much higher peak intensity, (2) a higher $V_{max}$ per second, and (3) a much higher intensity at each time point between 25 second and 120 seconds (end of the calcium measurement) than the compositions containing either of the ingredients alone. This demonstrates that fipronil and Blend 19 act synergistically in this cell system to affect intracellular calcium ion concentrations.

Blends listed in the Table 16, alone and in combination with fipronil, were tested in the same fashion.

TABLE 16

Figure 20:
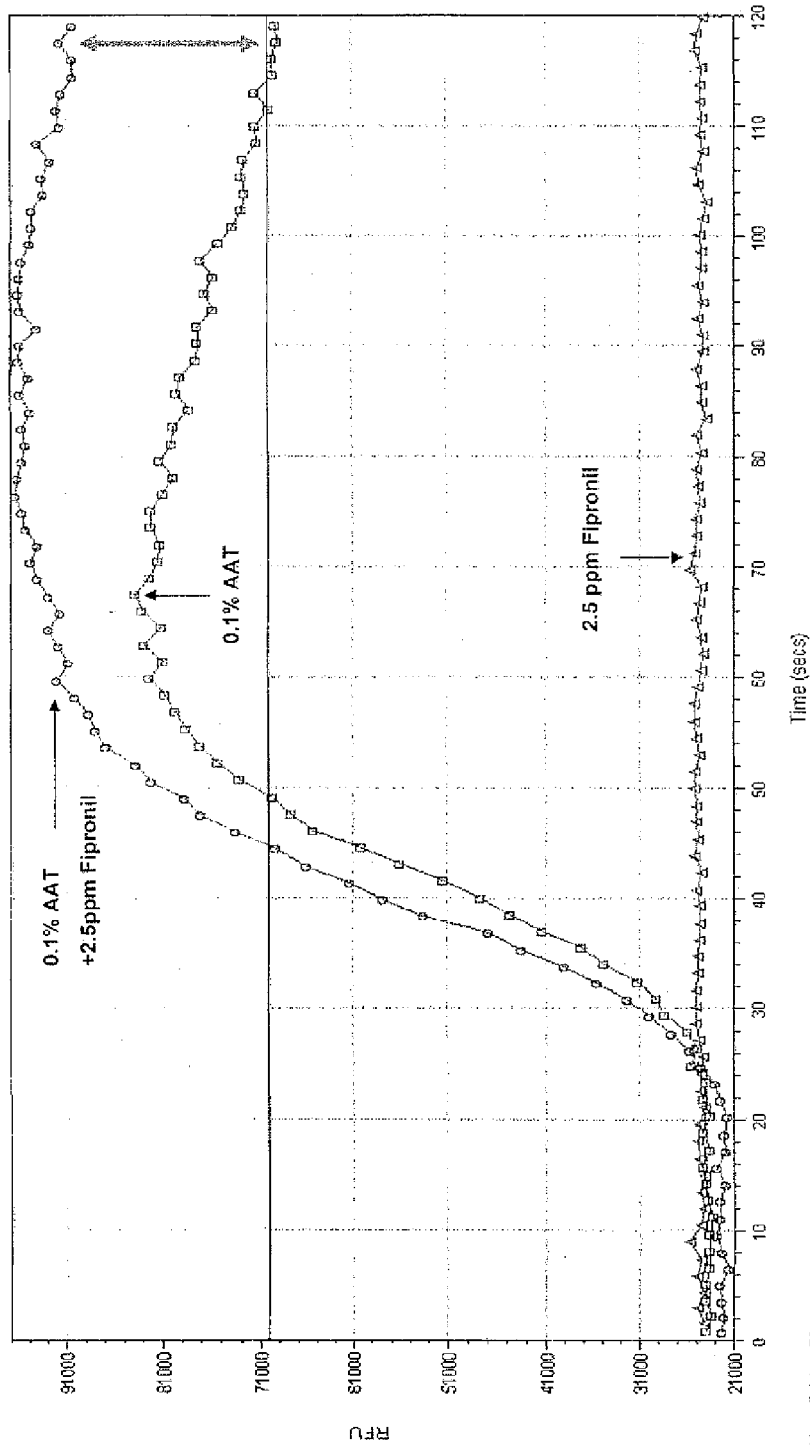
FIG. 20 shows fluorescence intensity curves corresponding to intracellular calcium ion concentrations, with the curve corresponding to the compositions containing 1) fipronil alone, 2) a test composition alone, and 3) the mixture of fipronil and the test composition. The test composition is Blend 42, and labeled as "AAT".
Figure 21:
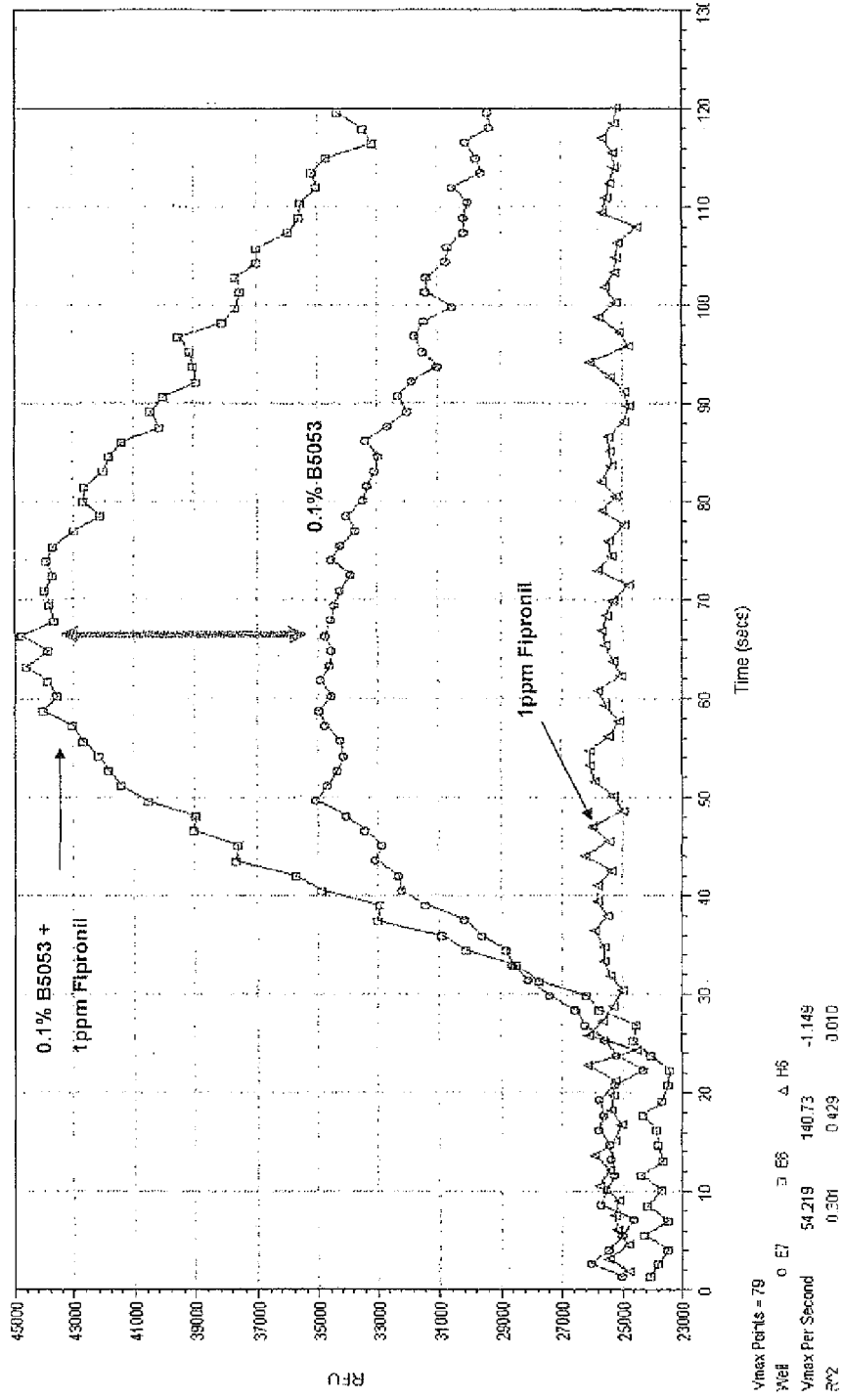
FIG. 21 shows fluorescence intensity curves corresponding to intracellular calcium ion concentrations, with the curve corresponding to the compositions containing 1) fipronil alone, 2) a test composition alone, and 3) the mixture of fipronil and the test composition. The test composition is Blend 39, and labeled as "B5053".

| Exemplified in Table 6 | Blend Concentration by Volume | Fipronil Concentration by Volume | Results Shown |
|---|---|---|---|
| Blend 19 | Ingredient Family 15 | 0.1% | 20 ppm | FIG. 19 |
| Blend 42 | Ingredient Family 3 | 0.1% | 2.5 ppm | FIG. 20 |
| Blend 39 | Ingredient Family 8 | 0.1% | 1 ppm | FIG. 21 |

These results demonstrate that fipronil and the blends act synergistically in this cell system to affect intracellular calcium ion concentrations. These combinations of ingredients, when applied to a pest expressing the tyramine receptor, also act synergistically to control the pest.

Example 22

Synergistic Effects of a Combination of a Blend and Fipronil on In vitro Calcium and Camp A Schneider cell line was produced that expressed a cell-surface tyramine receptor of Drosophila melanogaster, as described above. Cells of this line were exposed to two different compositions. The first composition contained fipronil at 1 ppm. The second solution contained a mixture of fipronil at 1 ppm and Blend 27 at 0.1% by volume. The results of this procedure are shown in Table 17 as changes in intracellular calcium concentrations and changes in intracellular cAMP concentrations induced by the mixture compared to fipronil alone.

As shown in Table 17 the composition containing the mixture of fipronil and Blend 27 exhibited greater changes in both intracellular calcium level and intracellular cAMP level. This demonstrates that fipronil and Blend 27 act synergistically in this cell system to affect intracellular calcium ion concentration and intracellular cAMP concentration.

Blends listed in the Table 17, alone and in combination with fipronil, were tested in the same fashion.

TABLE 17

| | Exemplified in Table 6 | Blend Concentration by Volume | Fipronil Concentration by Volume | $[Ca^{2+}]_i$ % Change as Compared to Fipronil Alone | $[cAMP]_i$ % Change as Compared to Fipronil Alone |
|---|---|---|---|---|---|
| Blend 27 | Ingredient Family 1 | 0.1% | 1 ppm | 150% | 130% |
| Blend 39 | Ingredient Family 8 | 0.1% | 1 ppm | 180% | 145% |
| Blend 42 | Ingredient Family 3 | 0.1% | 1 ppm | 333% | 170% |
| Blend 12 | Ingredient Family 9 | 0.1% | 1 ppm | 167% | −25% |

These results demonstrate that fipronil and the blends act synergistically in this cell system to affect intracellular calcium ion concentrations and cAMP concencentrations. These combinations of ingredients, when applied to a pest expressing the tyramine receptor, also act synergistically to control the pest.

Example 23

Synergistic Effects of a Combination of Blend 19 and Clothianidin on In vitro Calcium Mobilization A Schneider cell line was produced that expressed a cell-surface tyramine receptor of Drosophila melanogaster, as described above. Cells of this line were exposed to three different compositions. The first composition contained clothianidin (labeled "AMP Agent") at 0.01% by volume. The second solution contained Blend 19 at 5% by volume. The third composition contained a mixture of clothianidin at 0.01% by volume and Blend 19 at 0.1% by volume. Blend 19 is exemplified in Ingredient Family 15 in Table 6. The results of this procedure are shown in FIG. 22 as fluorescence intensity curves corresponding to intracellular calcium ion concentrations.

Figure 22:
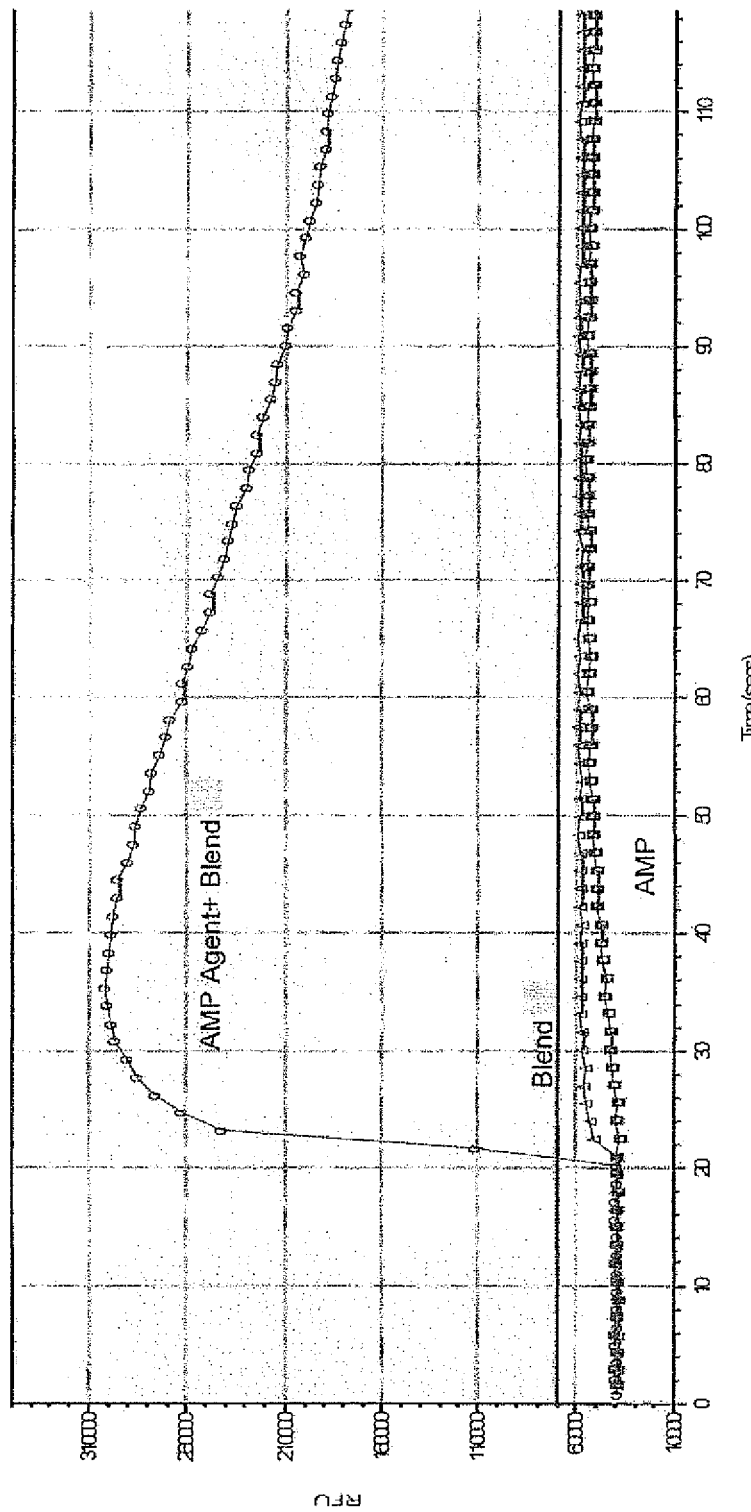
FIG. 22 shows fluorescence intensity curves corresponding to intracellular calcium ion concentrations, with the curve corresponding to the compositions containing 1) clothianidin alone, 2) a test composition alone, and 3) the mixture of clothianidin and the test composition. The test composition is Blend 19. Clothianidin is labeled as AMP Agent.

As shown in FIG. 22, the composition containing the mixture of fipronil and Blend 19 exhibited (1) a much higher peak intensity, (2) a higher $V_{max}$ per second, and (3) a much higher intensity at each time point between 20 second and 120 seconds (end of the calcium measurement) than the compositions containing either of the ingredients alone. This demonstrates that clothianidin and Blend 19 act synergistically in this cell system to affect intracellular calcium ion concentrations.

This combination of ingredients, when applied to a pest expressing the tyramine receptor, also acts synergistically to control the pest.

Example 24

Synergistic Effects of a Combination of Blend 7 and Abamectin on In vitro Calcium Mobilization A Schneider cell line was produced that expressed a cell-surface tyramine receptor of Drosophila melanogaster, as described above. Cells of this line were exposed to three different compositions. The first composition contained abamectin at 20 ppm. The second solution contained Blend 7 at 0.01% by volume. The third composition contained a mixture of abamectin at 20 ppm and Blend 7 at 0.01% by volume. The composition of Blend 7 was exemplified in Ingredient Family 5 of Table 6. Blend 7 is exemplified in Ingredient Family 5 in Table 6. The results of this procedure are shown in FIG. 23A as fluorescence intensity curves corresponding to intracellular calcium ion concentrations.

Figure 23:
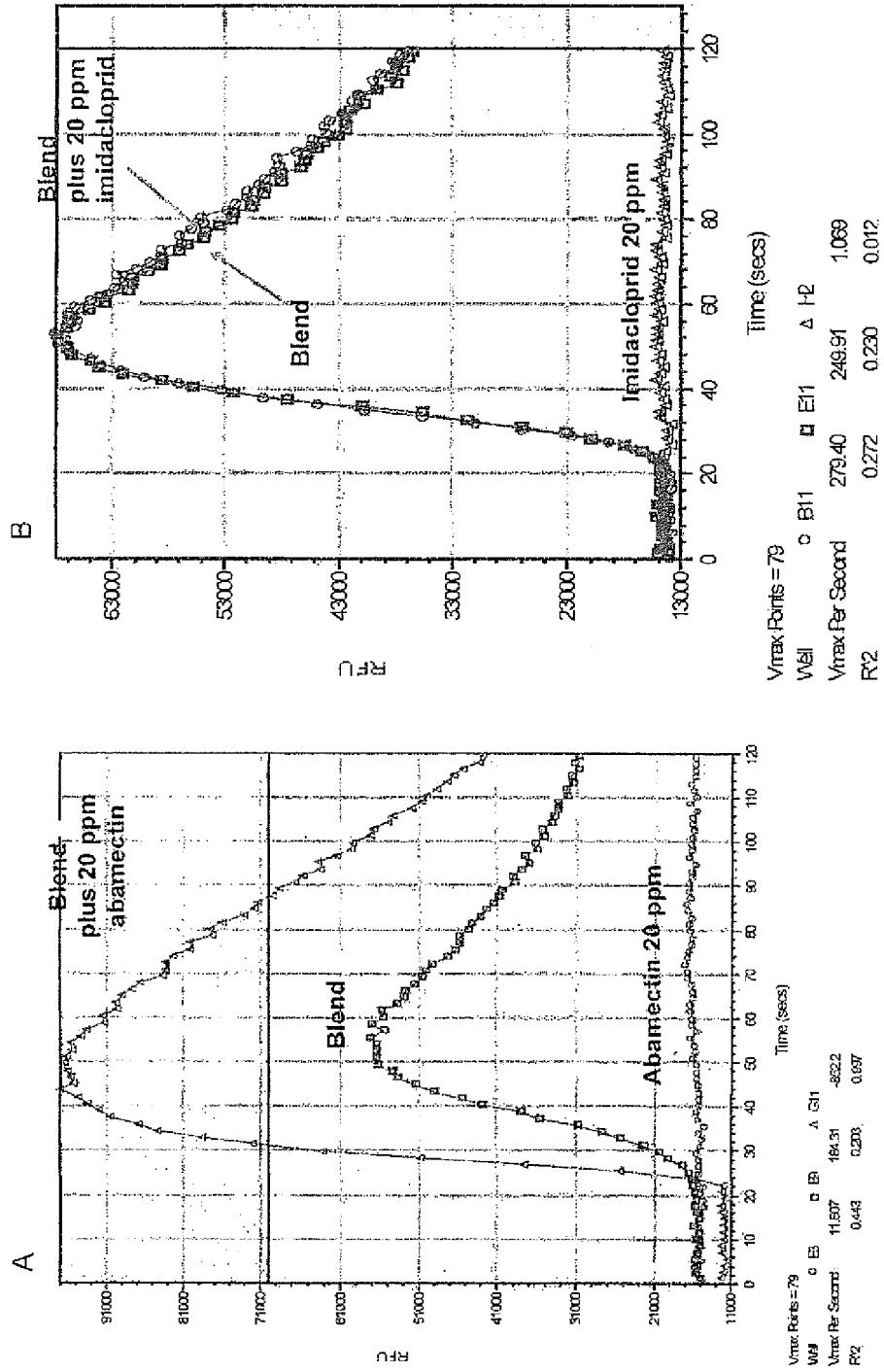
FIG. 23A shows fluorescence intensity curves corresponding to intracellular calcium ion concentrations, with the curve corresponding to the compositions containing 1) abamectin alone, 2) a test composition alone, and 3) the mixture of abamectin and the test composition. The test composition is Blend 7.
FIG. 23B shows fluorescence intensity curves corresponding to intracellular calcium ion concentrations, with the curve corresponding to the compositions containing 1) imidacloprid alone, 2) a test composition alone, and 3) the mixture of imidacloprid and the test composition. The test composition is Blend 7.

As shown in FIG. 23A, the composition containing the mixture of imidacloprid and Blend 7 exhibited (1) a much higher peak intensity, (2) a higher V. per second, and (3) a much higher intensity at each time point between 25 second and 120 seconds (end of the calcium measurement) than the compositions containing either of the ingredients alone. This demonstrates that imidacloprid and Blend 7 act synergistically in this cell system to affect intracellular calcium ion concentrations.

This combination of ingredients, when applied to a pest expressing the tyramine receptor, also acts synergistically to control the pest.

Example 25

Synergistic Effects of a Combination of Blend 11/Blend 39 and Vohimbine/Forskolin/Genistein on In vitro Calcium Mobilization A Schneider cell line was produced that expressed a cell-surface tyramine receptor of Drosophila melanogaster, as described above. Cells of this line were exposed to three different compositions. With reference to FIG. 24A, the first composition contained yohimbine at 100 ppm. With reference to FIG. 25A, the second solution contained Blend 11 at 0.1 mg/ml by volume, and the third composition contained a mixture of yohimbine at 100 ppm and Blend 11 at 0.1% by volume. Blend 11 was labeled as "B5028" and exemplified in Ingredient Family 2 of Table 6. The results of this procedure are shown in FIGS. 24A and 25A as fluorescence intensity curves corresponding to intracellular calcium ion concentrations.

As shown in FIG. 25A, the composition containing the mixture of yohimbine and Blend 11 exhibited (1) a higher peak intensity, (2) a higher $V_{max}$ per second, and (3) a higher intensity at each time point between 25 second and 120 seconds (end of the calcium measurement) than the compositions containing either of the ingredients alone. This demonstrates that yohimbine and Blend 11 act synergistically in this cell system to affect intracellular calcium ion concentrations.

Figure 25:
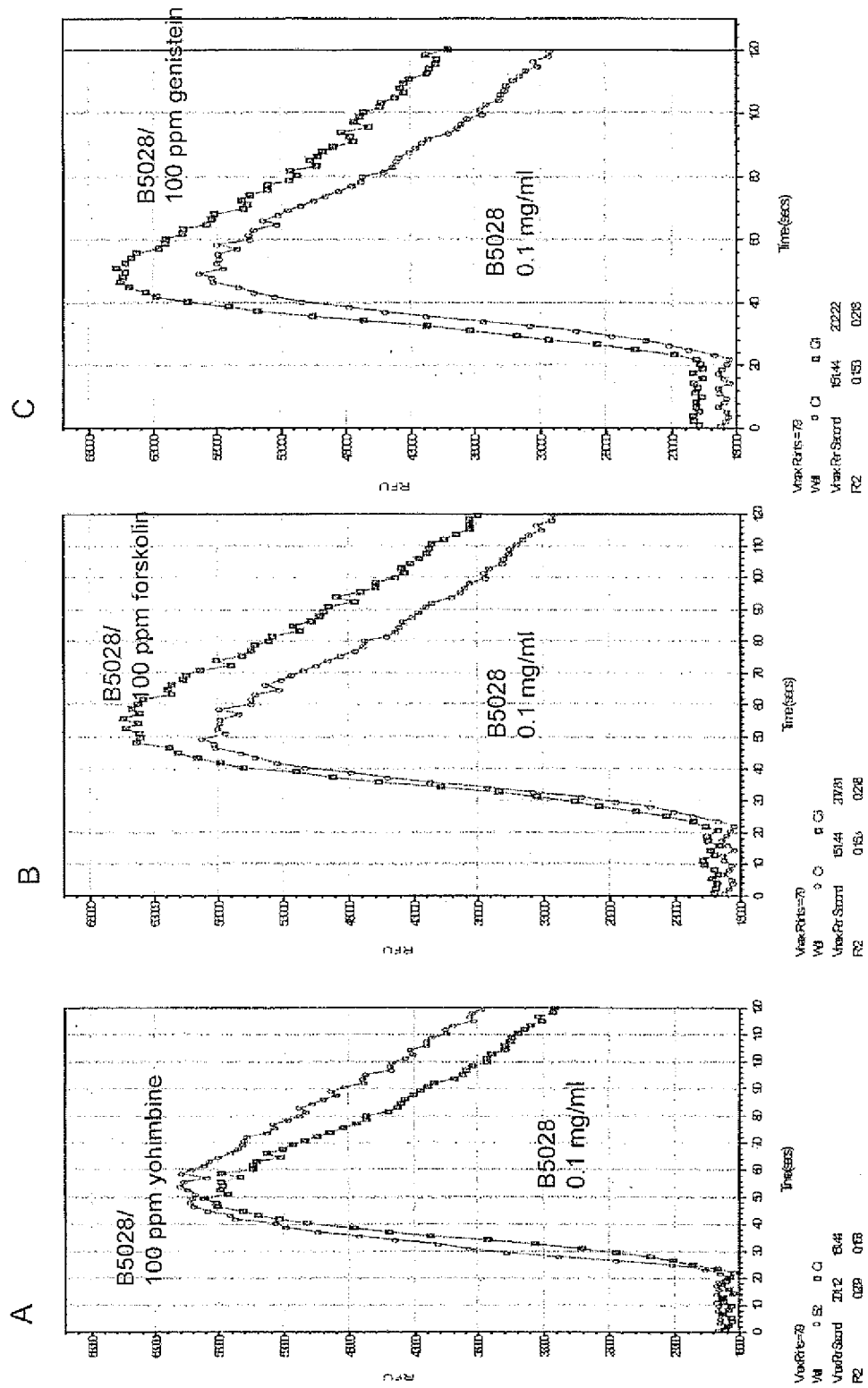
FIG. 25A shows fluorescence intensity curves corresponding to intracellular calcium ion concentrations, with the curve corresponding to the compositions containing 1) a test composition alone, and 2) the mixture of yohimbine and the test composition. The test composition is Blend 2, and labeled as "B5028".
FIG. 25B shows fluorescence intensity curves corresponding to intracellular calcium ion concentrations, with the curve corresponding to the compositions containing 1) a test composition alone, and 2) the mixture of forskolin and the test composition. The test composition is Blend 2, and labeled as "B5028".
FIG. 25C shows fluorescence intensity curves corresponding to intracellular calcium ion concentrations, with the curve corresponding to the compositions containing 1) a test composition alone, and 2) the mixture of genistein and the test composition. The test composition is Blend 2, and labeled as "B5028".

The synergistic effects of the combinations of Blend 11 at 0.1 mg/ml by volume with forskolin at 100 ppm and with genistein at 100 ppm were also tested in the same fashion, as shown in FIG. 25.

Figure 26:
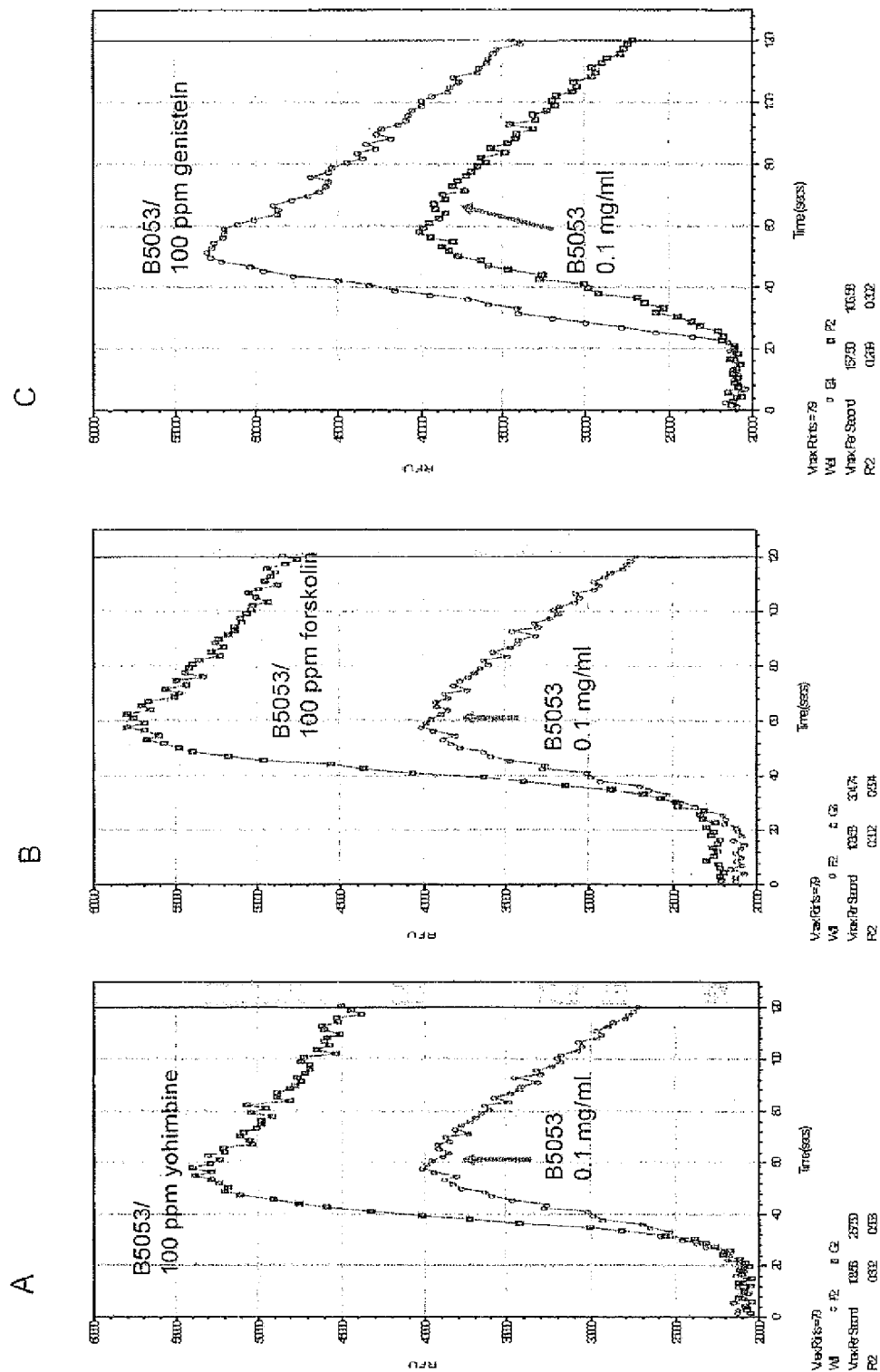
FIG. 26A shows fluorescence intensity curves corresponding to intracellular calcium ion concentrations, with the curve corresponding to the compositions containing 1) a test composition alone, and 2) the mixture of yohimbine and the test composition. The test composition is Blend 39, and labeled as "B5053".
FIG. 26B shows fluorescence intensity curves corresponding to intracellular calcium ion concentrations, with the curve corresponding to the compositions containing 1) a test composition alone, and 2) the mixture of forskolin and the test composition. The test composition is Blend 39, and labeled as "B5053".
FIG. 26C shows fluorescence intensity curves corresponding to intracellular calcium ion concentrations, with the curve corresponding to the compositions containing 1) a test composition alone, and 2) the mixture of genistein and the test composition. The test composition is Blend 39, and labeled as "B5053".

Similarly, the synergistic effects of the combinations of Blend 39 at 0.1 mg/ml by volume with forskolin at 100 ppm and with genistein at 100 ppm were tested in the same fashion, as shown in FIG. 26. Blend 39 was labeled as "B5053" and exemplified in Ingredient Family 8 of Table 6.

Figure 27:
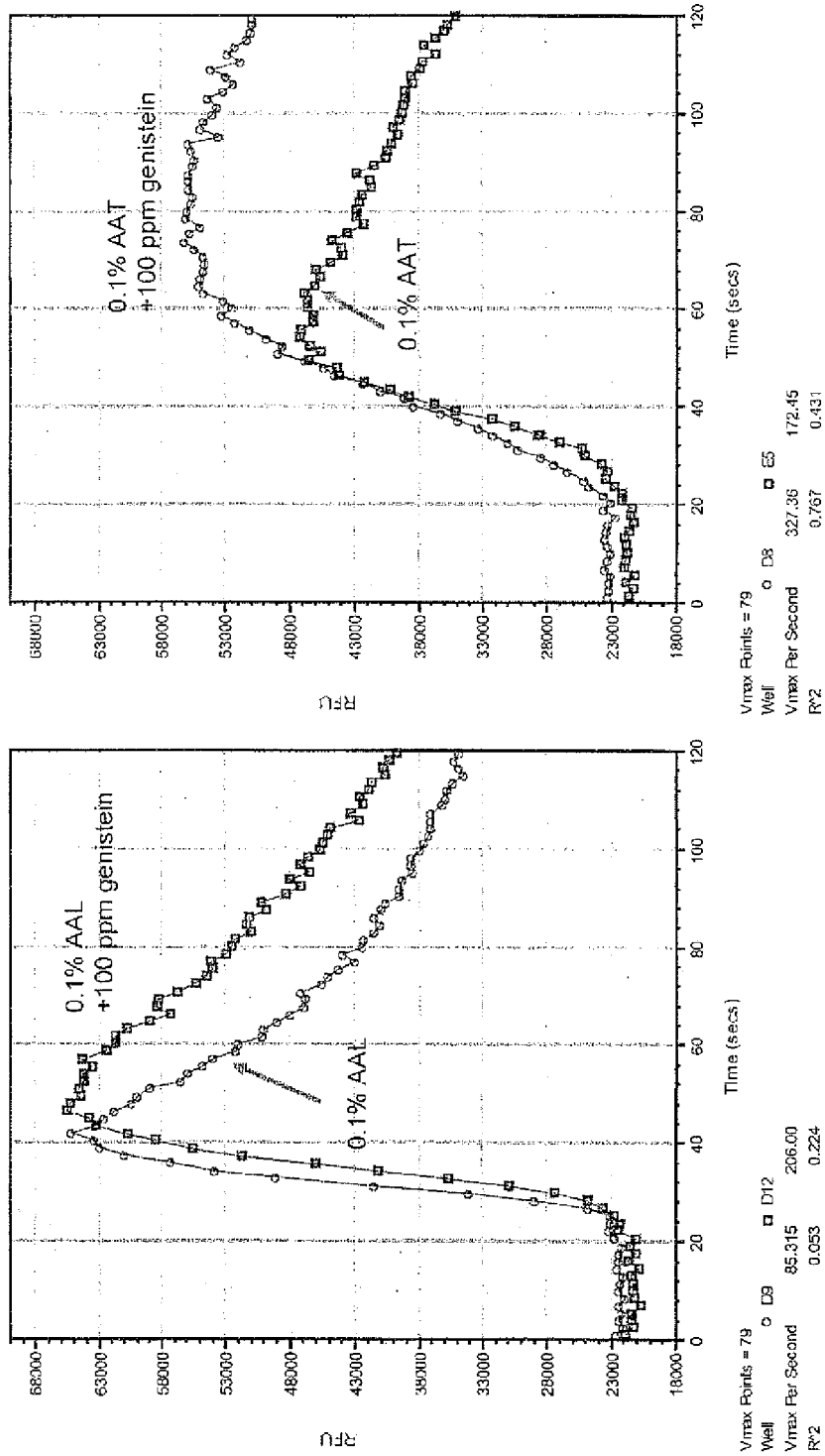
FIG. 27A shows fluorescence intensity curves corresponding to intracellular calcium ion concentrations, with the curve corresponding to the compositions containing 1) a test composition alone, and 2) the mixture of genistein and the test composition. The test composition is Blend 41, and labeled as "AAL".
FIG. 27B shows fluorescence intensity curves corresponding to intracellular calcium ion concentrations, with the curve corresponding to the compositions containing 1) a test composition alone, and 2) the mixture of genistein and the test composition. The test composition is Blend 42, and labeled as "AAT".

Similarly, the synergistic effects of the combinations of Blend 41 at 0.1 mg/ml with genistein at 100 ppm were tested in the same fashion, as shown in FIG. 27. Blend 41 was labeled as "AAL" and exemplified in Ingredient Family 13 of Table 6.

Furthermore, the synergistic effects of the combinations of Blend 42 at 0.1 mg/ml with genistein at 100 ppm were tested in the same fashion, as shown in FIG. 27. Blend 42 was labeled as "AAT" and exemplified in Ingredient Family 3 of Table 6.

The results demonstrate that these combinations of ingredients act synergistically in this cell system to affect intracellular calcium ion concentrations. These combinations of ingredients, when applied to a pest expressing the tyramine receptor, also act synergistically to control the pest.

Example 26

Negligible Effects of a Combination of a Blend and Imidacloprid on In vitro Calcium Mobilization A Schneider cell line was produced that expressed a cell-surface tyramine receptor of Drosophila melanogaster, as described above. Cells of this line were exposed to three different compositions. The first composition contained imidacloprid at 20 ppm. The second solution contained Blend 7 at 0.01% by volume. The third composition contained a mixture of imidacloprid at 20 ppm and Blend 7 at 0.01% by volume. The composition of Blend 7 was exemplified in Ingredient Family 5 of Table 6. The results of this procedure are shown in FIG. 23B as fluorescence intensity curves corresponding to intracellular calcium ion concentrations.

As shown in FIG. 23B, the intracellular calcium concentration profiles were nearly identical for the Blend 7 alone and Blend 7 with imidacloprid. This demonstrates that imidacloprid and Blend 7 do not act synergistically in this cell system to affect intracellular calcium ion concentrations.

Blends listed in the Table 18, alone and in combination with imidacloprid, were tested in the same fashion.

TABLE 18

| | Exemplified in Table 6 | Blend Concentration by Volume | Imidacloprid Concentration by Volume | Results Shown |
|---|---|---|---|---|
| Blend 7 | Ingredient Family 5 | 0.5% | 20 ppm | FIG. 23B |
| Blend 11 | Ingredient Family 2 | 0.5% | 20 ppm | FIG. 17D |
| Blend 39 | Ingredient Family 8 | 0.5% | 20 ppm | FIG. 18B |

As shown in FIGS. 23B, 17D and 18B, the intracellular calcium concentration profiles were nearly identical for the Blends 11 and 39 alone and each blend with imidacloprid. This demonstrates that imidacloprid and Blends 7, 11 and 39 do not act synergistically in this cell system to affect intracellular calcium ion concentrations.

Example 27

Negligible Effects of a Combination of Blend 27 and Yohimbine/Forskolin/Genistein on In vitro Calcium Mobilization A Schneider cell line was produced that expressed a cell-surface tyramine receptor of Drosophila melanogaster, as described above. Cells of this line were exposed to three different compositions. The first composition contained yohimbine at 100 ppm. The second solution contained Blend 27 at 0.1% by volume. The third composition contained a mixture of yohimbine at 100 ppm and Blend 27 at 0.1% by volume. Blend 27 was labeled as "B7001" and exemplified in Ingredient Family 1 of Table 6. The results of this procedure are shown in FIG. 28 as fluorescence intensity curves corresponding to intracellular calcium ion concentrations.

Figure 28:
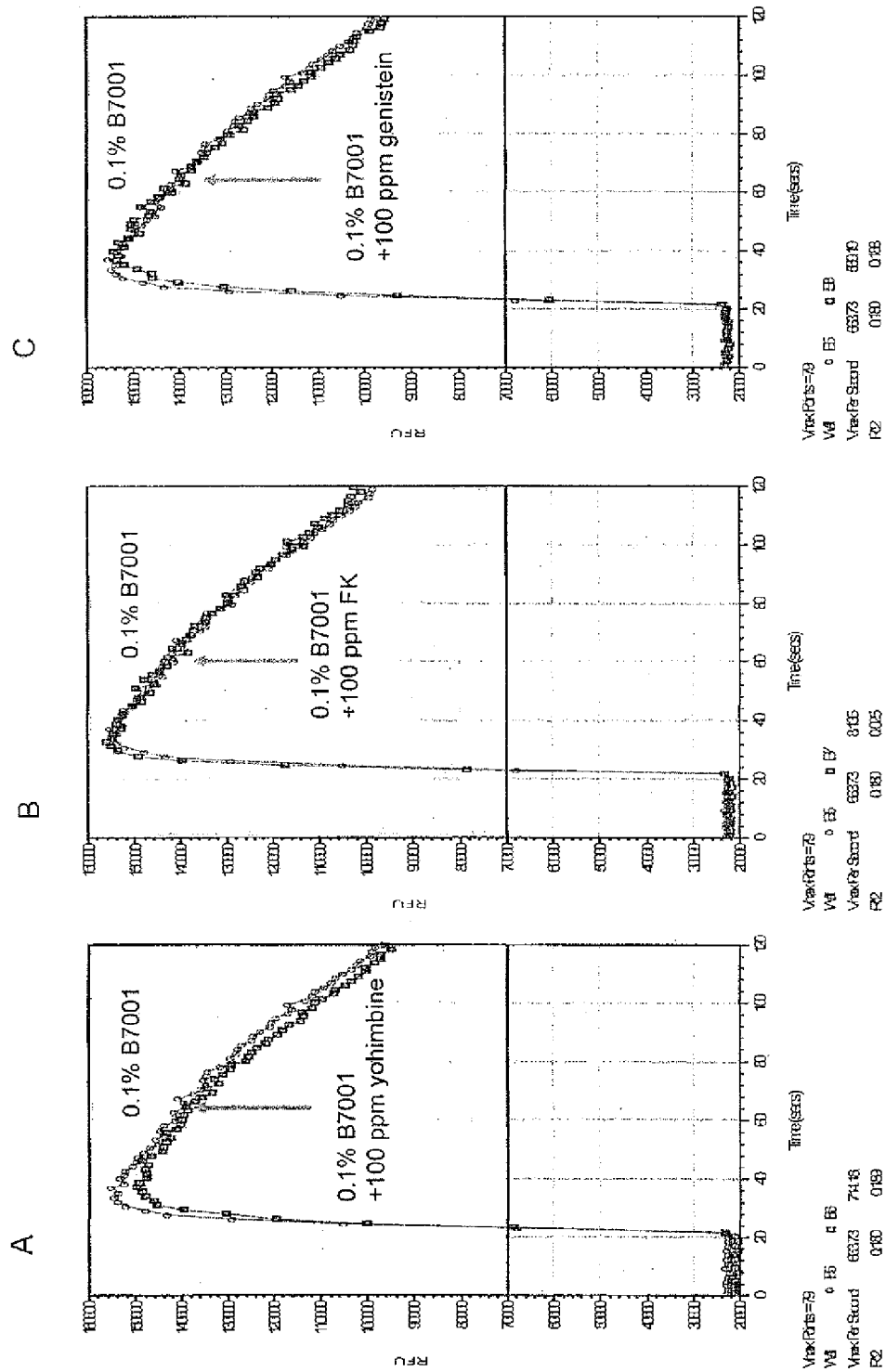
FIG. 28A shows fluorescence intensity curves corresponding to intracellular calcium ion concentrations, with the curve corresponding to the compositions containing 1) a test composition alone, and 2) the mixture of yohimbine and the test composition. The test composition is Blend 27, and labeled as "B7001".
FIG. 28B shows fluorescence intensity curves corresponding to intracellular calcium ion concentrations, with the curve corresponding to the compositions containing 1) a test composition alone, and 2) the mixture of forskolin (labeled "FK") and the test composition. The test composition is Blend 27, and labeled as "B7001".
FIG. 28C shows fluorescence intensity curves corresponding to intracellular calcium ion concentrations, with the curve corresponding to the compositions containing 1) a test composition alone, and 2) the mixture of genistein and the test composition. The test composition is Blend 27, and labeled as "B7001".

As shown in FIG. 28, the intracellular calcium concentration profiles for the Blend 27 alone and Blend 27 with yohimbine were nearly identical. This demonstrates that yohimbine and Blend 27 do not act synergistically in this cell system to affect intracellular calcium ion concentrations.

Similarly, the combination of Blend 27 at 0.1% by volume with forskolin at 100 ppm and with genistein at 100 ppm were tested in the same fashion, as shown in FIG. 28. This demonstrates that Blend 27 do not act synergistically with yohimbine, forskolin or genistein in this cell system to affect intracellular calcium ion concentrations.

Example 28

Inhibitive Effects of a Combination of Blend 58 and Yohimbine/Forskolin/Genistein on In vitro Calcium Mobilization A Schneider cell line was produced that expressed a cell-surface tyramine receptor of Drosophila melanogaster, as described above. Cells of this line were exposed to three different compositions. The first composition contained yohimbine at 100 ppm. The second solution contained Blend 58 at 0.1% by volume. The third composition contained a mixture of yohimbine at 100 ppm and Blend 58 at 0.1% by volume. Blend 58 was labeled as "B7002" and exemplified in Ingredient Family 14 of Table 6. The results of this procedure are shown in FIG. 29 as fluorescence intensity curves corresponding to intracellular calcium ion concentrations.

Figure 29:
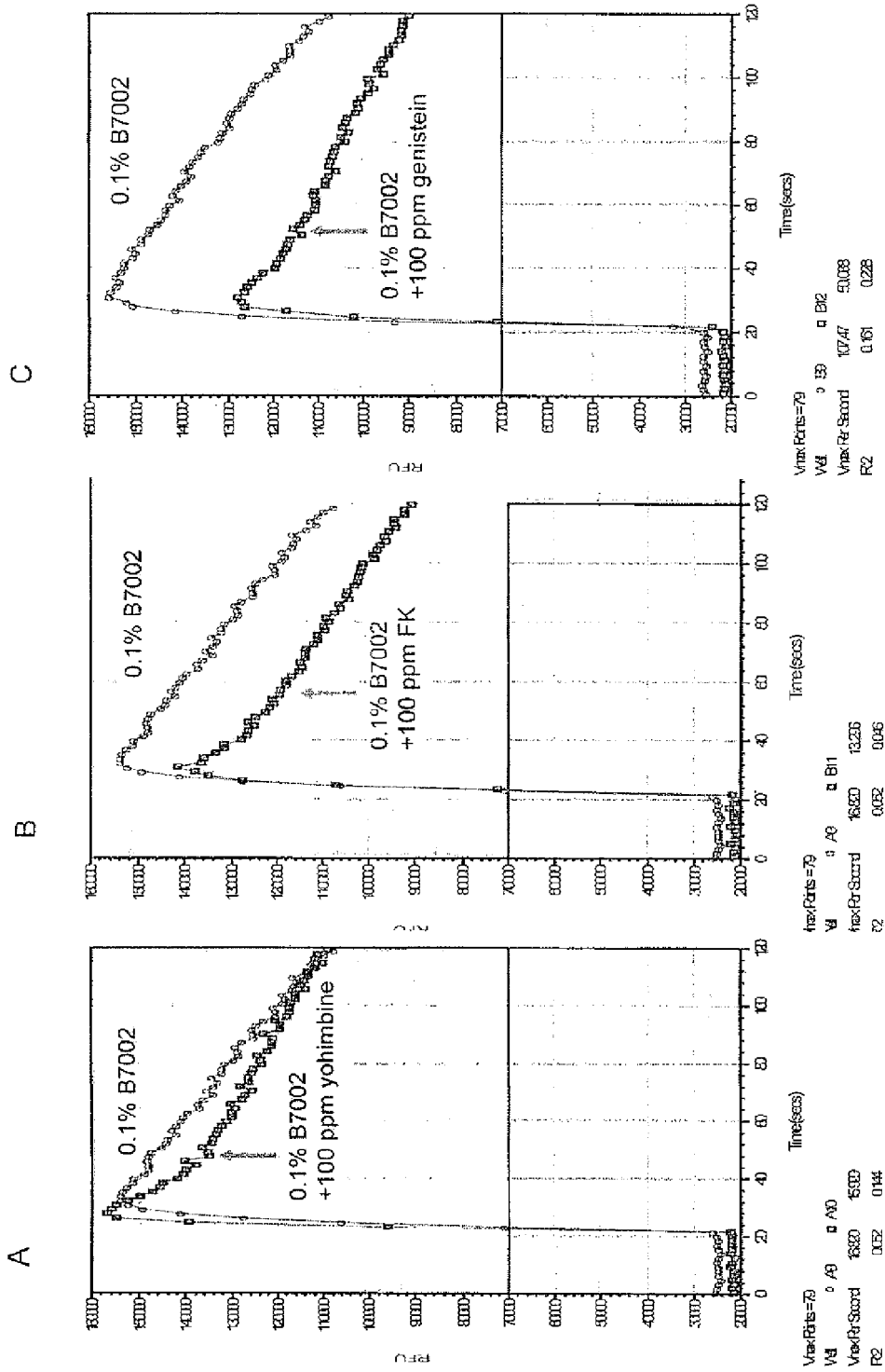
FIG. 29A shows fluorescence intensity curves corresponding to intracellular calcium ion concentrations, with the curve corresponding to the compositions containing 1) a test composition alone, and 2) the mixture of yohimbine and the test composition. The test composition is Blend 58, and labeled as "B7002".
FIG. 29B shows fluorescence intensity curves corresponding to intracellular calcium ion concentrations, with the curve corresponding to the compositions containing 1) a test composition alone, and 2) the mixture of forskolin (labeled "FK") and the test composition. The test composition is Blend 58, and labeled as "B7002".
FIG. 29C shows fluorescence intensity curves corresponding to intracellular calcium ion concentrations, with the curve corresponding to the compositions containing 1) a test composition alone, and 2) the mixture of genistein and the test composition. The test composition is Blend 58, and labeled as "B7002".

As shown in FIG. 29, the composition containing the mixture of yohimbine and Blend 58 exhibited (1) a lower peak intensity, (2) a lower $V_{max}$ per second, and (3) a lower intensity at each time point between 25 second and 100 seconds. This demonstrates that yohimbine and Blend 58 do not act synergistically in this cell system to affect intracellular calcium ion concentrations.

Similarly, the combination of Blend 58 at 0.1% by volume with forskolin at 100 ppm and with genistein at 100 ppm were tested in the same fashion, as shown in FIG. 29. The results demonstrate that Blend 58 does not act synergistically with forskolin or genistein in this cell system to affect intracellular calcium ion concentrations.

Example 29

Inhibitive Effects of a Combination of Anise Oil and Yohimbine/Forskolin/Genistein on In vitro Calcium Mobilization A Schneider cell line was produced that expressed a cell-surface tyramine receptor of *Drosophila melanogaster*, as described above. Cells of this line were exposed to three different compositions. The first composition contained yohimbine at 100 ppm. The second solution contained anise oil at 0.1% by volume. The third composition contained a mixture of yohimbine at 100 ppm and anise oil at 0.1% by volume. The results of this procedure are shown in FIG. 30A as fluorescence intensity curves corresponding to intracellular calcium ion concentrations.

As shown in FIG. 30A, the composition containing the mixture of fipronil and anise oil exhibited (1) a lower peak intensity, (2) a lower $V_{max}$ per second, and (3) a lower intensity at each time point between 35 second and 120 seconds. This demonstrates that yohimbine and anise oil do not act synergistically in this cell system to affect intracellular calcium ion concentrations.

Figure 30:
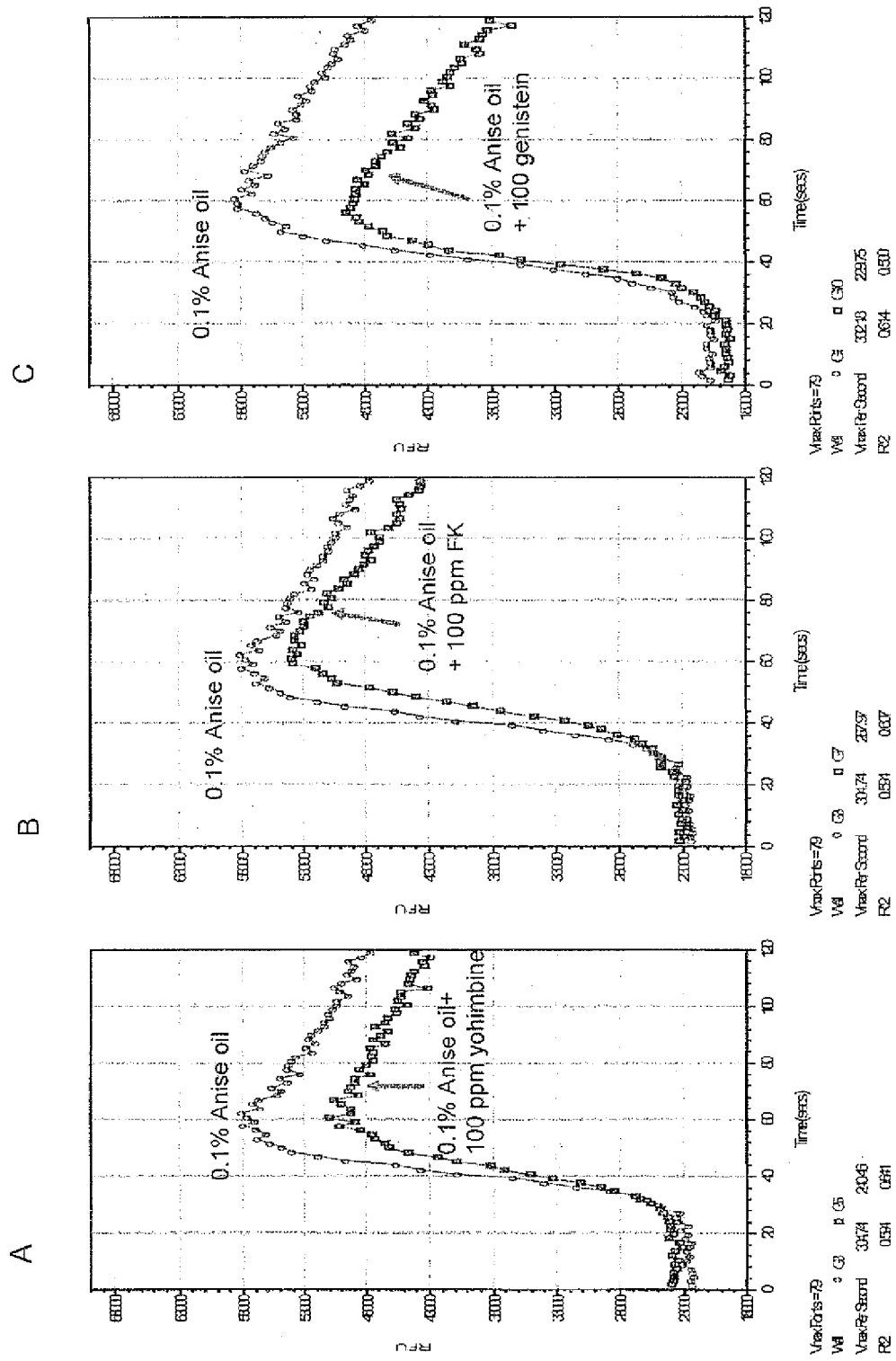
FIG. 30A shows shows fluorescence intensity curves corresponding to intracellular calcium ion concentrations, with the curve corresponding to the compositions containing 1) a test composition alone, and 2) the mixture of yohimbine and the test composition. The test composition is anise oil.
FIG. 30B shows shows fluorescence intensity curves corresponding to intracellular calcium ion concentrations, with the curve corresponding to the compositions containing 1) a test composition alone, and 2) the mixture of forskolin (labeled "FK") and the test composition. The test composition is anise oil.
FIG. 30C shows shows fluorescence intensity curves corresponding to intracellular calcium ion concentrations, with the curve corresponding to the compositions containing 1) a test composition alone, and 2) the mixture of genistein and the test composition. The test composition is anise oil.

Similarly, the combination of anise oil at 0.1% by volume with forskolin at 100 ppm and with genistein at 100 ppm were tested in the same fashion, as shown in FIG. 30. The results demonstrate that anise oil does not act synergistically with forskolin or genistein in this cell system to affect intracellular calcium ion concentrations.

Example 30

Figure 31:
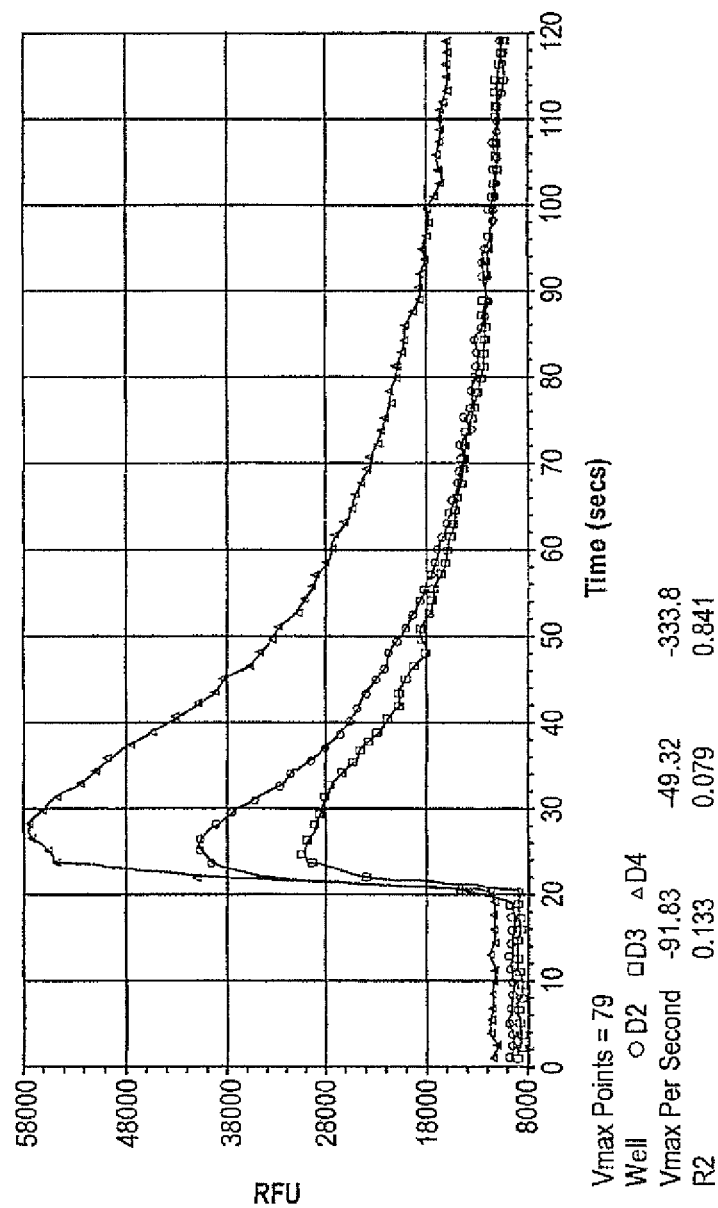
FIG. 31 shows fluorescence intensity curves corresponding to intracellular calcium ion concentrations, with the curve corresponding to the composition containing the mixture of imidacloprid and thyme oil indicated by triangles, the curve corresponding to the composition containing the thyme oil alone indicated by circles, and the curve corresponding to the composition containing imidacloprid alone indicated by squares.

In vitro Calcium Mobilization Effects of a Combination of Thyme Oil and Imidacloprid A Schneider cell line was produced that expressed a cell-surface tyramine receptor of *Drosophila melanogaster*, as described above. Cells of this line were exposed to three different compositions. The first composition contained imidacloprid at 1 mg/ml. The second solution contained thyme oil at 1 mg/ml. The third composition contained an approximately 50/50 mixture of imidacloprid and thyme oil, with the mixture contained at a concentration of 1 mg/ml. The results of this screening procedure are shown in FIG. 31 as fluorescence intensity curves corresponding to intracellular calcium ion concentrations. In FIG. 31, the curve corresponding to the composition containing the mixture of imidacloprid and thyme oil is indicated by triangles, the curve corresponding to the composition containing the thyme oil alone is indicated by circles, and the curve corresponding to the composition containing imidacloprid alone is indicated by squares. These curves may be obtained by the following method.

As shown in FIG. 31, the composition containing the mixture of imidacloprid and thyme oil exhibited a much higher peak intensity and $V_{max}$ per second than the compositions containing either of the ingredients alone. This demonstrates that imidacloprid and thyme oil act synergistically in this cell system to affect intracellular calcium ion concentrations.

This combination of ingredients, when applied to a pest expressing the tyramine receptor, also acts synergistically to control the pest.

Example 31

Figure 10:
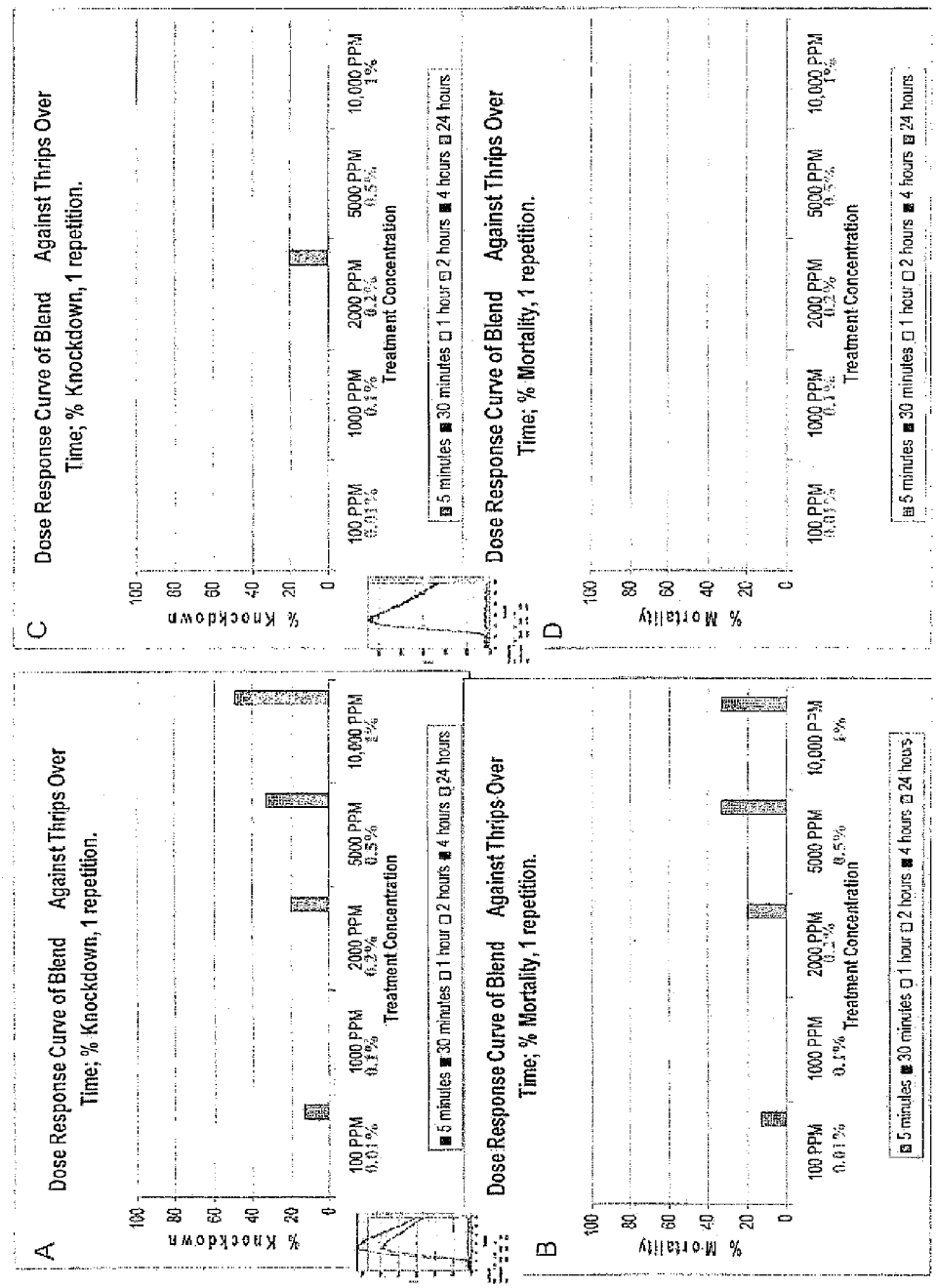
FIG. 10A shows a dose dependent pesticidal effect (knockdown) against thrips caused by Blend 11.
FIG. 10B shows a dose dependent pesticidal effect (mortality) against thrips caused by Blend 11.
FIG. 10C shows a dose dependent pesticidal effect (knockdown) against thrips caused by Blend 8.
FIG. 10D shows a dose dependent pesticidal effect (mortality) against thrips caused by Blend 8.

In vitro Calcium Mobilization Effects of a Combination of Thyme Oil and Fluoxastrobin A Schneider cell line was produced that expressed a cell-surface tyramine receptor of *Drosophila melanogaster*, as described above. Cells of this line were exposed to three different compositions. The first composition contained fluoxastrobin at 1 mg/ml. The second solution contained thyme oil at 1 mg/ml. The third composition contained an approximately 50/50 mixture of fluoxastrobin and thyme oil, with the mixture contained at a concentration of 1 mg/ml. The results of this screening procedure are shown in FIG. 10 as fluorescence intensity curves corresponding to intracellular calcium ion concentrations. In FIG. 10, the curve corresponding to the composition containing the mixture of fluoxastrobin and thyme oil is indicated by triangles, the curve corresponding to the composition containing the thyme oil alone is indicated by squares, and the curve corresponding to the composition containing fluoxastrobin alone is indicated by circles. These curves may be obtained by the method described above.

Figure 32:
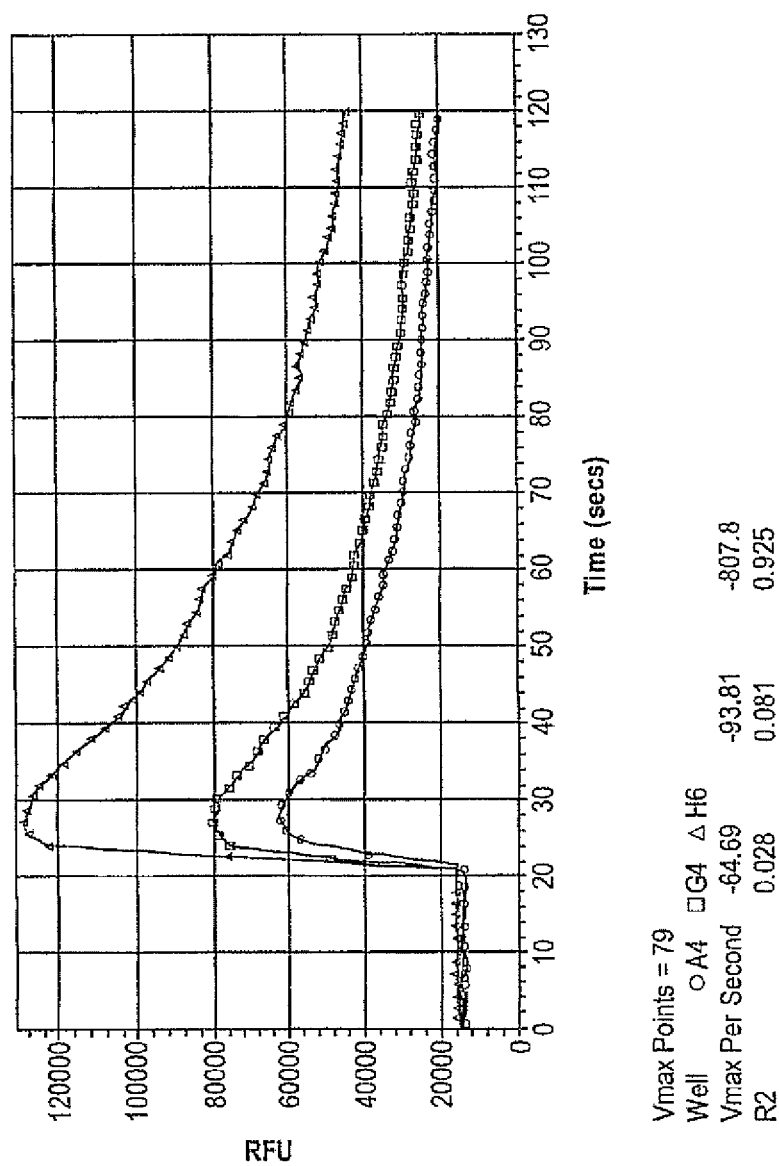
FIG. 32 shows fluorescence intensity curves corresponding to intracellular calcium ion concentrations, with the curve corresponding to the composition containing the mixture of fluoxastrobin and thyme oil indicated by triangles, the curve corresponding to the composition containing the thyme oil alone indicated by squares, and the curve corresponding to the composition containing fluoxastrobin alone indicated by circles.

As shown in FIG. 32, the composition containing the mixture of fluoxastrobin and thyme oil exhibited a much higher peak intensity and $V_{max}$ per second than the compositions containing either of the ingredients alone. This demonstrates that fluoxastrobin and thyme oil act synergistically in this cell system to affect intracellular calcium ion concentrations.

This combination of ingredients, when applied to a pest expressing the tyramine receptor, also acts synergistically to control the pest.

One of ordinary skill in the art will recognize that modifications and variations are possible without departing from the teachings of the invention. This description, and particularly the specific details of the exemplary embodiments disclosed, is provided primarily for clearness of understanding and no unnecessary limitations are to be understood therefrom, for modifications and other embodiments will become evident to those skilled in the art upon reading this disclosure and can be made without departing from the spirit or scope of the claimed invention.

What is claimed is:

1. A composition for controlling a target pest comprising a first agent and a second agent, wherein the first agent has a first activity against the target pest, the second agent has a second activity against the target pest, the composition has a third activity against the target pest, and the third activity reflects a synergistic interaction of the first agent and the second agent;

wherein the first agent comprises geraniol, isopropyl myristate, and thyme oil white; and wherein the second agent comprises imidacloprid.

2. The composition of claim 1, wherein the first agent is capable of interacting with a G-protein coupled receptor in the target pest, and wherein the second agent acts on a molecular target other than the receptor.

3. The composition of claim 1, wherein the first activity persists for a first period, the second activity persists for a second period, the third activity persists for a third period, and the third period is longer than either the first period or the second period.

4. The composition of claim 1, wherein the target pest is a species belonging to an animal order selected from the group consisting of Acari, Anoplura, Araneae, Blattaria, Blattodea, Coleoptera, Collembola, Diptera, Grylloptera, Hemiptera, Heteroptera, Homoptera, Hymenoptera, Isopoda, Isoptera, Lepidoptera, Mantodea, Mallophaga, Neuroptera, Odonata, Orthoptera, Psocoptera, Rhabditida, Siphonaptera, Symphyla, Thysanura, and Thysanontera.

5. A method of controlling a target pest, comprising administering an effective amount of the composition of claim 1 to the target pest or a substrate associated with the target pest, thereby achieving synergistic pest control.

6. A method of pest control comprising the steps of:

providing a target pest having at least one target G-protein coupled receptor; contacting the target pest with the composition of claim 1 comprising at least a first agent and a second agent, wherein the first agent is capable of interacting with the target receptor to trigger, disrupt or alter a biological function related to the binding of the target receptor with the first agent, and wherein the second agent is capable of interacting with a non-receptor molecule or step associated with cycling of the target receptor, to disrupt the cycling of the target receptor; wherein the first and second agents in combination cooperate to amplify the disrupted or altered function resulting from the binding of the target receptor by the first agent, resulting in synergistic control of the pest.

* * * * *

UNITED STATES PATENT AND TRADEMARK OFFICE
CERTIFICATE OF CORRECTION

PATENT NO.      : 8,691,256 B2
APPLICATION NO. : 12/936039
DATED           : April 8, 2014
INVENTOR(S)     : Essam Enan Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 358 days.

Signed and Sealed this

Twenty-ninth Day of September, 2015

Michelle K. Lee
*Director of the United States Patent and Trademark Office*